US012558416B2

(12) United States Patent
Chuah et al.

(10) Patent No.: US 12,558,416 B2
(45) Date of Patent: Feb. 24, 2026

(54) ENDOTHELIUM-SPECIFIC NUCLEIC ACID REGULATORY ELEMENTS AND METHODS AND USE THEREOF

(71) Applicant: Vrije Universiteit Brussel, Brussels (BE)

(72) Inventors: Marinee Chuah, Bierbeek (BE); Thierry Vandendriessche, Bierbeek (BE)

(73) Assignee: Vrije Universiteit Brussel, Brussels (BE)

( * ) Notice: Subject to any disclaimer, the term of this patent is extended or adjusted under 35 U.S.C. 154(b) by 810 days.

(21) Appl. No.: 17/815,136

(22) Filed: Jul. 26, 2022

(65) Prior Publication Data

US 2023/0051499 A1     Feb. 16, 2023

Related U.S. Application Data

(62) Division of application No. 16/065,629, filed as application No. PCT/EP2016/082314 on Dec. 22, 2016, now Pat. No. 11,446,375.

(30) Foreign Application Priority Data

Dec. 22, 2015    (WO) ........................ PCT/EP15/81075

(51) Int. Cl.
| | |
|---|---|
| *A61K 39/23* | (2006.01) |
| *C12N 15/67* | (2006.01) |
| *C12N 15/86* | (2006.01) |

(52) U.S. Cl.
CPC .............. *A61K 39/23* (2013.01); *C12N 15/67* (2013.01); *C12N 15/86* (2013.01); *C12N 2740/15043* (2013.01); *C12N 2750/14143* (2013.01); *C12N 2830/00* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 5,656,454 A | 8/1997 | Lee et al. |
| 6,524,815 B1 | 2/2003 | Huber et al. |
| 2005/0112110 A1 | 5/2005 | Harats et al. |
| 2007/0161031 A1 | 7/2007 | Trinklein et al. |
| 2011/0065100 A1 | 3/2011 | Aldred et al. |
| 2012/0301443 A1 | 11/2012 | Raffi et al. |
| 2014/0017215 A1 | 1/2014 | Ayares et al. |

FOREIGN PATENT DOCUMENTS

| | | |
|---|---|---|
| EP | 1 264 892 | 12/2002 |
| JP | 2005-204549 | 8/2005 |
| JP | 2015-109833 | 6/2015 |
| WO | 2008/073303 | 6/2008 |
| WO | 2011/090684 | 7/2011 |

OTHER PUBLICATIONS

Abel et al.,"Specific gene delivery to liver sinusoidal and artery endothelial cells." Blood. 122(12):2030-8 (Sep. 2013).
Altshoul et al., "Basic Local Alignment Search Tool," J Mol Biol 215:403-10 (1990).
Anliker et al., "Specific gene transfer to neurons, endothelial cells and hematopoietic progenitors with lentiviral vectors." Nat Methods. 7(11):929-35 (Nov. 2010; Epub Oct. 10, 2010).
Bhasin et al., "Bioinformatic identification and characterization of human endothelial cell-restricted genes," BMC Genomics, 11:342, pp. 1-18 (May 2010).
Buchholz et al. "Surface-Engineered Viral Vectors for Selective and Cell Type-Specific Gene Delivery." Trends Biotechnol. 33(12):777-90 (Dec. 2015; Epub Oct. 20, 2015).
Dai et al., "Identification of Synthetic Endothelial Cell-Specific Promoters by Use of a High-Throughput Screen," Journal of Virology 87(12):6209-21 (Jun. 2004).
DeLeve et al., "Liver sinusoidal endothelial cells and liver regeneration," J Clin. Invest. 123(5):1861-66 (May 2013; Epub May 1, 2013).
De Leeuw et al., "Sinusoidal endothelial cells of the liver: fine structure and function in relation to age." J Electron Microsc Tech. 14(3):218-36 (Mar. 1990).
Flynn et al., "Helper-dependent Adenoviral Vectors are Superior In Vitro to First-generation Vectors for Endothelial Cell-targeted Gene Therapy," Mol Ther. 18(12):2121-9 (Dec. 2010).
Godwin et al., "Towards endothelial cell-specific transgene expression in pigs: characterization of the pig ICAM-2 promoter," Xenotransplantation 13(6):515-21 (Nov. 2006).
Levitt et al., "Definition of an efficient synthetic poly(A) site." Genes Dev 3(7):1019-1025 (Jul. 1989).
Mavria et al., "Generation of a high titre retroviral vector for endothelial cell-specific gene expression in vivo," Gene Therapy 7(5):368-76 (Mar. 2000).
McCarty et al., "Self-complementary recombinant adeno-associated virus (scAAV) vectors promote efficient transduction independently of DNA synthesis," Gene Therapy 8(16):1248-54 (Aug. 2001).
McCarty et al., "Adeno-associated virus terminal repeat (TR) mutant generates self-complementary vectors to overcome the rate-limiting step to transduction in vivo," Gene Therapy 10(26):2112-8 (Dec. 2003).

(Continued)

*Primary Examiner* — Oluwatosin A Ogunbiyi
(74) *Attorney, Agent, or Firm* — McDonnell Boehnen Hulbert & Berghoff LLP

(57) ABSTRACT

The disclosure provides nucleic acid regulatory elements that are able to enhance endothelial cell-specific expression of genes, methods employing these regulatory elements and uses of these elements. Expression cassettes and vectors containing these nucleic acid regulatory elements are also disclosed. The nucleic acid regulatory elements, methods of employing these regulatory elements, uses of these elements, and expression cassettes and vectors containing these nucleic acid regulatory elements are particularly useful for applications using gene therapy, more particularly endothelial cell-directed gene therapy, and for vaccination purposes.

15 Claims, 11 Drawing Sheets

Specification includes a Sequence Listing.

(56)  References Cited

OTHER PUBLICATIONS

Modlich et al., "Increasing endothelial cell specific expression by the use of heterologous hypoxic and cytokine-Inducible enhancers," Gene Therapy 7(10):896-902 (May 2000).

Munch et al., "DARPins: an efficient targeting domain for lentiviral vectors." Mol Ther. 9(4):686-93 (Apr. 2011; Epub Jan. 11, 2011).

Munch et al., "Off-target-free gene delivery by affinity-purified receptor-targeted viral vectors." Nat Commun. 10;6:6246 (Feb. 2015).

Munch et al., "Overexpression of ABCG1 protein attenuates arteriosclerosis and endothelial dysfunction in atherosclerotic rabbits," Heart Int. 7(2): e12, pp. 108 (Jun. 2012).

Nathwani et al., "Sustained high-level expression of human factor IX (hFIX) after liver-targeted delivery of recombinant adeno-associated virus encoding the hFIX gene in rhesus macaques," Blood 100(5):1662-9 (Sep. 2002).

Nathwani et al., "Self-complementary adeno-associated virus vectors containing a novel liver-specific human factor IX expression cassette enable highly efficient transduction of murine and nonhuman primate liver," Blood 107 (7):2653-61 (Apr. 2006; Epub Dec. 1, 2005).

Nathwani et al, "Adenovirus-Associated Virus Vector-Mediated Gene Transferin Hemophilia B," N. Engl. J. Med. 365(25):2357-65 (Dec. 2011; Epub Dec. 10, 2011).

Neumann et al., "Liver sinusoidal endothelial cells induce immunosuppressive IL-10-producing Th1 cells via the Notch pathway." Eur J Immunol. 45(7):2008-16 (Jul. 2015; Epub May 12, 2015).

Nicol et al., "Use of in vivo phage display to engineer novel adenoviruses for targeted delivery to the cardiac vasculature." FEBS Lett. 583(12):2100-7 (Jun. 2009; Epub May 28, 2009).

Nicklin & Baker, "Efficient vascular endothelial gene transfer following intravenous adenovirus delivery." Mol Ther. 16(12):1904-5 (Dec. 2008).

Shahani et al., "Human liver sinusoidal endothelial cells but not hepatocytes contain factor VIII." J. Thromb. Hemost 12(1):36-42 (Jan. 2014).

Shahani et al., "Activation of human endothelial cells from specific vascular beds induces the release of a FVIII storage pool." Blood. 115(23):4902-9 (Jun. 2010; Epub Mar. 29, 2010).

Tatusov & Madden, "BLAST 2 Sequences, a new tool for comparing protein and nucleotide sequences," FEMS Microbiol Lett 174:247-50 (1999).

Vandendriessche et al., "Lentiviral vectors containing the human immunodeficiency virus type-1 central polypurine tract can efficiently transduce nondividing hepatocytes and antigen-presenting cells in vivo." Blood 100 (3):813-22 (Aug. 2002).

Vandendriessche et al., "Efficacy and safety of adeno-associated viral vectors based on serotype 8 and 9 vs. entiviral vectors for hemophilia B gene therapy." J Thromb Haemost. 5(1):16-24 (Jan. 2007; Epub Sep. 26, 2006).

Vandendriessche & Chuah, "Targeting endothelial cells by gene therapy." 122(12):1993-4 (Sep. 2013).

White et al., "Assessment of a novel, capsid-modified adenovirus with an improved vascular gene transfer profile." J Cardiothorac Surg. 8:183 pp. 1-8 (Aug. 2013).

White et al., "Targeted gene delivery to vascular tissue in vivo by tropism-modified adeno-associated virus vectors." Circulation. 109(4):513-9 (Feb. 2004; Epub Jan. 19, 2004).

Work et al., "Improved gene delivery to human saphenous vein cells and tissue using a peptide-modified adenoviral vector." Genet Vaccines Ther. 2(1):14 (Oct. 2004).

Work et al., "In vivo biopanning: A methodological approach to identifying novel targeting ligands for delivery of biological agents to the vasculature." Methods Mol Med. 108:395-413 (2005).

Work et al., "Vascular bed-targeted in vivo gene delivery using tropism-modified adeno-associated viruses." Mol Ther. 13(4):683-93 (Apr. 2006; Epub Jan. 4, 2006).

Wu et al., "Optimization of self-complementary AAV vectors for liver-directed expression results in sustained correction of hemophilia B at low vector dose," Mol Ther. 16(2):280-9 (Feb. 2009; Epub Dec. 4, 2007).

GenBank: CE 213087.1 "tigr-gss-dog-17000372777183 Dog Canine lupus familiaris genomic, genomic survey sequence" Entry created Sep. 25, 2003, one page.

The International Search Report from International Application No. PCT/EP2016/082314; dated Mar. 3, 2017, pp. 1-4.

Sequence Alignment SEQ 9 (RAFFI) and SEQ 1 (U.S. Appl. No. 16/065,629) (Year: 2020).

Papac-Milicevic N, Breuss JM, Zaujec J, Ryban L, Plyushch T, Wagner GA, Fenzl S, Dremsek P, Cabaravdic M, Steiner M, Glass CK. The interferon stimulated gene 12 inactivates vasculoprotective functions of NR4A nuclear receptors. Circulation research. Apr. 13, 2012;110(8):e50-63. (Year: 2012).

Rafii S, Kloss CC, Butler JM, et al. Human ESC-derived hemogenic endothelial cells undergo distinct waves of endothelial to hematopoietic transition. Blood, The Journal of the American Society of Hematology. Jan. 31, 2013; 121 (5):770-80. (Year: 2013).

Martensen et al., "The interferon alpha induced protein ISG12 is localized to the nuclear membrane," Eur J Biochem. 268(22):5947-54 (2001).

Genbank Accession No. AJ296088.1 "*Homo sapiens* promoter region of ISG12 gene," published on Jan. 7, 2002 retrieved from the internet https://www.ncbL.nlm.nih.gov/nuccore/AJ296088.1] [1 page].

Prandini MH, Dreher I, Bouillot S, Benkerri S, Moll T, Huber P. The human VE-cadherin promoter is subjected to organ-specific regulation and is activated in tumour angiogenesis. Oncogene. Apr. 2005;24(18):2992-3001. (Year: 2005).

Kren, B. T., Unger, G. M., Sjeklocha, L., et al. Nanocapsule-delivered Sleeping Beauty mediates therapeutic Factor VIII expression in liver sinusoidal endothelial cells of hemophilia A mice. The Journal of clinical investigation, 2009; 119(7), 2086-2099. (Year: 2009).

Zheng C, Baum BJ. Evaluation of promoters for use in tissue-specific gene delivery. Gene Therapy Protocols 2008 (pp. 205-219). Humana Press. (Year: 2008).

De Palma M, Venneri MA, Naldini L. In vivo targeting of tumor endothelial cells by systemic delivery of lentiviral vectors. Human gene therapy. Aug. 10, 2003; 14(12): 1193-206. (Year: 2003).

Dull T, Zufferey R, Kelly M, Mandel RJ, Nguyen M, Trono D, Naldini L. A third-generation lentivirus vector with a conditional packaging system. Journal of virology. Nov. 1, 1998 ;72(11 ):8463-71. (Year: 1998).

De Wet JR, Wood KV, Helinski DR, Deluca M. Cloning of firefly luciferase cDNA and the expression of active uciferase in *Escherichia coli*. Proceedings of the National Academy of Sciences. Dec. 1, 1985 ;82(23):7870-3. (Year: 1985).

Bert AG, Burrows J, Osborne CS, Cockerill PN. Generation of an improved luciferase reporter gene plasmid that employs a novel mechanism for high-copy replication. Plasmid. Sep. 1, 2000 ;44(2):173-82. (Year: 2000).

Kren, B. T., Unger, G. M., Sjeklocha, L., et al. Nanocapsule-delivered Sleeping Beauty mediates therapeutic Factor VIII expression in liver sinusoidal endothelial cells of hemophilia A mice. The Journal of clinical investigation, 2009; 119(7), 2086-2099. (Year: 2009).

Nabel EG. Gene therapy for cardiovascular disease. Circulation. Jan. 15, 1995;91 (2):541-8. (Year: 1995).

Luckow B, Schutz G. Cat constructions with multiple unique restriction sites for the functional analysis of eukaryotic promoters and regulatory elements. Nucleic Acids Research. Jul. 10, 1987;15(13):5490. (Year: 1987).

Zsvak Z, Ivies Z. Sleeping beauty transposition: biology and applications for molecular therapy. Molecular Therapy. Feb. 1, 2004 ;9(2) :147-56. (Year: 2004).

Bio Cat webpage (dated Aug. 16, 2015 biocat.com/genomics/piggybac-transposon-system) retrieved via Wayback Machine Apr. 9, 2021. (Year: 2015).

1

ENDOTHELIUM-SPECIFIC NUCLEIC ACID REGULATORY ELEMENTS AND METHODS AND USE THEREOF

CROSS REFERENCE TO RELATED APPLICATIONS

This application is a divisional of U.S. patent application Ser. No. 16/065,629, filed Jun. 22, 2018, now U.S. Pat. No. 11,446,375, issued Sep. 20, 2022, which is a U.S. National Phase of International Application No. PCT/EP2016/082314, filed Dec. 22, 2016, which claims priority to International Provisional Application No. PCT/EP2015/081075, filed Dec. 22, 2015, the disclosure of each of which is hereby incorporated by cross-reference in its entirety.

REFERENCE TO AN ELECTRONIC SEQUENCE LISTING

A computer readable form of the Sequence Listing is filed with this application by electronic submission and is incorporated into this application by reference in its entirety. The sequence listing submitted herewith is contained in the file created Jul. 26, 2022, entitled "18-920-US-DIV_Sequence-Listing.xml" and is 203 kilobytes in size.

FIELD

The present invention relates to nucleic acid regulatory elements that are able to enhance endothelial-specific expression of genes, methods employing these regulatory elements and use thereof. The invention further encompasses expression cassettes, vectors and pharmaceutical compositions comprising these regulatory elements. The present invention is particularly useful for applications using gene therapy, more particularly endothelial-directed gene therapy, and for vaccination purposes.

BACKGROUND

Endothelial cells form a single cell layer that lines all blood vessels and regulate exchanges between the bloodstream and the surrounding tissues. Signals from endothelial cells organize the growth and development of connective tissue cells that form the surrounding layers of the blood-vessel wall. New blood vessels can develop from the walls of existing small vessels by the outgrowth of endothelial cells, which have the capacity to form hollow capillary tubes even when isolated in culture. Endothelial cells of developing arteries and veins express different cell-surface proteins, which may control the way in which they link up to create a capillary bed. (Molecular Biology of the Cell. 4th Edition). A homeostatic mechanism ensures that blood vessels permeate every region of the body. Cells that are short of oxygen increase their concentration of hypoxia-inducible factor 1 (HIF-1), which stimulates the production of vascular endothelial growth factor (VEGF). VEGF acts on endothelial cells, causing them to proliferate and invade the hypoxic tissue to supply it with new blood vessels. (Molecular Biology of the Cell. 4th Edition).

Endothelial cell phenotypes vary between different organs, between different segments of the vascular loop within the same organ, and between neighbouring endothelial cells of the same organ and blood vessel type. In addition to differences in structure, endothelial cells show remarkable heterogeneity in function. For example, the endothelial cells in the liver, called liver sinusoidal endothelial cells (LSEC), form a continuous lining of the liver capillaries, or sinusoids, separating parenchymal cells and fat-storing cells from sinusoidal blood. LSECs represent unique, highly specialized endothelial cells in the body. LSECs differ in fine structure from endothelial cells lining larger blood vessels and from other capillary endothelia in that they lack a distinct basement membrane and also contain open pores, or fenestrae, in the thin cytoplasmic projections which constitute the sinusoidal wall. This distinctive morphology supports the protective role played by liver endothelium, the cells forming a general barrier against pathogenic agents and serving as a selective sieve for substances passing from the blood to parenchymal and fat-storing cells, and vice versa. Sinusoidal endothelial cells, furthermore, significantly participate in the metabolic and clearance functions of the liver. They have been shown to be involved in the endocytosis and metabolism of a wide range of macromolecules, including glycoproteins, lipoproteins, extracellular matrix components, and inert colloids, establishing endothelial cells as a vital link in the complex network of cellular interactions and cooperation in the liver.

In addition, LSECs have long been noted to contribute to liver regeneration after liver injury. In normal liver, the major cellular source of hepatocyte growth factor (HGF) is the hepatic stellate cell, but after liver injury, HGF expression has been thought to increase markedly in proliferating LSECs (DeLeve et al. Liver sinusoidal endothelial cells and liver regeneration J Clin. Invest. 2013). Another unexpected function of LSEC was recently reported (Shahani et al., J. Thromb. Hemost 2014), demonstrating that LSECs and not hepatocytes express coagulation factor VIII (FVIII). Moreover, endothelial cells, including LSECs, also express von Willebrand factor (vWF). It is known that secreted FVIII would be relatively unstable unless it is associated with vWF. Deficiency of FVIII, a co-factor in the intrinsic coagulation pathway, results in hemophilia A. Liver transplantation in both FVIII-deficient dogs and patients with hemophilia A corrects these disorders. Although the liver is known to be the main site of FVIII production, other organs are probably also important for the regulation of FVIII secretion. Recent studies have shown that lung endothelial cells can synthesize FVIII. Microvascular endothelial cells from lung, heart, intestine, and skin as well as endothelial cells from pulmonary artery constitutively secreted FVIII and released it after treatment with phorbol-myristate acetate and epinephrine. By contrast, endothelial cells from the aorta, umbilical artery and umbilical vein did not constitutively secrete FVIII or release it after treatment with agonists, probably because of a lack of FVIII synthesis. Extrahepatic endothelial cells from certain vascular beds therefore appear to be an important FVIII production and storage site with the potential to regulate FVIII secretion in chronic and acute conditions (Shahani et al. Blood. 2010 Jun. 10; 115(23): 4902-9). In addition, LSECs have also been reported to induce immunosuppressive IL-10-producing Th1 cells via the Notch pathway (Neumann et al. Eur J Immunol. 2015 July; 45(7):2008-16) suggesting an important immune-modulatory role. Therefore, LSEC dysfunction has been regarded as a key event in multiple liver disorders. Future studies are likely to disclose more fully the role of LSEC in the regulation of liver hemodynamics, in liver metabolism and blood clearance, in the maintenance of hepatic structure, in the pathogenesis of various liver diseases, and in the aging process in the liver (De Leeuw et al. J Electron Microsc Tech. 1990 March; 14(3):218-36).

The endothelium is involved in many disease states, either as a primary determinant of pathophysiology or as a secondary target. In particular, endothelial cell dysfunction can be caused by acquired, complex multifactorial, genetic or infectious diseases. In some cases, the underlying endothelial cell defect can be life-threatening, for which no effective cure is presently available. Dysfunction of the vascular endothelium is a hallmark of many human diseases. The endothelium is directly involved in many different diseases including peripheral vascular disease, stroke, heart disease, diabetes, insulin resistance, chronic kidney failure, tumor growth, metastasis, venous thrombosis, and severe viral infectious diseases. Consequently, the endothelium has substantial untapped potential as a therapeutic target. In particular, endothelial cells are attractive target cells for gene therapy to enable robust and/or sustained expression of the cognate therapeutic genes.

In particular, endothelial dysfunction is one of the major pathophysiological mechanisms that leads towards coronary artery disease and other atherosclerotic diseases. Atherosclerosis is a progressive vascular disease characterized by the accumulation of lipids, inflammatory cells, and fibrous elements. In Western societies, it is the underlying cause of approximately 50% of all deaths. Dysfunction or injury of vascular endothelial cells is critical for the development of atherosclerosis. The endothelium functions as a selectively permeable barrier between blood and tissues as it can regulate transcytosis and generate effector molecules such us nitric oxide (NO) that regulate thrombosis, inflammation, vascular tone and vascular remodeling. For example, overexpression of STAMP2 suppresses atherosclerosis and stabilizes plaques in diabetic mice. Similarly, it had been reported that over-expression of ABCG1 by somatic gene transfer to the atherosclerotic vessel wall results in a significant improvement of plaque morphology and composition, and of vascular function in vivo (Heart Int. 2012 Jun. 5; 7(2): e12.).

Endothelial cells also play a key role in angiogenesis and vasculogenesis. Angiogenesis is the physiological process through which new blood vessels form from pre-existing vessels. This is distinct from vasculogenesis, which is the de novo formation of endothelial cells from mesoderm cell precursors. Angiogenesis and vasculogenesis are normal and vital processes in growth and development. However, they also represent a fundamental step in cancer progression, justifying the use of angiogenesis or vasculogenesis inhibitors in the treatment of cancer. Conversely, promoting angiogenesis and vasculogenesis may benefit the treatment of ischemia which is associated with decrease in blood supply to certain organs or tissues. Consequently, the delivery of genes into endothelial cells that either promote or inhibit angiogenesis and/or vasculogenesis opens new perspectives for the treatment of cardiovascular disease and cancer, respectively. This includes a plethora of therapeutic genes including VEGF, PLGF, FGF, sFLT1, antibodies directed against these factors and their cognate receptors, cytokines, chemokines, etc.

Furthermore, endothelial cells are also promising targets for gene therapy to express therapeutic proteins that are missing or defective in genetic disorders that result from mutations in the respective genes. For example, this includes FVIII, vWF or ADAMTS13 (a disintegrin and metalloproteinase with a thrombospondin type 1 motif, member 13). As mentioned above, hemophilia A is due to a deficiency in FVIII. Moreover, deficiency in vWF causes a bleeding diathesis in patients suffering from von Willebrand disease (VWD). Conversely, a deficiency in ADAMTS13 is linked to the development of microvascular thrombosis characteristic of thrombotic thrombocytopenic purpura (TTP). Consequently, to establish an effective cure for these genetic diseases, robust expression of FVIII, vWF or ADAMTS13 in the endothelial cells is required. In addition, given their proximity to the blood, endothelial cells are also ideally suited to express other therapeutic proteins that are normally not expressed by endothelial cells but that can be directly secreted in the blood. This includes, but is not limited to, other coagulation factors (e.g. factor VII, IX, XI etc.), serum proteins (α1-antitrypsin, AAT, antibodies, growth factors etc.).

Finally, endothelial cells also play a key role in viral infection. For example, the Ebola virus is an aggressive pathogen that causes a highly lethal hemorrhagic fever syndrome in humans and nonhuman primates. The virus infects microvascular endothelial cells and compromises vascular integrity. Infection of endothelial cells also induces a cytopathic effect and damage to the endothelial barrier. Similarly, Dengue virus causes leakage of the vascular endothelium, resulting in dengue hemorrhagic fever and dengue shock syndrome. The endothelial cell lining of the vasculature regulates capillary permeability and is altered by immune and chemokine responses which affect fluid barrier functions of the endothelium. Human endothelial cells are susceptible to infection by dengue virus Following attachment to human endothelial cell receptors, dengue virus causes a productive infection that has the potential to increase viral dissemination and viremia. This provides the potential for dengue virus-infected endothelial cells to directly alter barrier functions of the endothelium, contribute to enhancement of immune cell activation, and serve as potential targets of immune responses which play a central role in dengue pathogenesis.

Hence, there is a need to establish effective cures by gene therapy to enable robust expression of the cognate therapeutic genes in the endothelial cells. This requires the development of potent expression cassettes containing the genes of interest. Consequently, there is a need to identify robust nucleic acid regulatory elements capable of substantially increasing transcription in the endothelium.

SUMMARY OF THE INVENTION

To achieve a robust and specific expression in endothelial cells, the inventors have developed a computational approach to identify robust nucleic acid regulatory elements such as cis-regulatory elements (CREs) that are capable of substantially increasing transcription in endothelial cells (also called EC-CREs or EC-REs) when combined with an endothelial specific promoter. Endothelial specific nucleic acid regulatory elements were identified in silico and subsequently validated in in vitro cell lines and also in vivo in mice.

These nucleic acid regulatory elements are critically important for the regulation of gene expression in an endothelial cell type-specific manner. They are typically composed of clusters of transcription factor binding site (TFBS) motifs. The types and arrangement of TFBS and epigenetic modification patterns influence gene expression levels and specificity. Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take into account the importance of including evolutionary conserved regulatory motifs into the expression modules. The development of nucleic acid regulatory elements that can lead to robust and specific expression in endothelial cells will be very useful for achieving safe and efficient gene delivery to endothelial cells for the treatment of disorders related to endothelial cell dysfunction.

The present inventors have relied on a computational approach (cf. FIG. 1) to identify robust nucleic acid regulatory elements that boost gene expression at the transcriptional level in endothelial cells (designated herein as "EC"). This requires the following to computational steps: (1) endothelial cell-specific genes were identified that are highly and specifically expressed based on expression data from endothelial cells; (2) publicly available databases (ENSEMBL) were used for extracting the sequences upstream of the Transcriptional Start Site (TSS) of the selected genes. 3) These sequences were then submitted into UCSC Genome Browser Database for locating the transcription start site in human genome. To extract the corresponding endothelial cell nucleic acid regulatory elements, defined herein as the nucleic acid regulatory elements, the sequences were selected based on the following criteria: a) rich TFBS content, b) epigenetic signatures associated with high DNase hypersensitivity or chromatin accessibility (i.e. histone modifications), and c) evolutionary conserved clusters of TFBS associated with highly expressed endothelial cell-specific genes.

As shown in the experimental section, the inventors identified nucleic acid regulatory elements that will specifically enhance gene expression in endothelial cells.

The endothelial cell regulatory elements will subsequently be validated in vivo, yielding efficient and tissue-specific gene expression. This approach hence, allows for the use of lower and thus safer vector doses, while maximizing therapeutic efficacy.

The invention therefore provides the following aspects:

Aspect 1. A nucleic acid regulatory element for enhancing endothelial cell-specific gene expression comprising, consisting essentially of, or consisting of the sequence selected from the group consisting of: SEQ ID NO:1 to 33, or a sequence having at least 80%, preferably at least 85%, more preferably at least 90%, even more preferably at least 95%, such as 95%, 96%, 97%, 98%, or 99%, identity to any of these sequences. In a preferred embodiment of said aspect, said nucleic acid regulatory element for enhancing endothelial cell-specific gene expression comprises, consists essentially of, or consists of the sequence of SEQ ID NO.22, or a sequence having at least 80%, preferably at least 85%, more preferably at least 90%, even more preferably at least 95%, such as 95%, 96%, 97%, 98%, or 99%, identity to any of these sequences.

Aspect 2. The nucleic acid regulatory element according to aspect 1, having a maximal length of 1000 nucleotides, preferably 800 nucleotides, more preferably 700 nucleotides, most preferably of 610 nucleotides, still comprising the regulatory element defined by any one of SEQ ID Nos: 1 to 33.

Aspect 3. A nucleic acid regulatory element for enhancing gene expression in endothelial cells comprising, consisting essentially of, or consisting of the complement of a sequence as defined by any one of SEQ ID Nos: 1 to 33, or hybridizing under stringent conditions to a sequence as defined by any one of SEQ ID Nos: 1 to 33.

Aspect 4. Use of the nucleic acid regulatory element according to any one aspects 1 to 3 in a nucleic acid expression cassette, or a vector, more particularly for enhancing gene expression in endothelial cells of said nucleic acid expression cassette or vector.

Aspect 5. A nucleic acid expression cassette comprising at least one, such as one, two, three, four, five or more, nucleic acid regulatory elements according to any one of aspects 1 to 3, operably linked to a promoter.

Aspect 6. The nucleic acid expression cassette according to aspect 5, wherein the nucleic acid regulatory element is operably linked to a promoter and a transgene.

Aspect 7. The nucleic acid expression cassette according any one of aspects 5 or 6, wherein the promoter is an endothelial cell-specific promoter, such as the promotor of any one of the genes selected from the group comprising: IF127, ICAM2, VWF, EDN1, ENG, ECSCR, CDH5 (vascular endothelial cadherin promoter, cadherin 5 type 2), PECAM1, HHIP, TIE1 and HYAL2.

Aspect 8. The nucleic acid expression cassette according to any one of aspects 5 to 7, wherein the transgene encodes a therapeutic protein or an immunogenic protein.

Aspect 9. The nucleic acid expression cassette according to any one of aspects 5 to 8, wherein the transgene encodes a secretable protein or a structural protein.

Aspect 10. The nucleic acid expression cassette according to aspect 8 or 9, wherein said transgene is selected from the group comprising: hepatocyte growth factor (HGF), coagulation factor VIII (FVIII), coagulation factor VII (FVII), tissue factor (TF), tissue factor pathway inhibitor (TFPI), coagulation factor IX (FIX), coagulation factor XI (FXI), von Willebrand factor (vWF), ADAMTS13, VEGF, PLGF, FGF, sFLT1, α1-antitrypsin, AAT, apolipoprotein A-I (apoA-I), matrix metalloproteinases including but not limited to matrix metalloproteinase-3 (TIMP-3), nitric oxide synthase (NOS), antibodies, growth factors, cytokines, chemokines and antibodies, including but not limited to antibodies directed against any one of said transgenes, factors and their cognate receptors or against any secreted protein or viral protein, small interfering RNA, guide RNA, endonuclease, and Cas9.

Aspect 11. The nucleic acid expression cassette according to any one of aspects 5 to 10, further comprising a poly-adenylation signal, preferably the Simian Virus 40 (SV40) polyadenylation signal, a synthetic polyadenylation signal or a bovine growth hormone polyadenylation signal.

Aspect 12. A vector comprising the nucleic acid regulatory element according to any one of aspects 1 to 3, or the nucleic acid expression cassette according to any one of aspects 5 to 11.

Aspect 13. The vector according to aspect 12, which is a viral vector, preferably a lentiviral vector (LV), an adeno-associated viral (AAV) vector, or an adenoviral vector (AV). In specific examples of said aspect, the vector is a self- or non-self inactivating lentiviral vector, preferably a self inactivating lentiviral vector.

In specific examples the LV has the following components: EC-CRE-PM-TG, with EC-CRE being one of the newly identified regulatory sequences as defined in SEQ ID Nos 1-33; PM being an endothelial cell-specific promotor such as, but not limited to, those referred to in aspect 7, and TG being a transgene such as, but not limited to, the transgenes identified herein and in particular those defined in aspect 10.

Taking the example with endothelial cell-specific promotor ICAM2, and using the self inactivating lentiviral vector backbone pCDH, the vector can be:

pCDH-CDH5-EC-CRE1a-ICAM2-TG, such as wherein the TG is any one of those identified in aspect 10, pCDH-CDH5-EC-CRE1b-ICAM2-TG, such as wherein the TG is any one of those identified in aspect 10,
pCDH-CDH5-EC-CRE1c-ICAM2-TG, such as wherein the TG is any one of those identified in aspect 10,
pCDH-CDH5-EC-CRE1d-ICAM2-TG, such as wherein the TG is any one of those identified in aspect 10,
pCDH-CDH5-EC-CRE1e-ICAM2-TG, such as wherein the TG is any one of those identified in aspect 10,
pCDH-HYAL2-EC-CRE1f-ICAM2-TG, such as wherein the TG is any one of those identified in aspect 10,
pCDH-ECSCR-EC-CRE1a-ICAM2-TG, such as wherein the TG is any one of those identified in aspect 10,
pCDH-ECSCR-EC-CRE1b-ICAM2-TG, such as wherein the TG is any one of those identified in aspect 10,
pCDH-EDN1-EC-CRE1a-ICAM2-TG, such as wherein the TG is any one of those identified in aspect 10,
pCDH-ENG-EC-CRE1a-ICAM2-TG, such as wherein the TG is any one of those identified in aspect 10,
pCDH-ENG-EC-CRE1b-ICAM2-TG, such as wherein the TG is any one of those identified in aspect 10,
pCDH-ENG-EC-CRE1c-ICAM2-TG, such as wherein the TG is any one of those identified in aspect 10,
pCDH-HHIP-EC-CRE1a-ICAM2-TG, such as wherein the TG is any one of those identified in aspect 10,
pCDH-HHIP-EC-CRE1b-ICAM2-TG, such as wherein the TG is any one of those identified in aspect 10,
pCDH-HYAL2-EC-CRE1a-ICAM2-TG, such as wherein the TG is any one of those identified in aspect 10,
pCDH-HYAL2-EC-CRE1b-ICAM2-TG, such as wherein the TG is any one of those identified in aspect 10,
pCDH-HYAL2-EC-CRE1c-ICAM2-TG, such as wherein the TG is any one of those identified in aspect 10,
pCDH-ICAM2-EC-CRE1a-ICAM2-TG, such as wherein the TG is any one of those identified in aspect 10,
pCDH-ICAM2-EC-CRE1b-ICAM2-TG, such as wherein the TG is any one of those identified in aspect 10,
pCDH-ICAM2-EC-CRE1c-ICAM2-TG, such as wherein the TG is any one of those identified in aspect 10,
pCDH-IFI27-EC-CRE1a-ICAM2-TG, such as wherein the TG is any one of those identified in aspect 10,
pCDH-IFI27-EC-CRE1b-ICAM2-TG, such as wherein the TG is any one of those identified in aspect 10,
pCDH-PECAM1-EC-CRE1a-ICAM2-TG, such as wherein the TG is any one of those identified in aspect 10,
pCDH-TIE1-EC-CRE1a-ICAM2-TG, such as wherein the TG is any one of those identified in aspect 10,
pCDH-TIE1-EC-CRE1b-ICAM2-TG, such as wherein the TG is any one of those identified in aspect 10,
pCDH-VWF-EC-CRE1a-ICAM2-TG, such as wherein the TG is any one of those identified in aspect 10, or
pCDH-VWF-EC-CRE1b-ICAM2-TG, such as wherein the TG is any one of those identified in aspect 10.

In anyone of said VL constructs, the ICAM2-promotor can be replaced by another endothelial cell specific promotor, such as, but not limited to those exemplified in aspect 7. In anyone of said VL constructs, the vector backbone can be exchanged by another suitable backbone such as those known to the person skilled in the art.

Aspect 14. The vector according to aspect 12, which is a non-viral vector, preferably a plasmid, a minicircle, an episomal vector, or a transposon-based vector, such as a PiggyBac-based vector or a Sleeping Beauty-based vector.

Aspect 15. A pharmaceutical composition comprising the nucleic acid expression cassette according to any one of aspects 5 to 11, or the vector according to any one of aspects 12 to 14, and a pharmaceutically acceptable carrier.

Aspect 16. The nucleic acid regulatory element according to any one of aspects 1 to 3, the nucleic acid expression cassette according to any one of aspects 5 to 11, the vector according to any one of aspects 12 to 14, or the pharmaceutical composition according to aspect 15 for use in medicine, more preferably for use in gene therapy, in particular for use in treating endothelial cell dysfunction, preferably such as any one of the diseases or disorders selected from the group comprising: liver diseases, hemophilia A, von Willebrand disease, microvascular thrombosis, thrombotic thrombocytopenic purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer and viral infectious diseases such as Ebola, Dengue and Dengue hemorrhagic fever.

Aspect 17. The nucleic acid regulatory element according to any one of aspects 1 to 3, the nucleic acid expression cassette according to any one of aspects 4 to 11, the vector according to any one of aspects 12 to 14, or the pharmaceutical composition according to aspect 15 for use as a vaccine, preferably a prophylactic vaccine, or for use in vaccination therapy, preferably prophylactic vaccination. Alternatively, said nucleic acid regulatory element according to any one of aspects 1 to 3, the nucleic acid expression cassette according to any one of aspects 4 to 11, the vector according to any one of aspects 12 to 14, or the pharmaceutical composition according to aspect 15 can be for use in induction of immunotolerance to the transgene.

Aspect 18. A method, preferably an in vivo method, for expressing a transgene product in endothelial cells, comprising:
    introducing the nucleic acid expression cassette according to any one of aspects 4 to 11, or the vector according to any one of aspects 12 to 14, comprising the nucleic acid regulatory element according to any one of aspects 1 to 3, into the cells; and Aspect 19. A method, preferably an in vitro or ex vivo method, for expressing a transgene product in endothelial cells, comprising:
    introducing the nucleic acid expression cassette according to any one of aspects 4 to 11, or the vector according to any one of aspects 12 to 14, comprising the nucleic acid regulatory element according to any one of aspects 1 to 3, into the cells; and
    expressing the transgene product in the cells.

Aspect 20. A method for treating an endothelial cell-related disease or disorder comprising the administration of a therapeutically effective amount of the nucleic acid expression cassette according to any one of aspects 5 to 11, the vector according to any one of aspects 12 to 14, or the pharmaceutical composition according to aspect 15, each comprising the nucleic acid regulatory element according to any one of aspects 1 to 3, to a subject in need thereof.

Aspect 21. The method according to aspect 20, wherein said endothelial cell-related disease or disorder is selected from the group comprising: endothelial cell dysfunction, preferably such as any one of the diseases or disorders selected from the group comprising: liver diseases, hemophilia A, von Willebrand disease, microvascular thrombosis, thrombotic thrombocytopenic purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer and viral infectious diseases such as Ebola Dengue and Dengue hemorrhagic fever.

As shown in the experimental section (Example 1), the inventors identified nucleic acid regulatory elements that will specifically enhance gene expression in endothelial cells. The endothelial specific regulatory elements were subsequently be validated in vitro and in vivo assays in mice. The details of the in vitro and in vivo validation are described in Example 2 to 6 below. The successful use of the endothelial CREs will hence, allows for the use of lower and thus safer vector doses, while maximizing therapeutic efficacy.

Figure 2:
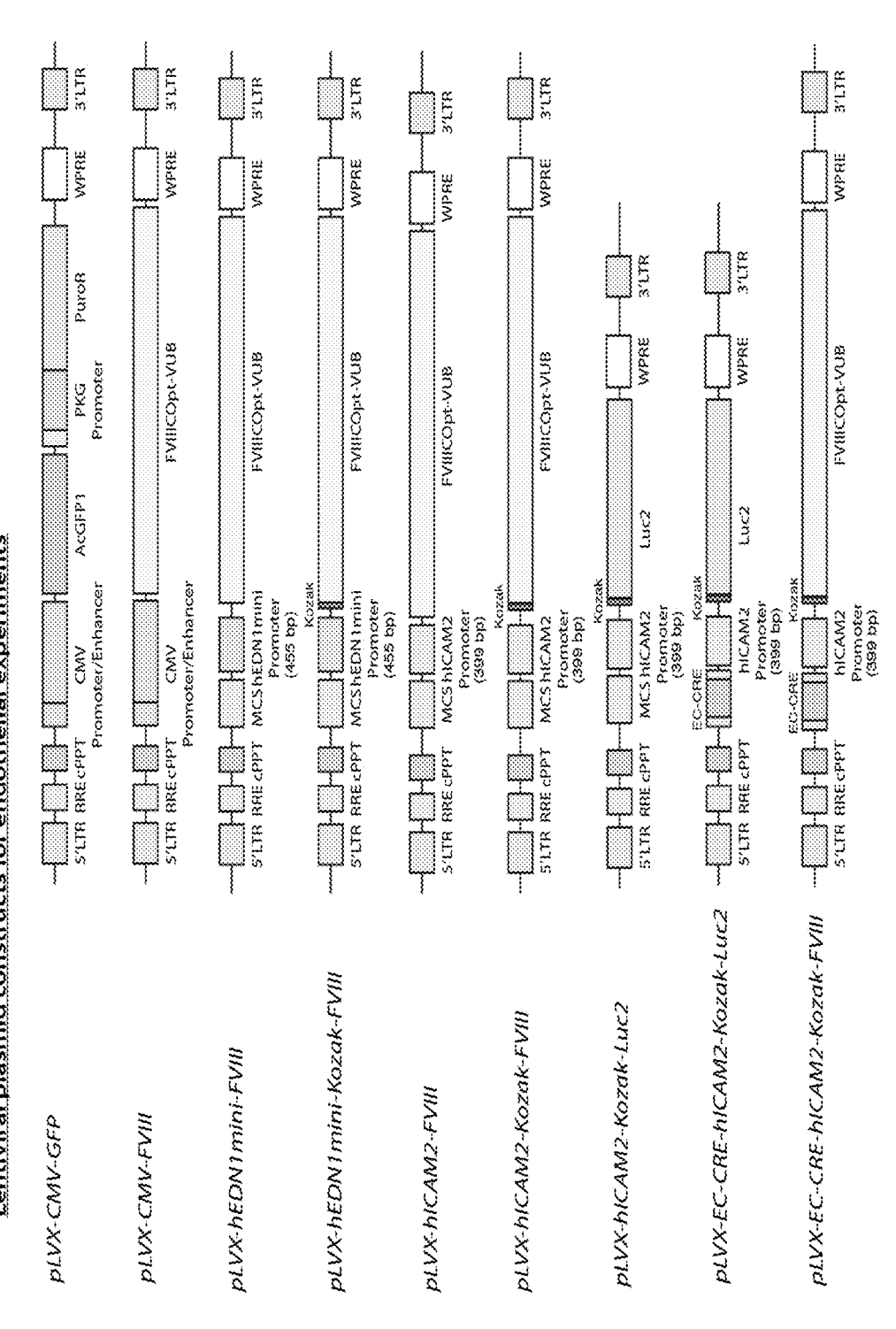

FIG. 2: Lentiviral vector design

Lentiviral vectors were produced as described previously (VandenDriessche et al., Blood 2002). Briefly, the lentiviral vector-containing plasmids were cotransfected with a VSV-G expression plasmid, a gag-pol and Rev expression plasmid. Lentiviruses were produced by transient co-transfection of HEK293T (293T) cells using supplemented Dulbecco modified Eagle medium (Invitrogen) with 10% heat-inactivated fetal bovine serum (Invitrogen) and 1% penicillin/streptomycin. A total of 60 µg lentiviral plasmid was used for transfection of one double-tray culture chamber: 60 µg lentiviral plasmid, 30 µg pRSV-REV, 30 µg pMDLg/pRRE and 30 µg pCMV-VSV-G. Plasmid was pre-complexed with calcium phosphate (Calcium phosphate transfection kit, Invitrogen) for 30 minutes at room temperature. Transfection media was added to the cells for 16 hours and then replaced by fresh medium containing NU-serum (Invitrogen) and Sodium Butyrate (Sigma). Viral supernatant was harvested 48 and 72 hours after transfection and concentrated using a Centricon concentrator (Millipore) (2000 rpm for 1 hours at 4° C.). Aliquots of viruses were stored at −80° C. The physical titer in nanograms per microliter of all LVs was determined using a p24 colorimetric enzyme-linked immunosorbent assay (ELISA) kit (Cell Biolabs) according to the manufacturer's instructions. This value was then used to calculate an estimated vector titer equivalent in transducing units (TU) per milliliter. Polybrene (8 µg/mL) was added to the concentrated vectors to enhance transduction.

Figure 3A:
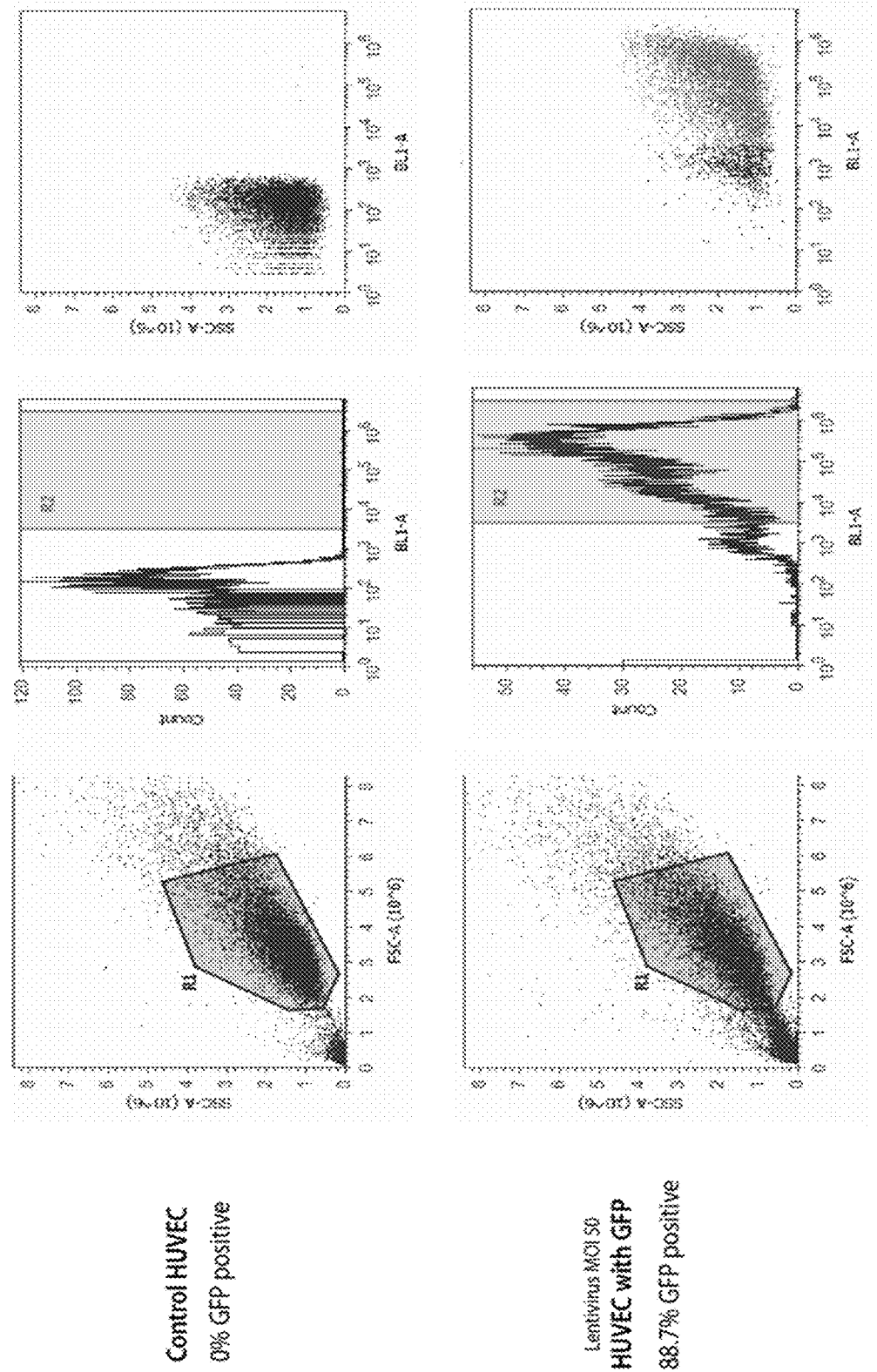
Figure 3B:
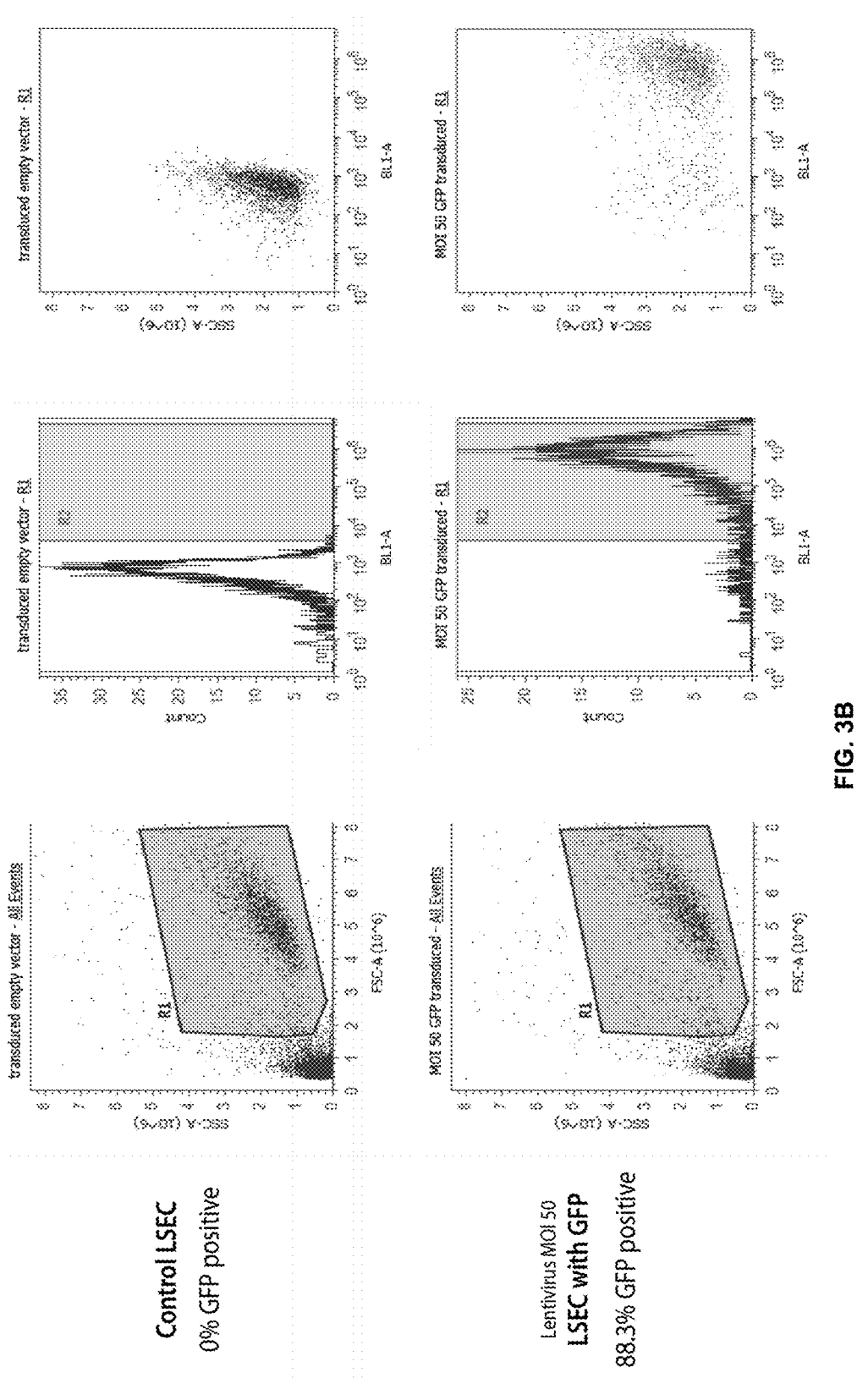

FIGS. 3A-3B: Flow cytometry analysis of HUVECs and LSECs transduced with LV CMV-GFP vector (MOI 50) at 72 hr timepoint post transduction.

Figure 4:
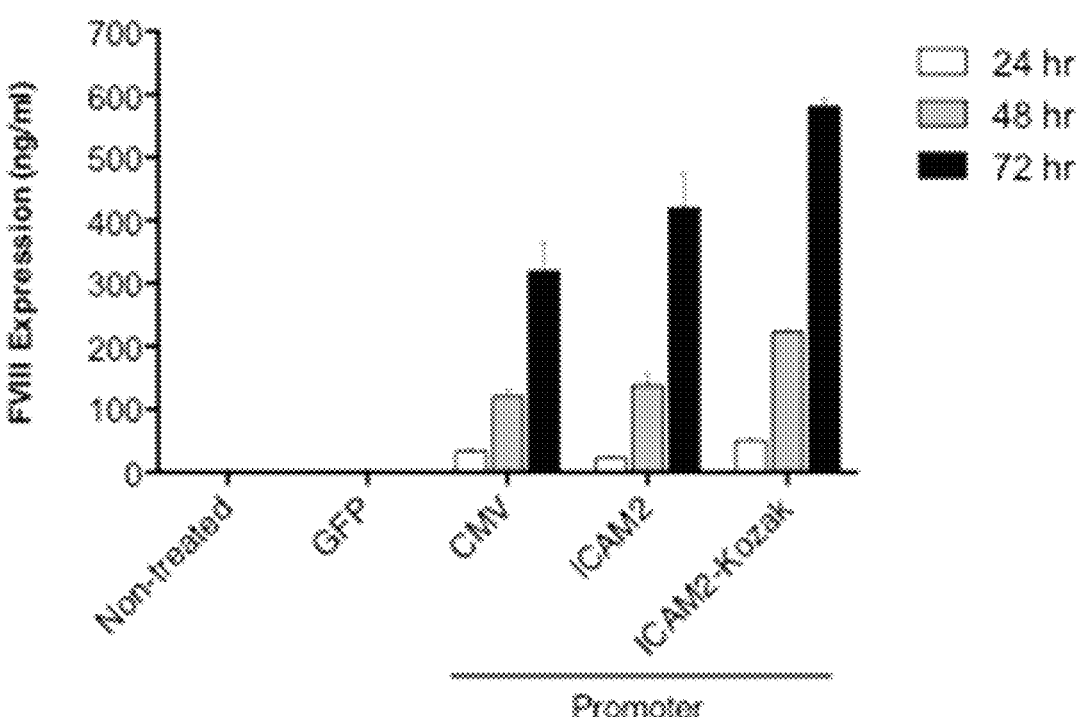
Figure 4:
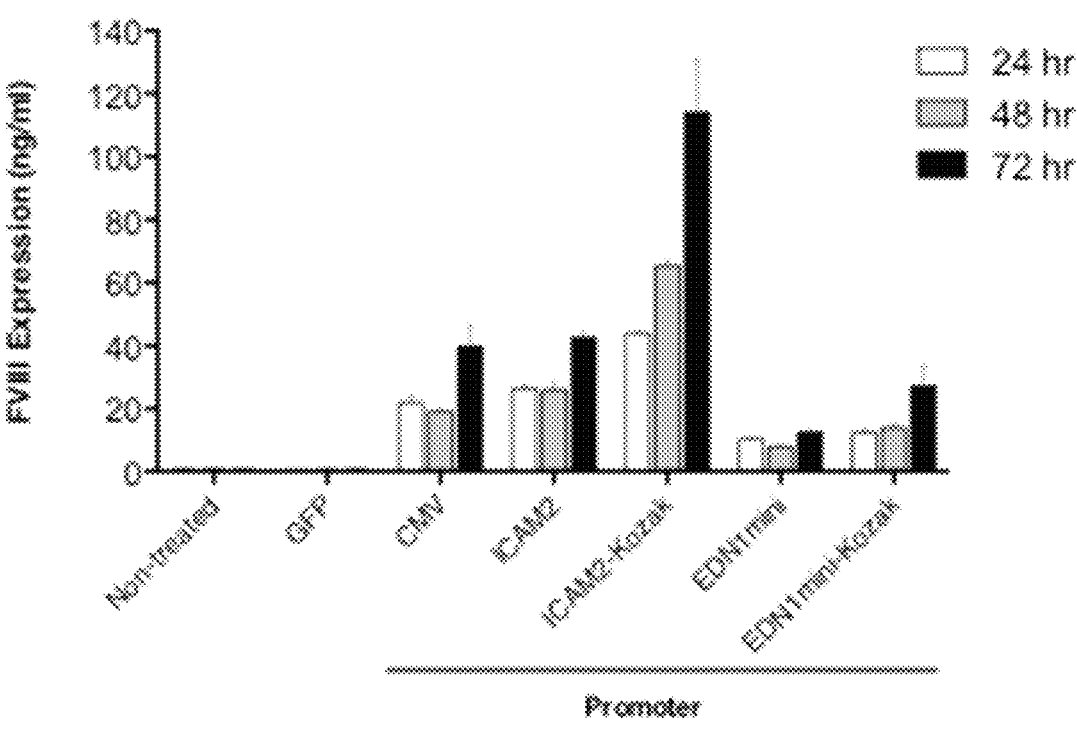

FIG. 4: FVIII antigen expression expressed in ng/ml in HUVECs and LSECS transduced with different lentiviral vector designs. FVIII antigen expression levels were determined. at 24, 48 and 72 hrs after transduction.

Figure 5:
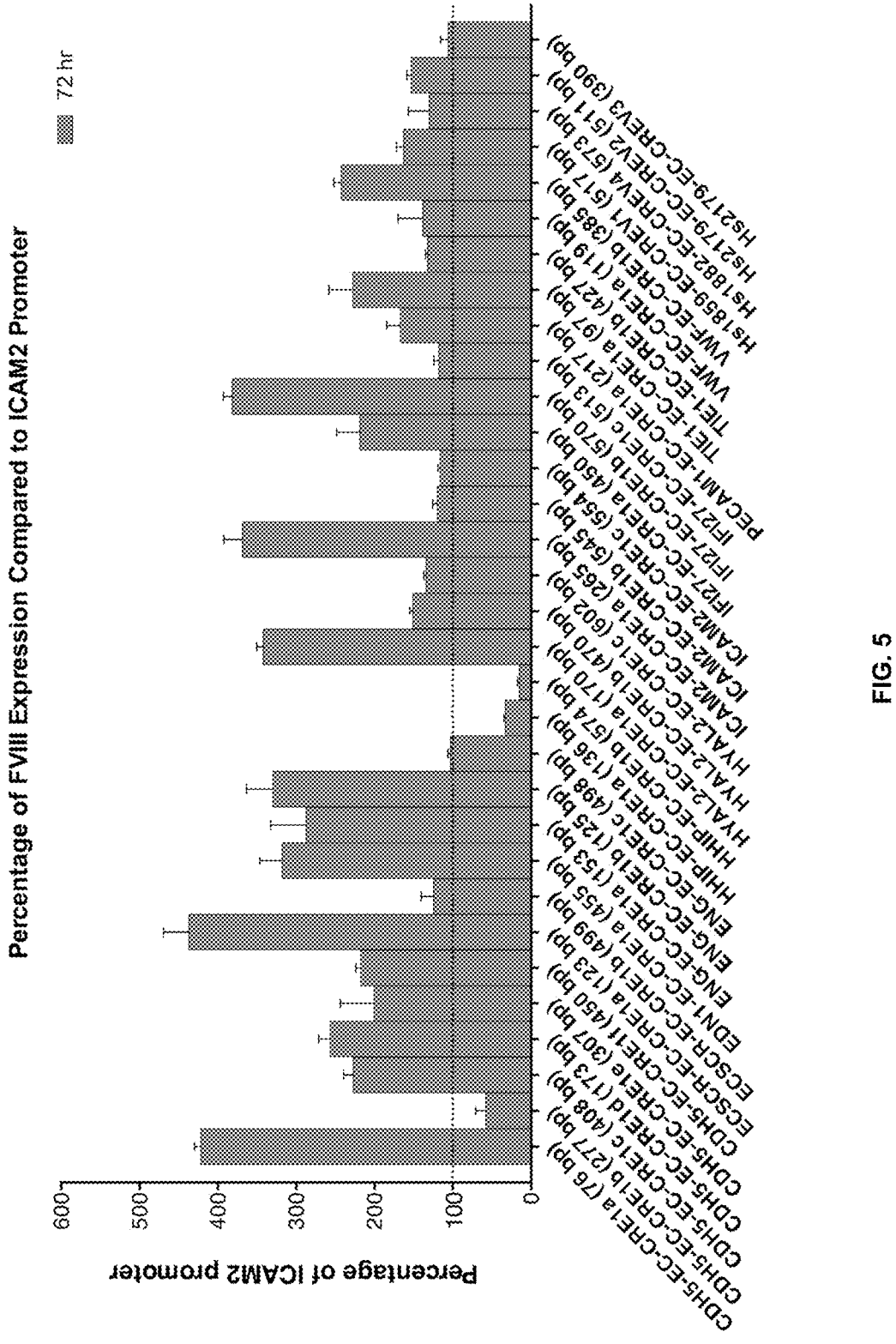

FIG. 5: The FVIII expression levels of each EC-CRE-ICAM2-FVIII construct in HUVECs. The percentage compared to the ICAM2 construct without EC-CREs. The expression values were represented as mean with standard error of mean (SEM; n=3 for each group).

Figure 6:
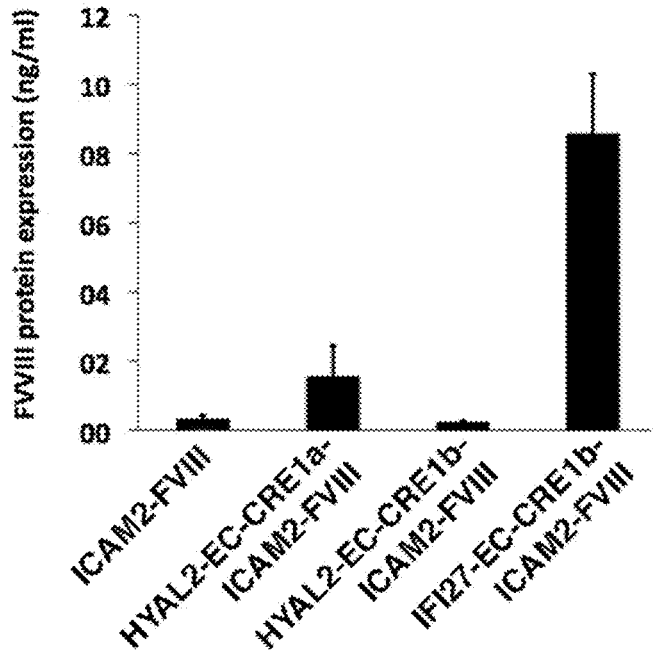

FIG. 6: FVIII expression after lentiviral in vivo transduction. FVIII protein expression was determined using a human FVIII-specific ELISA on the plasma samples collected 5 weeks after lentiviral vector injection. The mice cohorts (n=4 mice per cohort) include ICAM2-FVIII (no CRE control), HYAL2-EC-CRE1a-ICAM2-FVIII, HYAL2-EC-CRE1b-ICAM2-FVIII & IF127-EC-CRE1b-ICAM2-FVIII.

Figure 7:
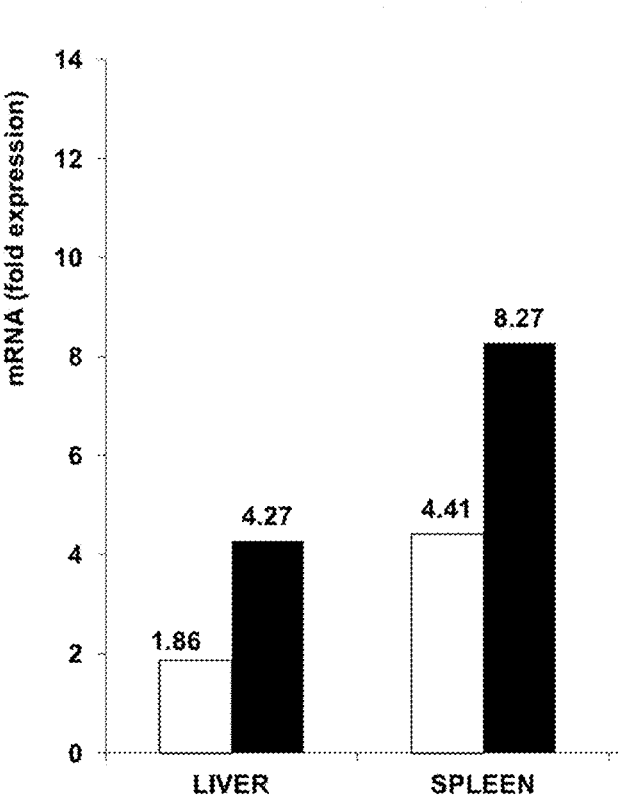

FIG. 7: mRNA analysis of the CD146-positive endothelial cells isolated from liver and spleen. The human FVIII expression encoded by the lentiviral vector was normalized to endogenous mouse GAPDH expression.

FIGS. 8A-8D: plasmid maps of lentiviral vectors

Figure 8A:
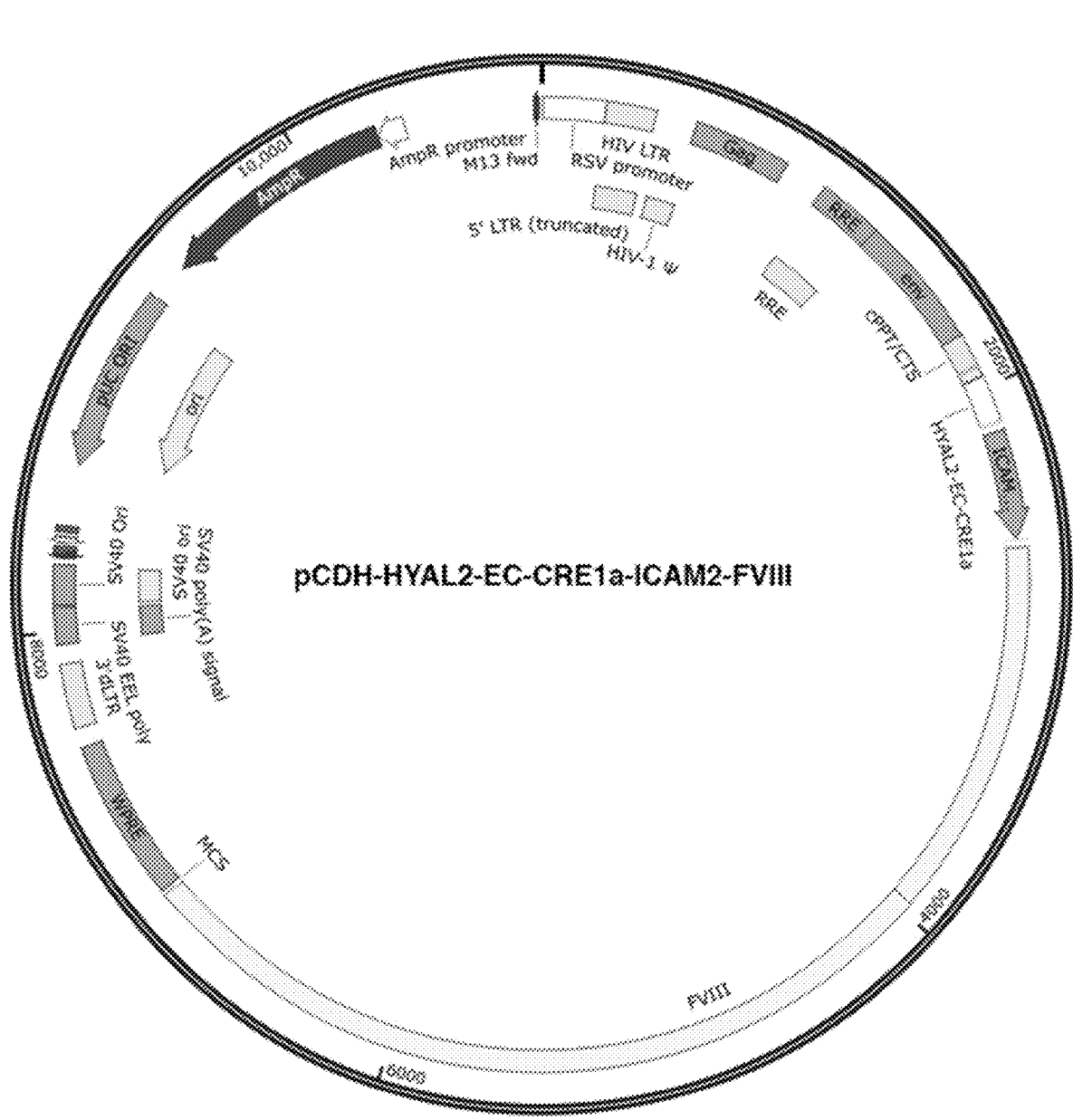
Figure 8B:
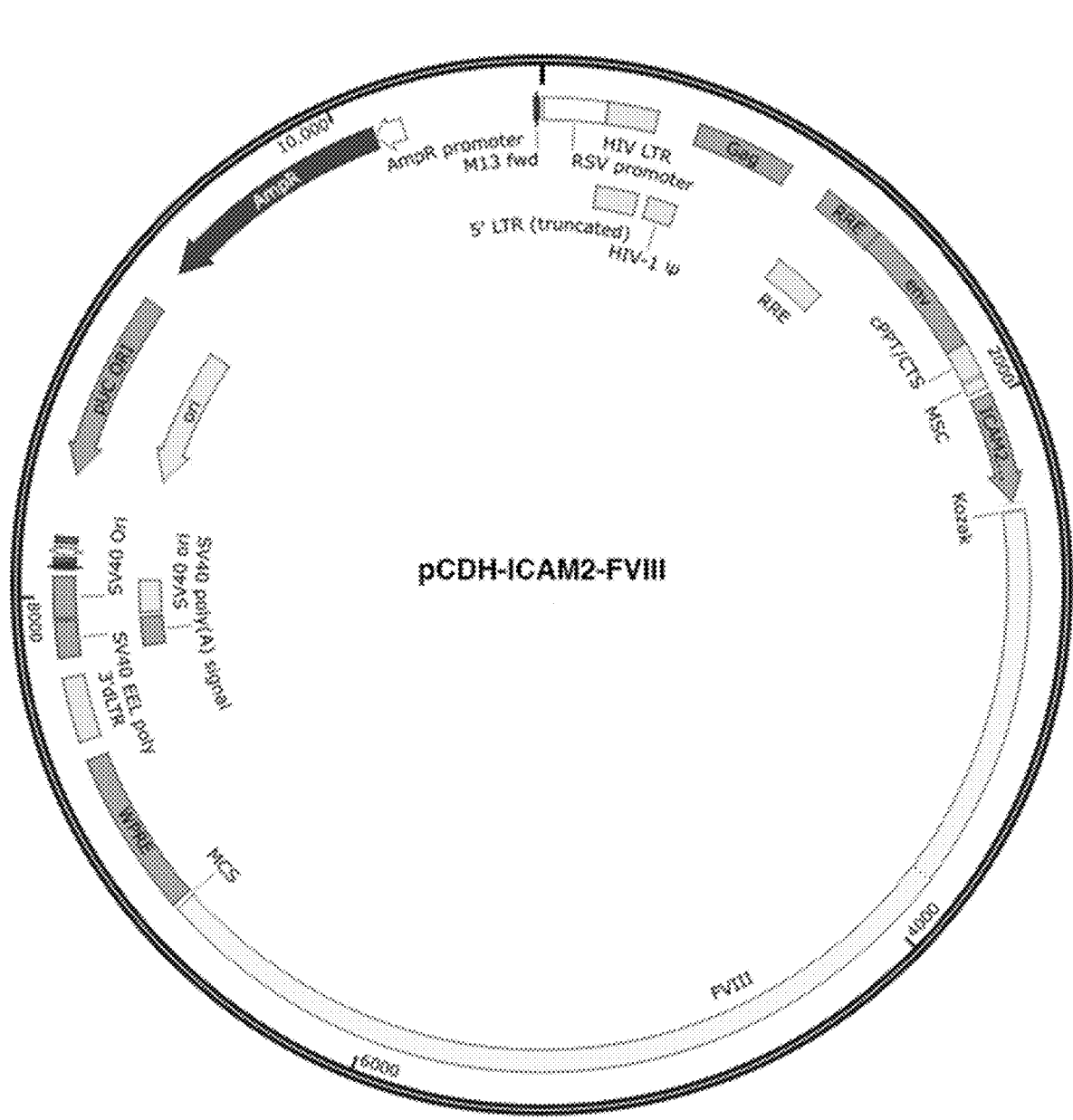
Figure 8C:
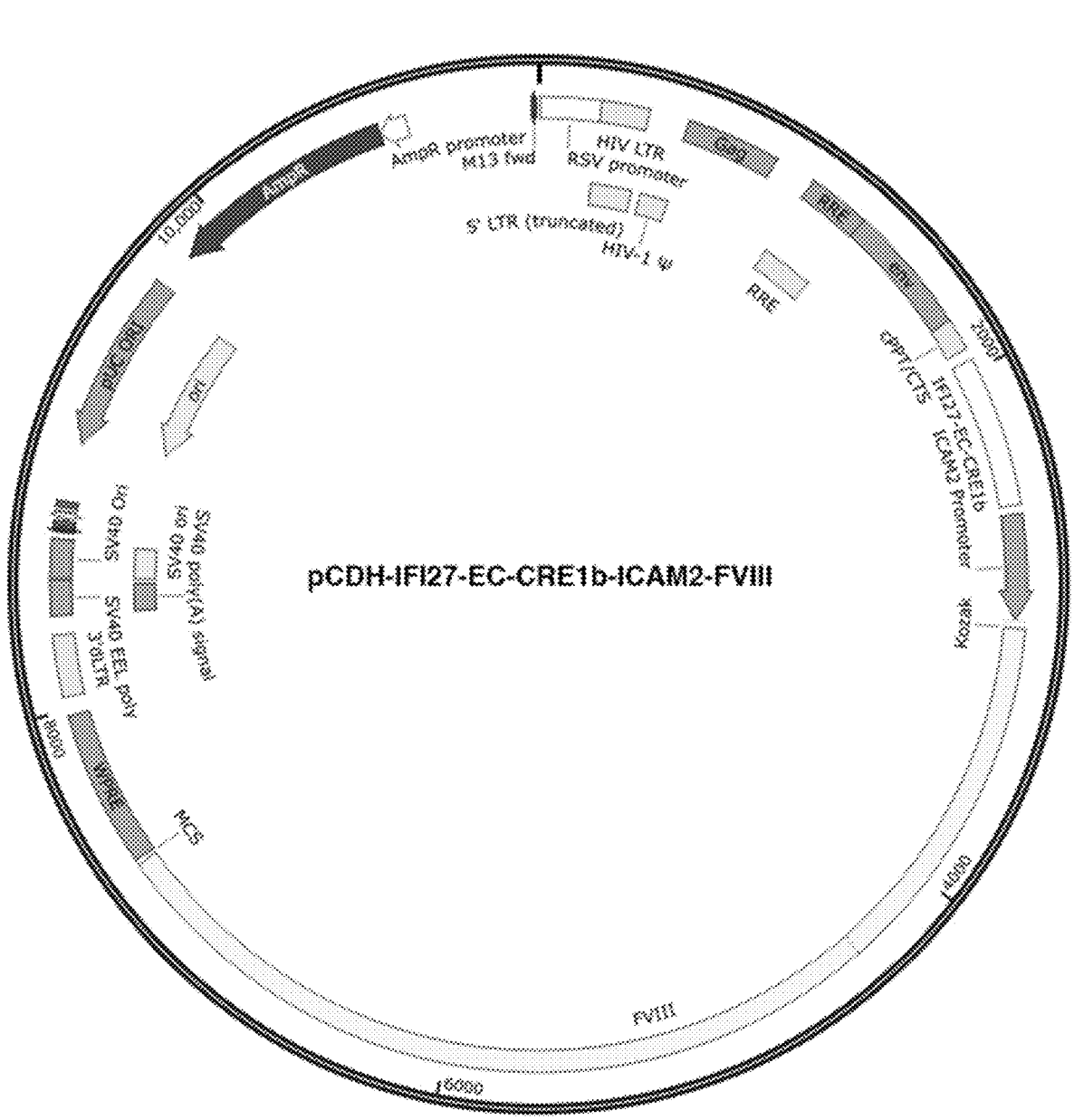
Figure 8D:

All endothelial CRE's were cloned, in a self inactivating the lentiviral vectors called pCDH as shown in the map. FIG. 8A: pCDH-HYAL2-EC-CRE1a-ICAM2-FVIII (SEQ ID NO. 50); FIG. 8B: pCDH-ICAM2-FVIII (SEQ ID NO. 49); FIG. 8C: pCDH-IFI27-EC-CRE1b-ICAM2-FVIII (SEQ ID NO. 52); FIG. 8D: pCDH-HYAL2-EC-CRE1b-ICAM2-FVIII (SEQ ID NO. 51).

DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any or etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter alia to well-known textbooks, including, e.g., "Molecular Cloning: A Laboratory Manual, 2nd Ed." (Sambrook et al., 1989), "Current Protocols in Molecular Biology" (Ausubel et al., 1987).

In one aspect, the invention relates to a nucleic acid regulatory element for enhancing gene expression in endothelial cells or tissue comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of: a sequence selected from the group consisting of: SEQ ID NO:1 to 33, a sequence having at least 80%, preferably at least 85%, more preferably at least 90%, even more preferably at least 95%, such as 95%, 96%, 97%, 98%, or 99%, identity to any of these sequences, or a functional fragment of a sequence selected from the group consisting of: SEQ ID NO:1 to 33.

Tables 2 and 3 below depict the core nucleotide sequence of the different nucleic acid regulatory elements for enhancing gene expression in endothelial cells or tissue. Table 1 lists the corresponding genes and lengths.

A 'nucleic acid regulatory element', 'cis-acting regulatory element', 'CRE' or 'regulatory element' as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for an endothelial cell-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory elements hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for or such as: POLR2A, Pol2(b), GATA2, GATA-2, FOS, c-Fos, NR3C1, Freac-2, MAX, FOX2P, MYC, SRY, SOX9, SRF, JUN, TEAD4, EZH2, TBP, TCF7L2, SPI1, RELA, JUND, MXI1, JUNB, BHLHE40, RCOR1, TCF12, TAL1, EP300, HDAC2, GTF2F1, SIN3AK20, FOSL2, ETS1, CTBP2, GATA3, CEBPB, FOXA1, YY1, RFX5, TAF1, REST, ELF1, CTCF, SMC3, FOXP2, RUNX3, NRF1, HDAC6, IRF4, PAX5, RAD21, WRNIP1, ERalpha_a, PU.1, TCF4, TAL1, HDAC2, GATA3, Mxi1, GTF2F1, ELF1, NRSF, CTCF, SMC3, Ini1, IRF4, PAX5, CTCF, Pol2-4H8, YY1, CTCF, FOXO1, FOXJ2, GATA-X, Gfi-1, Hand1/E47, MAZ, USF1, REST, TFAP2A, TFAP2C, CHD2, ZNF274, BACH1, EBF, EBF1, ATF2:c-Jun, CREB1, ATF, Tax/CREB, CREB1, EGR1, NF-kappaB, c-Rel, Pax-3, FOXO4, SOX5, GR, ZNF263, Lmo2 complex, AP-4, HEN1, E2F6, PML, TRIM28, SMARCA4, RBBP5, NRF2F, TBL1XR1, STAT5A, MAFF, REST, JUND, IRF1, MAFK, eGFP-JunDATF1, ARID3A, ATF3, E2F6, GATA2, GATA-1, Brg1, TAL1, JunB, NR2F2, HDAC8, BCL3, ATF2, CBX3, HNF4, FOXA2, KAP1, UBTF, GABP, GABPA, BCLAF1, SP1, FOXM1, MEF2A, ZNF143, ZBTB7A, NANOG, CTCFL, NFKB, CCNT2, EBF1, FOXA1, Max, c-Myc, STAT1, STAT2, MZF1, SMARCC1, E2F4, FOSL1, STAT3, P300, AP2gamma, MafF1, JunD, AP2alpha, FOXA2, HMGN3, ZBTB33, P300, Nkx2-2, Nkx2-5, SRF, YY1, HTF, CHX10, HNF1, OCT, Ncx, AP-2rep, Lmo2 complex, SOX5, GATA-1, CDP CR1, Cart-1, NFIV, RXRA, SREBP1, MYBL2, HNF4G, HNF4A, HEY1, ZEB1, PHF8, CHD1, PU-1, RSRFC4, MEF-2, and/ or Lyf-1. The nucleic acid regulatory elements described herein can comprise any one or more of said TFBS, or combinations thereof. Transcription factor binding sites may be found in databases such as Transfac®.

Sequences disclosed herein may be part of sequences of regulatory elements capable of controlling transcription of endothelial cell-specific genes in vivo. Particular examples for endothelial-specific regulatory elements may in particular be controlling the following genes: IF127, ICAM2, VWF, EDN1, ENG, ECSCR, CDH5, PECAM1, HHIP, TIE1 or HYAL2.

Accordingly, in embodiments, the nucleic acid regulatory elements disclosed herein comprise a sequence from CDH5 regulatory elements, i.e. regulatory elements that control expression of the CDH5 gene (Cadherin 5 or VE-cadherin gene) in vivo, e.g. regulatory elements comprising any one or more of SEQ ID NOs: 1 to 6, or functional fragments thereof. In other embodiments, the nucleic acid regulatory elements disclosed herein comprise a sequence from ECSCR regulatory elements, i.e. regulatory elements that control expression of the ECSCR gene (Endothelial Cell-Specific Chemotaxis Regulator gene) in vivo, e.g. regulatory elements comprising any one or more of SEQ ID NOs: 7 or 8, or functional fragments thereof. In other embodiments, the nucleic acid regulatory elements disclosed herein comprise a sequence from EDN1 regulatory elements, i.e. regulatory elements that control expression of the EDN1 gene (Endothelin 1 gene) in vivo, e.g. regulatory elements comprising SEQ ID NO: 9, or functional fragments thereof. In other embodiments, the nucleic acid regulatory elements disclosed herein comprise a sequence from ENG regulatory elements, i.e. regulatory elements that control expression of the ENG gene (Endoglin gene) in vivo, e.g. regulatory elements comprising any one or more of SEQ ID NOs: 10 to 12, or functional fragments thereof. In other embodiments, the nucleic acid regulatory elements disclosed herein comprise a sequence from HHIP regulatory elements, i.e. regulatory elements that control expression of the HHIP gene (Hedgehog Interacting Protein gene) in vivo, e.g. regulatory elements comprising any one or more of SEQ ID NOs: 13 or 14, or functional fragments thereof. In other embodiments, the nucleic acid regulatory elements disclosed herein comprise a sequence from HYAL2 regulatory elements, i.e. regulatory elements that control expression of the HYAL2 gene (Hyaluronoglucosaminidase 2 gene) in vivo, e.g. regulatory elements comprising any one or more of SEQ ID NOs: 15 to 17, or functional fragments thereof. In other embodiments, the nucleic acid regulatory elements disclosed herein comprise a sequence from ICAM2 regulatory elements, i.e. regulatory elements that control expression of the ICAM2 gene (Intercellular Adhesion Molecule 2 gene) in vivo, e.g. regulatory elements comprising any one or more of SEQ ID NOs: 18 to 20, or functional fragments thereof. In other embodiments, the nucleic acid regulatory elements disclosed herein comprise a sequence from IF127 regulatory elements, i.e. regulatory elements that control expression of the IF127 gene (Interferon, Alpha-Inducible Protein 27 gene) in vivo, e.g. regulatory elements comprising any one or more of SEQ ID NOs: 21 to 23, or functional fragments thereof. In other embodiments, the nucleic acid regulatory elements disclosed herein comprise a sequence from PECAM1 regulatory elements, i.e. regulatory elements that control expression of the PECAM1 gene (Platelet/Endothelial Cell Adhesion Molecule 1 gene) in vivo, e.g. regulatory elements comprising SEQ ID NO: 24, or functional fragments thereof. In other embodiments, the nucleic acid regulatory elements disclosed herein comprise a sequence from TIE1 regulatory elements, i.e. regulatory elements that control expression of the TIE1 gene (Tyrosine Kinase With Immunoglobulin-Like And EGF-Like Domains 1 gene) in vivo, e.g. regulatory elements comprising any one or more of SEQ ID NOs: 25 or 26, or functional fragments thereof. In other embodiments, the nucleic acid regulatory elements disclosed herein comprise a sequence from VWF regulatory elements, i.e. regulatory elements that control expression of the VWF gene (Von Willebrand Factor gene) in vivo, e.g. regulatory elements comprising any one or more of SEQ ID NOs: 27 or 28, or functional fragments thereof. In other embodiments, the nucleic acid regulatory elements disclosed herein comprise a sequence comprising any one or more of SEQ ID NOs: 29 to 33, or functional fragments thereof.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term 'functional fragment' as used in the application refers to fragments of the regulatory element sequences disclosed herein that retain the capability of regulating endothelial cell-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

"endothelial cell-specific expression" as used in the application, refers to the preferential or predominant expression of a (trans)gene (as RNA and/or polypeptide) in endothelial cells and tissue comprising or built from endothelial cells, as compared to other (i.e. non-endothelial) cells or tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within endothelial cells or endothelial tissue.

The term "endothelial cell" as used herein encompasses all endothelial cell types, such as the cells forming a single cell layer that lines all blood vessels and regulates exchanges between the bloodstream and the surrounding tissues. Many endothelial cell types exist and their phenotypes vary between different organs, between different segments of the vascular loop within the same organ, and between neighbouring endothelial cells of the same organ and blood vessel type. Non-limiting examples of such endothelial cells are: liver sinusoidal endothelial cells (LSEC), (micro)vascular endothelial cells from e.g. lung, heart, intestine, skin, retina, arterial endothelial cells, such as endothelial cells from pulmonary artery, the aorta, umbilical artery and umbilical vein, extrahepatic endothelial cells from certain vascular beds, blood-brain barrier ECs, bone marrow ECs, and high endothelial venule cells (HEVs).

According to a particular embodiment, endothelial cell specific expression entails that there is less than 10%, less than 5%, less than 2% or even less than 1% 'leakage' of expressed gene product to other organs or tissue than those comprising or built by endothelial cells, such as muscle, heart, lung, liver, brain, kidney and/or spleen.

The same applies mutatis mutandis for endothelial progenitor cell (EPC)-specific expression, which may be considered as a particular form of endothelial cell-specific expression. Hence, throughout the application, where endothelial cell-specific is mentioned in the context of expression, endothelial progenitor cell (EPC)-specific expression is also explicitly envisaged.

In embodiments, the invention relates to a nucleic acid regulatory element for enhancing gene expression in endothelial cells or tissue derived therefrom comprising, consisting essentially of, or consisting of a sequence selected from the group consisting of: SEQ ID NO:1 to 33; a sequence having at least 80%, preferably at least 85%, more preferably at least 90%, even more preferably at least 95%, such as 95%, 96%, 97%, 98%, or 99%, identity to any of the sequences selected from the group consisting of SEQ ID NO: 1 to 33; or a functional fragment thereof, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 2, 3, 4, or 5, more preferably at least 10 or at least 15 transcription factor binding sites (TFBS) such as those TFBS that are present in the sequence from which it is derived.

It is also possible to make nucleic acid regulatory elements that comprise an artificial sequence by combining two or more identical or different sequences disclosed herein or functional fragments thereof. Accordingly, in certain embodiments a nucleic acid regulatory element for enhancing gene expression in endothelial cells is provided comprising at least two sequences selected from the group consisting of: SEQ ID NO:1-33.

For example, disclosed herein is a nucleic acid regulatory element comprising, consisting to essentially of, or consisting of 2, 3, 4, or 5 repeats, e.g. tandem repeats, of any one of SEQ ID NOs:1 to 33, or combinations thereof.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing endothelial cell-specific gene expression, in particular endothelial cell-specific gene expression, comprising binding sites for e.g. Sp1, EGR-1, ETS and GATA. Further for example, also disclosed herein is a nucleic acid regulatory element for enhancing endothelial cell-specific gene expression, in particular comprising binding sites for one or more of: Sp1, EGR-1, ETS and GATA and combinations thereof. In some embodiments, these nucleic acid regulatory elements comprise at least two, such as 2, 3, 4, or more copies of any one or more of the recited TFBSs.

In some embodiments, the vector used is a lentiviral vector. In other embodiments, the vector used is an adeno-associated viral vector. In yet other embodiment, the vector used is an adenoviral vector. In case a lentiviral vector is used, it can be a self inactivating or a non self-inactivating lentiviral vector. A self inactivating lentiviral vector is sometimes preferred for clinical use since it is considered safer.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing endothelial cell-specific gene expression comprising, consisting essentially of, or consisting of the complement of a sequence described herein, in particular a sequence selected from the group consisting of: SEQ ID NOs:1 to 33; a sequence having at least 80%, preferably at least 85%, more preferably at least 90%, even more preferably at least 95%, such as 95%, 96%, 97%, 98%, or 99%, identity to any of these sequences; or a functional fragment thereof as defined herein.

Also disclosed herein is a nucleic acid regulatory element for enhancing endothelial cell-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NOs:1 to 33; a sequence having at least 90%, preferably at least 95%, such as 95%, 96%, 97%, 98%, or 99%, identity to any of these sequences; a functional fragment thereof as defined herein; or to its complement. Said nucleic acid regulatory elements do not need to be of equal length as the sequence they hybridize to.

In preferred embodiments, the size of said hybridizing nucleic acid regulatory element does not differ more than 25% in length, in particular 20% in length, more in particular 15% in length, most in particular 10% in length from the sequence it hybridizes to.

The expression 'hybridize under stringent conditions' refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 1500 nucleotides or less, 1000 nucleotides or less, 900 nucleotides or less, 800 nucleotides or less, 700 nucleotides or less, more preferably 610 nucleotides or less, such as 550 nucleotides or less, 500 nucleotides or less, 450 nucleotides or less, 400 nucleotides or less, 350 nucleotides or less, or 300 nucleotides or less (i.e. the nucleic acid regulatory element has a maximal length of 1500 nucleotides, 1000 nucleotides, 900 nucleotides, 800 nucleotides, 700 nucleotides, preferably 610 nucleotides, such as 550 nucleotides, 500 nucleotides, 450 nucleotides, 400 nucleotides, 350 nucleotides, or 300 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 200 nucleotides, 250 nucleotides, 300 nucleotides, 350 nucleotides or 400 nucleotides.

In certain embodiments, the invention provides for a nucleic acid regulatory element of 1000 nucleotides or less, preferably 900 nucleotides or less, preferably 800 nucleotides or less, preferably 700 nucleotides or less of a sequence selected from the group consisting of: SEQ ID NOs:1 to 33; a sequence having at least 80%, preferably at least 85%, more preferably at least 90%, even more preferably at least 95%, such as 95%, 96%, 97%, 98%, or 99%, identity to any of said sequences; or a functional fragment thereof as defined herein.

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each other such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By "modulate" is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this need not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein. In alternative embodiments, the nucleic acid expression cassette comprises two or more, such as, e.g., 2, 3, 4, 5, 6, 7, 8, 9, or 10, nucleic acid regulatory elements as described herein, i.e. they are combined modularly to enhance their regulatory (and/or enhancing) effect. In further embodiments, at least two of the two or more nucleic acid regulatory elements are identical or substantially identical. In yet further embodiments, all of the two or more regulatory elements are identical or substantially identical. The copies of the identical or substantially identical nucleic acid regulatory elements may be provided as tandem repeats in the nucleic acid expression cassette. In alternative further embodiments, at least two of the two or more nucleic acid regulatory elements are different from each other, that is to say, are defined by a different SEQ ID NO. The nucleic acid expression cassette may also comprise a combination of identical and substantially identical nucleic acid regulatory elements and non-identical nucleic acid regulatory elements.

For example, the nucleic acid expression cassette may comprise a nucleic acid regulatory element comprising SEQ ID NO:1, and a nucleic acid regulatory element comprising any one or more of SEQ ID Nos: 2 to 33. Alternatively, this can be done for remaining regulatory elements defined by SEQ ID NOs:2 to 33, which can be combine with any one or more of the other regulatory elements.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of endothelial cell-specific expression in vivo (and/or in vitro in cell lines derived from endothelial cell- or tissue) of the transgene, and/or (2) can increase the level of expression of the transgene in endothelial cells (and/or in vitro in cell lines derived from endothelial cells or tissue).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

Non-limiting exemplary endothelial cell-specific promoters are: the promotors of the genes depicted in Table 1 below, more preferably the In particularly preferred embodiments, the promoter is a mammalian promoter, in particular a murine or human promoter.

In preferred embodiments, the promoter is from the vascular-endothelial cadherin gene, in particular the murine or human cadherin-5 gene, such as the promoter as defined in SEQ ID NO: 34 (cf. Table 4).

In preferred embodiments, the promoter is from the endothelin-1 gene, in particular the murine or human endothelin-1 gene, such as the promoter as defined in SEQ ID NO: 35 (cf. Table 4).

In preferred embodiments, the promoter is from the endoglin gene, in particular the murine or human endoglin gene, such as the promoter as defined in SEQ ID NO: 36 (cf. Table 4).

In preferred embodiments, the promoter is from the Fms-Related Tyrosine Kinase 1 gene, in particular the murine or human Fms-Related Tyrosine Kinase 1 gene, such as the promoter as defined in SEQ ID NO: 37 (cf. Table 4).

In preferred embodiments, the promoter is from the Intercellular Adhesion Molecule 2 gene, in particular the murine or Intercellular Adhesion Molecule 2 gene (ICAM2), such as the promoter as defined in SEQ ID NO: 38 (cf. Table 4).

Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less. One particular non-limiting example of such a minimal promotor is the EDN1mini promoter (cf. Table 4).

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, antisense RNA, RNA aptamers, ZFN, TALEN, CRISPR/Cas9 or similar DNA or RNA cutters, etc.

How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular mammal, in which it is introduced, e.g. in cases where the nucleic acid expression cassette is used for gene therapy).

The transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e.e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein. The therapeutic protein may be a secretable protein. Non-limiting examples of secretable proteins, in particular secretable therapeutic proteins, include hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin, AAT, apolipoprotein A-I (apoA-I), matrix metalloproteinases including but not limited to matrix metalloproteinase-3 (TIMP-3), insulin, erythropoietin, lipoprotein lipase, nitric oxide synthase (NOS), antibodies or nanobodies, including but not limited to antibodies directed against any one of said transgenes, factors and their cognate receptors or against any secreted protein or viral protein, small interfering RNA, guide RNA, endonuclease, and Cas9, growth factors, cytokines, chemokines, plasma factors etc. The therapeutic protein may also be a structural protein. Non-limiting examples of structural proteins, in particular structural therapeutic proteins, include proteins modulating vascular relaxation and vasoconstriction, atherosclerosis. In preferred embodiments, the transgene comprises the nitric oxide synthase (NOS).

In embodiments, the transgene encodes an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein, but may not be necessary. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron. Preferably, the intron is MVM intron.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit β-globin (mRBG) gene, and the synthetic polyA s(SPA) site as described in Levitt et al. (1989, Genes Dev 3:1019-1025). Preferably, the polyadenylation signal is derived from SV40 (i.e. SV40 pA).

In particular embodiments, the invention provides a nucleic acid expression cassette comprising, consisting essentially of, or consisting of a nucleic acid regulatory element selected from the group consisting of SEQ ID NO: 1 to 33 or a sequence having 95% identity to said sequence, operably linked to a promoter, preferably a promoter selected from the group consisting of the promoter from the cadherin-5, endothelin-1, endoglin, Fms-Related Tyrosine Kinase 1, or Intercellular Adhesion Molecule 1 gene or the promoter, and a transgene, preferably a transgene encoding a luciferase. In yet further embodiments the nucleic acid expression cassette further comprises a polyadenylation signal, preferably a polyadenylation signal derived from SV40.

In particular embodiments, the invention provides a nucleic acid expression cassette comprising, consisting essentially of, or consisting of a nucleic acid regulatory element selected from the group consisting of SEQ ID NO: 1 to 33 or a sequence having 95% identity to said sequence, operably linked to a promoter, preferably the promoter from the cadherin-5, endothelin-1, endoglin, Fms-Related Tyrosine Kinase 1, or Intercellular Adhesion Molecule 1 gene, and a transgene, preferably a transgene encoding a therapeutic or structural protein as defined herein. In yet further embodiments, the nucleic acid expression cassette further comprises a polyadenylation signal. In particular embodiments, any one of the following transgenes can introduced: secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), matrix metalloproteinases including but not limited to matrix metalloproteinase-3 (TIMP-3) (TIMP-3), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, modulating vascular relaxation and vasoconstriction, atherosclerosis. In preferred embodiments, the transgene comprises the nitric oxide synthase (NOS).

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably a lentiviral vector. Lentiviral vectors are preferably derived from the human immune deficiency virus (HIV) though other lentiviral vectors based on other lentiviruses could also be used (including but not limited to Equine infectious anemia virus). Lentiviral vectors can transduce endothelial cells. Production of lentiviral vectors can be achieved by (VandenDriessche et al. J. Thromb Hemostasis, 2007) transient co-transfected of lentiviral vector plasmids encoding to the gene of interest with the gag-pol, rev and env-encoding helper constructs. Typically, a heterologous envelope is used such as the vesicular stomatitis virus G glycoprotein (VSV-G) or an endotheliotropic envelope including but not limited to envelopes that confer antibody or nanobody (i.e. single chain antibody)-mediated endothelial retargeting targeting specific endothelial cell surface markers (VandenDriessche & Chuah, Blood. 2013 Sep. 19; 122(12):1993-4; Abel et al., Blood. 2013 Sep. 19; 122(12):2030-8; Buchholz et al. Trends Biotechnol. 2015 December; 33(12):777-90; Munch et al., Mol Ther. 2011 April; 19(4):686-93; Anliker et al., Nat Methods. 2010 November; 7(11):929-35).

In another embodiment the vector is an adeno-associated viral (AAV) vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), although the use of single-stranded AAV vectors (ssAAV) are also encompassed herein.

Production of AAV vector particles can e.g. be achieved by transient co-transfection of AAV-vector and AAV helper constructs, encoding AAV capsids into HEK293 cells, followed by a purification step based on cesium chloride (CsCl) density gradient ultracentrifugation, as described (Vanden Driessche et al., 2007). Capsids can also be derived from different serotypes or are specifically modified to enhance endothelial cell transduction either by evolution or selection, antibody (nanobody engineering) or the use of DARPin (Work et al., Mol Ther. 2006 April; 13(4):683-93; Munch et al., Nat Commun. 2015 Feb. 10; 6:6246; Buchholz et al., Trends Biotechnol. 2015 December; 33(12):777-90; White et al. Circulation. 2004 Feb. 3; 109(4):513-9.)

In yet another embodiment the vector is an adenoviral vector. Adenoviral vectors are preferably derived from the human adenovirus 5 serotype or from other serotypes that display increased tropism to endothelial cells, including but not limited to Ad5T*F35++(White et al., J Cardiothorac Surg. 2013 Aug. 9; 8:183. doi: 10.1186/1749-8090-8-183). Alternatively, the capsid can be engineered to enhance the endotheliotropic properties of the adenoviral vectors including but not limited to the references below (Nicol et al., FEBS Lett. 2009 Jun. 18; 583(12):2100-7; Nicklin and Baker, Mol Ther. 2008 December; 16(12):1904-5; Work et al., Methods Mol Med. 2005; 108:395-413; Work et al., Genet Vaccines Ther. 2004 Oct. 8; 2(1):14). They can be derived from either early-generation or helper-dependent adenoviral vectors (Mol Ther. 2010 December; 18(12): 2121-9). Production of these vectors has after transfection of adenoviral vector and helper constructs in HEK293T cells has been described previously (Mol Ther. 2010 December; 18(12):2121-9).

Since the nucleic acid regulatory elements are de facto modular, also combinations of the best endothelial cell-specific nucleic acid regulatory elements with any other endothelial cell-specific nucleic acid regulatory elements to maximize expression in the desired target tissue are tested. Consequently, this can lead to the generation of a versatile endothelial cell-specific nucleic acid regulatory element platform tailor-made for diseases that affect endothelial cells and tissues encompassing those. Furthermore, the endothelial cell-specific nucleic acid regulatory elements can also be combined with other promoters or nucleic acid regulatory elements active in other target tissues.

In other embodiments, the vector is a non-viral vector, preferably a plasmid, a minicircle, or a transposon-based vector, such as a Sleeping Beauty(SB)-based vector or piggyBac(PB)-based vector.

In yet other embodiments, the vector comprises viral and non-viral elements.

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 33, a promoter, preferably the promoter from the cadherin-5, endothelin-1, endoglin, Fms-Related Tyrosine Kinase 1, or Intercellular Adhesion Molecule 1 gene, a transgene, preferably a transgene encoding a therapeutic structural or secretable protein, and a polyadenylation signal. In particular, any one of the following transgenes can introduced: secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), apolipoprotein A-I (apoA-I), matrix metalloproteinases including but not limited to matrix metalloproteinase-3 (TIMP-3) (TIMP-3), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, including proteins modulating vascular relaxation, vasoconstriction or atherosclerosis. In preferred embodiments, the transgene comprises the nitric oxide synthase (NOS).

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 33, a promoter, preferably the promoter from the cadherin-5, endothelin-1, endoglin, Fms-Related Tyrosine Kinase 1, or Intercellular Adhesion Molecule 1 gene, a transgene, preferably a transgene encoding secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), apolipoprotein A-I (apoA-I), matrix metalloproteinases including but not limited to matrix metalloproteinase-3 (TIMP-3) (TIMP-3), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, including proteins modulating vascular relaxation, vasoconstriction or atherosclerosis. In preferred embodiments, the transgene comprises the nitric oxide synthase (NOS).

The nucleic acid expression cassettes and vectors disclosed herein may be used, for example, to express proteins that are normally expressed and utilized in endothelial cells (i.e. structural proteins), or to express proteins that are expressed in endothelial cells and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), Corynebacterium parvum, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder such as a disease or disorder related to endothelial cells.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement. In embodiments, the nucleic acid regulatory elements according to any one of SEQ ID Nos: 1-33, the nucleic acid expression cassettes, the vectors, or the pharmaceutical compositions described herein may be for use in gene therapy, in particular endothelial cell-directed gene therapy.

Also disclosed herein is the use of the nucleic acid regulatory elements according to any one of SEQ ID Nos: 1-33, the nucleic acid expression cassettes, the vectors, or the pharmaceutical compositions described herein for the manufacture of a medicament for gene therapy, in particular endothelial cell-directed gene therapy.

Also disclosed herein is a method for gene therapy, in particular endothelial cell-directed gene therapy in a subject in need of said gene therapy comprising:

introducing in the subject, in particular in endothelial cells or tissue of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID Nos: 1-33, operably linked to a promoter and a transgene; and expressing a therapeutically effective amount of the transgene product in the subject, in particular in endothelial tissue or cells of the subject.

The transgene product may be any one of the following transgenes can introduced: secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, $\alpha$1-antitrypsin (AAT), apolipoprotein A-I (apoA-I), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, including proteins modulating vascular relaxation, vasoconstriction or atherosclerosis, In preferred embodiments, the transgene comprises the nitric oxide synthase (NOS).

Alternatively, the transgene product may be RNA, such as siRNA, or a nuclease such as ZFN, TALEN, CRISPR/Cas9 or similar DNA or RNA editing systems.

Exemplary diseases and disorders that may benefit from gene therapy using the nucleic acid regulatory elements, the nucleic acid expression cassettes, the vectors, or the pharmaceutical compositions described herein include: liver diseases, hemophilia A, von Willebrand disease, microvascular thrombosis, thrombotic thrombocytopenic purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer and viral infectious diseases such as Ebola, Dengue fever and dengue hemorrhagic fever.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993). In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of medicament or a vaccine, in particular for the manufacture of a prophylactic vaccine.

Also disclosed herein is a method of vaccination, in particular prophylactic vaccination, of a subject in need of said vaccination comprising:

introducing in the subject, in particular in endothelial tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID Nos: 1 to 33, operably linked to a promoter and a transgene; and expressing an immunologically effective amount of the transgene product in the subject, in particular in endothelial cells or tissue of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Preferably, the higher expression remains specific to endothelial tissues or cells. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

Also disclosed herein is the use of the nucleic acid regulatory elements according to SEQ ID Nos: 1 to 33, or the nucleic acid expression cassettes, or the vectors disclosed herein comprising said nucleic acid regulatory elements, for transfecting or transducing endothelial cells.

Further disclosed herein is the use of the nucleic acid expression cassettes or the vectors disclosed herein comprising the nucleic acid regulatory elements according to SEQ ID Nos: 1 to 33, for expressing a transgene product in endothelial cells, wherein the nucleic acid expression cassette or the vector comprises said nucleic acid regulatory element disclosed herein operably linked to a promoter and a transgene.

Further disclosed herein is a method for expressing a transgene product in endothelial cells, comprising:

transfecting or transducing said cells with a nucleic acid expression cassette or a vector disclosed herein, wherein the nucleic acid expression cassette or the vector comprises a nucleic acid regulatory element according to any one of SEQ ID Nos: 1 to 33, operably linked to a promoter and a transgene; and
    expressing the transgene product in said cells.

Non-viral transfection or viral vector-mediated transduction of endothelial cells may be performed by in vitro, ex vivo or in vivo procedures. The in vitro approach requires the in vitro transfection or transduction of endothelial cells, e.g. cells previously harvested from a subject, cell lines or cells differentiated from e.g. induced pluripotent stem cells or embryonic cells. The ex vivo approach requires harvesting of the endothelial cells from a subject, in vitro transfection or transduction, and optionally re-introduction of the transfected cells into the subject. The in vivo approach requires the administration of the nucleic acid expression cassette or the vector disclosed herein into a subject. In preferred embodiments, the transfection of the endothelial cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into endothelial cell precursors or endothelial cells, transgenic models for over-expression of proteins in endothelial cells or their precursors, etc.

The invention is further explained by the following non-limiting examples

EXAMPLES

Example 1: Identification of Endothelial Cell-Specific Nucleic Acid Regulatory Elements To identify the endothelial cell genes that are highly expressed, we followed several steps. First, we obtained the list of genes that are highly expressed in endothelial cells from the publication of Bhasin et al., 2010 (Genomics 2010, 11:342) showing 104 genes that were identified as endothelial-restricted genes. Subsequently, the specificity and robustness of expression of the endothelial-restricted genes was compared to that of 6 types of endothelial cells (i.e. LSEC: Liver Sinusoid Endothelial cells, HCAEC: Coronary Artery Endothelial cells, HMVEC: Dermal Microvascular Endothelial cells, HUVEC: Human Umblilical Vein Endothelial cells, IEn: Iliac Artery Endothelial cells, RE: Retinal Endothelial cells) based on the Reference Database of Gene Expression Analysis (RefExA). We identified 11 genes (Table 1) from this endothelial-restricted gene list that are highly expressed and specific among these quintessential endothelial cell types. Consequently, these 11 genes were then used for designing the endothelial-specific cis-regulatory elements (CREs: Table 2)

TABLE 1

| Highly expressed genes in endothelial cells | |
| --- | --- |
| Highly expressed genes in endothelial cells | ENSEMBL Acc. No |
| IFI27 | ENSG00000165949 |
| ICAM2 | ENSG00000108622 |
| VWF | ENSG00000110799 |
| EDN1 | ENSG00000078401 |
| ENG | ENSG00000106991 |
| ECSCR | ENSG00000279686 |
| CDH5 | ENSG00000179776 |
| PECAM1 | ENSG00000261371 |
| HHIP | ENSG00000164161 |
| TIE1 | ENSG00000066056 |
| HYAL2 | ENSG00000068001 |

Figure 1:
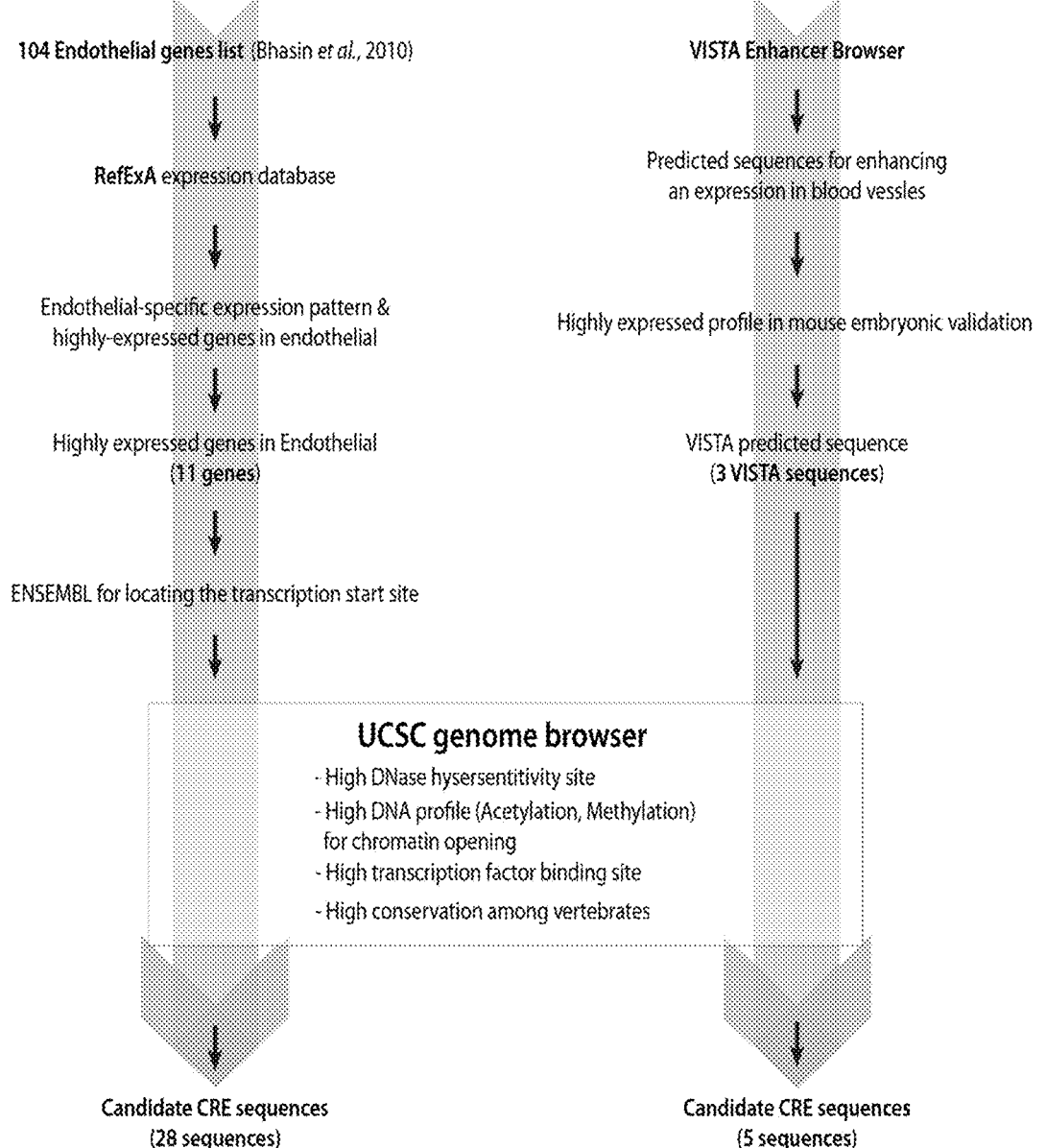
FIG. 1: The selection strategies of endothelial-specific CREs

Candidate CREs were selected using the University of California Santa Cruz (UCSC) Genome Browser database based on i) high DNase hypersensitivity sites; ii) high content of epigenetic markers associated with open chromatin (acetylation, methylation); iii) high content of transcription factor binding sites; iv) strong evolutionary conservation. The ideal CREs were expected to exhibit co-existence of predicted motifs together with DNase clusters, high conservation level in vertebrates, and explicit histone modification patterns. Therefore, 28 potential CRE sequences were selected based on those criteria (FIG. 1 and Table 2).

TABLE 2

The EC-CREs sequence for highly expression in endothelial cells.

| Gene | EC-CRE | Size (bp) | Sequence |
|---|---|---|---|
| CDH5 | EC-CRE1a | 76 | GCCCTCACAAAGGAACAATAACAGG AAACCATCCCAGGGGGAAGTGGGCC AGGGCCAGCTGGAAAACCTGAAGGG G (SEQ ID NO: 1) |
| CDH5 | EC-CRE1b | 277 | GGCCGAGGCAGCCGCCCACCGCAGG GCCTGCCTATCTGCAGCCAGCCCAG CCCTCACAAAGGAACAATAACAGGA AACCATCCCAGGGGGAAGTGGGCCA GGGCCAGCTGGAAAACCTGAAGGGG AGGCAGCCAGGCCTCCCTCGCCAGC GGGGTGTGGCTCCCCTCCAAAGACG GTCGGCTGACAGGCTCCACAGAGCT CCACTCACGCTCAGCCCTGGACGGA CAGGCAGTCCAACGGAACAGAAACA TCCCTCAGCCCACAGGCACGGTGAG TG (SEQ ID NO: 2) |
| CDH5 | EC-CRE1c | 408 | GCTTCCTCCTCTGCTACTAATCTGG TCTCACAGACCATCCCATTTCCTGC TAGCCCACCAGCCGCCTTCCTTGCT CCCAATGACACTTCCTGGCCTTGTG CCCTCCTGTTACCTCCTTTGCCTCC AGAGAGGTTGGAGCAGAGGCTGGGC AGTGCCAGAAATCAGGCATGAAATC CTCAGGGGGACCAAGGAGGCACCAG CCTCCCTCCCACAGTCTCAGCTACC TCTGCTACGGTGACCCCCAGCCCCA CCCCTGGGGCCCACAGCTCATGCCT GGCTCACCATTCCTTTGTTTATGGA CCACAGGAACAGTCGTTTTCAGGGC AGAGTCAACTTCCTCATGGACTGGG AGTACAAAGGGAATTGGCAGATGGT GCCAGGACAGGCCCTGTCCCCATCT GCCACAGC (SEQ ID NO: 3) |
| CDH5 | EC-CRE1d | 173 | GCTTCCTCCTCTGCTACTAATCTGG TCTCACAGACCATCCCATTTCCTGC TAGCCCACCAGCCGCCTTCCTTGCT CCCAATGACACTTCCTGGCCTTGTG CCCTCCTGTTACCTCCTTTGCCTCC AGAGAGGTTGGAGCAGAGGCTGGGC AGTGCCAGAAATCAGGCATGAAA (SEQ ID NO: 4) |
| CDH5 | EC-CRE1e | 307 | CCCAGCTGAGGGCTGGTGCCAGAGC CGTGTCTGCTTGCCCCATCAAGAGG TGGGAGGGATTGATCCACCTTCCTG CCCCACAGATGGTGCAGCCTCCAAC CTATTGTTTTCCAGGACGCTTCGGT GGAGAGCACAAGGAATGTAGGGTCT AGAAACAGGAAGCCCTGGCTTCCGC TGGACAAGGTTTCCTCCAGACTCAG GCCTGCCCTCCAGACAACAAGGCAG GGCCCTTGGTCCCACCCTGCCCTGC CTGGCTCACTGGGCCACCCCAAGGA AGGCCTTGCCCTCTCTGGGCTTCTG CATGTGA (SEQ ID NO: 5) |
| CDH5 | EC-CRE1f | 450 | AGGTATCCACCAAGGGGCCCAAGAG CTGCTGAGCCCCTGAGCAGCCCTAC |

TABLE 2-continued

The EC-CREs sequence for highly expression in endothelial cells.

| Gene | EC-CRE | Size (bp) | Sequence |
|---|---|---|---|
| | | | CAATTTCAGCTTATGGTGGTGAGGG GTAGGGGAGGTGTATACTGGCCTGG AAGGGGTTAAGCTGCCCGCCTGCAG CCTCAGCCTGAGCTATTGTGTTGCC AAACAAGGGCCGGACATGAGGGCAG GAAGCCAGCAGGGGCCACACATTTT CTGCAAAGTTGGATGATTCACTGCT GACTTGGGGACACCCAGGGGACAGA GGGGACACCATCCCAGGAAGAATCT TAGGCTCATTTTGCCCACATGGACC CATGACTGTTCCCTGTATCCTCTCT CTGCACCCCCTCAGTCACACTGAAG CAACTATGAGAATTCCCATTTGACA GATGGGACCATCGAGGCTGAGGGAA GCTGTGCAGCCAGTCCAAGGTCACA CAACCAACACAAGGTAGAAGCAGGG (SEQ ID NO: 6) |
| ECSCR | EC-CRE1a | 123 | AGGGCCCCTGGGAGCTGGTCCCAATG TGTTTCCTTCTATTCTTTTGACAGG AAGCTCCTGGAGAGCCAGTCCCCAC CCCCATCCCGCCCCAGCACTCCCTC TCTCTTCTCCACTATGGACAGAG (SEQ ID NO: 7) |
| ECSCR | EC-CRE1b | 499 | TAGGGCCTCTCTGAAAGATGTGGGG AGTCCTATCTGCATTGGGATCCCTG AGGAGGGAGAGGAATGTGGAGAATT CAGGGTCCAGGGAGCATGGGTGACT GGTGGGCTGGGCTTCCAGGCTGAAT CATGGGAAAGGAGAACCTGGTCTGA AACAGTACTGGGCGGGATTGGTGTT AGATTCCAGGAAAACCCCCAGGCGG TCTGTGGTGGAACCTGATGGACCCT CAGAAGGGAAGAGAATGGGGATGGG GCCAGGTTGCCATGGTTGGTCATTG TGCATAGGCACTAGAGGCCATGCTG GGTGGGCACAGTCGCTGCTGCAGCC TCACATCCTCATCTGGACATGGCTG AGCAGGGCCCCTGGAGCTGGTCCCA ATGTGTTTCCTTCTATTCTTTTGAC AGGAAGCTCCTGGAGAGCCAGTCCC CACCCCCATCCCGCCCCAGCACTCC CTCTCTCTTCTCCACTATGGACAGA GCCTCCACTGAGCTGCTGCCTGCC (SEQ ID NO: 8) |
| EDN1 | EC-CRE1a | 455 | GAGACATAAAAGGAAAATGAAGCGA GCAACAATTAAAAAAAATTCCCCGC ACACAACAATACAATCTATTTAAAC TGTGGCTCATACTTTTCATACCAAT GGTATGACTTTTTTTCTGGAGTCCC CTCTTCTGATTCTTGAACTCCGGGG CTGGCAGCTTGCAAAGGGGAAGCGG ACTCCAGCACTGCACGGGCAGGTTT AGCAAAGGTCTCTAATGGGTATTTT CTTTTTCTTAGCCCTGCCCCCGAAT TGTCAGACGGCGGGCGTCTGCCTCT GAAGTTAGCAGTGATTTCCTTTCGG GCCTGGCCTTATCTCCGGCTGCACG TTGCCTGTTGGTGACTAATAACACA ATAACATTGTCTGGGGCTGGAATAA AGTCGGAGCTGTTTACCCCCACTCT AATAGGGGTTCAATATAAAAAGCCG GCAGAGAGCTGTCCAAGTCAGACGC GCCTC (SEQ ID NO: 9) |
| ENG | EC-CRE1a | 153 | TGTCCACTTCTCCTGACCCCTCGGC CGCCACCCCAGAAGGCTGGAGCAGG GACGCCGTCGCTCCGGCCGCCTGCT CCCCTCGGGTCCCCGTGCGAGCCCA CGCCGGCCCCGGTGCCCGCCCGCAG CCCTGCCACTGGACACAGGATAAGG |

TABLE 2-continued

The EC-CREs sequence for highly expression
in endothelial cells.

| Gene | EC-CRE | Size (bp) | Sequence |
|---|---|---|---|
| | | | CCC (SEQ ID NO: 10) |
| ENG | EC-CRE1b | 125 | GGGCCCCCCACCCAGTGACAAAGCC CGTGGCACTTCCTCTACCCGGTTGG CAGGCGGCCTGGCCCAGCCCCTTCT CTAAGGAAGCGCATTTCCTGCCTCC CTGGGCCGGCCGGGCTGGATGAGCC (SEQ ID NO: 11) |
| ENG | EC-CRE1c | 498 | GGGATGGGAGGGTGGGGTGCTTGGG GAGACAAGCCTAGAGCCTGGGCCCT CCCACCCCACTGCCTCCCCCCATCC CAGGGCCCCCCACCCAGTGACAAAG CCCGTGGCACTTCCTCTACCCGGTT GGCAGGCGGCCTGGCCCAGCCCCTT CTCTAAGGAAGCGCATTTCCTGCCT CCCTGGGCCGGCCGGGCTGGATGAG CCAGGGAGCTCCCTGCTGCCGGTCAT ACCACAGCCTTCATCTGCGCCCTGG GGCCAGGACTGCTGCTGTCACTGCC ATCCATTGGAGCCCAGCACCCCCTC CCCGCCCATCCTTCGGACAGCAACT CCAGCCCAGCCCCGCGTCCCTGTGT CCACTTCTCCTGACCCCTCGGCCGC CACCCCAGAAGGCTGGAGCAGGGAC GCCGTCGCTCCGGCCGCCTGCTCCC CTCGGGTCCCCGTGCGAGCCCACGC CGGCCCCGGTGCCCGCCCGCAGCCC TGCCACTGGACACAGGATAAGGC (SEQ ID NO: 12) |
| HHIP | EC-CRE1a | 136 | AGCGGTGACGTCAAGGGGCGCGCTG TGGCAGCACCTCCCCGCGCGCTAGT TAAAAAGAAGAAGAAAAGAGGGAAC GAAACATGAGAGGCTGTGTGAGAAG CTGCAGCCGCCGGCAGAGGAGACCT CAGCATCATCT (SEQ ID NO: 13) |
| HHIP | EC-CRE1b | 574 | CTGGGCGGGGGCGCGCGAGAAGCGG TGACGTCAAGGGGCGCGCTGTGGCA GCACCTCCCCGCGCGCTAGTTAAAA AGAAGAAGAAAAGAGGGAACGAAAC ATGAGAGGCTGTGTGAGAAGCTGCA GCCGCCGGCAGAGGAGACCTCAGCA TCATCTAGAGCCCAGCGCTGGCCCT GCCTCCGCCTGCCCCGCCGCCGCCG TCGCCGTTTCTGTTCCTGCTACTGT CCCACCTAAACAACTCCCGTTACAC GGACAAGTGAACATCTGTGGCTGTC CTCTCCTTTTCTTCCTCCTCCTTCCA ACTCCTTCTCCTCCTCCCACTTCCC AGCCGCAGCAGAAAGCCCCCAACCC AACTGACACTGGCACAACTGCAAAC GGTGTCATCCGCACAACTTTATCTC GCTCCTCGGGCTCCCCTAAGGCATT GGACCCATCGCCGCGTCTTTTATTT TTTGCAAAGTTGCATCGCTGTACAT ATTTTTGTCCCCGCCACCTCCCTCT GTCTCTGGAGTGCCCTACAGCCCCG CAAACTCCTCCTGGAGCTGCGCCCT AGTGCCCCTGCTGGGCAGTGGCGT (SEQ ID NO: 14) |
| HYAL2 | EC-CRE1a | 170 | AGGGAACTCCCTGTGCTGGGCCTAC CCAGCTGACCCCATCGCTGGAAACA ATGGGGGTCAGGCAACACTTCCCCA CTCTCTCCCGCCGGCTGTGCTCAC TTCCTTCCTGCTGGCTGCCTGAGGA AGTGTCCCTGCCCTGGGACAGTCTG GCCTAGCCTTTGTTTCCCCG (SEQ ID NO: 15) |

TABLE 2-continued

The EC-CREs sequence for highly expression
in endothelial cells.

| Gene | EC-CRE | Size (bp) | Sequence |
|---|---|---|---|
| HYAL2 | EC-CRE1b | 470 | GACAGGCTTCTGAGTGTAGGGAGCT GGTCTGCCAGTCTTTCGGAGGTTTG AACTTGTCAAGGCTAGGGCAGGATC ACCATATCCAGCCTGGACTTGCAGT TCTGTGGGGTGCCTCCCCATACCCC CATAAGATGCCAAACATGAGGCCCT GTCATCCTCCATGGTCCCCCTCTAC TGGCTGTTCAAGGCCCAGGGCTCTC CCATGCCAGATAGCATCCTGTCTCC TACCACCACTGTCCCAGCCTGAGGG AACTCCCTGTGCTGGGCCCTACCCAG CTGACCCCATCGCTGGAAACAATGG GGGTCAGGCAACACTTCCCCACTCT CTCCCGCCGGGCTGTGCTCACTTCC TTCCTGCTGGCTGCCTGAGGAAGTG TCCCTGCCCTGGGACAGTCTGGCCT AGCCTTTGTTTCCCCGGGGGTCCCC ACCCATGGAGCTTTCAAGGCTTCTG GCCCCTGTGAAGCCAGCACA (SEQ ID NO: 16) |
| HYAL2 | EC-CRE1c | 602 | CAGTGGAAAAAAACGGACTCAGCTA CTGGAAGTCCCCCCGACCCTCCCCC CAAGGCTAGTTCCCTTCTTGGGCAC CTGCTCTGGGGGACCATCAGCTGAA CGACCCCCAAGTATTTTGACTCCCA AAAGCACCACCACCTGACCCCATCC TCTCACACCCTACTGGATTTGAGGA TGGGCCCCAATCCTAGGGAAGGAGT GAAGAGGTTCCCTAGTGTTGGAAGC TGTGGGTGTGGGGGAGATTGGCACC TGATCCTGAGCCCATAGCCTTCCTG TCACCTGGCGCAGCTGGCGGGGCCA GATCCTACTCGGGAAGGGTGGGGAG GGCAGCCAGCCAGCAGGGCATTCTG GAGGGAAACAGGGTCAAGGCGATCT CCTCCCCCACGCCTGTTCCTGGCCC TTTCCTCTCAGGGGGCAGCAGGAAG TGAGGAGAAAGGGCTGGGATGGGAG GCGGGAGCGGATGGGAGGGGAATGGG GTTTATCAAGTCCTCGGCGAGCTGC CCAACGGGCAGCAGCTGGCGCAAGT AGCCTAGCTGGAGAGGCTCACCCCA GGAAGGAGGGAGGGCCACCGACCTAC TGGGCCGACGGACTCCCACACAGGT GA (SEQ ID NO: 17) |
| ICAM2 | EC-CRE1a | 265 | CTTGCATAGATGGCCAGCGTTCATA CTTTCTGCTTGTTTGTACAAAGTCA TTCTTCTAGAGTAATTGTTGTAAAA TTGCTAGGCAAGGTGGCAGGTCTGA TAAGATTTGATGACGTAATGGCTCT TAGTCGCTAATAAGAGGCTTTTGTG GAGTGGCGTGTCACAGCCAGCGAAG GCTCAGCTCTGTGATCTTCGCCTGC CTCACTTGGGGGACCAGAAGGCAGC TTGTCTTGGAACTGCCTCATTCACA GAAGACCCCATTGAG (SEQ ID NO: 18) |
| ICAM2 | EC-CRE1b | 545 | TTTACCTAGCATGATCTTGGCAGTT CAAAGAGGAATGTGCCAGAAACCAA GCAAAGAAGAAAAAGAAATAAATGG AAATGGAAAGTGATCTGCTCAGAGG CCACAAAGTTGAGGGAGGAGGTTTC CAGAGTGGGATTTGGCCCAAATGTT GCCTGAGGAAGTACGTAAAGGGGTC TCAACTCTGGCTACACAACAGAACA GCAGGACTGTGTGTGCAGCTCACGA AGTGGGTACACAGGGTAATCTGCAA GTTCTGGGTGGATCTAGCACCTGGA TTGTTAAAACTTGCATAGATGGCCA GCGTTCATACTTTCTGCTTGTTTGT |

TABLE 2-continued

The EC-CREs sequence for highly expression
in endothelial cells.

| Gene | EC-CRE | Size (bp) | Sequence |
|---|---|---|---|
| | | | ACAAAGTCATTCTTCTAGAGTAATT GTTGTAAAATTGCTAGGCAAGGTGG CAGGTCTGATAAGATTTGATGACGT AATGGCTCTTAGTCGCTAATAAGAG GCTTTTTGTGGAGTGGCGTGTCACAG CCAGCGAAGGCTCAGCTCTGTGATC TTCGCCTGCCTCACTTGGGGGACCA GAAGGCAGCTTGTCTTGGAACTGCC TCATTCACAGAAGACCCCAT (SEQ ID NO: 19) |
| ICAM2 | EC-CRE1c | 554 | ATGGCAGCTGGCAGGTGCCTTCACG TCCAGGGTTTCCAGAGAGAAAGCAT CTCTCCTCCGCAGAGACCCTCCCAC GCTCTCCCTCCCTCAAATTAGTGCA TCTACATAGACCGCCCTCCTTATAA ACAGTCTCTCAGGGGATCCTAGCCC ATTCCAAATCTACCTGTGATTGCAG AATCGCAAGGAATGTGATTTACCGC AGATCGCGGGGCGTCGTGTCTTTTA GGGGACCTGCTCACTTTGGCCACTA GGTGGCGGGCAGTGCAGCCCCTGCT CCTGTCGACCCTGAGCGTTCAGCGT TTCCGCCGCCTCCGCCCCACTCCGT AGGGGGAGCTGATGAGATGAGGTTG AGGTCCAGGAAGACGTCAAGGGCTT GGTTTTGTAAACAACTCCATTCCTC GCTCGCTGATAAGTTTTCTAAGTGA TGCATATTCACAACCTTGTCCCATC CAAGGACCCAAGAATTAACACATTA CATAATATGGACAGCCCCCTCCTGT CCAACGGGCATGATTTTGGGGTCTG ATATTCTGTGGATCTGTGCAATAGT CAAC (SEQ ID NO: 20) |
| IFI27 | EC-CRE1a | 450 | AGACTTTTTTTGAAAAACGGAACAT CTGCCTATCGCAAGGACTACTATTA TTCTGAAAATCACCTTCTTCATTAG AAAGTAATATTTATCATTTTATTAT AGAACTTTGATCTTACTTCTTGTGA CTTCATTCTGCGTAGAGCACACTCC CATCCTTGAATTAAATGACAAAGCA TTTTATATTAACTGACAATGACTGA TGCCATGGGCAAATCCTATTTCTGT AAATAACTGAATTTTCTTCTGGACT GCGCATGAGGGGAGAAAGATGTCTG CAGTTTCGGTTTCCTGGAAAATGAA ACCTATCTCATTTGTTGCCTGTGTC AAGGGGCAGTGCTTCAGTCGGGGTG GAGCTGCTTAAAAGGCCTGGGATCA CACCCTTTGGGAACACATCCAAGCT TAAGACGGTGAGGTCAGCTTCACAT TCTCAGGAACTCTCCTTCTTTGGGT (SEQ ID NO: 21) |
| IFI27 | EC-CRE1b | 570 | GAGACTTTTTTTGAAAAACGGAACA TCTGCCTATCGCAAGGACTACTATT ATTCTGAAAATCACCTTCTTCATTA GAAAGTAATATTTATCATTTTATTA TAGAACTTTGATCTTACTTCTTGTG ACTTCATTCTGCGTAGAGCACACTC CCATCCTTGAATTAAATGACAAAGC ATTTTATATTAACTGACAATGACTG ATGCCATGGGCAAATCCTATTTCTG TAAATAACTGAATTTTCTTCTGGAC TGCGCATGAGGGGAGAAAGATGTCT GCAGTTTCGGTTTCCTGGAAAATGA AACCTATCTCATTTGTTGCCTGTGT CAAGGGGCAGTGCTTCAGTCGGGGT GGAGCTGCTTAAAAGGCCTGGGATC ACACCCTTTGGGAACACATCCAAGC TTAAGACGGTGAGGTCAGCTTCACA TTCTCAGGAACTCTCCTTCTTTGGG |

TABLE 2-continued

The EC-CREs sequence for highly expression
in endothelial cells.

| Gene | EC-CRE | Size (bp) | Sequence |
|---|---|---|---|
| | | | TAAGACTGGGAGGGTGGGCAGGAGC TACCCTTCCCGTGGCCCCGGACCTT GGGTGGGCTGTGGGCTCAGGGAGCG GAGGGGAGGCCTTAAGCATCCACTC TCTGCCCGGTGTTTTTGTTC (SEQ ID NO: 22) |
| IFI27 | EC-CRE1c | 513 | AGGTGGGGGATGAGGGGCTAAGTATG AACCAAGGAGCTAGAAATACAGCAC TGGAAGCTGGAAGCAGGGGGCTTGG AGACTGGGAGCTGGAGTGCGTGTGG GCAGGGTGTGGCAGCAGCCGGCAGA GGCCATTTCCCCTTGGCAGAACATT CACCATGTGACCCTGAGCATGTCTT TGAACTCCTCTGAGCTCCTGTTTCC TCTCCAGAGAAAAGGCTGGTAATGC CCATTCAGGGTTATGGTCAGGATTG CATAGGGTGAAACAATAGAGATTGA ACACAGTAGACATGAAAGAGATGCC AGGGCTCAGCTCCCTTTGGTTTAGT TGCTTCCAGTGTGCTCTGTGGCAAC ACCACGGAGCCCTAGAGCTGTCTCT TTGAGCCGCTCTGAATGTGCCTCTT ACATAATCTCCTGGGCAACATCTGC TCCCCTAATGAGATTTGCTCCCCAG CAAAGATAAGAAACTTGCCAACCAC TCCCCTGGTCCAGCATTTGGCCAAG GCAGACACTGAGG (SEQ ID NO: 23) |
| PECA M1 | EC-CRE1a | 217 | ACCTCACTCAATGCATGGAAGTTGA CACAATGGCTCAACATTAGCGTTGG GCTGATTCATCATTTGGCTGTTGAC ACCAGCCTCTGGCCCAGCCAGGACA GAAAAAGGGCCCCTGAGGAACTTCT GGCTCTGTTCCCTCTATGGGGGAGG GGCAGTGGACTTGTGATAAGACAGG GTGTTAGGGTGAGGTGGACTTGGGG AAACAGGATATTTCTAA (SEQ ID NO: 24) |
| TIE1 | EC-CRE1a | 97 | GGGGGGGAGGGGAGACCCCAGAACAA TGTCCCCCACCCCACCCCCCTCCTC AATAGGCGGAAGCCACTGGCTTCCT CCCTTTCCTGCCTCCTGCCTCC (SEQ ID NO: 25) |
| TIE1 | EC-CRE1b | 427 | GTGTGTTTGTGCCGGGGGGAGGGGA GACCCCAGAACAATGTCCCCCACCC CACCCCCCTCCTCAATAGGCGGAAG CCACTGGCTTCCTCCCTTTCCTGCC TCCTGCCTCCTTTGTGCCAGCAAGA CTGAGTACTGGAGAGAGACAGGGGA TGGGAAAAATCAGTCCAGCTGTCCC CAGGTCTGCCCTTACCATAACCTTC CCCCCACCTCAAGTGACTCCTCCCA GGCCACACCCATCCCCAGCCTTGTG GGGGCCAGATTGGGGGGCCTAGAGG CTCAAAGGCAGAATGAGTCCTCCCA CCCCCTACCCTGCCACCCCTCCCAC CCAAGCCACCTCATTTCCTCTTCCT CCCCAGCACCGACCCACACTGACCA ACACAGGCTGAGCAGTCAGGCCCAC AGCATCTGACCCCAGGCCCAGCTCG TC (SEQ ID NO: 26) |
| VWF | EC-CRE1a | 119 | CTACAAAGCTTTATCAGCTTGGAGG TACTTCTAATACCATTTCCTTTCAT TGTTTCCTTTTGGTAATTAAAAGGA GGCCAATCCCCTGTTGTGGCAGCTC ACAGCTATTGTGGTGGGAA (SEQ ID NO: 27) |

TABLE 2-continued

The EC-CREs sequence for highly expression
in endothelial cells.

| Gene | EC-CRE | Size (bp) | Sequence |
|---|---|---|---|
| VWF | EC-CRE1b | 385 | CTGCCAGGAGGTCTCCCTCCAAACT CTACAAAGCTTTATCAGCTTGGAGG TACTTCTAATACCATTTCCTTTCAT TGTTTCCTTTTGGTAATTAAAAGGA GGCCAATCCCCTGTTGTGGCAGCTC ACAGCTATTGTGGTGGGAAAGGGAG GGTGGTTGGTGGATGTCACAGCTTG GGCTTTATCTCCCCCAGCAGTGGGG ACTCCACAGCCCCTGGGCTACATAA CAGCAAGACAGTCCGGAGCTGTAGC AGACCTGATTGAGCCTTTGCAGCAG CTGAGAGCATGGCCTAGGGTGGGCG GCACCATTGTCCAGCAGCTGAGTTT CCCAGGGACCTTGGAGATAGCCGCA GCCCTCATTTGCAGGGGAAGGTATG GCCTTTGGAA (SEQ ID NO: 28) |

Alternatively, the VISTA enhancer browser (enhancer.l-bl.gov) was also applied, a central resource for experimentally validated human and mouse non-coding fragments with gene enhancer activity. This also provided the predicted DNA elements associated with high expression in blood vessels. The predicted sequences from VISTA were selected based on the validated data using mouse embryonic staining. Up to 3 VISTA sequences were selected from these validated data. However, since the DNA fragment sizes were too large to be accommodated into a viral vector, the selected sequences were further trimmed down or separated into sub-fragments using the UCSC genome browser using the aforementioned criteria. This resulted in 5 CREs derived from the 3 selected VISTA sequences (Table 3). All of the endothelial-specific CREs sequences were further validated both in vitro and in vivo to investigate their specificity and robustness in endothelial cells.

TABLE 3

The EC-CREs sequence for highly expression
in endothelial cells from VISTA
Enhancer browser.

| VISTA code | EC-CRE | Size (bp) | Sequence |
|---|---|---|---|
| Hs1859 | EC-CRE-V1 | 517 | GCCATTGGCTGGTCCTTCACTGACA GCAGAAACTTGGCCAATGGCAATCA ATCAGGGGGCCCGCGCTGCCTTAAA TACCAGCAGAGCAAACAGCCTCAGA CAAAGCTGCGCCGTGTATCAATTAC CGAGAGGCTGCGTGCTCCTCTGGGC GGAGGGAGCCGGAGCGAGCGGCCAG GGCTGCTGCCCCAGCTGATAAGGGC CCGCATTGTTCGGGGACAGCTGGCA GCCCGATAAGGGCCTGCTCGCCCGA GATAATGGCAGTGGGCAGGCGCCTC GCGGCAGTTTAGAATTTCTTGGGTC TCCAAGAAAGGTTCTATTAAGCCCA CTGACCCCAATTGAATATTAATTAG CTAATTAACGGATTTATTGTTCCAC GCCATTTCTGGAGAGGCCATTTTTT TTCGAGTGCCATTATTTTTGTAAAT GATTTTTCGCATTGTTCATAATTGA ATCTTTGCAGCTGCCAGCATCTTCT GCATGATTTGGCAAAAAAAAGGAAG CAGAAGCACTTAGGGTT (SEQ ID NO: 29) |

TABLE 3-continued

The EC-CREs sequence for highly expression
in endothelial cells from VISTA
Enhancer browser.

| VISTA code | EC-CRE | Size (bp) | Sequence |
|---|---|---|---|
| Hs2179 | EC-CRE-V2 | 511 | CCCCTAATAAACAGGAAGGCATCCG CGCCATTAGTATCCATCCTTTTCAG AGCATCTGAGACCTGTCTGGACCAT CAAAGCCATCCCCAGCCCCCAGGAG CCTACTGGAGGAGACACCAGCCTCG CCAAAACAATTCTCCATTGTGTTCT TCCCCTTAGAAATCATGGGTTTGTA AACAGGCCCTTACATTTCAGCAGGT CCTGCCCTGGCTTTGTGCTGGTGTG TTGTTTTTTCTTCCCTGAACAATGT CCTTTCCAGTAGGGCCAGCCGTTCA CACCATTGTCTGAGACCCTTGGACT ACAGGAAACATCACCAGATTCTTAT CAGTTGGGGGCAGGAGTGGGGGGGT GAACAGATGAGATCATGTCCACAGA GCAAGTGGCTGGTGTGCCACGTCAT TCCCCATGCCTTCATCTGTGAGAGC AGAGCCCGCTCGCCCTCCATCAATC TGGGCTTCATGTGTCCAGAGTCCAG TCCCCTCTATTTGGTGGTAGACACC TGGACTCTGTT (SEQ ID NO: 30) |
| Hs2179 | EC-CRE-V3 | 390 | TCCTACAGTTATGGGTCTGTCTTTC CTGCTAGATCAGAAGCTCCAGGGAC CTGTCTGTCTTATTAACCTTTCTTC CCCTCATGATGCCTGGCCCAGGACT CCACGTTCAGAGGCAGTTTAATGTC TACAGAACTGATGGATGCTCCATAC CCTGTATTCATAAGCCTGTGTTTTG CTGCCAAACACCAGAGGGCACTGTT AGCATGTCGATGAAGATTATAAACC CTCAGACCTGGAAGGCTGGGAAAGG CTTATGAAAATCTTGCTTCTGTTTT GGGATTACATAAGACTTATTGCGCC TCAATTGTTCTAAACACATCTGTTC GAGTTTATTCATGAGGCACGTTCCT GTTGGGGTTAGAGATGAGTTTGAAA GCTCCCCGTCACAGG (SEQ ID NO: 31) |
| Hs1882 | EC-CRE-V4 | 573 | AGGGACTGTTGGGCAGCCCCAGACT GGCACAGGTGGATCGGGTGCCTAGG CAGGGGGTGGTGAGTTATGGCGCAG CTGTCTTGGTGGCTGGGGGGAGCAG GGATAAGGGTGGACTTCTTAGTGAC CGCTCTCTGCCCCAGGAGGTAGAGT CCTGGGGGCTGGGCTGGCCTGAGAG ACGCCCCCTCATCCTTTCCAGGGTG AGGTACGAGGGCTCCGCCCCCTCCT GATATCACCAGGCCTAGGGCAGCAT CCTGATGGGGGAGGGGCAAGTGACC CGGGCCCTGGACTGCAGGAACAGCC CCTCCTCCACTGGTGGAGTTCCCAC TTCCTGCGGAAGGAACTATGTTAGA AGTTGTGTATATGGGGTGGGGGTTG GGTGTGGGTGGCGGGGGGCCTGGGT GGGGTCCACTGAGTCGCCTCCCCTG TCTCCCTGCACTTCCTCCTGGAGGA AATGGGGACAACAGGATGAAGTGAG GGCCTGCTGAGCCCAGGGCTGCCAC CTGGGAGTGAAGCCGGGGCAGGCTG CAGGGTCCGGGCCCTTCTGTGTGGG CAGGTGGAAGTGGTGGGGATGCA (SEQ ID NO: 32) |
| Hs1882 | EC-CRE-V5 | 441 | GGGGAGAGGGTGTGGGGTGGGGTGG GGAGAGGGGTGGGGTGGGGTGGGGG AGAGGGGATGGGATGGCATGGGGGG ATGTGGCAGTGAGGAGGCTGGGCCC TTGGAGCTGCCGAGTGCAGGGGCCT GGAGGACTCCGGGAAGGCGTCCTAG TGCATCAAGCGTGGGCTTGGCCTGC |

TABLE 3-continued

The EC-CREs sequence for highly expression
in endothelial cells from VISTA
Enhancer browser.

| VISTA code | EC-CRE | Size (bp) | Sequence |
|---|---|---|---|
| | | | TTGGGTCTCCCCTCCTGGCCCCCCT<br>AGCAATGGGCGGACTTGGGCCCGCT<br>CTGGGAGGATTCCAGGAACGGCTCC<br>TGCCTGGTTATAAATAGACTTCTCC<br>GAAAGGCCTGGGGCTGTGCCAGCTG<br>CAGCAGGTGCCTCCCAGGCCCGGCC<br>AGAGGGCCCCAGGCAAGGGGGTGGA<br>GCCCGGGTGGGGGTGATGAGGATGC<br>TGGGGTCCACTTTTGTAGCGCCAGA<br>GGCGACGGGCTCTGTCTGGTTGTAG<br>CATCACAGAGCTTGAT<br>(SEQ ID NO: 33) |

Example 2: Lentiviral Transduction of Human Endothelial Cells In Vitro

To validate the potential endothelial cell-specific CREs, we first validated a robust endothelial-specific promoter. The selected endothelial cell-specific CREs were cloned upstream of this promoter. We identified several human endothelial-specific promoter such as the human CDH5 promoter (1,303 bp) and human EDN1 promoter (455 bp) (The sequence of the CDH5 was obtained from Genecopoeia (www.genecopoeia.com) and for EDN1mini promoter, we selected the promoter sequence using the same concept as we select the CREs from UCSC). In addition, we also identified several endothelial promoters that are commercially available (Invivogen, USA) such as the as ENG promoter (888 bp), FLT1 promoter (1,037 bp), and ICAM2 promoter (399 bp). The sequences of these promoters are provided in Table 4. The endothelial-specific promoters were cloned into the lentiviral vector plasmid upstream of the FVIII or GFP reporter gene (FIG. 2).

Nine different lentiviral constructs were generated (designated as:
1) pLVX-CMV-GFP (SEQ ID NO:40),
2) pLVX-CMV-FVIII (SEQ ID NO:41),
3) pLVX-hEDN1mini-FVIII (SEQ ID NO:42),
4) pLVX-hEDN1mini-Kozak-FVIII (SEQ ID NO:43),
5) pLVX-hICAM2-FVIII (SEQ ID NO:44),
6) pLVX-hICAM2-Kozak-FVIII (SEQ ID NO:45)
7) pLVX-hICAM2-Kozak-Luc2 (SEQ ID NO:46)
8) pLVX-EC-CRE-h(uman)ICAM2-Kozak-Luc2 (SEQ ID NO:47)
9) pLVX-EC-CRE-h(uman)ICAM2-Kozak-FVIII (SEQ ID NO:48), by conventional cloning. pLVX can also be a pCDH backbone or another (lenti)viral backbone.

TABLE 4

Endothelial-specific promoter sequences

| Promoter | Host Species | Size (bp) | Sequence | Source |
|---|---|---|---|---|
| CDH5 | Human | 1303 | GCTTGCCCAGCTATA<br>TAATAAAACAAGTTT<br>GGGACTTCCCAACCA<br>TTCACCCATGGAAAA<br>ACAGAAGCAACTCTT<br>CAAAGGACAGATTCC<br>CAGGATCTGCCCTGG | Genecopoeia |

TABLE 4-continued

Endothelial-specific promoter sequences

| Promoter | Host Species | Size (bp) | Sequence | Source |
|---|---|---|---|---|
| | | | GAGATTCCAAATCAG<br>TTGATCTGGGGTGAG<br>CCCAGTCCTCTGTAG<br>TTTTTAGAAGCTCCT<br>CCTATGTCTCTCCTG<br>GTCAGCAGAATCTTG<br>GCCCCTCCCTTCCCC<br>CCAGCCTCTTGGTTC<br>TTCTGGGCTCTGATC<br>CAGCCTCAGCGTCAC<br>TGTCTTCCACGCCCC<br>TCTTTGATTCTCGTT<br>TATGTCAAAAGCCTT<br>GTGAGGATGAGGCTG<br>TGATTATCCCCATTT<br>TACAGATGAGGAAAC<br>TGTGGCTCCAGGATG<br>ACACAACTGGCCAGA<br>GGTCACATCAGAAGC<br>AGAGCTGGGTCACTT<br>GACTCCACCCAATAT<br>CCCTAAATGCAAACA<br>TCCCCTACAGACCGA<br>GGCTGGCACCTTAGA<br>GCTGGAGTCCATGCC<br>CGCTCTGACCAGGAG<br>AAGCCAACCTGGTCC<br>TCCAGAGCCAAGAGC<br>TTCTGTCCCTTTCCC<br>ATCTCCTGAAGCCTC<br>CCTGTCACCTTTAAA<br>GTCCATTCCCACAAA<br>GACATCATGGGATCA<br>CCACAGAAAATCAAG<br>CTCTGGGGCTAGGCT<br>GACCCCAGCTAGATT<br>TTTGGCTCTTTTATA<br>CCCCAGCTGGGTGGA<br>CAAGCACCTTAAACC<br>CGCTGAGCCTCAGCT<br>TCCCGGGCTATAAAA<br>TGGGGGTGATGACAC<br>CTGCCTGTAGCATTC<br>CAAGGAGGGTTAAAT<br>GTGATGCTGCAGCCA<br>AGGGTCCCCACAGCC<br>AGGCTCTTTGCAGGT<br>GCTGGGTTCAGAGTC<br>CCAGAGCTGAGGCCG<br>GGAGTAGGGGTTCAA<br>GTGGGGTGCCCCAGG<br>CAGGGTCCAGTGCCA<br>GCCCTCTGTGGAGAC<br>AGCCATCCGGGGCCG<br>AGGCAGCCGCCCACC<br>GCAGGGCCTGCCTAT<br>CTGCAGCCAGCCCAG<br>CCCTCACAAAGGAAC<br>AATAACAGGAAACCA<br>TCCCAGGGGGAAGTG<br>GGCCAGGGCCAGCTG<br>GAAAACCTGAAGGGG<br>AGGCAGCCAGGCCTC<br>CCTCGCCAGCGGGGT<br>GTGGCTCCCCTCCAA<br>AGACGGTCGGCTGAC<br>AGGCTCCACAGAGCT<br>CCACTCACGCTCAGC<br>CCTGGACGGACAGGC<br>AGTCCAACGGAACAG<br>AAACATCCCTCAGCC<br>CACAGGCACGGTGAG<br>TGGGGGCTCCCACAC<br>TCCCCTCCACCCCAA<br>ACCCGCCACCCTGCG | |

TABLE 4-continued

Endothelial-specific promoter sequences

| Promoter | Host Species | Size (bp) | Sequence | Source |
|---|---|---|---|---|
| | | | CCCAAGATGGGAGGG | |
| | | | TCCTCAGCTTCCCCA | |
| | | | TCTGTAGAATGGGCA | |
| | | | TCGTCCCACTCCCAT | |
| | | | GACAGAGAGGCTC | |
| | | | (SEQ ID NO: 34) | |
| EDN1 | Human | 455 | GAGACATAAAAGGAA | UCSC |
| | | | AATGAAGCGAGCAAC | |
| | | | AATTAAAAAAAATTC | |
| | | | CCCGCACACAACAAT | |
| | | | ACAATCTATTTAAAC | |
| | | | TGTGGCTCATACTTT | |
| | | | TCATACCAATGGTAT | |
| | | | GACTTTTTTTCTGGA | |
| | | | GTCCCCTCTTCTGAT | |
| | | | TCTTGAACTCCGGGG | |
| | | | CTGGCAGCTTGCAAA | |
| | | | GGGGAAGCGGACTCC | |
| | | | AGCACTGCACGGGCA | |
| | | | GGTTTAGCAAAGGTC | |
| | | | TCTAATGGGTATTTT | |
| | | | CTTTTTCTTAGCCCT | |
| | | | GCCCCCGAATTGTCA | |
| | | | GACGGCGGGCGTCTG | |
| | | | CCTCTGAAGTTAGCA | |
| | | | GTGATTTCCTTTCGG | |
| | | | GCCTGGCCTTATCTC | |
| | | | CGGCTGCACGTTGCC | |
| | | | TGTTGGTGACTAATA | |
| | | | ACACAATAACATTGT | |
| | | | CTGGGGCTGGAATAA | |
| | | | AGTCGGAGCTGTTTA | |
| | | | CCCCCACTCTAATAG | |
| | | | GGGTTCAATATAAAA | |
| | | | AGCCGGCAGAGAGCT | |
| | | | GTCCAAGTCAGACGC | |
| | | | GCCTC | |
| | | | (SEQ ID NO: 35) | |
| ENG | Human | 888 | CGCCTTGCTGTGCCA | Invivogen |
| | | | CTTTGGGACTTCCCT | Inc. |
| | | | CCCTAGCCTGAGCTT | |
| | | | CAGTTTTCCTGCCTG | |
| | | | TTAGGCAGCCCCATG | |
| | | | TCAACTGCACTTAGT | |
| | | | AGGCCGGGTTTGATG | |
| | | | CCCGACAAGACGTGA | |
| | | | AGTGGTGGAGGTGGG | |
| | | | CAGGATCCCAGCGCT | |
| | | | ACCATCTTCTTGAAC | |
| | | | CAGTGATCTCAACAC | |
| | | | ATCGGATTTCTGTTT | |
| | | | CCTCATCTGCAAAAT | |
| | | | GGGATCAGTGAGCTC | |
| | | | AGGTGGGTCACAAAT | |
| | | | TCTACAGGAACTACT | |
| | | | TTAGCCAAGCCCGGC | |
| | | | CCCCTGAAAGTTCCC | |
| | | | CTCGGTGGGCTGTTA | |
| | | | GGGTGATTGTTTTCA | |
| | | | TCTGTGGGGCTCCCT | |
| | | | GATGCGTCCCACCCA | |
| | | | CCAGCCTTGGAGAGG | |
| | | | GTGGGATGGGAGGGT | |
| | | | GGGGTGCTTGGGGAG | |
| | | | ACAAGCCTAGAGCCT | |
| | | | GGGCCCTCCCACCCC | |
| | | | ACTGCCTCCCCCCAT | |
| | | | CCCAGGGCCCCCCAC | |
| | | | CCAGTGACAAAGCCC | |
| | | | GTGGCACTTCCTCTA | |
| | | | CCCGGTTGGCAGGCG | |
| | | | GCCTGGCCCAGCCCC | |
| | | | TTCTCTAAGGAAGCG | |

TABLE 4-continued

Endothelial-specific promoter sequences

| Promoter | Host Species | Size (bp) | Sequence | Source |
|---|---|---|---|---|
| | | | CATTTCCTGCCTCCC | |
| | | | TGGGCCGGCCGGGCT | |
| | | | GGATGAGCCGGGAGC | |
| | | | TCCCTGCTGCCGGTC | |
| | | | ATACCACAGCCTTCA | |
| | | | TCTGCGCCCTGGGGC | |
| | | | CAGGACTGCTGCTGT | |
| | | | CACTGCCATCCATTG | |
| | | | GAGCCCAGCACCCCC | |
| | | | TCCCCGCCCATCCTT | |
| | | | CGGACAGCAACTCCA | |
| | | | GCCCAGCCCCGCGTC | |
| | | | CCTGTGTCCACTTCT | |
| | | | CCTGACCCCTCGGCC | |
| | | | GCCACCCCAGAAGGC | |
| | | | TGGAGCAGGGACGCC | |
| | | | GTCGCTCCGGCCGCC | |
| | | | TGCTCCCCTCGGGTC | |
| | | | CCCGTGCGAGCCCAC | |
| | | | GCCGGCCCCGGTGCC | |
| | | | CGCCCGCAGCCCTGC | |
| | | | CACTGGACACAGGAT | |
| | | | AAGGCCCAGCGCACA | |
| | | | GGCCCCCACGTGGAC | |
| | | | ACC | |
| | | | (SEQ ID NO: 36) | |
| FLT1 | Human | 1037 | TTTGCTTCTAGGAAG | Invivogen |
| | | | CAGAAGACTGAGGAA | Inc. |
| | | | ATGACTTGGGCGGGT | |
| | | | GCATCAATGCGGCCA | |
| | | | AAAAAGACACGGACA | |
| | | | CGCTCCCCTGGGACC | |
| | | | TGAGCTGGTTCGCAG | |
| | | | TCTTCCCAAAGGTGC | |
| | | | CAAGCAAGCGTCAGT | |
| | | | TCCCCTCAGGCGCTC | |
| | | | CAGGTTCAGTGCCTT | |
| | | | GTGCCGAGGGTCTCC | |
| | | | GGTGCCTTCCTAGAC | |
| | | | TTCTCGGGACAGTCT | |
| | | | GAAGGGGTCAGGAGC | |
| | | | GGCGGGACAGCGCGG | |
| | | | GAAGAGCAGGCAAGG | |
| | | | GGAGACAGCCGGACT | |
| | | | GCGCCTCAGTCCTCC | |
| | | | GTGCCAAGAACACCG | |
| | | | TCGCGGAGGCGCGGC | |
| | | | CAGCTTCCCTTGGAT | |
| | | | CGGACTTTCCGCCCC | |
| | | | TAGGGCCAGGCGGCG | |
| | | | GAGCTTCAGCCTTGT | |
| | | | CCCTTCCCCAGTTTC | |
| | | | GGGCGGCCCCCAGAG | |
| | | | CTGAGTAAGCCGGGT | |
| | | | GGAGGGAGTCTGCAA | |
| | | | GGATTTCCTGAGCGC | |
| | | | GATGGGCAGGAGGAG | |
| | | | GGGCAAGGGCAAGAG | |
| | | | GGCGCGGAGCAAAGA | |
| | | | CCCTGAACCTGCCGG | |
| | | | GGCCGCGCTCCCGGG | |
| | | | CCCGCGTCGCCAGCA | |
| | | | CCTCCCCACGCGCGC | |
| | | | TCGGCCCCGGGCCAC | |
| | | | CCGCCCTCGTCGGCC | |
| | | | CCCGCCCCTCTCCGT | |
| | | | AGCCGCAGGGAAGCG | |
| | | | AGCCTGGGAGGAAGA | |
| | | | AGAGGGTAGGTGGGG | |
| | | | AGGCGGATGAGGGGT | |
| | | | GGGGGACCCCTTGAC | |
| | | | GTCACCAGAAGGAGG | |
| | | | TGCCGGGGTAGGAAG | |
| | | | TGGGCTGGGGAAAGG | |

TABLE 4-continued

Endothelial-specific promoter sequences

| Promoter | Host Species | Size (bp) | Sequence | Source |
|---|---|---|---|---|
| | | | TTATAAATCGCCCCC GCCCTCGGCTGCTCT TCATCGAGGTCCGCG GGAGGCTCGGAGCGC GCCAGGCGGACACTC CTCTCGGCTCCTCCC CGGCAGCGGCGGCGG CTCGGAGCGGGCTCC GGGGCTCGGGTGCAG CGGCCAGCGGGCGCC TGGCGGCGAGGATTA CCCGGGGAAGTGGTT GTCTCCTGGCTGGAG CCGCGAGACGGGCGC TCAGGGCGCGGGGCC GGCGGCGGCGAACAA GAGGACGGACTCTGG CGGCCGGGTCGTTGG CCGCGGGGAGCGCGG GCACCGGGCGAGCAG GCCGCGTCGCGCTCA CC (SEQ ID NO: 37) | |
| ICAM2 | Human | 399 | GTCTCCCAGGCATGA CTCCAACAATGCATC CCATGGGATTTGGGG TTCCCCAGATCTGGG GCTTGTAGGCCTGAC TCTCCCCTGTGCACA CGTCTCATACACGCA TGCGTGCACCCATTG CCTGCCCCGCCCCTT GCACAGGGAGTCAGC AGGGAGGACTGGGTT ATGCCCTGCTTATCA GCAGCTTCCCAGCTT CCTCTGCCTGGATTC TTAGAGGCCTGGGGT CCTAGAACGAGCTGG TGCACGTGGCTTCCC AAAGATCTCTCAGAT AATGAGAGGAAATGC AGTCATCAGTTTGCA GAAGGCTAGGGATTC TGGGCCATAGCTCAG ACCTGCGCCCACCAT CTCCCTCCAGGCAGC CCTTGGCTGGTCCCT GCGAGCCCGTGGAGA CTGCCAGTC (SEQ ID NO: 38) | Invivogen Inc. |

The Kozak consensus sequence is present in eukaryotic mRNA and is known to improve expression by enhancing translation initiation. Consequently, we introduce the Kozak consensus sequence (i.e. GCCACC, SEQ ID NO:39) upstream of the FVIII or LUC2 gene within the lentiviral vector plasmids.

HUVECs or LSECs were transduced at a multiplicity of infection (MOI)=50. Culture medium was collected at 24, 48, and 72 hrs and FVIII levels were subsequently measured in the conditioned medium using a human FVIII-specific ELISA, according to the manufacturer's instructions (Asserachrome). Using flow cytometry, the results showed that more than nearly 90% of HUVEC and LSEC cells were transduced compared to non-transduced HUVECs (FIG. 3). Relatively robust FVIII expression could be achieved in transduced HUVECs and LSECs with CMV, ICAM2 and EDN1mini. The Kozak translational consensus sequence significantly enhanced FVIII expression levels (FIG. 4). In particular, the Kozak consensus optimized ICAM2 construct yielded the highest FVIII expression in both HUVECs and LSECs. These results confirmed the robustness of the selected promoters in endothelial cells.

Example 3: In Vitro Validation of
Endothelial-Specific (EC) CREs in Transfected
HUVECs To validate whether the different EC-CREs identified by genome-wide computational analysis, led to enhanced FVIII expression when coupled to an EC-specific human ICAM2 promoter, human umbilical vein endothelial cells (HUVECs) were transfected in vitro with the corresponding lentiviral vector constructs: pCDH-EC-CRE-ICAM2-FVIII, with EC-CRE representing the respective regulatory elements named in FIG. 5, which were cloned upstream of the ICAM2 promoter driving the human FVIII gene in a pCDH lentiviral self-inactivating backbone. FIG. 8 shows 4 examples of such expression cassettes comprising HYAL2-EC-CRE1a (FIG. 8a— SEQ ID NO. 50), HYAL2-EC-CRE1b (FIG. 8d— SEQ ID NO. 51) and IF127-EC-CRE1b (FIG. 8c— SEQ ID NO. 52). The control vector (without EC-CRE) is depicted in FIG. 8b (SEQ ID NO. 49). Analogously, the person skilled in the art would be capable of cloning the other EC-CRE's in a similar manner in the expression vector backbone.

HUVECs were seeded at $1.5 \times 10^5$ cells/well of 6-well plate transfected 24 hr later with cationic lipid-based Lipofectamine 3000 (Invitrogen, USA). For HUVECs, 2.5 microgram of each plasmid were mixed with 3.75 microliter of Lipofectamine reagents. The P3000 reagent was mixed with each plasmid at 2 microliter per 1 microgram of plasmid and incubated at room temperature for 5 mins before adding to the HUVECs. Sixteen hours after transfection, the cell culture medium was removed and then replaced with fresh medium. 72 hrs later 100 microliter of the culture medium was collected and stored in −80° C. for FVIII quantification using a human FVIII-specific ELISA (Asserachrome). The results showed that about 70% of the CRMs resulted in increased FVIII expression in transfected HUVECs in vitro, relative to the control lentiviral vector without CRE (i.e. 23 out of 32). (FIG. 5).

Example 4: In Vivo Validation of
Endothelial-Specific (EC) CREs Following
Lentiviral Transduction in Mice Next, it was validated whether the EC-CREs identified by genome-wide computational analysis, led to enhanced FVIII expression in mice in vivo. Self-inactivating lentiviral vectors were used to express the human codon usage optimized B-domain deleted FVIII from an EC-specific human ICAM2 promoter. To test the impact of the EC-CRE on FVIII expression, the HYAL2-EC-CRE1a (SEQ ID NO. 50), HYAL2-EC-CRE1b (SEQ ID NO. 51) and IF127-EC-CRE1b (SEQ ID NO. 52) elements were cloned upstream of the ICAM2 promoter driving the human FVIII gene. Said expression cassettes comprise respectively the EC-CRE's HYAL2-EC-CRE1a, HYAL2-EC-CRE1b and IF127-EC-CRE1b. Analogously, the person skilled in the art would be capable of cloning the other EC-CRE's in a similar manner in an expression vector backbone. In these examples the pCDH-ICAM2-FVIII backbone is used. A lentiviral vector identical in design but without any upstream EC-CRE was used as control (SEQ ID NO. 49) to compare FVIII expression levels. Lentiviral vector particles were manufactured by

45 | 46 transient cotransfection of HEK293 packaging cells with lentiviral vector and helper plasmids (Cyagen, USA). Vector titer was determined and expressed in Transducing Units per ml (TU/ml). Lentiviral vectors were retro-orbitally injected in 2 day-old neonatal CB17-SCID mice (Taconic). The vector preparation was supplemented with 40 microgram/ml polybrene in a total volume of 80 microliter. A total vector dose of $1 \times 10^8$TU was used. Plasma was collected 5 weeks post-injection and FVIII was measured using a human FVIII-specific ELISA.

A significant increase was detected in FVIII expression in vivo when the EC-CRE were present compared to a control lentiviral vector without EC-CRE (FIG. 6). In particular, a 27-fold increase in FVIII could be detected following in vivo transduction with lentiviral vectors containing the IF127-EC-CRE1b compared to a control lentiviral vector without EC-CRE (ICAM2-FVIII). Similarly, the HYAL2-EC-CRE1a also boosted FVIII expression, but to a lesser extent (5-fold). This is consistent with the increased FVIII expression following in vitro HUVEC transfection with the IF127-EC-CRE1b and HYAL2-EC-CRE1a vectors compared to controls without EC-CRE (ICAM2-FVIII) (FIG. 5). HYAL2-EC-CRE1b did not increase FVIII expression in vivo, consistent with the lower levels of FVIII expression in transfected HUVECs in vitro (FIG. 5).

Example 5: Confirmation of Increased Gene Expression by EC-CRE in Organ-Derived Endothelial Cells Isolated from Lentivirally Transduced Mice The mice were injected with the lentiviral vectors containing the ICAM2-FVIII (no CRE control—SEQ ID NO. 49) or IFI27-EC-CRE1b-ICAM2-FVIII (SEQ ID NO. 52) expression cassette. After euthanization, the liver and spleen were processed to obtain their respective endothelial populations (i.e. liver sinusoidal endothelial cells, splenic endothelial cells). First, a single cell suspension was obtained from the liver and spleen tissue using the GentleMACS dissociator (Product no—130-093-235, Miltenyi Biotec) according to the manufacturer's protocol (Liver Dissociation Kit: Product code: 130-105-807; Miltenyi Biotec.—www.miltenyibiotec.com/en/products-and-services/macs-sample-preparation/sample-dissociation/tissue-dissociation-kits/liver-dissociation-kit-mouse.aspx), spleen (Spleen Dissociation Kit: Product code: 130-095-926; Miltenyi Biotec.—www.miltenyibiotec.com/en/products-and-services/macs-sample-preparation/sample-dissociation/tissue-dissociation-kits/spleen-dissociation-kit-mouse. aspx). Subsequently, the single cell suspension from each organ was subjected to MACS cell separation technology (Miltenyi Biotec) to sort out the respective endothelial populations. The single cell suspension obtained from liver and spleen were therefore tagged with CD146 microbeads, according to the manufacturer's instructions (Product code: 130-092-007; Miltenyi Biotec.-www.miltenyibiotec.com/en/products-and-services/macs-cell-separation/cell-separation-reagents/endothelial-cells/cd146-lsec-microbeads-mouse.aspx), allowing positive selection of the respective liver-derived and splenic endothelial cells. One to $1.6 \times 106$ CD146-positive endothelial cells were obtained from the liver and $6.9-8.1 \times 105$ CD146-positive endothelial cells were obtained from the spleen. The isolated cells were plated at a density of 25000 cells/well of 48 well plates in 200 microliter of Endothelial Basal Medium supplemented with growth factors.

Subsequently, the single cell suspension from each organ was subjected to MACS cell separation technology (Miltenyi Biotec) to sort out the respective endothelial populations. The single cell suspension obtained from liver and spleen were therefore tagged with CD146 microbeads, according to the manufacturer's instructions (Product code: 130-092-007; Miltenyi Biotec. —http://www.miltenyibiotec.com/en/products-and-services/macs-cell-separation/cell-separation-reagents/endothelial-cells/cd146-lsec-microbeads-mouse.aspx), allowing positive selection of the respective liver-derived and splenic endothelial cells. One to $1.6 \times 10^6$ CD146-positive endothelial cells were obtained from the liver and $6.9-8.1 \times 10^5$ CD146-positive endothelial cells were obtained from the spleen. The isolated cells were plated at a density of 25000 cells/well of 48 well plates in 200 microliter of Endothelial Basal Medium supplemented with growth factors.

Total RNA was isolated from the cells using RNeasy Micro Kit (Qiagen) according to manufacturer's instruction. Isolated RNA concentrations were measured using Nanodrop 1000 (Thermo scientific, MA, USA). Complementary DNA (cDNA) was synthesized from 75 ng-35 ng isolated RNA using Superscript III First-Strand synthesis system (Invitrogen) according to manufacturer's instructions. The qRT-PCR was performed using SYBR Green qPCR mix (Life technology) in a qPCR ABI Prism 7900HT (Applied Biosystems, Foster City/CA, USA) using FVIII specific primers 5'-AACGGCTACGTGAACAGAAG-3' (forward—SEQ ID NO. 53) and 5'-GATAGGGCTGATTTCCAGGC-3' (reverse—SEQ ID NO. 54). The expression levels were normalized to GAPDH (glyceraldehyde-3-phosphate dehydrogenase) mRNA expression, obtained by using the forward primer 5'-GAAGGTGAAGGTCGGAGTC-3' (SEQ ID NO. 55) and reverse primer 5'-GAAGATGGTGATGG-GATTTC-3' (SEQ ID NO. 56).

The results showed that the IF127-EC-CRE1b element enhanced FVIII expression in CD146-positive endothelial cells obtained from liver or spleen, as reflected by increased FVIII mRNA levels in mice injected with the lentiviral vector containing the IF127-EC-CRE1b-ICAM2-FVIII cassette compared to the ICAM2-FVIII control (FIG. 7).

The invention claimed is:

1. A method for treating or preventing an endothelial cell-related disease or disorder, the method comprising:

i) administering a therapeutically effective amount of a nucleic acid expression cassette; a vector comprising said nucleic acid expression cassette; or a pharmaceutical composition comprising said nucleic acid expression cassette or said vector, and a pharmaceutically acceptable carrier, to a subject in need thereof, wherein said nucleic acid expression cassette comprises one or more nucleic acid regulatory element for enhancing endothelial cell-specific gene expression comprising the sequence of SEQ ID NO: 22, operably linked to a promoter.

2. The method according to claim 1, wherein the nucleic acid regulatory element has a maximal length of about 1000 nucleotides, still comprising said regulatory element.

3. The method according to claim 1, wherein the nucleic acid regulatory element is operably linked to a promoter and a transgene.

4. The method according to claim 1, wherein the promoter is an endothelial cell-specific promoter selected from the group consisting of: IFI27, ICAM2, VWF, EDN1, ENG, ECSCR, CDH5, PECAM1, HHIP, TIE1 and HYAL2.

5. The method according to claim 3, wherein the transgene encodes a therapeutic protein or an immunogenic protein.

6. The method according to claim 3, wherein the transgene encodes hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, a1-antitrypsin (AAT), apolipoprotein A-l (apoA-l), matrix metalloproteinase-3 (TIMP-3), insulin, nitric oxide synthase (NOS), growth factors, antibodies directed against any one of said transgenes, factors and their cognate receptors or against any secreted protein or viral protein, small interfering RNA, guide RNA, endonuclease, or Cas9.

7. The method according to claim 3, wherein the transgene encodes coagulation factor VIII (FVIII).

8. The method according to claim 1, wherein the nucleic acid expression cassette further comprises a polyadenylation signal.

9. The nucleic acid expression cassette according to claim 8, wherein the polyadenylation signal is the Simian Virus 40 (SV40) polyadenylation signal.

10. The method according to claim 1, wherein the vector is a lentiviral vector, an adeno-associated viral (AAV) vector, or a adenoviral vector.

11. The method according to claim 1, wherein the vector is a plasmid, a minicircle, an episomal vector, or a transposon-based vector.

12. The method according to claim 11, wherein the transposon-based vector is a PiggyBac-based vector or a Sleeping Beauty-based vector.

13. The method according to claim 1, wherein said endothelial cell-related disease or disorder is selected from the group comprising: liver diseases, hemophilia A, von Willebrand disease, cardiovascular disease, microvascular thrombosis, thrombotic thrombocytopenia purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer, Ebola, Dengue and Dengue hemorrhagic fever.

14. A method for enhancing transgene expression in endothelial cells in a subject undergoing endothelial cell-directed gene therapy, the method comprising:

i) administering to the subject a nucleic acid expression cassette; a vector comprising said nucleic acid expression cassette; or a pharmaceutical composition comprising said nucleic acid expression cassette or said vector, and a pharmaceutically acceptable carrier, wherein said nucleic acid expression cassette comprises one or more nucleic acid regulatory element for enhancing endothelial cell-specific gene expression comprising the sequence of SEQ ID NO: 22, operably linked to a promoter and a transgene; and ii) expressing a therapeutically effective amount of the transgene product in endothelial cells of the subject.

15. A method for vaccinating a subject, the method comprising:

i) administering to the subject a nucleic acid expression cassette; a vector comprising said nucleic acid expression cassette; or a pharmaceutical composition comprising said nucleic acid expression cassette or said vector, and a pharmaceutically acceptable carrier, wherein said nucleic acid expression cassette comprises one or more nucleic acid regulatory element for enhancing endothelial cell-specific gene expression comprising the sequence of SEQ ID NO: 22, operably linked to a promoter and a transgene; and ii) expressing an immunologically effective amount of the transgene product in endothelial cells of the subject.

* * * * *

SEQUENCE LISTING

```
Sequence total quantity: 56
SEQ ID NO: 1          moltype = DNA  length = 76
FEATURE               Location/Qualifiers
source                1..76
                      mol_type = other DNA
                      organism = Homo sapiens
SEQUENCE: 1
gccctcacaa aggaacaata acaggaaacc atcccagggg gaagtgggcc agggccagct   60
ggaaaacctg aagggg                                                   76
```

```
SEQ ID NO: 2          moltype = DNA   length = 277
FEATURE               Location/Qualifiers
source                1..277
                      mol_type = other DNA
                      organism = Homo sapiens
SEQUENCE: 2
ggccgaggca gccgcccacc gcagggcctg cctatctgca gccagcccag ccctcacaaa   60
ggaacaataa caggaaacca tcccaggggg aagtgggcca gggccagctg gaaaacctga  120
aggggaggca gccaggcctc cctcgccagc ggggtgtggc tccctccaa agacggtcgg   180
ctgacaggct ccacagagct ccactcacgc tcagccctgg acggacaggc agtccaacgg  240
aacagaaaca tccctcagcc cacaggcacg gtgagtg                           277

SEQ ID NO: 3          moltype = DNA   length = 408
FEATURE               Location/Qualifiers
source                1..408
                      mol_type = other DNA
                      organism = Homo sapiens
SEQUENCE: 3
gcttcctcct ctgctactaa tctggtctca cagaccatcc catttcctgc tagcccacca   60
gccgccttcc ttgctcccaa tgacacttcc tggccttgtg ccctcctgtt acctcctttg  120
cctccagaga ggttggagca gaggctgggc agtgccagaa atcaggcatg aaatcctcag  180
ggggaccaag gaggcaccag cctccctccc acagtctcag ctacctctgc tacggtgacc  240
cccagcccca ccctgggggc ccacagctca tgcctggctc accattcctt tgtttatgga  300
ccacaggaac agtcgttttc agggcagagt caacttcctc atggactggg agtacaaagg  360
gaattggcag atggtgccag acaggccct gtccccatct gccacagc                408

SEQ ID NO: 4          moltype = DNA   length = 173
FEATURE               Location/Qualifiers
source                1..173
                      mol_type = other DNA
                      organism = Homo sapiens
SEQUENCE: 4
gcttcctcct ctgctactaa tctggtctca cagaccatcc catttcctgc tagcccacca   60
gccgccttcc ttgctcccaa tgacacttcc tggccttgtg ccctcctgtt acctcctttg  120
cctccagaga ggttggagca gaggctgggc agtgccagaa atcaggcatg aaa          173

SEQ ID NO: 5          moltype = DNA   length = 307
FEATURE               Location/Qualifiers
source                1..307
                      mol_type = other DNA
                      organism = Homo sapiens
SEQUENCE: 5
cccagctgag ggctggtgcc agagccgtgt ctgcttgccc catcaagagg tgggagggat   60
tgatccacct tcctgcccca cagatggtgc agcctccaac ctattgtttt ccaggacgct  120
tcggtggaga gcacaaggaa tgtagggtct agaaacagga agccctggct ccgctggac   180
aaggtttcct ccagactcag gcctgccctc cagacaacaa ggcagggccc ttggtccac   240
cctgccctgc ctggctcact gggccacccc aaggaaggcc ttgccctctc tgggcttctg  300
catgtga                                                            307

SEQ ID NO: 6          moltype = DNA   length = 450
FEATURE               Location/Qualifiers
source                1..450
                      mol_type = other DNA
                      organism = Homo sapiens
SEQUENCE: 6
aggtatccac caaggggccc aaagagctgct gagcccctga gcagccctac caatttcagc  60
ttatggtggt gaggggtagg ggaggtgtat actggcctgg aaggggttaa gctgcccgcc  120
tgcagcctca gcctgagcta ttgtgttgcc aaacaagggc cggacatgag ggcaggaagc  180
cagcaggggc cacacatttt ctgcaaagtt ggatgattca ctgctgactt ggggacaccc  240
aggggacaga ggggacacca tcccaggaag aatcttaggc tcattttgcc cacatggacc  300
catgactgtt ccctgtatcc tctctctgca cccctcagt cacactgaag caactatgag   360
aattcccatt tgacagatgg gaccatcgag gctgagggaa gctgtgcagc cagtccaagg  420
tcacacaacc aacacaaggt agaagcaggg                                   450

SEQ ID NO: 7          moltype = DNA   length = 123
FEATURE               Location/Qualifiers
source                1..123
                      mol_type = other DNA
                      organism = Homo sapiens
SEQUENCE: 7
agggcccctg gagctggtcc caatgtgttt ccttctattc ttttgacagg aagctcctgg   60
agagccagtc cccacccca tcccgcccca gcactccctc tctcttctcc actatggaca   120
gag                                                                 123

SEQ ID NO: 8          moltype = DNA   length = 499
FEATURE               Location/Qualifiers
source                1..499
                      mol_type = other DNA
                      organism = Homo sapiens
```

```
SEQUENCE: 8
tagggcctct ctgaaagatg tggggagtcc tatctgcatt gggatccctg aggagggaga    60
ggaatgtgga gaattcaggg tccagggagc atgggtgact ggtgggctgg gcttccaggc   120
tgaatcatgg gaaaggagaa cctggtctga aacagtactg ggcgggattg gtgttagatt   180
ccaggaaaac ccccaggcgg tctgtggtgg aacctggtg accctcagaa gggaagagaa    240
tggggatggg gccaggttgc catggttggt cattgtgcat aggcactaga ggccatgctg   300
ggtgggcaca gtcgctgctg cagcctcaca tcctcatctg gacatggctg agcagggccc   360
ctggagctga tcccaatgtg tttccttcta ttctttttgac aggaagctcc tggagagcca   420
gtccccaccc ccatcccgcc ccagcactcc ctctctcttc tccactatgg acagagcctc   480
cactgagctg ctgcctgcc                                                499

SEQ ID NO: 9              moltype = DNA  length = 455
FEATURE                   Location/Qualifiers
source                    1..455
                          mol_type = other DNA
                          organism = Homo sapiens
SEQUENCE: 9
gagacataaa aggaaaatga agcgagcaac aattaaaaaa aattccccgc acacaacaat    60
acaatctatt taaactgtgg ctcatacttt tcataccaat ggtatgactt tttttctgga   120
gtccctctt ctgattcttg aactccgggg ctggcagctt gcaaagggga agcggactcc     180
agcactgcac gggcaggttt agcaaaggtc tctaatgggg attttctttt tcttagccct   240
gccccgaat tgtcagacgg cgggcgtctg cctctgaagt tagcagtgat ttcctttcgg     300
gcctggcctt atctccggct gcacgttgcc tgttggtgac taataacaca ataacattgt   360
ctggggctgg aataaagtcg gagctgttta cccccactct aataggggtt caatataaaa   420
agccggcaga gagctgtcca agtcagacgc gcctc                               455

SEQ ID NO: 10             moltype = DNA  length = 153
FEATURE                   Location/Qualifiers
source                    1..153
                          mol_type = other DNA
                          organism = Homo sapiens
SEQUENCE: 10
tgtccacttc tcctgacccc tcggccgcca ccccagaagg ctggagcagg gacgccgtcg    60
ctccggccgc ctgctcccct cgggtccccg tgcgagccca cgccggcccc ggtgcccgcc   120
cgcagccctg ccactggaca caggataagg ccc                                153

SEQ ID NO: 11             moltype = DNA  length = 125
FEATURE                   Location/Qualifiers
source                    1..125
                          mol_type = other DNA
                          organism = Homo sapiens
SEQUENCE: 11
gggcccccca cccagtgaca aagcccgtgg cacttcctct acccggttgg caggcggcct    60
ggcccagccc cttctctaag gaagcgcatt tcctgcctcc ctgggccggc cgggctggat   120
gagcc                                                               125

SEQ ID NO: 12             moltype = DNA  length = 498
FEATURE                   Location/Qualifiers
source                    1..498
                          mol_type = other DNA
                          organism = Homo sapiens
SEQUENCE: 12
gggatgggag ggtggggtgc ttggggagac aagcctagag cctgggccct cccacccac     60
tgcctccccc catcccaggg ccccccaccc agtgacaaag cccgtggcac ttcctctacc   120
cggttggcag gcggcctggc ccagcccctt ctctaaggag gcgcatttcc tgcctccctg   180
ggccggccgg gctggatgag gcaggagctc cctgctgccg gtcataccac agccttcatc   240
tgcgccctgg ggccaggact gctgctgtca ctgccatcca ttggagccca gcaccccctc   300
cccgcccatc cttcggacag caactccagc ccagccccgc gtcctgtgt ccacttctct     360
tgaccctcg gccgccaccc cagaaggctg agcagggac gccgtcgctc cggccgcctg      420
ctccctcgg gtccccgtgc gagcccacgc cggccccggt gccgccgc agccctgcca       480
ctggacacag gataaggc                                                 498

SEQ ID NO: 13             moltype = DNA  length = 136
FEATURE                   Location/Qualifiers
source                    1..136
                          mol_type = other DNA
                          organism = Homo sapiens
SEQUENCE: 13
agcggtgacg tcaaggggcg cgctgtggca gcacctcccc gcgcgctagt taaaaagaag    60
aagaaaagag ggaacgaaac atgagaggct gtgtgagaag ctgcagccgc cggcagagga   120
gacctcagca tcatct                                                   136

SEQ ID NO: 14             moltype = DNA  length = 574
FEATURE                   Location/Qualifiers
source                    1..574
                          mol_type = other DNA
                          organism = Homo sapiens
SEQUENCE: 14
ctgggcgggg gcgcgcgaga agcggtgacg tcaaggggcg cgctgtggca gcacctcccc    60
```

```
gcgcgctagt taaaaagaag aagaaaagag ggaacgaaac atgagaggct gtgtgagaag   120
ctgcagccgc cggcagagga gacctcagca tcatctagag cccagcgctg gccctgcctc   180
cgcctgcccc gccgccgccg tcgccgtttc tgttcctgct actgtcccac ctaaacaact   240
cccgttacac ggacaagtga acatctgtgg ctgtcctctc cttttcttcc tcctcttcca   300
actccttctc ctcctcccac ttcccagccg cagcagaaag cccccaaccc aactgacact   360
ggcacaactg caaacggtgt catccgcaca actttatctc gctcctcggg ctcccctaag   420
gcattggacc catcgccgcg tctttttattt tttgcaaagt tgcatcgctg tacatatttt   480
tgtccccgcc acctccctct gtctctggag tgccctacag ccccgcaaac tcctcctgga   540
gctgcgccct agtgcccctg ctgggcagtg gcgt                                574

SEQ ID NO: 15           moltype = DNA   length = 170
FEATURE                 Location/Qualifiers
source                  1..170
                        mol_type = other DNA
                        organism = Homo sapiens
SEQUENCE: 15
agggaactcc ctgtgctggg cctacccagc tgaccccatc gctggaaaca atgggggtca    60
ggcaacactt ccccactctc tcccgccggg ctgtgctcac ttccttcctg ctggctgcct   120
gaggaagtgt ccctgccctg ggacagtctg gcctagcctt tgtttccccg                170

SEQ ID NO: 16           moltype = DNA   length = 470
FEATURE                 Location/Qualifiers
source                  1..470
                        mol_type = other DNA
                        organism = Homo sapiens
SEQUENCE: 16
gacaggcttc tgagtgtagg gagctggtct gccagtcttt cggaggtttg aacttgtcaa    60
ggctagggca ggatcaccat atccagcctg gacttgcagt tctgtggggt gcctccccat   120
accccccataa gatgccaaac atgaggccct gtcatcctcc atggtccccc tctactggct   180
gttcaaggcc cagggctctc ccatgccaga tagcatcctg tctcctacca ccactgtccc   240
agcctgaggg aactccctgt gctgggccta cccagctgac cccatcgctg gaaacaatgg   300
gggtcaggca acacttcccc actctctccc gccgggctgt gctcacttcc ttcctgctgg   360
ctgcctgagg aagtgtccct gccctgggac agtctggcct agcctttgtt tccccggggg   420
tccccacccca tggagctttc aaggcttctg gccctgtga agccagcaca                470

SEQ ID NO: 17           moltype = DNA   length = 602
FEATURE                 Location/Qualifiers
source                  1..602
                        mol_type = other DNA
                        organism = Homo sapiens
SEQUENCE: 17
cagtggaaaa aaacggactc agctactgga agtccccccg accctccccc caaggctagt    60
tcccttcttg ggcacctgct ctgggggacc atcagctgaa cgacccccaa gtattttgac   120
tcccaaaagc accaccacct gaccccatcc tctcacaccc tactggattt gaggatgggc   180
cccaatccta gggaaggagt gaagaggttc cctagtgttg gaagctgtgg gtgtggggga   240
gattggcacc tgatcctgag cccatagcct tcctgtcacc tggcgcagct ggcggggcca   300
gatcctactc gggaagggtg gggagggcag ccagccagca ggcattctg gagggaaaca   360
gggtcaaggc gatctcctcc cccacgcctg ttcctggccc tttcctctca gggggcagca   420
ggaagtgagg agaaagggct gggatgggag gcgggagcgg atgggaggga atggggttta   480
tcaagtcctc ggcgagctgc ccaacgggca gcagctggcg caagtagcct agctggagag   540
gctcacccca ggaaggaggg aggccaccga cctactgggc cgacggactc ccacacaggt   600
ga                                                                    602

SEQ ID NO: 18           moltype = DNA   length = 265
FEATURE                 Location/Qualifiers
source                  1..265
                        mol_type = other DNA
                        organism = Homo sapiens
SEQUENCE: 18
cttgcataga tggccagcgt tcatactttc tgcttgtttg tacaaagtca ttcttctaga    60
gtaattgttg taaaattgct aggcaaggtg gcaggtctga taagatttga tgacgtaatg   120
gctcttagtc gctaataaga ggctttgtgt gagtggcgtg tcacagccag cgaaggctca   180
gctctgtgat cttcgcctgc ctcacttggg ggaccagaag gcagcttgtc ttggaactgc   240
ctcattcaca gaagacccca ttgag                                          265

SEQ ID NO: 19           moltype = DNA   length = 545
FEATURE                 Location/Qualifiers
source                  1..545
                        mol_type = other DNA
                        organism = Homo sapiens
SEQUENCE: 19
tttacctagc atgatcttgg cagttcaaag aggaatgtgc cagaaaccaa gcaaagaaga    60
aaaagaaata aatggaaatg gaaagtgatc tgctcagagg ccacaaagtt gagggaggag   120
gtttccagag tgggatttgg cccaaatgtt gcctgaggaa gtacgtaaag gggtctcaac   180
tctggctaca caacagaaca gcaggactgt gtgtgcagct cacgaagtgg gtacacaggg   240
taatctgcaa gttctgggtg gatctagcac ctggattgtt aaaacttgca tagatggcca   300
gcgttcatac tttctgcttg tttgtacaaa gtcattcttc tagagtaatt gttgtaaaat   360
tgctaggcaa ggtggcaggt ctgataagat ttgatgacgt aatggctctt agtcgctaat   420
aagaggcttt tgtggagtgg cgtgtcacag ccagcgaagg ctcagctctg tgatcttcgc   480
```

```
ctgcctcact tggggggacca gaaggcagct tgtcttggaa ctgcctcatt cacagaagac   540
cccat                                                                 545

SEQ ID NO: 20           moltype = DNA  length = 554
FEATURE                 Location/Qualifiers
source                  1..554
                        mol_type = other DNA
                        organism = Homo sapiens
SEQUENCE: 20
atggcagctg gcaggtgcct tcacgtccag ggtttccaga gagaaagcat ctctcctccg   60
cagagaccct cccacgctct ccctccctca aattagtgca tctacataga ccgccctcct   120
tataaacagt ctctcagggg atcctagccc attccaaatc tacctgtgat tgcagaatcg   180
caaggaatgt gatttaccgc agatcgcggg gcgtcgtgtc ttttagggga cctgctcact   240
ttggccacta ggtggcgggc agtgcagccc ctgctcctgt cgaccctgag cgttcagcgt   300
ttccgccgcc tccgccccac tccgtagggg gagctgatga gatgaggttg aggtccagga   360
agacgtcaag ggcttggttt tgtaaacaac tccattcctc gctcgctgat aagtttctca   420
agtgatgcat attcacaacc ttgtcccatc caaggaccca agaattaaca cattacataa   480
tatggacagc cccctcctgt ccaacgggca tgattttggg gtctgatatt ctgtggatct   540
gtgcaatagt caac                                                       554

SEQ ID NO: 21           moltype = DNA  length = 450
FEATURE                 Location/Qualifiers
source                  1..450
                        mol_type = other DNA
                        organism = Homo sapiens
SEQUENCE: 21
agactttttt tgaaaaacgg aacatctgcc tatcgcaagg actactatta ttctgaaaat   60
caccttcttc attagaaagt aatatttatc attttattat agaactttga tcttacttct   120
tgtgacttca ttctgcgtag agcacactcc catccttgaa ttaaatgaca aagcatttta   180
tattaactga caatgactga tgccatgggc aaatcctatt tctgtaaata actgaatttt   240
cttctggact gcgcatgagg ggagaaagat gtctgcagtt tcggtttcct ggaaaatgaa   300
acctatctca tttgttgcct gtgtcaaggg gcagtgcttc agtcggggtg gagctgctta   360
aaaggcctgg gatcacaccc tttgggaaca catccaagct taagacggtg aggtcagctt   420
cacattctca ggaactctcc ttctttgggt                                      450

SEQ ID NO: 22           moltype = DNA  length = 570
FEATURE                 Location/Qualifiers
source                  1..570
                        mol_type = other DNA
                        organism = Homo sapiens
SEQUENCE: 22
gagactttt ttgaaaaacg gaacatctgc ctatcgcaag gactactatt attctgaaaa    60
tcaccttctt cattagaaag taatatttat cattttatta tagaactttg atcttacttc   120
ttgtgacttc attctgcgta gagcacactc ccatccttga attaaatgac aaagcatttt   180
atattaactg acaatgactg atgccatggg caaatcctat ttctgtaaat aactgaattt   240
tcttctggac tgcgcatgag gggagaaaga tgtctgcagt ttcggtttcc tggaaaatga   300
aacctatctc atttgttgcc tgtgtcaagg ggcagtgctt cagtcggggt ggagctgctt   360
aaaaggcctg ggatcacacc ctttgggaac acatccaagc ttaagacggt gaggtcagct   420
tcacattctc aggaactctc cttctttggg taagactggg agggtgggca ggagctaccc   480
ttcccgtggc cccggacctt gggtgggctg tgggctcagg gagcggaggg gaggccttaa   540
gcatccactc tctgcccggt gttttttgttc                                     570

SEQ ID NO: 23           moltype = DNA  length = 513
FEATURE                 Location/Qualifiers
source                  1..513
                        mol_type = other DNA
                        organism = Homo sapiens
SEQUENCE: 23
aggtggggat gaggggctaa gtatgaacca aggagctaga aatacagcac tggaagctgg   60
aagcaggggg cttggagact gggagctgga gtgcgtgtgg gcagggtgtg gcagcagccg   120
gcagaggcca tttcccttg gcagaacatt caccatgtga ccctgagcat gtctttgaac   180
tcctctgagc tcctgtttcc tctccagaga aaaggctggt aatgcccatt cagggttatg   240
gtcaggattg cataggggtga aacaatagag attgaacaca gtagacatga aagagatgcc   300
agggctcagc tcccttttggt ttagttgctt ccagtgtgct ctgtggcaac accacggagc   360
cctagagctg tctctttgag ccgctctgaa tgtgcctctt acataatctc ctgggcaaca   420
tctgctcccc taatgagatt tgctccccag caaagataag aaacttgcca accactcccc   480
tggtccagca tttggccaag gcagacactg agg                                  513

SEQ ID NO: 24           moltype = DNA  length = 217
FEATURE                 Location/Qualifiers
source                  1..217
                        mol_type = other DNA
                        organism = Homo sapiens
SEQUENCE: 24
acctcactca atgcatggaa gttgacacaa tggctcaaca ttagcgttgg gctgattcat   60
catttggctg ttgacaccag cctctggccc agccaggaca gaaaaagggc ccctgaggaa   120
cttctggctc tgttccctct atggggggagg ggcagtggac ttgtgataag acagggtgtt   180
agggtgaggt ggacttgggg aaacaggata tttctaa                              217
```

```
SEQ ID NO: 25            moltype = DNA   length = 97
FEATURE                  Location/Qualifiers
source                   1..97
                         mol_type = other DNA
                         organism = Homo sapiens
SEQUENCE: 25
ggggggaggg gagaccccag aacaatgtcc cccaccccac cccctcctc aataggcgga   60
agccactggc ttcctccctt tcctgcctcc tgcctcc                           97

SEQ ID NO: 26            moltype = DNA   length = 427
FEATURE                  Location/Qualifiers
source                   1..427
                         mol_type = other DNA
                         organism = Homo sapiens
SEQUENCE: 26
gtgtgtttgt gccgggggga ggggagaccc cagaacaatg tcccccaccc caccccctc   60
ctcaataggc ggaagccact ggcttcctcc ctttcctgcc tcctgcctcc tttgtgccag  120
caagactgag tactggagag agacagggga tgggaaaaat cagtccagct gtccccaggt  180
ctgcccttac cataaccttc cccccacctc aagtgactcc tcccaggcca cacccatccc  240
cagccttgtg ggggccagat tgggggggcct agaggctcaa aggcagaatg agtcctccca  300
cccccctaccc tgccaccccct cccacccaag ccacctcatt tcctcttcct ccccagcacc  360
gacccacact gaccaacaca ggctgagcag tcaggccac agcatctgac cccaggccca  420
gctcgtc                                                            427

SEQ ID NO: 27            moltype = DNA   length = 119
FEATURE                  Location/Qualifiers
source                   1..119
                         mol_type = other DNA
                         organism = Homo sapiens
SEQUENCE: 27
ctacaaagct ttatcagctt ggaggtactt ctaataccat ttcctttcat tgtttccttt   60
tggtaattaa aaggaggcca atccctgtt gtggcagctc acagctattg tggtgggaa    119

SEQ ID NO: 28            moltype = DNA   length = 385
FEATURE                  Location/Qualifiers
source                   1..385
                         mol_type = other DNA
                         organism = Homo sapiens
SEQUENCE: 28
ctgccaggag gtctccctcc aaactctaca aagctttatc agcttggagg tacttctaat   60
accatttcct ttcattgttt ccttttggta attaaaagga ggccaatccc ctgttgtggc  120
agctcacagc tattgtggtg ggaaagggag ggtggttggt ggatgtcaca gcttgggctt  180
tatctcccccc agcagtgggg actccacagc ccctgggcta cataacagca agacagtccg  240
gagctgtagc agacctgatt gagcctttgc agcagctgag agcatggcct agggtggggcg  300
gcaccattgt ccagcagctg agtttcccag ggaccttgga gatagccgca gccctcattt  360
gcaggggaag gtatggcctt tggaa                                        385

SEQ ID NO: 29            moltype = DNA   length = 517
FEATURE                  Location/Qualifiers
source                   1..517
                         mol_type = other DNA
                         organism = Homo sapiens
SEQUENCE: 29
gccattggct ggtccttcac tgacagcaga aacttggcca atggcaatca atcagggggc   60
ccgcgctgcc ttaaatacca gcagagcaaa cagcctcaga caaagctgcg ccgtgtatca  120
attaccgaga ggctgcgtgc tcctctgggc ggagggagcc ggagcgagcg gccagggctg  180
ctgccccagc tgataaagggc ccgcattgtt cggggacagc tggcagcccg ataagggcct  240
gctcgcccga dataatggca gtgggcaggc gcctcgcggc agtttagaat ttcttgggtc  300
tccaagaaag gttctattaa gcccactgac cccaattgaa tattaattag ctaattaacg  360
gatttattgt tccacgccat ttctggagag gccattttt ttcgagtgcc attatttttg  420
taaatgattt ttcgcattgt tcataattga atctttgcag ctgccagcat cttctgcatg  480
atttggcaaa aaaaaggaag cagaagcact tagggtt                           517

SEQ ID NO: 30            moltype = DNA   length = 511
FEATURE                  Location/Qualifiers
source                   1..511
                         mol_type = other DNA
                         organism = Homo sapiens
SEQUENCE: 30
cccctaataa acaggaaggc atccgcgcca ttagtatcca tccttttcag agcatctgag   60
acctgtctgg accatcaaag ccatccccag ccccaggag cctactggag gagacaccag  120
cctcgccaaa acaattctcc attgtgttct tcccccttaga aatcatgggt ttgtaaacag  180
gcccttacat ttcagcaggt cctgccctgg ctttgtgctg gtgtgttgtt ttttcttccc  240
tgaacaatgt cctttccagt agggccagcc gttcacacca ttgtctgaga cccttggact  300
acaggaaaca tcaccagatt cttatcagtt ggggggcagga gtggggggggt gaacagatga  360
gatcatgtcc acagagcaag tggctggtgt gccacgtcat tccccatgcc ttcatctgtg  420
agagcagagc ccgctcgccc tccatcaatc tgggcttcat gtgtccagag tccagtcccc  480
tctatttggt ggtagacacc tggactctgt t                                 511
```

-continued

```
SEQ ID NO: 31          moltype = DNA   length = 390
FEATURE                Location/Qualifiers
source                 1..390
                       mol_type = other DNA
                       organism = Homo sapiens
SEQUENCE: 31
tcctacagtt atgggtctgt ctttcctgct agatcagaag ctccagggac ctgtctgtct    60
tattaacctt tcttcccctc atgatgcctg gcccaggact ccacgttcag aggcagttta   120
atgtctacag aactgatgga tgctccatac cctgtattca taagcctgtg ttttgctgcc   180
aaacaccaga gggcactgtt agcatgtcga tgaagattat aaaccctcag acctggaagg   240
ctgggaaagg cttatgaaaa tcttgcttct gttttgggat tacataagac ttattgcgcc   300
tcaattgttc taaacacatc tgttcgagtt tattcatgag gcacgttcct gttggggtta   360
gagatgagtt tgaaagctcc ccgtcacagg                                    390

SEQ ID NO: 32          moltype = DNA   length = 573
FEATURE                Location/Qualifiers
source                 1..573
                       mol_type = other DNA
                       organism = Homo sapiens
SEQUENCE: 32
agggactgtt gggcagcccc agactggcac aggtggatcg ggtgcctagg caggggtgg     60
tgagttatgg cgcagctgtc ttggtggctg ggggagacag ggataagggt ggacttctta   120
gtgaccgctc tctgccccag gaggtagagt cctggggggct gggctggcct gagagacgcc   180
ccctcatcct ttccagggtg aggtacgagg gctccgcccc ctcctgatat caccaggcct   240
agggcagcat cctgatgggg gagggcaag tgacccgggc cctggactgc aggaacagcc    300
cctcctccac tggtggagtt cccacttcct gcggaaggaa ctatgttaga agttgtgtat   360
atggggtggg ggttgggtgt gggtggcggg gggcctgggt ggggtccact gagtcgcctc   420
ccctgtctcc ctgcacttcc tcctggagga aatggggaca acaggatgaa gtgagggcct   480
gctgagccca gggctgccac ctgggagtga agccgggggca ggctgcaggg tccgggccct   540
tctgtgtggg caggtggaag tggtggggat gca                                573

SEQ ID NO: 33          moltype = DNA   length = 441
FEATURE                Location/Qualifiers
source                 1..441
                       mol_type = other DNA
                       organism = Homo sapiens
SEQUENCE: 33
ggggagaggg tgtggggtgg ggtgggggaga gggtgtgggg tggggtgggg agaggggatg    60
ggatggcatg ggggggatgtg gcagtgagga ggctgggtcc ttggagctgc cgagtgcagg   120
ggcctggagg actccgggaa ggcgtcctag tgcatcaagc gtgggcttgg cctgcttggg   180
tctcccctcc tggcccccct agcaatgggc ggacttgggc ccgctctggg aggattccag   240
gaacggctcc tgcctggtta taaatagact tctccgaaag gcctggggct gtgccagctg   300
cagcaggtgc ctcccaggcc cggccagagg gccccaggca aggggggtgga gcccgggtgg   360
gggtgatgag gatgctgggg tccactttg tagcgccaga ggcgacgggc tctgtctggt    420
tgtagcatca cagagcttga t                                             441

SEQ ID NO: 34          moltype = DNA   length = 1303
FEATURE                Location/Qualifiers
source                 1..1303
                       mol_type = other DNA
                       organism = Homo sapiens
SEQUENCE: 34
gcttgcccag ctatataata aaacaagttt gggacttccc aaccattcac ccatggaaaa    60
acagaagcaa ctcttcaaag gacagattcc caggatctgc cctgggagat tccaaatcag   120
ttgatctggg gtgagcccag tcctctgtag tttttagaag ctcctcctat gtctctcctg   180
gtcagcagaa tcttggcccc tcccttcccc ccagcctctt ggttcttctg ggctctgatc   240
cagcctcagc gtcactgtct tccacgcccc tctttgattc tcgtttatgt caaaagcctt   300
gtgaggatga ggctgtgatt atccccattt tacagatgag gaaactgtgg ctccaggatg   360
acacaactgg ccagaggtca catcagaagc agagctgggt cacttgactc cacccaatat   420
ccctaaatgc aaacatcccc tacagaccga ggctggcacc ttagagctgg agtccatgcc   480
cgctctgacc aggagaagcc aacctggtcc tccagagcca agagcttctg tcccttttccc   540
atctcctgaa gcctccctgt cacctttaaa gtccattccc acaaagacat catgggatca   600
ccacagaaaa tcaagctctg gggctaggct gaccccagct agattttttgg ctctttttata   660
ccccagctgg gtggacaagc accttaaacc cgctgaccct cagcttcccg ggctataaaa   720
tgggggtgat gacacctgcc tgtagcattc caaggagggt taaatgtgat gctgcagcca   780
agggtccccca cagccaggct cttttgcaggt gctgggttca gagtcccaga ctgaggccg    840
ggagtagggg ttcaagtggg gtgccccagg cagggtccag tgccagccct ctgtggagac   900
agccatccgg ggccgaggca gccgcccacc gcagggcctg cctatctgca gccagcccag   960
ccctcacaaa ggaacaataa caggaaacca tcccaggggg aagtgggcca gggccagctg   1020
gaaaacctga aggggaggca gccaggcctc cctcgccagc ggggtgtggc tccctccaa    1080
agacggtcgg ctgacaggct ccacagagct ccactcacgc tcagccctgg acggacaggc   1140
agtccaacgg aacagaaaca tccctcagcc cacaggcacg gtgagtgggg gctcccacac   1200
tccccctccac cccaaacccg ccaccctgcg cccaagatgg gagggtcctc agcttcccca   1260
tctgtagaat gggcatcgtc ccactccat gacagagagg ctc                      1303

SEQ ID NO: 35          moltype = DNA   length = 455
FEATURE                Location/Qualifiers
source                 1..455
                       mol_type = other DNA
```

-continued

```
                         organism = Homo sapiens
SEQUENCE: 35
gagacataaa aggaaaatga agcgagcaac aattaaaaaa aattccccgc acacaacaat    60
acaatctatt taaactgtgg ctcatacttt tcataccaat ggtatgactt tttttctgga   120
gtcccctctt ctgattcttg aactccgggg ctggcagctt gcaaaggga agcggactcc   180
agcactgcac gggcaggttt agcaaaggtc tctaatgggt attttctttt cttagccct   240
gcccccgaat tgtcagacgg cgggcgtctg cctctgaagt tagcagtgat ttcctttcgg   300
gcctggcctt atctccggct gcacgttgcc tgttggtgac taataacaca ataacattgt   360
ctggggctgg aataaagtcg gagctgttta cccccactct aataggggtt caatataaaa   420
agccggcaga gagctgtcca agtcagacgc gcctc                             455

SEQ ID NO: 36            moltype = DNA   length = 888
FEATURE                  Location/Qualifiers
source                   1..888
                         mol_type = other DNA
                         organism = Homo sapiens
SEQUENCE: 36
cgccttgctg tgccactttg ggacttccct ccctagcctg agcttcagtt ttcctgcctg    60
ttaggcagcc ccatgtcaac tgcacttagt aggccgggtt tgatgcccga caagacgtga   120
agtggtggag gtgggcagga tcccagcgct accatcttct tgaaccagtg atctcaacac   180
atcggatttc tgtttcctca tctgcaaaat gggatcagtg agctcaggtg ggtcacaaat   240
tctacaggaa ctactttagc caagcccggc ccctgaaag ttccctcgg tgggctgtta   300
gggtgattgt tttcatctgt ggggctccct gatgcgtccc acccaccagc cttggagagg   360
gtgggatggg agggtggggt gcttggggag acaagcctag agcctgggcc ctcccacccc   420
actgcctccc cccatcccag ggcccccac ccagtgacaa agcccgtggc acttcctcta   480
cccggttggc aggcggcctg gcccagcccc ttctctaagg aagcgcattt cctgcctccc   540
tgggccggcc gggctggatg agccgggagc tccctgctgc cggtcatacc acagccttca   600
tctgcgccct ggggccagga ctgctgctgt cactgccatc cattggagcc cagcacccc   660
tccccgccca tccttcggac agcaactcca gcccagcccc gcgtccctgt gtccacttct   720
cctgacccct cggccgccac cccagaaggc tggagcaggg acgccgtcgc tccggccgcc   780
tgctcccctc gggtccccgt gcgagcccac gccggcccg gtgcccgccc gcagccctgc   840
cactggacac aggataaggc ccagcgcaca ggccccacg tggacacc                 888

SEQ ID NO: 37            moltype = DNA   length = 1037
FEATURE                  Location/Qualifiers
source                   1..1037
                         mol_type = other DNA
                         organism = Homo sapiens
SEQUENCE: 37
tttgcttcta ggaagcagaa gactgaggaa atgacttggg cgggtgcatc aatgcggcca    60
aaaaagacac ggacacgctc ccctgggacc tgagctggtt cgcagtcttc ccaaaggtgc   120
caagcaagcg tcagttcccc tcaggcgctc caggttcagt gccttgtgcc gagggtctcc   180
ggtgccttcc tagacttctc gggacagtct gaaggggtca ggagcggcgg gacagcgcgg   240
gaagagcagg caaggggaga cagccggact gcgcctcagt cctccgtgcc aagaacaccg   300
tcgcggaggc gcggccagct tcccttggat cggactttcc gcccctaggg ccaggcggcg   360
gagcttcagc cttgtcccTT ccccagtttc gggcggcccc cagagctgag taagccgggt   420
ggagggagtc tgcaaggatt tcctgagcgc gatgggcagg aggagggca agggcaagag   480
ggcgcggagc aaagaccctg aacctgccgg ggccgcgctc ccgggcccgc gtcgccagca   540
cctccccacg cgcgctcggc cccgggccac ccgccctcgt cggcccccgc ccctctccgt   600
agccgcaggg aagcgagcct gggaggaaga agagggtagg tggggaggcg gatgaggggt   660
ggggacccc ttgacgtcac cagaaggagg tgccggggta ggaagtgggc tggggaaagg   720
ttataaatcg cccccgccct cggctgctct tcatcgaggt ccgcgggagg ctcggagcgc   780
gccaggcgga cactcctctc ggctcctccc cggcagcggc ggcggctcgg agcgggctcc   840
ggggctcggg tgcagcggcc agcgggcgcc tggcggcgag gattacccgg ggaagtggtt   900
gtctcctggc tggagccgcg agacgggcgc tcagggcgcg gggccggcgg cggcgaacaa   960
gaggacggac tctggcggcc gggtcgttgg ccgcggggag cgcgggcacc gggcgagcag  1020
gccgcgtcgc gctcacc                                                 1037

SEQ ID NO: 38            moltype = DNA   length = 399
FEATURE                  Location/Qualifiers
source                   1..399
                         mol_type = other DNA
                         organism = Homo sapiens
SEQUENCE: 38
gtctcccagg catgactcca acaatgcatc ccatgggatt tggggttccc cagatctggg    60
gcttgtaggc ctgactctcc cctgtgcaca cgtctcatac acgcatgcgt gcacccattg   120
cctgccccgc cccttgcaca gggagtcagc agggaggact gggttatgcc ctgcttatca   180
gcagcttccc agcttcctct gcctggattc ttagaggcct ggggtcctag aacgagctgg   240
tgcacgtgca ttcccaaaga tctctcagat aatgagagga aatgcagtca tcagtttgca   300
gaaggctagg gattctgggc catagctcag acctgcgccc accatctccc tccaggcagc   360
ccttggctgg tccctgcgag cccgtggaga ctgccagtc                        399

SEQ ID NO: 39            moltype =   length =
SEQUENCE: 39
000

SEQ ID NO: 40            moltype = DNA   length = 8834
FEATURE                  Location/Qualifiers
misc_feature             1..8834
```

```
                      note = vector
source                1..8834
                      mol_type = other DNA
                      organism = synthetic construct
SEQUENCE: 40
tggaagggct aattcactcc caaagaagac aagatatcct tgatctgtgg atctaccaca   60
cacaaggcta cttccctgat tagcagaact acacaccagg gccagggtc agatatccac    120
tgacctttgg atggtgctac aagctagtac cagttgagcc agataaggta gaagaggcca   180
ataaaggaga gaacaccagc ttgttacacc ctgtgagcct gcatgggatg gatgacccag   240
agagagaagt gttagagtgg aggtttgaca gccgcctagc atttcatcac gtggcccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agacccttt agtcagtgtg gaaaatctct agcagtggcg cccgaacagg gacttgaaag   660
cgaaaggaa accagaggag ctctctcgac gcaggactcg gcttgctgaa gcgcgcacgg   720
caagagggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaatataa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttga   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaaa cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacg tatcgccttt aaaagaaaag   2040
gggggattgg ggggtacagt gcaggggaaa gaatagtaga cataatagca acagacatac   2100
aaactaaaga actacaaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaaactgccca cttggcagta catcaagtgt atcatatgcc aagtacgccc cctattgacg   2400
tcaatgacgg taaatggccc gcctggcatt atgcccagta catgacctta cgggactttc   2460
ctacttggca gtacatctac gtattagtca tcgctattac catggtgatg cggttttggc   2520
agtacaccaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tagctagagg atctaccggt cgccaccatg gtgagcaagg   2820
gcgccgagct gttcaccggc atcgtgccca tcctgatcga gctgaatggc gatgtgaatg   2880
gccacaagtt cagcgtgagc ggcgagggcg agggcgatgc cacctacggc aagctgaccc   2940
tgaagttcat ctgcaccacc ggcaagctgc ctgtgccctg gcccaccctg gtgaccaccc   3000
tgagctacgg cgtgcagtgc ttctcacgct accccgatca catgaagcag cacgacttct   3060
tcaagagcgc catgcctgag ggctacatcc aggagcgcac catcttcttc gaggatgacg   3120
gcaactacaa gtcgcgcgcc gaggtgaagt tcgagggcga taccctggtg aatcgcatcg   3180
agctgaccgg caccgatttc aaggaggatg gcaacatcct gggcaataag atggagtaca   3240
actacaacgc ccacaatgtg tacatcatga ccgacaaggc caagaatggc atcaaggtga   3300
acttcaagat ccgccacaac atcgaggatg gcagcgtgca gctggccgac cactaccagc   3360
agaatacccc catcggcgat ggccctgtgc tgctgcccga taaccactac ctgtccaccc   3420
agagcgccct gtccaaggac cccaacgaga gcgcgatca catgatctac ttcggcttcg   3480
tgaccgccgc cgccatcacc cacggcatgg atgagctgta caagtccgga ctcagatctc   3540
gagctcaagc ttcgaattct gcagtcgacg gtaccgcggg cccgggatcc accggatcta   3600
gataactgat cataattcta ccgggtaggg gaggcgcttt tcccaaggca gtctggagca   3660
tgcgctttag cagccccgct gggcacttgg cgctacacaa gtggcctctg cctcgcaca   3720
cattccacat ccaccggtag cgccaaccg gctccgttcc ttggtggccc cttcgcgcca   3780
ccttctactc ctcccctagt caggaagttc ccccccgcct cagcctcgc gtcgtgcagg   3840
acgtgacaaa tggaagtagc acgtctcact agtctcgtgc agatggacag caccgctgag   3900
caatggaagc gggtaggcct ttggggcagc ggccaatagc agctttgctc cttcgctttc   3960
tgggctcaga ggctgggaag gggtgggtcc ggggggcgggc tcaggggcgg ctcaggggc   4020
ggggcgggc cccgaaggtc ctccggaggc ccggcattct gcacgcttca aaagcgcacg   4080
tctgccgcgc tgttctcctc ttcctcatct ccgggcctt gaccctgcag cccaagctta   4140
ccatgaccga gtacaagccc acggtgcgcc tcgccaccg cgacgacgtc cccagggccg   4200
tacgcaccct cgccgccgcg ttcgccgact accccgccac gcgccacacc gtcgatccgg   4260
accgccacat cgagcgggtc accgagctgc aagaactctt cctcacgcgc gtcgggctcg   4320
acatcggcaa ggtgtgggtc gcggacgacg gcgccgcggt ggcggtctgg accacgccgg   4380
agagcgtcga agcggggggcg gtgttcgccg agatcggccc gcgcatggcc gagttgagcg   4440
```

-continued

```
gttcccggct ggccgcgcag caacagatgg aaggcctcct ggcgccgcac cggcccaagg  4500
agcccgcgtg gttcctggcc accgtcggcg tctcgcccga ccaccagggc aagggtctgg  4560
gcagcgccgt cgtgctcccc ggagtggagg cggccgagcg cgccggggtg cccgccttcc  4620
tggagacctc cgcgccccgc aacctcccct tctacgagcg gctcggcttc accgtcaccg  4680
ccgacgtcga ggtgcccgaa ggaccgcgca cctggtgcat gacccgcaag ccgggtgcct  4740
gaccgcgtct ggaacaatca acctctggat tacaaaattt gtgaaagatt gactggtatt  4800
cttaactatg ttgctccttt tacgctatgt ggatacgctg ctttaatgcc tttgtatcat  4860
gctattgctt cccgtatggc tttcattttc tcctccttgt ataaatcctg gttgctgtct  4920
ctttatgagg agttgtggcc cgttgtcagg caacgtggcg tggtgtgcac tgtgtttgct  4980
gacgcaaccc ccactggttg gggcattgcc accacctgtc agctcctttc cgggactttc  5040
gctttccccc tccctattgc cacggcggaa ctcatcgccg cctgccttgc ccgctgctgg  5100
acaggggctc ggctgttggg cactgacaat tccgtggtgt tgtcggggaa gctgacgtcc  5160
tttccatggc tgctcgcctg tgttgccacc tggattctgc gcgggacgtc cttctgctac  5220
gtcccttcgg ccctcaatcc agcggacctt ccttcccgcg cctgcctgcc ggctctgcgg  5280
cctcttccgc gtcttcgcct cgccctcag acgagtcgga tctccctttg ggccgcctcc  5340
ccgcctggaa ttaattctgc agtcgagacc tagaaaaaca tggagcaatc acaagtagca  5400
atacagcagc taccaatgct gattgtgcct ggctagaagc acaagaggag gaggaggtgg  5460
gttttttccag tcacacctca ggtacctttta agaccaatga cttacaaggc agctgtagat  5520
cttagccact ttttaaaaga aaagagggga ctggaagggc taattcactc ccaacgaaga  5580
caagatatcc ttgatctgtg gatctaccac acacaaggct acttccctga ttagcagaac  5640
tacacaccag ggccaggggt cagatatcca ctgacctttg gatggtgcta caagctagta  5700
ccagttgagc cagataaggt agaagaggcc aataaaggag agaacaccag cttgttacac  5760
cctgtgagcc tgcatgggat ggatgacccg gagagagaag tgttagagtg gaggtttgac  5820
agccgcctag catttcatca cgtggcccga gagctgcatc cggagtactt caagaactgc  5880
tgatatcgag cttgctacaa gggactttcc gctggggact ttccaggag gcgtggcctg  5940
ggcgggactg gggagtggcg agccctcaga tcctgcatat aagcagctgc tttttgcctg  6000
tactgggtct ctctggttag accagatctg agcctgggag ctctctggct aactagggaa  6060
cccactgctt aagcctcaat aaagcttgcc ttgagtgctt caagtagtgt gtgcccgtct  6120
gttgtgtgac tctggtaact agagatccct cagacccttt tagtcagtgt ggaaaatctc  6180
tagcagtagt agttcatgtc atcttattat tcagtattta taacttgcaa agaaatgaat  6240
atcagagagt gagaggcctt gacattgcta gcgtttttacc gtcgacctct agctagagct  6300
tggcgtaatc atggtcatag ctgtttcctg tgtgaaattg ttatccgctc acaattccac  6360
acaacatacg agccggaagc ataaagtgta aagcctgggg tgcctaatga gtgagctaac  6420
tcacattaat tgcgttgcgc tcactgcccg ctttccagtc gggaaacctg tcgtgccagc  6480
tgcattaatg aatcggccaa cgcgcgggga gaggcggttt gcgtattggg cgctcttccg  6540
cttcctcgct cactgactcg ctgcgctcgg tcgttcggct gcggcgagcg gtatcagctc  6600
actcaaaggc ggtaatacgg ttatccacag aatcagggga taacgcagga agaacatgt  6660
gagcaaaagg ccagcaaaag gccaggaacc gtaaaaaggc cgcgttgctg gcgtttttcc  6720
ataggctccg cccccctgac gagcatcaca aaaatcgacg ctcaagtcag aggtggcgaa  6780
acccgacagg actataaaga taccaggcgt ttccccctgg aagctccctc gtgcgctctc  6840
ctgttccgac cctgccgctt accggatacc tgtccgcctt tctcccttcg ggaagcgtgg  6900
cgctttctca tagctcacgc tgtaggtatc tcagttcggt gtaggtcgtt cgctccaagc  6960
tgggctgtgt gcacgaaccc cccgttcagc ccgaccgctg cgccttatcc ggtaactatc  7020
gtcttgagtc caacccggta agacacgact tatcgccact ggcagcagcc actggtaaca  7080
ggattagcag agcgaggtat gtaggcggtg ctacagagtt cttgaagtgg tggcctaact  7140
acggctacac tagaagaaca gtatttggta tctgcgctct gctgaagcca gttaccttcg  7200
gaaaaagagt tggtagctct tgatccggca aacaaaccac cgctggtagc ggttttttcg  7260
tttgcaagca gcagattacg cgcagaaaaa aaggatctca agaagatcct ttgatctttt  7320
ctacggggtc tgacgctcag tggaacgaaa actcacgtta agggatttg gtcatgagat  7380
tatcaaaaag gatcttcacc tagatccttt taaattaaaa atgaagtttt aaatcaatct  7440
aaagtatata tgagtaaact tggtctgaca gttaccaatg cttaatcagt gaggcaccta  7500
tctcagcgat ctgtctattt cgttcatcca tagttgcctg actccccgtc gtgtagataa  7560
ctacgatacg ggagggctta ccatctggcc ccagtgctgc aatgataccg cgagacccac  7620
gctcaccggc tccagattta tcagcaataa accagccagc cggaagggcc gagcgcagaa  7680
gtggtcctgc aactttatcc gcctccatcc agtctattaa ttgttgccgg gaagctagag  7740
taagtagttc gccagttaat agtttgcgca acgttgttgc cattgctaca ggcatcgtgg  7800
tgtcacgctc gtcgtttggt atggcttcat tcagctccgg ttcccaacga tcaaggcgag  7860
ttacatgatc ccccatgttg tgcaaaaaag cggttagctc cttcggtcct ccgatcgttg  7920
tcagaagtaa gttggccgca gtgttatcac tcatggttat ggcagcactg cataattctc  7980
ttactgtcat gccatccgta agatgctttt ctgtgactgg tgagtactca accaagtcat  8040
tctgagaata gtgtatgcgg cgaccgagtt gctcttgccc ggcgtcaata cgggataata  8100
ccgcgccaca tagcagaact ttaaaagtgc tcatcattgg aaaacgttct cggggcgaa  8160
aactctcaag gatcttaccg ctgttgagat ccagttcgat gtaacccact cgtgcaccca  8220
actgatcttc agcatctttt actttcacca gcgtttctgg gtgagcaaaa acaggaaggc  8280
aaaatgccgc aaaaaaggga ataagggcga cacggaaatg ttgaatactc atactcttcc  8340
tttttcaata ttattgaagc atttatcagg gttattgtct catgagcgga tacatatttg  8400
aatgtattta gaaaaataaa caaataggg ttccgcgcac atttccccga aaagtgccac  8460
ctgacgtcga cggatcggga gatcaacttg tttattgcag cttataatgg ttacaaataa  8520
agcaatagca tcacaaattt cacaaataaa gcatttttt cactgcattc tagttgtggt  8580
ttgtccaaac tcatcaatgt atcttatcat gtctggatca actggataac tcaagctaac  8640
caaaatcatc ccaaacttcc caccccatac cctattacca ctgccaatta cctagtggtt  8700
tcatttactc taaacctgtg attcctctga attatttta ttttaaagaa attgtatttg  8760
ttaaatatgt actacaaact tagtagtttt taaagaaatt gtatttgtta aatatgtact  8820
acaaacttag tagt                                                    8834
```

```
SEQ ID NO: 41        moltype = DNA  length = 11329
FEATURE              Location/Qualifiers
misc_feature         1..11329
                     note = vector
```

-continued

```
source                    1..11329
                          mol_type = other DNA
                          organism = synthetic construct
SEQUENCE: 41
tggaagggct aattcactcc caaagaagac aagatatcct tgatctgtgg atctaccaca   60
cacaaggcta cttccctgat tagcagaact acacaccagg gccagggggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agacccttttt agtcagtgtg gaaaatctct agcagtggcg cccgaacagg gacttgaaag  660
cgaaagggaa accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca ggggggaaaga aaaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaacccccg aggggacccg acaggcccga aggaatagaa gaagaaggtg gagagagaga 1980
cagagacaga tccattcgat tagtgaacgg atctcgacgg tatcgccttt aaaagaaaag 2040
gggggattgg ggggtacagt gcaggggaaa gaatagtaga cataatagca acagacatac 2100
aaactaaaga attacaaaaa caaattacaa aaattcaaaa ttttcgggtt tattacaggg 2160
acagcagaga tccagtttat cgataagctt gggagttccg cgttacataa cttacggtaa 2220
atggcccgcc tggctgaccg cccaacgacc cccgcccatt gacgtcaata atgacgtatg 2280
ttcccatagt aacgccaata gggactttcc attgacgtca atgggtggag tatttacggt 2340
aaactgccca cttggcagta catcaagtgt atcatatgcc aagtacgccc cctattgacg 2400
tcaatgacgg taaatggccc gcctggcatt atgcccagta catgacctta tgggactttc 2460
ctacttggca gtacatctac gtattagtca tcgctattac catggtgatg cggttttggc 2520
agtacatcaa tgggcgtgga tagcggtttg actcacgggg atttccaagt ctccaccccca 2580
ttgacgtcaa tgggagtttg ttttggcacc aaaatcaacg ggactttcca aaatgtcgta 2640
acaactccgc cccattgacg caaatgggcg gtaggcgtgt acggtgggag gtctatataa 2700
gcagagctcg tttagtgaac cgtcagatcg cctggagacg ccatccacgc tgtttttgacc 2760
tccatagaag acaccgactc tactagagga tcgctagcgc taccggactc agatctcgag 2820
ctcaagcttc gaattctgca gtcgacggta ccgcgggccc ggatgcagat cgagctgtcc 2880
acctgctttt ttctgtgcct gctgcgggttc tgcttcagcg ccacccggcg gtactacctg 2940
ggcgccgtgg agctgtcctg ggactacatg cagagcgacc tgggcgagct gcccgtggac 3000
gcccggttcc cccccagagt gcccaagagc ttccccttca acaccagcgt ggtgtacaag 3060
aaaaccctgt tcgtggagtt caccgaccac ctgttcaata tcgccaagcc caggccccccc 3120
tggatggggcc tgctgggccc caccatccag gccgaggtgt acgacaccgt ggtgatcacc 3180
ctgaagaaca tggccagcca ccccgtgagc ctgcacgccg tgggcgtgag ctactggaag 3240
gccagcgagg gcgccgagta cgacgaccag accagccagc gggagaaaga agatgacaag 3300
gtgttccctg gcggcagcca cacctacgtg tggcaggtgc tgaaagaaaa cggcccccatg 3360
gcctccgacc ccctgtgcct gacctacagc tacctgagcc acgtggacct ggtgaaggac 3420
ctgaacagcg gcctgatcgg cgctctgctc gtctgccggg agggcagcct ggccaaagag 3480
aaaacccaga ccctgcacaa gttcatcctg ctgttcgccg tgttcgacga gggcaagagc 3540
tggcacagcg agacaaagaa cagcctgatg caggaccggg acgccgcctc tgccagagcc 3600
tggcccaaga tgcacaccgt gaacggctac gtgaacagaa gcctgccggg cctgattggc 3660
tgccaccgga gagcgtgta ctggcacgtg atcggcatgg gcaccacacc cgaggtgcac 3720
agcatctttc tggaagggca cacctttctg gtccggaacc accggcaggc cagcctggaa 3780
atcagccccta tcaccttcct gaccgcccag acactgctga tggacctggg ccagttcctg 3840
ctgtttttgcc acatcagctc tcaccagcac gacggcatgg aagcctacgt gaaggtggac 3900
tcttgccccg aggaacccca gctgcgggatg aagaacaacg aggaagccga ggactacgac 3960
gacgacctga ccgacagcga gatggacgtg gtgcggttcg acgacgacaa cagccccagc 4020
ttcatccaga tcagaagcgt ggccaagaag caccccaaga cctgggtgca ctatatcgcc 4080
gccgaggaag aggactggga ctacgcccccc ctggtgctgg cccccgacga cagaagctac 4140
aagagccagt acctgaacaa tggcccccag cggatcgacg gaagtacaa gaagtacgag 4200
ttcatggccc acaccgacga cattcagaag acccgggagg ccatccagca cgagagcggc 4260
atcctgggcc ccctgctgta cggcgaagtg ggcgacacac tgctgatcat cttcaagaac 4320
caggctagcg gccctacaa catctacccc cacggcatca ccgacgtgcg gcccctgtac 4380
agcaggcggc tgcccaaggg cgtgaagcac ctgaaggact ccccatcct gcccggcgag 4440
atcttcaagt acaagtggac cgtgaccgtg gaggacggcg ccaccaagag cgaccccaga 4500
```

-continued

```
tgcctgaccc ggtactacag cagcttcgtg aacatggaac gggacctggc ctccgggctg    4560
atcggacctc tgctgatctg ctacaaagaa agcgtggacc agcggggcaa ccagatcatg    4620
agcgacaagc ggaacgtgat cctgttcagc gtgttcgatg agaaccggtc ctggtatctg    4680
accgagaaca tccagcggtt tctgcccaac cctgccggcg tgcagctgga agatcccgag    4740
ttccaggcca gcaacatcat gcactccatc aatggctacg tgttcgactc tctgcagctc    4800
tccgtgtgtc tgcacgaggt ggcctactgg tacatcctga gcatcggcgc ccagaccgac    4860
ttcctgagcg tgttcttcag cggctacacc ttcaagcaca agatggtgta cgaggacacc    4920
ctgaccctgt tccctttcag cggcgagaca gtgttcatga gcatggaaaa ccccggcctg    4980
tggattctgg gctgccacaa cagcgacttc cggaaccggg gcatgaccgc cctgctgaag    5040
gtgtccagct gcgacaagaa caccggcgac tactacgagg acagctacga ggatatcagc    5100
gcctacctgc tgtccaagaa caacgccatc gaaccccgga gcttcagcca gaaccccccc    5160
gtgctgacgc gtcaccagcg ggagatcacc cggacaaccc tgcagtccga ccaggaagag    5220
atcgattacg acgacaccat cagcgtggag atgaagaaag aggatttcga tatctacgac    5280
gaggacgaga accagagccc cagaagcttc cagaagaaa cccggcacta cttcattgcc    5340
gccgtggaga ggctgtggga ctacggcatg agttctagcc cccacgtgct gcggaaccgg    5400
gcccagagcg gcagcgtgcc ccagttcaag aaagtggtgt tccaggaatt cacagacggc    5460
agcttcaccc agcctctgta tagaggcgag ctgaacgagc acctggggct gctggggccc    5520
tacatcaggg ccgaagtgga ggacaacatc atggtgacct tccggaatca ggccagcaga    5580
ccctactcct tctacagcag cctgatcagc tacgaagagg accagcggca gggcgccgaa    5640
ccccggaaga acttcgtgaa gcccaacgaa accaagaccc acttctggaa agtgcagcac    5700
cacatggccc ccaccaagga cgagttcgac tgcaaggcct gggcctactt cagcgacgtg    5760
gatctggaaa aggacgtgca ctctggactg attggcccac tcctggtctg ccacactaac    5820
accctcaacc ccgccacgg ccgccaggtg accgtgcagg aattcgccct gttcttcacc    5880
atcttcgacg agacaaagtc ctggtacttc accgagaata tggaacggaa ctgcagagcc    5940
ccctgcaaca tccagatgga agatcctacc ttcaaagaga actaccggtt ccacgccatc    6000
aacggctaca tcatggacac cctgcctggc ctggtgatgg cccaggacca gagaatccgg    6060
tggtatctgc tgtccatggg cagcaacgag aatatccaca gcatccactt cagcggccac    6120
gtgttcaccg tgcggaagaa agaagagtac aagatggccc tgtacaacct gtaccccggc    6180
gtgttcgaga cagtggagat gctgcccagc aaggccggca tctggcgggt ggagtgtctg    6240
atcggcgagc acctgcacgc tggcatgagc accctgtttc tggtgtacag caacaagtgc    6300
cagacccccac tgggcatggc ctctggccac atccggggact tccagatcac cgcctccggc    6360
cagtacggcc agtgggcccc caagctggcc agactgcact acagcggcag catcaacgcc    6420
tggtccacca aagagcccct tcagctggatc aaggtggacc tgctggcccc tatgatcatc    6480
cacggcatta gacccaggg cgccaggcag aagttcagca gcctgtacat cagccagttc    6540
atcatcatgt acagcctgga cggcaagaag tggcagacct accggggcaa cagcaccggc    6600
accctgatgg tgttcttcgg caatgtggac agcagcggca tcaagcacaa catcttcaac    6660
ccccccatca ttgcccggta catccggctg cacccccacc actacagcat tagatccaca    6720
ctgagaatgg aactgatggg ctgcgacctg aactcctgca gcatgcctct gggcatggaa    6780
agcaaggcca tcagcgacgc ccagatcaca gccagcagct acttcaccaa catgttcgcc    6840
acctggtccc cctccaaggc caggctgcac ctgcagggcc ggtccaacgc ctggcggcct    6900
caggtcaaca accccaaaga atggctgcag gtggacttttc agaaaaccat gaaggtgacc    6960
ggcgtgacca cccagggcgt gaaaagcctg ctgaccagca tgtacgtgaa agagtttctg    7020
atcagcagct ctcaggatgg ccaccagtgg acctgttct ttcagaacgg caaggtgaaa    7080
gtgttccagg gcaaccagga ctccttcacc cccgtggtga actccctgga cccccccctg    7140
ctgacccgct acctgagaat ccacccccag tcttgggtgc accagatcgc cctcaggatg    7200
gaagtcctgg gatgtgaggc ccaggatctg tactgatgac gtctggaaca atcaacctct    7260
ggattacaaa atttgtgaaa gattgactgg tattcttaac tatgttgctc cttttacgct    7320
atgtggatac gctgctttaa tgcctttgta tcatgctatt gcttcccgta tggctttcat    7380
tttctcctcc ttgtataaat cctggttgct gtctctttat gaggagttgt ggcccgttgt    7440
caggcaacgt ggcgtggtgt gcactgtgtt tgctgacgca acccccactg gttggggcat    7500
tgccaccacc tgtcagctcc tttccgggac tttcgctttc ccctccccta ttgccacggc    7560
ggaactcatc gccgcctgcc ttgcccgctg ctggacaggg gctcggctgt tgggcactga    7620
caattccgtg gtgttgtcgg ggaagctgac gtcctttcca tggctgctcg cctgtgttgc    7680
cacctggatt ctgcgcggga cgtccttctg ctacgtccct tcggccctca atccagcgga    7740
ccttccttcc cgcggcctgc tgccggctct gcggcctctt ccttcgccc tcggcctctc    7800
tcagacgagt cggatctccc tttgggccgc ctccccgcct ggaattaatt ctgcagtcga    7860
gacctagaaa aacatggagc aatcacaagt agcaatacag cagctaccaa tgctgattgt    7920
gcctggctag aagcacaaga ggaggaggag gtgggttttc cagtcacacc tcaggtacct    7980
ttaagaccaa tgacttacaa ggcagctgta gatcttagcc acttttttaa agaaaagagg    8040
ggactggaag ggctaattca ctcccaacga agacaagata tccttgatct gtggatctac    8100
cacacacaag gctacttccc tgattagcag aactacacac cagggccagg ggtcagatat    8160
ccactgacct ttggatggtg ctacaagcta gtaccagttg agcagataa ggtagaagag    8220
gccaataaag gagagaacac cagcttgtta caccctgtga gcctgcatgg gatggatgac    8280
ccggagagag aagtgttaga gtggaggttt gacagccgc tagcatttca tcacgtggcc    8340
cgagagctgc atccggagta cttcaagaac tgctgatatc gagcttgcta caagggactt    8400
tccgctgggg actttccagg gaggcgtggc ctgggcggga ctggggagtg cgagccctc    8460
agatcctgca tataagcagc tgcttttttgc ctgtactggg tctctctggt tagaccagat    8520
ctgagcctgg gagctctctg gctaactagg gaacccactg cttaagcctc aataaagctt    8580
gccttgagtg cttcaagtag tgtgtgcccg tctgttgtgt gactctggta actagagatc    8640
cctcagaccc ttttagtcag tgtggaaaat ctctagcagt agtagttcat gtcatcttat    8700
tattcagtat ttataacttg caaagaaatg aatatcagag agtgagaggc cttgacattg    8760
ctagcgtttt accgtcgacc tctagctaga gcttggcgta atcatggtca tagctgtttc    8820
ctgtgtgaaa ttgttatccg ctcacaattc cacacaacat acgagccgga agcataaagt    8880
gtaaagcctg gggtgcctaa tgagtgagct aactcacatt aattgcgttg cgctcactgc    8940
ccgctttcca gtcgggaaac ctgtcgtgcc agctgcatta atgaatcggc caacgcgcgg    9000
ggagaggcgg tttgcgtatt gggcgctctt ccgcttcctc gctcactgac tcgctgcgct    9060
cggtcgttcg gctgcggcga gcggtatcag ctcactcaaa ggcggtaata cggttatcca    9120
cagaatcagg ggataacgca ggaaagaaca tgtgagcaaa aggccagcaa aaggccagga    9180
accgtaaaaa ggccgcgttg ctggcgtttt tccataggct ccgcccccct gacgagcatc    9240
```

-continued

```
acaaaaatcg acgctcaagt cagaggtggc gaaacccgac aggactataa agataccagg   9300
cgtttccccc tggaagctcc ctcgtgcgct ctcctgttcc gaccctgccg cttaccggat   9360
acctgtccgc ctttctccct tcgggaagcg tggcgctttc tcatagctca cgctgtaggt   9420
atctcagttc ggtgtaggtc gttcgctcca agctgggctg tgtgcacgaa ccccccgttc   9480
agcccgaccg ctgcgcctta tccggtaact atcgtcttga gtccaacccg gtaagacacg   9540
acttatcgcc actggcagca gccactggta acaggattag cagagcgagg tatgtaggcg   9600
gtgctacaga gttcttgaag tggtggccta actacggcta cactagaaga acagtatttg   9660
gtatctgcgc tctgctgaag ccagttacct tcggaaaaag agttggtagc tcttgatccg   9720
gcaaacaaac caccgctggt agcggtggtt tttttgtttg caagcagcag attacgcgca   9780
gaaaaaaagg atctcaagaa gatcctttga tcttttctac ggggtctgac gctcagtgga   9840
acgaaaactc acgttaaggg attttggtca tgagattatc aaaaaggatc ttcacctaga   9900
tccttttaaa ttaaaaatga agttttaaat caatctaaag tatatatgag taaacttggt   9960
ctgacagtta ccaatgctta atcagtgagg cacctatctc agcgatctgt ctatttcgtt   10020
catccatagt tgcctgactc cccgtcgtgt agataactac gatacgggag ggcttaccat   10080
ctggccccag tgctgcaatg ataccgcgag acccacgctc accggctcca gatttatcag   10140
caataaacca gccagccgga agggccgagc gcagaagtgg tcctgcaact ttatccgcct   10200
ccatccagtc tattaattgt tgccgggaag ctagagtaag tagttcgcca gttaatagtt   10260
tgcgcaacgt tgttgccatt gctacaggca tcgtggtgtc acgctcgtcg tttggtatgg   10320
cttcattcag ctccggttcc caacgatcaa ggcgagttac atgatccccc atgttgtgca   10380
aaaaagcggt tagctccttc ggtcctccga tcgttgtcag aagtaagttg gccgcagtgt   10440
tatcactcat ggttatggca gcactgcata attctcttac tgtcatgcca tccgtaagat   10500
gcttttctgt gactggtgag tactcaacca agtcattctg agaatagtgt atgcggcgac   10560
cgagttgctc ttgcccggcg tcaatacggg ataataccgc gccacatagc agaactttaa   10620
aagtgctcat cattggaaaa cgttcttcgg ggcgaaaact ctcaaggatc ttaccgctgt   10680
tgagatccag ttcgatgtaa cccactcgtg cacccaactg atcttcagca tcttttactt   10740
tcaccagcgt ttctgggtga gcaaaaacag gaaggcaaaa tgccgcaaaa aagggaataa   10800
gggcgacacg aaaatgttga atactcatac tcttcctttt tcaatattat tgaagcattt   10860
atcaggggtta ttgtctcatg agcggataca tatttgaatg tatttagaaa aataaacaaa   10920
tagggggttcc gcgcacattt ccccgaaaag tgccacctga cgtcgacgga tcgggagatc   10980
aacttgttta ttgcagctta taatggttac aaataaagca atagcatcac aaatttcaca   11040
aataaagcat ttttttcact gcattctagt tgtggtttgt ccaaactcat caatgtatct   11100
tatcatgtct ggatcaactg gataactcaa gctaaccaaa atcatcccaa acttcccacc   11160
ccatacccta ttaccactgc caattacctg tggtttcatt tactctaaac ctgtgattcc   11220
tctgaattat tttcatttta aagaaattgt atttgttaaa tatgtactac aaacttagta   11280
gttttttaaag aaattgtatt tgttaaatat gtactacaaa cttagtagt            11329
```

```
SEQ ID NO: 42          moltype = DNA   length = 11220
FEATURE                Location/Qualifiers
misc_feature           1..11220
                       note = vector
source                 1..11220
                       mol_type = other DNA
                       organism = synthetic construct
SEQUENCE: 42
tggaagggct aattcactcc caaagaagac aagatatcct tgatctgtgg atctaccaca   60
cacaaggcta cttccctgat tagcagaact acacaccagg gccaggggtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgaccgg   240
agagagaagt gttagagtgg aggtttgaca gccgcctagc atttcatcac gtggcccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agacccttttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaatataa attaaaacat atagtatggg   900
caagcagggg gctagaacga ttcgcagtta atcctggcct gttagaaaca tcagaaggct   960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac caccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttttgctgt   1860
acttttctata gtgaatagag ttaggcaggg atattcacca ttatcgtttc agacccacct   1920
cccaacccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aagggggggat tggggggtac agtgcagggg aaagaatagt   2100
```

-continued

```
agacataata gcaacagaca tacaaactaa agaattacaa aaacaaatta caaaaattca    2160
aaattttcgg gtttattaca gggacagcag agatccagtt tggatcgata agcttgatat    2220
cgaattcctg cgcggccgct tcgaacgcgc gcgatgcatc atatgcgtac gcggtctaga    2280
actagtgaga cataaaagga aaatgaagcg agcaacaatt aaaaaaaatt ccccgcacac    2340
aacaatacaa tctatttaaa ctgtggctca tacttttcat accaatggta tgactttttt    2400
tctggagtcc cctcttctga ttcttgaact ccggggctgg cagcttgcaa aggggaagcg    2460
gactccagca ctgcacgggc aggtttagca aaggtctcta atgggtattt tcttttttctt    2520
agccctgccc ccgaattgtc agacggcggg cgtctgcctc tgaagttagc agtgatttcc    2580
tttcgggcct ggccttatct ccggctgcac gttgcctgtt ggtgactaat aacacaataa    2640
cattgtctgg ggctggaata aagtcggagc tgtttacccc cactctaata ggggttcaat    2700
ataaaaagcc ggcagagagc tgtccaagtc agacgcgcct cagcgctgga tccatgcaga    2760
tcgagctgtc cacctgcttt tttctgtgcc tgctgcggtt ctgcttcagc gccaccggc    2820
ggtactacct gggcgccgtg gagctgtcct gggactacat gcagagcgac ctgggcgagc    2880
tgcccgtgga cgccggttc cccccccagag tgcccaagag cttcccccttc aacaccaggc    2940
tggtgtacaa gaaaaccctg ttcgtggagt tcaccgacca cctgttcaat atcgccaagc    3000
ccaggcccc ctgatgggc ctgctgggcc ccaccatcca ggccgaggtg tacgacaccg    3060
tggtgatcac cctgaagaac atggccagcc accccgtgag cctgcacgcc gtgggcgtga    3120
gctactggaa ggccagcgag ggcgccgagt acgacgacca gaccagccag cgggagaaag    3180
aagatgacaa ggtgttccct ggcggcagcc acacctacg gtggcaggtg ctgaaagaaa    3240
acggccccat ggcctccgac cccctgtgcc tgacctacag ctacctgagc cacgtggacc    3300
tggtgaagga cctgaacagc ggcctgatcg gcgctctgct cgtctgccgg gagggcagcc    3360
tggccaaaga gaaaacccag accctgcaca agttcatcct gctgttcgcc gtgttcgaca    3420
agggcaagag ctggcacagc gagacaaaga acagcctgat gcaggaccgg gacgccgcct    3480
ctgccagagc ctggcccaag atgcacaccg tgaacggcta cgtgaacaga agcctgcccg    3540
gcctgattgc ctgccaccgg aagagcgtgt actggcacgt gatcggcatg ggcaccacac    3600
ccgaggtgca cagcatcttt ctggaagggc acacctttct ggtccggaac caccggcagg    3660
ccagcctgga aatcagccct atcaccttcc tgaccgccca gacactgctg atggacctgg    3720
gccagttcct gctgtttttgc cacatcagct ctcaccagca cgacggcatg gaagcctacg    3780
tgaaggtgga ctcttgcccc gaggaacccc agctgcggat gaagaacaac gaggaagccg    3840
aggactacga cgacgacctg accgacagcg agatggacgt ggtgcggttc gacgacgaca    3900
acagccccag cttcatccag atcagaagcg tggccaagaa gcaccccaag acctgggtgc    3960
actatatcgc cgccgaggaa gaggactggg actacgcccc cctggtgctg gcccccgacg    4020
acagaagcta caagagccag tacctgaaca atggcccca gcggatcggc cggaagtaca    4080
agaaagtgcg gttcatggcc tacaccgacg agacattcaa gacccgggag gccatccagc    4140
acgagacgcg catcctgggc cccctgctgt acggcgaagt gggcgacaca ctgctgatca    4200
tcttcaagaa ccaggctagc cggccctaca acatctaccc ccacggcatc accgacgtgc    4260
ggcccctgta cagcaggcgg ctgcccaagg gcgtgaagca cctgaaggac ttccccatcc    4320
tgcccggcga gatcttcaag tacaagtgga ccgtgaccgt ggaggacggc cccaccaaga    4380
gcgaccccag atgcctgacc cggtactaca gcagcttcgt gaacatggac aggaggacctg    4440
cctccgggct gatcggacct ctgctgatct gctacaaaga aagcgtggac cagcggggca    4500
accagatcat gagcgacaag cggaacgtga tcctgttcag cgtgttcgat gagaaccggt    4560
cctggtatct gaccgagaac atccagcggt ttctgcccaa ccctgccggc gtgcagctgg    4620
aagatcccga gttccaggcc agcaacatca tgcactccat caatgcctac caatgttcgact    4680
ctctgcagct ctccgtgtgt ctgcacgagg tggcctactg gtacatcctg agcatcggcg    4740
cccagaccga cttcctgagc gtgttcttca gcggctacac cttcaagcac aagatggtgt    4800
acgaggacac cctgacctg ttccctttca gcggcgagac agtgttcatg agcatggaaa    4860
accccgcct gtggattctg ggctgccaca acagcgacct ccggaaccgg gacgatgaccg    4920
ccctgctgaa ggtgtccagc tgcgacaaga acaccggcga ctactacgcg gacagctacg    4980
aggatatcag cgcctacctg ctgtccaaga acaacgccat cgaacccgg agcttcagcc    5040
agaacccccc cgtgctgacg cgtcaccagc gggagatcac ccgacaacc ctgcagtccg    5100
accaggaaga gatcgattac gacgacacca tcagcgtgga gatgaagaaa gaggatttcg    5160
atatctacga cgaggacgag aaccagagcc ccagaagctt ccagaagaaa acccggcact    5220
acttcattgc cgccgtggag aggctgtggg actacggcat gagttctagc ccccacgtgc    5280
tgcggaaccg ggcccagagc ggcagcgtgc cccagttcaa gaaagtggtg ttccaggaat    5340
tcacagacgg cagcttcacc cagcctctgt atagaggcga gctgaacgag cacctggggc    5400
tgctgggggc ctacatcagg gccgaagtgg aggacaacat catggtgacc ttccggaatc    5460
aggccagcag accctactcc ttctacagca gcctgatcag ctacgaagag gaccagcggc    5520
agggcgccga accccggaag aacttcgtga agcccaacga aaccaagacc tacttctgga    5580
aagtgcagca ccacatggcc cccaccaagg acgagttcga ctgcaaggcc tgggcctact    5640
tcagcgacgt ggatctggaa aaggacgtgc actctggact gattggccca ctcctggtct    5700
gccacactaa caccctcaac cccgcccacg gccgccaggt gaccgtgcag gaattcgccc    5760
tgttcttcac catcttcgac gagacaaagt cctggtactt caccgagaat atggaacgga    5820
actgcagagc ccccctgcaac atccagatgg aagatcctac cttcaaagag aactaccggt    5880
tccacgccat caacggctac atcatggaca ccctgcctgg cctggttgac ggcccaggacc    5940
agagaatccg gtggtatctg ctgtccatgg gcagcaacga gaatatccac agcatccact    6000
tcagcggcca cgtgttcacc gtgcggaaga aggaagagta caagatggcc ctgtacaacc    6060
tgtaccccgg cgtgttcgag acagtggaga tgctgcccag caaggccggc atctggcggg    6120
tggagtgtct gatcggcgag caccctgcacg ctggcatgag caccctgttt ctggtgtaca    6180
gcaacaagtg ccagacccca ctgggcatgg cctctggcca catctgggac ttccagatca    6240
ccgcctccgg ccagtacggc cagtgggccc ccaagctggc cagactgcac tacagcggca    6300
gcatcaacgc ctggtccacc aaaagagcct tcagctggat caaggtggac ctgctggccc    6360
ctatgatcat ccacggcatt aagacccagg cgccaggca gaagttcagc agcctgtaca    6420
tcagccagtt catcatcatg tacagcctgg acggcaagaa gtggcagacc taccggggca    6480
acagcacagg caccctgatg gtgttcttcg gcaatgtgga cagcagcggc atcaagcaca    6540
acatcttcaa cccccccatc attgcccggt acatccggct gcaccccacc cactacagca    6600
ttagatccac actgagaatg gaactgatgg gctgcgacct gaactcctgc agcatgcctc    6660
tgggcatgga aagcaaggcc atcagcgacg cccagatcac agccagcagc tacttcacca    6720
acatgttcgc cacctggtcc ccctccaagg ccaggctgca cctgcagggc cggtccaacg    6780
cctggcggcc tcaggtcaac aaccccaaag aatggctgca ggtggacttt cagaaaacca    6840
```

```
tgaaggtgac cggcgtgacc acccagggcg tgaaaagcct gctgaccagc atgtacgtga   6900
aagagtttct gatcagcagc tctcaggatg gccaccagtg gaccctgttc tttcagaacg   6960
gcaaggtgaa agtgttccag ggcaaccagg actccttcac ccccgtggtg aactccctgg   7020
accccccct gctgacccgc tacctgagaa tccacccca gtcttgggtg caccagatcg   7080
ccctcaggat ggaagtcctg ggatgtgagg cccaggatct gtactgatga cgtctggaac   7140
aatcaacctc tggattacaa aatttgtgaa agattgactg gtattcttaa ctatgttgct   7200
ccttttacgc tatgtggata cgctgcttta atgcctttgt atcatgctat tgcttcccgt   7260
atggctttca ttttctcctc cttgtataaa tcctggttgc tgtctcttta tgaggagttg   7320
tggcccgttg tcaggcaacg tggcgtggtg tgcactgtgt ttgctgacgc aacccccact   7380
ggttggggca ttgccaccac ctgtcagctc ctttccggga ctttcgcttt ccccctccct   7440
attgccacgg cggaactcat cgccgcctgc cttgcccgct gctggacagg ggctcggctg   7500
ttgggcactg acaattccgt ggtgttgtcg gggaagctga cgtcctttcc atggctgctc   7560
gcctgtgttg ccacctggat tctgcgcggg acgtccttct gctacgtccc ttcggccctc   7620
aatccagcgg accttccttc ccgcggcctg ctgccggctc tgcggcctct tccgcgtctt   7680
cgccttcgcc ctcagacgag tcggatctcc ctttgggccg cctccccgcc tggaattaat   7740
tctgcagtcg agacctagaa aaacatggag caatcacaag tagcaataca gcagctacca   7800
atgctgattg tgcctggcta gaagcacaag aggaggagga ggtgggtttt ccagtcacac   7860
ctcaggtacc tttaagacca atgacttaca aggcagctgt agatcttagc cacttttaa   7920
aagaaaagag gggactggaa gggctaattc actcccaacg aagacaagat atccttgatc   7980
tgtggatcta ccacacacaa ggctacttcc ctgattagca gaactacaca ccagggccag   8040
gggtcagata tccactgacc tttggatggt gctacaagct agtaccagtt gagccagata   8100
aggtagaaga ggccaataaa ggagagaaca ccagcttgtt acaccctgtg agcctgcatg   8160
ggatgatga cccggagaga gaagtgttag agtggaggtt tgacagccgc ctagcatttc   8220
atcacgtggc ccgagagctg catccggagt acttcaagaa ctgctgatat cgagcttgct   8280
acaagggact ttccgctggg gactttccag ggaggcgtgg cctgggcggg actggggagt   8340
ggcgagccct cagatcctgc atataagcag ctgcttttg cctgtactgg gtctctctgg   8400
ttagaccaga tctgagcctg ggagctctct ggctaactag ggaacccact gcttaagcct   8460
caataaagct tgccttgagt gcttcaagta gtgtgtgccc gtctgttgtg tgactctggt   8520
aactagagat ccctcagacc cttttagtca gtgtggaaaa tctctagcag tagtagttca   8580
tgtcatctta ttattcagta tttataactt gcaaagaaat gaatatcaga gagtgagagg   8640
ccttgacatt gctagcgttt taccgtcgac ctctagctag agcttggcgt aatcatggtc   8700
atagctgttt cctgtgtgaa attgttatcc gctcacaatt ccacacaaca tacgagccgg   8760
aagcataaag tgtaaagcct ggggtgccta atgagtgagc taactcacat taattgcgtt   8820
gcgctcactg cccgctttcc agtcgggaaa cctgtcgtgc cagctgcatt aatgaatcgg   8880
ccaacgcgcg gggagaggcg gtttgcgtat tgggcgctct tccgcttcct cgctcactga   8940
ctcgctgcgc tcggtcgttc ggctgcggcg agcggtatca gctcactcaa aggcggtaat   9000
acggttatcc acagaatcag gggataacgc aggaaagaac atgtgagcaa aaggccagca   9060
aaaggccagg aaccgtaaaa aggccgcgtt gctggcgttt ttccataggc tccgcccccc   9120
tgacgagcat cacaaaaatc gacgctcaag tcagaggtgg cgaaacccga caggactata   9180
aagataccag gcgtttcccc ctggaagctc cctcgtgcgc tctcctgttc cgaccctgcc   9240
gcttaccgga tacctgtccg cctttctccc ttcgggaagc gtggcgcttt ctcatagctc   9300
acgctgtagg tatctcagtt cggtgtaggt cgttcgctcc aagctgggct gtgtgcacga   9360
accccccgtt cagcccgacc gctgcgcctt atccggtaac tatcgtcttg agtccaaccc   9420
ggtaagacac gacttatcgc cactggcagc agccactggt aacaggatta gcagagcgag   9480
gtatgtaggc ggtgctacag agttcttgaa gtggtggcct aactacggct acactagaag   9540
aacagtattt ggtatctgcg ctctgctgaa gccagttacc ttcggaaaaa gagttggtag   9600
ctcttgatcc ggcaaacaaa ccaccgctgg tagcggtggt ttttttgttt gcaagcagca   9660
gattacgcgc agaaaaaaag gatctcaaga agatcctttg atcttttcta cggggtctga   9720
cgctcagtgg aacgaaaact cacgttaagg gattttggtc atgagattat caaaaaggat   9780
cttcacctag atccttttaa attaaaaatg aagttttaaa tcaatctaaa gtatatatga   9840
gtaaacttgg tctgacagtt accaatgctt aatcagtgag gcacctatct cagcgatctg   9900
tctatttcgt tcatccatag ttgcctgact ccccgtcgtg tagataacta cgatacggga   9960
gggcttacca tctggcccca gtgctgcaat gataccgcga gacccacgct caccggctcc  10020
agatttatca gcaataaacc agccagccgg aagggccgag cgcagaagtg gtcctgcaac  10080
tttatccgcc tccatccagt ctattaattg ttgccgggaa gctagagtaa gtagttcgcc  10140
agttaatagt ttgcgcaacg ttgttgccat tgctacaggc atcgtggtgt cacgctcgtc  10200
gtttggtatg gcttcattca gctccggttc ccaacgatca aggcgagtta catgatcccc  10260
catgttgtgc aaaaaagcgg ttagctcctt cggtcctccg atcgttgtca gaagtaagtt  10320
ggccgcagtg ttatcactca tggttatggc agcactgcat aattctctta ctgtcatgcc  10380
atccgtaaga tgcttttctg tgactggtga gtactcaacc aagtcattct gagaatagtg  10440
tatgcggcga ccgagttgct cttgcccggc gtcaatacgg gataataccg cgccacatag  10500
cagaacttta aaagtgctca tcattggaaa acgttcttcg gggcgaaaac tctcaaggat  10560
cttaccgctg ttgagatcca gttcgatgta acccactcgt gcacccaact gatcttcagc  10620
atcttttact tcaccagcg tttctgggtg agcaaaaaca ggaaggcaaa atgccgcaaa  10680
aaagggaata agggcgacac ggaaatgttg aatactcata ctcttccttt ttcaatatta  10740
ttgaagcatt tatcagggtt attgtctcat gagcggatac atatttgaat gtatttagaa  10800
aaataaacaa ataggggttc cgcgcacatt ccccgaaaa gtgccacctg acgtcgacgg  10860
atcgggagat caacttgttt attgcagctt ataatggtta caaataaagc aatagcatca  10920
caaatttcac aaataaagca tttttttcac tgcattctag ttgtggtttg tccaaactca  10980
tcaatgtatc ttatcatgtc tggatcaact ggataactca agctaaccaa aatcatccca  11040
aacttcccac cccataccct attaccactg ccaattacct gtggtttcat ttactctaaa  11100
cctgtgattc ctctgaatta ttttcatttt aaagaaattg tatttgttaa atatgtacta  11160
caaacttagt agttttttaaa gaaattgtat ttgttaaata tgtactacaa acttagtagt  11220
```

SEQ ID NO: 43        moltype = DNA   length = 11236
FEATURE              Location/Qualifiers
misc_feature        1..11236
                    note = vector
source              1..11236

```
                   mol_type = other DNA
                   organism = synthetic construct
SEQUENCE: 43
tggaagggct aattcactcc caaagaagac aagatatcct tgatctgtgg atctaccaca   60
cacaaggcta cttccctgat tagcagaact acacaccagg gccaggggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctgggggactt tccagggagg cgtggcctgs gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agacccttt agtcagtgtg gaaaatctct agcagtggcg cccgaacagg gacttgaaag  660
cgaaagggaa accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca gggggaaaga aaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagagagaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag tttttgctgt  1860
actttctata gtgaatagag ttaggcaggg atattcacca ttatcgtttc agacccacct  1920
cccaaccccg aggggggacc cgacaggccc gaaggaatag aagaagaagg tggagagaga  1980
gacagagaca gatccattcg attagtgaac ggatctcgac ggtcgccaaa tggcagtatt  2040
catccacaat tttaaaagaa aaggggggat tggggggtac agtgcagggg aaagaatagt  2100
agacataata gcaacagaca tacaaactaa agaattacaa aaacaaatta caaaaattca  2160
aaattttcgg gtttattaca gggacagcag agatccagtt tggatcgata gcttgatat  2220
cgaattcctg cgcggccgct tcgaacgcgc gcgatgcatc atatgcgtac gcggtctaga  2280
actagtgaga cataaaagga aaatgaagcg agcaacaatt aaaaaaaatt ccccgcacac  2340
aacaatacaa tctatttaaa ctgtgagtca tacttttcat accaatggta tgacttttt  2400
tctggagtcc cctcttctga ttcttgaact ccggggctgg cagcttgcaa aggggaagcg  2460
gactccagca ctgcacgggc aggtttagca aaggtctcta atgggtattt tcttttttctt  2520
agccctgccc ccgaattgtc agacggcggg cgtctgcctc tgaagttagc agtgatttcc  2580
tttcgggcct ggccttatct ccggctgcac gttgcctgtt ggtgactaat aacacaataa  2640
cattgtctgg ggctggaata aagtcggagc tgtttacccc cactctaata ggggttcaat  2700
ataaaaagcc ggcagagagc tgtccaagtc agacgcgcct cagcgctgga tctcgggctc  2760
gaggccacca tgcagatcga gctgtccacc tgcttttttc tgtgcctgct gcggttctgc  2820
ttcagcgcca cccggcggta ctacctgggc gccgtggagc tgtcctggga ctacatgcag  2880
agcgacctgg gcgagctgcc cgtggacgcc cggttccccc ccagagtgcc caagagcttc  2940
cccttcaaca ccagcgtggt gtacaagaaa accctgttcg tggagttcac cgaccacctg  3000
ttcaatatcg ccaagcccag gccccctgg atgggcctgc tgggccccac catccaggcc  3060
gaggtgtacg acaccgtggt gatcaccctg aagaacatgg ccagccaccc cgtgagcctg  3120
cacgccgtgg gcgtgagcta ctggaaggcc agcgagggcg ccgagtacga cgaccagacc  3180
agccagcggg agaagaagaag tgacaaggtg ttccctggcg gcagccacac ctacgtgtgg  3240
caggtgctga agaaaacgg ccccatggcc tccgaccccc tgtgcctgac ctacagctac  3300
ctgagccacg tggacctggt gaaggacctg aacagcggcc tgatcggcgc tctgctcgtc  3360
tgccggggagg gcagcctggc caaagagaaa acccagagac tgcacaagtt catcctgctg  3420
ttcgccgtgt tcgacgaggg caagagctgg cacagcgaga caaagaacag cctgatgcag  3480
gaccgggacg ccgcctctgc cagagcctgg cccaagatgc acaccgtgaa cggctacgtg  3540
aacagaagcc tgcccggcct gattggctgc caccggaaga gcgtgtactg gcacgtgatc  3600
ggcatggaa ccacacccga ggtgcacagc atctttctgg aagggcacac ctttctgggt  3660
cggaaccacc ggcaggccag cctggaaatc agccctatca ccttcctgac cgcccagaca  3720
ctgctgatgg acctgggcca gttcctgctg ttttgccaca tcagctctca ccagcacgac  3780
ggcatggaag cctacgtgaa ggtggactct tgccccgagg aaccccagct gcggatgaag  3840
aacaacgagg aagccgagga ctacgacgac gacctgaccg acagcgagat ggacgtggtg  3900
cggttcgacg acgacaacag ccccagcttc atccagatca gaagcgtggc caagaagcac  3960
cccaagacct gggtgcacta tatcgccgcc gaggaagagg actgggacta cgcccccctg  4020
gtgctggccc ccgacgacag aagctacaag agccagtacc tgaacaatgg cccccagcgg  4080
atcggccgga gtacaagaa agtgcggttc atggcctaca ccgacgagac attcaagacc  4140
cgggaggcca tccagcacga gcggcatc ctgggccccc tgctgtacgg cgaagtgggc  4200
gacacactgc tgatcatctt caagaaccag gctagcaga ctaccccac ctaccccac  4260
ggcatcaccg acgtgcggcc cctgtacagc aggcggctgc ccaagggcgt gaagcacctg  4320
aaggacttcc ccatcctgcc cggcgagatc ttcaagtaca gtggaccgt gaccgtggag  4380
gacggcccca ccaagagcga ccccagatgc ctgacccgt actacagcag cttcgtgaac  4440
atggaacggg acctggcctc cgggctgatc ggacctctgc tgatctgcta caagaaagc  4500
gtggaccagc ggggcaacca gatcatgagc gacaagcgga acgtgatcct gttcagcgtg  4560
```

```
ttcgatgaga accggtcctg gtatctgacc gagaacatcc agcggtttct gcccaaccct   4620
gccggcgtgc agctggaaga tcccgagttc caggccagca acatcatgca ctccatcaat   4680
ggctacgtgt tcgactctct gcagctctcc gtgtgtctgc acgaggtggc ctactggtac   4740
atcctgagca tcggcgccca gaccgacttc ctgagcgtgt tcttcagcgg ctacaccttc   4800
aagcacaaga tggtgtacga ggacaccctg accctgttcc ctttcagcgg cgagacagtg   4860
ttcatgagca tggaaaaccc cggcctgtgg attctgggct gccacaacag cgacttccgg   4920
aaccggggca tgaccgccct gctgaaggtg tccagctgcg acaagaacac cggcgactac   4980
tacgaggaca gctacgagga tatcagcgcc tacctgctgt ccaagaacaa cgccatcgaa   5040
ccccggagct tcagccagaa ccccccccgtg ctgacgcgtc accagcggga gatcacccgg   5100
acaaccctgc agtccgacca ggaagagatc gattacgacg acaccatcag cgtggagatg   5160
aagaaagagg atttcgatat ctacgacgag gacgagaacc agagcccccag aagcttccag   5220
aagaaaaccc ggcactactt cattgccgcc gtggagaggc tgtgggacta cggcatgagt   5280
tctagcccccc acgtgctgcg gaaccgggcc cagagcggca gcgtgcccca gttcaagaaa   5340
gtggtgttcc aggaattcac agacggcagc ttcacccagc ctctgtatag aggcgagctg   5400
aacgagcacc tggggctgct ggggccctac atcagggccg aagtggagga caacatcatg   5460
gtgaccttcc ggaatcaggc cagcagaccc tactccttct acagcagcct gatcagctac   5520
gaagaggacc agcggcaggg cgccgaaccc cggaagaact tcgtgaagcc caacgaaacc   5580
aagacctact tctggaaagt gcagcaccac atggccccca ccaaggacga gttcgactgc   5640
aaggcctggg cctacttcag cgacgtggat ctggaaaagg acgtgcactc tggactgatt   5700
ggcccactcc tggtctgcca cactaacacc ctcaaccccg cccacggccg ccaggtgacc   5760
gtgcaggaat tcgccctgtt cttcaccatc ttcgacgaga caaagtcctg gtacttcacc   5820
gagaatatgg aacggaactg cagagccccc tgcaacatcc agatggaaga tcctaccttc   5880
aaagagaact accggttcca cgccatcaac ggctacatca tggacaccct gcctggcctg   5940
gtgatggccc aggaccagag aatccggtgg tatctgctgt ccatgggcag caacgagaat   6000
atccacagca tccacttcag cggccacgtg ttcaccgtgc ggaagaaaga agagtacaag   6060
atggccctgt acaacctgta ccccggcgtg ttcgagacag ttggagatgct gcccagcaag   6120
gccggcatct ggcgggtgga gtgtctgatc ggcgagcacc tgcacgctgg catgagcacc   6180
ctgtttctgg tgtacagcaa caagtgccag accccactgg gcatggcctc tggccacatc   6240
cgggacttcc agatcaccgc ctccggccag tacggccagt gggcccccaa gctggccaga   6300
ctgcactaca gcggcagcat caacgcctgg tccaccaaag agcccttcag ctggatcaag   6360
gtggacctgc tggcccctat gatcatccac ggcattaaga cccagggcgc caggcagaag   6420
ttcagcagcc tgtacatcag ccagttcatc atcatgtaca gcctggacgg caagaagtgg   6480
cagacctacc ggggcaacag caccggcacc ctgatggtgt tcttcggcaa tgtggacagc   6540
agcggcatca agcacaacat cttcaacccc cccatcattg cccggtacat ccggctgcac   6600
cccacccact acagcattag atccacactg agaatggaac tgatgtgggctg cgacctgaac   6660
tcctgcagca tgcctctggg catggaaagc aaggccatca gcgacgccca gatcacagcc   6720
agcagctact tcaccaacat gttcgccacc tggtcccccct ccaaggccag gctgcacctg   6780
cagggccggt ccaacgcctg gcgggcctcag gtcaacaacc ccaaagaatg gctgcaggtg   6840
gactttcaga aaccatgaa ggtgaccggc gtgaccaccc agggccgtgaa aagcctgctg   6900
accagcatgt acgtgaaaga gtttctgatc agcagctctc aggatggcca ccagtggacc   6960
ctgttctttc agaacggcaa ggtgaaagtg ttccagggca accaggactc cttcacccccc   7020
gtggtgaact ccctggaccc ccccctgctg acccgctacc tgagaatcca cccccagtct   7080
tgggtgcaac agatcgccct caggatggaa gtcctggcgt gtgaggccca ggatctgtac   7140
tgatgacgtc tggaacaatc aacctctgga ttacaaaatt tgtgaaagat tgactggtat   7200
tcttaactat gttgctcctt ttacgctatg tggatacgct gctttaatgc ctttgtatca   7260
tgctattgct tcccgtatgg ctttcatttt ctcctccttg tataaatcct ggttgctgtc   7320
tctttatgag gagttgtggc ccgttgtcag gcaacgtggc gtggtgtgca ctgtgtttgc   7380
tgacgcaacc cccactggtt ggggcattgc caccacctgt cagctccttt ccgggacttt   7440
cgctttcccc ctccctattg ccacggcgga actcatcgcc gcctgccttg cccgctgctg   7500
gacaggggct cggctgttgg gcactgacaa ttccgtggtg ttgtcgggga agctgacgtc   7560
ctttccatgg ctgctcgcct gtgttgccac ctggattctg cgcgggacgt ccttctgcta   7620
cgtcccttcg ccctcaatc cagcggacct tccttcccgc ggcctgctgc cggctctgcg   7680
gcctcttccg cgtcttcgcc ttcgccctca gacgagtcgg atctccctt gggccgcctc   7740
cccgcctgga attaattctg cagtcgagac ctagaaaaac atggagcaat cacaagtagc   7800
aatacagcag ctaccaatgc tgattgtgcc tggctagaaa cacaagagga ggaggaggtg   7860
ggttttccag tcacacctca ggtacctttta agaccaatga cttacaaggc agctgtagat   7920
cttagccact tttttaaaaga aaagaggggga ctggaagggc taattcactc ccaacgaaga   7980
caagatatcc ttgatctgtg gatctaccac acacaaggct acttccctga ttagcagaac   8040
tacacaccag ggccaggggt cagatatcca ctgacctttg gatggtgcta caagctagta   8100
ccagttgagc cagataaggt agaagaggcc aataaaggag agaacaccag cttgttacac   8160
cctgtgagcc tgcatgggat ggatgacccg gagagagaag tgttagagtg gaggtttgac   8220
agccgcctag catttcatca cgtggcccga gagctgcatc cggagtactt caagaactgc   8280
tgatatcgag cttgctacaa gggactttcc gctggggact ttccagggag gcgtggcctg   8340
ggcgggactg gggagtggcg agccctcaga tcctgcatat aagcagctgc tttttgcctg   8400
tactgggtct ctctggttag accagatctg agcctgggag ctctctggct aactagggaa   8460
cccactgctt aagcctcaat aaagcttgcc ttgagtgctt caagtagtgt gtgcccgtct   8520
gttgtgtgac tctggtaact agagatccct cagacccttt tagtcagtgt ggaaaatctc   8580
tagcagtagt agttcatgtc atcttattat tcagtattta taacttgcaa agaaatgaat   8640
atcagagagt gagaggcctt gacattgcta gcgttttacc gtcgacctct agctagagct   8700
tggcgtaatc atggtcatag ctgtttcctg tgtgaaattg ttatccgctc acaattccac   8760
acaacatacg agccggaagc ataaagtgta aagcctgggg tgcctaatga gtgagctaac   8820
tcacattaat tgcgttgcgc tcactgcccg ctttccagtc gggaaacctg tcgtgccagc   8880
tgcattaatg aatcggccaa cgcgcgggga gaggcggttt gcgtattggg cgctcttccg   8940
cttcctcgct cactgactcg ctgcgctcgg tcgttcggct gcggcgagcg gtatcagctc   9000
actcaaaggc ggtaatacgg ttatccacag aatcagggga taacgcagga aagaacatgt   9060
gagcaaaagg ccagcaaaag gccaggaacc gtaaaaaggc cgcgttgctg gcgtttttcc   9120
ataggctccg cccccctgac gagcatcaca aaaatcgacg ctcaagtcag aggtggcgaa   9180
acccgacagg actataaaga taccaggcgt ttccccctgg aagctccctc gtgcgctctc   9240
ctgttccgac cctgccgctt accggatacc tgtccgcctt tctcccttcg ggaagcgtgg   9300
```

```
cgctttctca tagctcacgc tgtaggtatc tcagttcggt gtaggtcgtt cgctccaagc   9360
tgggctgtgt gcacgaaccc cccgttcagc ccgaccgctg cgccttatcc ggtaactatc   9420
gtcttgagtc caacccggta agacacgact tatcgccact ggcagcagcc actggtaaca   9480
ggattagcag agcgaggtat gtaggcggtg ctacagagtt cttgaagtgg tggcctaact   9540
acggctacac tagaagaaca gtatttggta tctgcgctct gctgaagcca gttaccttcg   9600
gaaaaagagt tggtagctct tgatccggca aacaaaccac cgctggtagc ggtggttttt   9660
ttgtttgcaa gcagcagatt acgcgcagaa aaaaaggatc tcaagaagat cctttgatct   9720
tttctacggg gtctgacgct cagtggaacg aaaactcacg ttaagggatt ttggtcatga   9780
gattatcaaa aaggatcttc acctagatcc ttttaaatta aaaatgaagt tttaaatcaa   9840
tctaaagtat atatgagtaa acttggtctg acagttacca atgcttaatc agtgaggcac   9900
ctatctcagc gatctgtcta tttcgttcat ccatagttgc ctgactcccc gtcgtgtaga   9960
taactacgat acgggagggc ttaccatctg gccccagtgc tgcaatgata ccgcgagacc  10020
cacgctcacc ggctccagat ttatcagcaa taaaccagcc agccgaagg gccgagcgca  10080
gaagtggtcc tgcaacttta tccgcctcca tccagtctat taattgttgc cgggaagcta  10140
gagtaagtag ttcgccagtt aatagtttgc gcaacgttgt tgccattgct acaggcatcg  10200
tggtgtcacg ctcgtcgttt ggtatggctt cattcagctc cggttcccaa cgatcaaggc  10260
gagttacatg atcccccatg ttgtgcaaaa aagcggttag ctccttcggt cctccgatcg  10320
ttgtcagaag taagttggcc gcagtgttat cactcatggt tatggcagca ctgcataatt  10380
ctcttactgt catgccatcc gtaagatgct tttctgtgac tggtgagtac tcaaccaagt  10440
cattctgaga atagtgtatg cggcgaccga gttgctcttg cccggcgtca tacgggata  10500
ataccgcgcc acatagcaga actttaaaag tgctcatcat tggaaaacgt tcttcggggc  10560
gaaaactctc aaggatctta ccgctgttga gatccagttc gatgtaaccc actcgtgcac  10620
ccaactgatc ttcagcatct tttactttca ccagcgtttc tgggtgagca aaaacaggaa  10680
ggcaaaatgc cgcaaaaaag ggaataaggg cgacacggaa atgttgaata ctcatactct  10740
tcctttttca atattattga agcatttatc agggttattg tctcatgagc ggatacatat  10800
ttgaatgtat ttagaaaaat aaacaaatag gggttccgcg cacatttccc cgaaaagtgc  10860
cacctgacgt cgacggatcg ggagatcaac ttgtttattg cagcttataa tggttacaaa  10920
taaagcaata gcatcacaaa tttcacaaat aaagcatttt tttcactgca ttctagttgt  10980
ggtttgtcca aactcatcaa tgtatcttat catgtctgga tcaactggat aactcaagct  11040
aaccaaaatc atcccaaact tcccacccca taccctatta ccactgccaa ttacctgtgg  11100
tttcatttac tctaaacctg tgattcctct gaattatttt cattttaaag aaattgtatt  11160
tgttaaatat gtactacaaa cttagtagtt tttaaagaaa ttgtatttgt taaatatgta  11220
ctacaaactt agtagt                                                   11236
```

```
SEQ ID NO: 44          moltype = DNA  length = 11177
FEATURE                Location/Qualifiers
misc_feature           1..11177
                       note = vector
source                 1..11177
                       mol_type = other DNA
                       organism = synthetic construct
SEQUENCE: 44
tggaagggct aattcactcc caaagaagac aagatatcct tgatctgtgg atctaccaca   60
cacaaggcta cttccctgat tagcagaact acacaccagg gccaggggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agaccctttt agtcagtgtg gaaaatctct agcagtggcg cccgaacagg gacttgaaag  660
cgaaaggga accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca gggggaaaga aaaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga gaggagcatt gttccttggg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag ttttttgctgt 1860
actttctata gtgaatagag ttaggcaggg atattcacca ttatcgtttc agacccacct 1920
cccaaccccg aggggggacc cgacaggccc gaaggaatag aagaagaagg tggagagaca 1980
gacagagaca gatccattcg attagtgaac ggatctcgac ggtcgccaaa tggcagtatt 2040
catccacaat tttaaaagaa aaggggggat tggggggtac agtgcagggg aaagaatagt 2100
agacataata gcaacagaca tacaaactaa agaattacaa aaacaaatta caaaaattca 2160
aaattttcgg gtttattaca gggacagcag agatccagtt tggatcgata agcttgatat 2220
```

-continued

```
cgaattcctg cgcggccgct tcgaacgcgc gcgatgcatc atatgcgtac gcggtctaga   2280
attcctgcag ggcccactag tctcccaggc atgactccaa caatgcatcc catgggattt   2340
ggggttcccc agatctgggg cttgtaggcc tgactctccc ctgtgcacac gtctcataca   2400
cgcatgcgtg cacccattgc ctgccccgcc ccttgcacag ggagtcagca gggaggactg   2460
ggttatgccc tgcttatcag cagcttccca gcttcctctg cctggattct tagaggcctg   2520
gggtcctaga acgagctggt gcacgtggct tcccaaagat ctctcagata atgagaggaa   2580
atgcagtcat cagtttgcag aaggctaggg attctgggcc atagctcaga cctgcgccca   2640
ccatctccct ccaggcagcc cttggctggt ccctgcgagc ccgtggagac tgccagtcag   2700
cgctggatcc atgcagatcg agctgtccac ctgctttttt ctgtgcctgc tgcggttctg   2760
cttcagcgcc acccggccgt actacctggg cgccgtggag ctgtcctggg actacatgca   2820
gagcgacctg ggcgagctgc ccgtggacgc ccggttcccc cccagagtgc ccaagagctt   2880
cccccttcaac accagcgtgg tgtacaagaa aaccctgttc gtggagttca ccgaccacct   2940
gttcaatatc gccaagccca ggcccccctg gatgggcctg ctgggcccca ccatccaggc   3000
cgaggtgtac gacaccgtgg tgatcaccct gaagaacatg gccagccacc cgtgagcct    3060
gcacgccgtg ggcgtgagct actggaaggc cagcgagggc gccgagtacg acgaccagac   3120
cagccagcgg gagaaagaag atgacaaggt gttccctggc ggcagccaca cctacgtgtg   3180
gcaggtgctg aaagaaaacg gccccatggc ctccgacccc ctgtgcctga cctacagcta   3240
cctgagccac gtggacctga tgaaggacct gaacagcggc ctgatcggcg ctctgctcgt   3300
ctgccgggag ggcagcctgg ccaaagagaa aaccccagacc ctgcacaagt tcatcctgct   3360
gttcgccgtg ttcgacgagg gcaagagctg gcacagcgag acaaagaaca gcctgatgca   3420
ggaccgggac gccgcctctg ccagagcctg gcccaagatg cacaccgtga acggctacgt   3480
gaacagaagc ctgcccggcc tgattggctg ccaccggaag ggcgtgtact ggcacgtgat   3540
cggcatgggc accacacccg aggtgcacag catctttctg gaagggcaca cctttctggt   3600
ccggaaccac cggcaggcca gcctggaaat cagccctatc accttcctga ccgcccagac   3660
actgctgatg gacctgggcc agttcctgct gttttgccac atcagctctc accagcacga   3720
cggcatggaa gcctacgtga aggtggactc ttgccccgag caacacccag tgcggatgaa   3780
gaacaacgag gaagccgagg actacgacga cgacctgacc gacagcgaga tggacgtggt   3840
gcggttcgac gacgacaaca gccccagctt catccagatc agaagcgtgg ccaagaagca   3900
ccccaagacc tgggtgcact atatcgccgc cgaggaagag gactgggact acgcccccct   3960
ggtgctggcc cccgacgaca gaagctacaa gagccagtac ctgaacaatg gcccccagcg   4020
gatcggccgg aagtacaaga aagtgcggtt catggcctac accgacgaga cattcaagac   4080
ccgggaggcc atccagcacg agagcggcat cctgggcccc ctgctgtacg gcgaagtggg   4140
cgacacactg ctgatcatct tcaagaacca ggctagccgg ccctacaaca tctacccca    4200
cggcatcacc gacgtgcggc ccctgtacag caggcggctg ccaaagggcg tgaagcacct   4260
gaaggacttc cccatcctgc ccggcgagat cttcaagtac aagtggaccg tgaccgtgga   4320
ggacggcccc accaagagcg accccagatg cctgacccgg tactacagca gcttcgtgaa   4380
catgaacgg gacctggcct ccgggctgat cggacctctg ctgatctgct acaaagaaag   4440
cgtggaccag cggggcaacc agatcatgag cgacaagcgg aacgtgatcc tgttcagcgt   4500
gttcgatgag aaccggtcct ggtatctgac cgagaacatc cagcggtttc tgcccaaccc   4560
tgccggcgtg cagctggaag atcccgagtt ccaggccagc aacatcatgc actccatcaa   4620
tggctacgtg ttcgactctc tgcagctctc cgtgtgtctg cacgaggtgg cctactggta   4680
catcctgagc atcggcgccc agaccgactt cctgagcgtg ttcttcagcg gctacacctt   4740
caagcacaag atggtgtacg aggacaccct gacccttgttc ccttcagcg gcgagacagt   4800
gttcatgagc atggaaaacc ccggcctgtg gattctgggc tgccacaaca gcgacttccg   4860
gaaccggggc atgaccgccc tgctgaaggt gtccagctgc gacaagaaca ccggcgacta   4920
ctacgaggac agctacgagg atatcagcgc ctacctgctg tccaagaaca acgccatcga   4980
accccggacc ttcagccaga acccccccgt gctgacgcgt caccagcggg agatcacccg   5040
gacaaccctg cagtccgacc aggaagagat cgattacgac gacaccatca gcgtggagat   5100
gaagaaagag gatttcgata tctacgacga ggacgagaac cagagcccca gaagcttcca   5160
gaagaaaccc cggcactact tcattgccgc cgtggagagg ctgtgggact acggcatgag   5220
ttctgacccc cacgtgctgc ggaaccgggc ccagagcggc agcgtgcccc agttcaagaa   5280
agtggtgttc caggaattca cagacgcag cttcacccag cctctgtata gaggcgagct   5340
gaacgagcac ctggggctgc tggggcccta catcagggcc gaagtggagg acaacatcat   5400
ggtgaccttc cggaatcagg ccagcagacc ctactccttc tacagcagcc tgatcagcta   5460
cgaagaggac cagcggcagg gcgccgaacc ccggaagaac ttcgtgaagc ccaacgaaac   5520
caagacctac ttctggaaag tgcagcacca catggccccc accaaggacg agttcgactg   5580
caaggcctgg gcctacttca gcgacgtgga tctggaaaag gacgtgcact ctggactgat   5640
tggcccactc ctggtctgcc acactaacac cctcaacccc gcccacgccc gccaggtgac   5700
cgtgcaggaa ttcgccctgt tcttcaccat cttcgacgag acaaagtcct ggtacttcac   5760
cgagaatatg gaacggaact gcagagcccc ctgcaacatc cagatggaag atcctacctt   5820
caaaagagaac taccggttcc acgccatcaa cggctacatc atggacaccc tgcctggcct   5880
ggtgatggcc caggaccaga gaatccggtg gtatctgctg tccatgggca gcaacgagaa   5940
tatccacagc atccacttca gcgcggccac gttcaccgtg cggaagaaag aagagtacaa   6000
gatggcccctg tacaacctgt accccggcgt gttcgagaca gtggagatgc tgcccagcaa   6060
ggccggcatc tggcgggtgg agtgtctgat cggcgagcac ctgcacgctg catgagcac    6120
cctgtttctg gtgtacagca acaagtgcca gaccccactg ggcatggcct ctggccacat   6180
ccgggacttc cagatcaccg cctccggcca gtacggccag tgggcccca agctggccag   6240
actgcactac agcggcagca tcaacgcctg gtccaccaaa gagcccttca gctggatcaa   6300
ggtggacctg ctggccccta tgatcatcca cggcattaag acccagggcg ccgccagaa    6360
gttcagcagc ctgtacatca gccagttcat catcatgtac agcctggacg gcaagaagtg   6420
gcagacctac cgggcgcaaca gcaccggcac cctgatggtg ttcttcggca atgtggacag   6480
cagcggcatc aagcacaaca tcttcaaccc ccccatcatt gccccggtaca tccggctgca   6540
ccccacccac tacagcatta atccacact gagaatggaa ctgatgggct gcgacctgaa   6600
ctcctgcagc atgcctctgg gcatggaaag caaggccatc agcgacgccc agatcacagc   6660
cagcagctac ttcaccaaca tgttcgccac ctggtccccc tccaaggcca ggctgcacct   6720
gcagggccgg tccaacgcct ggcggcctca ggtcaacaac cccaaagaat ggctgcaggt   6780
ggactttcag aaaccatga aggtgaccgg cgtgaccacc cagggcgtga aaagcctgct   6840
gaccagcatg tacgtgaaag agtttctgat cagcagctct caggatggcc accagtggac   6900
cctgttcttt cagaacggca aggtgaaagt gttccagggc aaccaggact ccttcacccc   6960
```

-continued

```
cgtggtgaac tccctggacc cccccctgct gacccgctac ctgagaatcc accccccagtc    7020
ttgggtgcac cagatcgccc tcaggatgga agtcctggga tgtgaggccc aggatctgta    7080
ctgatgacgt ctggaacaat caacctctgg attacaaaat ttgtgaaaga ttgactggta    7140
ttcttaacta tgttgctcct tttacgctat gtggatacgc tgctttaatg cctttgtatc    7200
atgctattgc ttcccgtatg gctttcattt tctcctcctt gtataaatcc tggttgctgt    7260
ctctttatga ggagttgtgg cccgttgtca ggcaacgtgg cgtggtgtgc actgtgtttg    7320
ctgacgcaac ccccactggt tggggcattg ccaccacctg tcagctcctt tccgggactt    7380
tcgctttccc cctccctatt gccacggcgg aactcatcgc cgcctgcctt gcccgctgct    7440
ggacaggggc tcggctgttg ggcactgaca attccgtggt gttgtcgggg aagctgacgt    7500
cctttccatg gctgctcgcc tgtgttgcca cctggattct gcgcgggacg tccttctgct    7560
acgtcccttc ggccctcaat ccagcggacc ttccttcccg cggcctgctg ccggctctgc    7620
ggcctcttcc gcgtcttcgc cttcgccctc agacgagtcg gatctccctt tgggccgcct    7680
ccccgcctgg aattaattct gcagtcgaga cctagaaaaa catggagcaa tcacaagtag    7740
caatacagca gctaccaatg ctgattgtgc ctggctagaa gcacaagagg aggaggaggt    7800
gggtttccca gtcacacctc aggtaccttt aagaccaatg acttacaagg cagctgtaga    7860
tcttagccac ttttttaaaag aaaagagggg actggaaggg ctaattcact cccaacgaag    7920
acaagatatc cttgatctgt ggatctacca cacacaaggc tacttccctg attagcagaa    7980
ctacacacca gggccagggg tcagatatcc actgaccttt ggatggtgct acaagctagt    8040
accagttgag ccagataagg tagaagaggc caataaaagga gagaacacca gcttgttaca    8100
ccctgtgagc ctgcatggga tggatgaccc ggagagagaa gtgttagagt ggaggtttga    8160
cagccgccta gcatttcatc acgtggcccg agagctgcat ccggagtact tcaagaactg    8220
ctgatatcga gcttgctaca agggactttc cgctggggac tttccagggg ggcgtggcct    8280
gggcgggact ggggagtggc gagccctcag atcctgcata taagcagctg cttttttgcct    8340
gtactgggtc tctctggtta gaccagatct gagcctggga gctctctggc taactaggga    8400
acccactgct taagcctcaa taaagcttgc cttgagtgct tcaagtagtg tgtgcccgtc    8460
tgttgtgtga ctctggtaac tagagatccc tcagacccctt ttagtcagtg tggaaaatct    8520
ctagcagtag tagttcatgt catcttatta ttcagtattt ataacttgca aagaaatgaa    8580
tatcagagag tgagaggcct tgacattgct agcgtttttac cgtcgacctc tagctagagc    8640
ttggcgtaat catggtcata gctgtttcct gtgtgaaatt gttatccgct cacaattcca    8700
cacaacatac gagccggaag cataaagtgt aaagcctggg gtgcctaatg agtgagctaa    8760
ctcacattaa ttgcgttgcg ctcactgccc gctttccagt cgggaaacct gtcgtgccag    8820
ctgcattaat gaatcggcca acgcgcgggg agaggcggtt tgcgtattgg gcgctcttcc    8880
gcttcctcgc tcactgactc gctgcgctcg gtcgttcggc tgcggcgagc ggtatcagct    8940
cactcaaagg cggtaatacg gttatccaca gaatcagggg ataacgcagg aagaacatg    9000
tgagcaaaag gccagcaaaa ggccaggaac cgtaaaaagg ccgcgttgct ggcgtttttc    9060
cataggctcc gcccccctga cgagcatcac aaaaatcgac gctcaagtca gaggtggcga    9120
aacccgacag gactataaag ataccaggcg tttccccctg gaagctccct cgtgcgctct    9180
cctgttccga ccctgccgct taccggatac ctgtccgcct ttctcccttc gggaagcgtg    9240
gcgctttctc atagctcacg ctgtaggtat ctcagttcgg tgtaggtcgt tcgctccaag    9300
ctgggctgtg tgcacgaacc ccccgttcag cccgaccgct gcgccttatc cggtaactat    9360
cgtcttgagt ccaacccggt aagacacgac ttatcgccac tggcagcagc cactggtaac    9420
aggattagca gagcgaggta tgtaggcggt gctacagagt tcttgaagtg gtggcctaac    9480
tacggctaca ctagaagaac agtatttggt atctgcgctc tgctgaagcc agttaccttc    9540
ggaaaaagag ttggtagctc ttgatccggc aaacaaacca ccgctggtag cggtggtttt    9600
tttgtttgca agcagcagat tacgcgcaga aaaaaaggat ctcaagaaga tcctttgatc    9660
ttttctacgg ggtctgacgc tcagtggaac gaaaactcac gttaagggat tttggtcatg    9720
agattatcaa aaaggatctt cacctagatc cttttaaatt aaaaatgaag ttttaaatca    9780
atctaaagta tatatgagta aacttggtct gacagttacc aatgcttaat cagtgaggca    9840
cctatctcag cgatctgtct atttcgttca tccatagttg cctgactccc cgtcgtgtag    9900
ataactacga tacgggaggg cttaccatct ggccccagtg ctgcaatgat accgcgagac    9960
ccacgctcac cggctccaga tttatcagca ataaaccagc cagccggaag ggccgagcgc    10020
agaagtggtc ctgcaacttt atccgcctcc atccagtcta ttaattgttg ccgggaagct    10080
agagtaagta gttcgccagt taatagtttg cgcaacgttg ttgccattgc tacaggcatc    10140
gtggtgtcac gctcgtcgtt tggtatggct tcattcagct ccggttccca acgatcaagg    10200
cgagttacat gatccccccat gttgtgcaaa aaagcggtta gctccttcgg tcctccgatc    10260
gttgtcagaa gtaagttggc cgcagtgtta tcactcatgg ttatggcagc actgcataat    10320
tctcttactg tcatgccatc cgtaagatgc ttttctgtga ctggtgagta ctcaaccaag    10380
tcattctgag aatagtgtat gcggcgaccg agttgctctt gcccggcgtc aatacgggat    10440
aataccgcgc cacatagcag aactttaaaa gtgctcatca ttggaaaacg ttcttcgggg    10500
cgaaaactct caaggatctt accgctgttg agatccagtt cgatgtaacc cactcgtgca    10560
cccaactgat cttcagcatc ttttactttc accagcgttt ctgggtgagc aaaaacagga    10620
aggcaaaatg ccgcaaaaaa gggaataagg gcgacacgga aatgttgaat actcatactc    10680
ttcctttttc aatattattg aagcatttat cagggttatt gtctcatgag cggatacata    10740
tttgaatgta tttagaaaaa taaacaaata ggggttccgc gcacatttcc ccgaaaagtg    10800
ccacctgacg tcgacggatc gggagatcaa cttgtttatt gcagcttata atggttacaa    10860
ataaagcaat agcatcacaa atttcacaaa taaagcattt ttttcactgc attctagttg    10920
tggtttgtcc aaactcatca atgtatctta tcatgtctgg atcaactgga taactcaagc    10980
taaccaaaat catcccaaac ttcccacccc ataccctatt accactgcca attacctgtg    11040
gtttcattta ctctaaacct gtgattcctc tgaattattt tcattttaaa gaaattgtat    11100
ttgttaaata tgtactacaa acttagtagt ttttaaagaa attgtatttg ttaaatatgt    11160
actacaaact tagtagt                                                     11177
```

SEQ ID NO: 45        moltype = DNA   length = 11196
FEATURE              Location/Qualifiers
misc_feature        1..11196
                     note = vector
source              1..11196
                     mol_type = other DNA
                     organism = synthetic construct -continued

```
SEQUENCE: 45
tggaagggct aattcactcc caaagaagac aagatatcct tgatctgtgg atctaccaca    60
cacaaggcta cttccctgat tagcagaact acacaccagg gccagggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat    1020
cattatataa tacagtagca accctctatt gtgtgcatca aaggatagag ataaaagaca    1080
ccaaggaagc tttagacaag atagaggaag agcaaaacaa aagtaagacc accgcacagc    1140
aagcggccgg ccgctgatct tcagacctgg aggaggagat atgagggaca attggagaag    1200
tgaattatat aaatataaag tagtaaaaat tgaaccatta ggagtagcac caccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttgggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag tttttgctgt    1860
actttctata gtgaatagag ttaggcaggg atattcacca ttatcgtttc agacccacct    1920
cccaacccg agggggacc cgacaggccc gaaggaatag aagaagaagg tggagagaga    1980
gacagagaca gatccattcg attagtgaac ggatctcgac ggtcgccaaa tggcagtatt    2040
catccacaat tttaaaagaa aaggggggat tggggggtac agtgcagggg aaagaatagt    2100
agacataata gcaacagaca tacaaactaa agaattacaa aaacaaatta caaaaattca    2160
aaattttcgg gtttattaca gggacagcag agatccagtt tggatcgata agcttgatat    2220
cgaattcctg cgcggccgct tcgaacgcgc gcgatgcatc atatgcgtac gcggtctaga    2280
attcctgcag ggcccactag tctcccaggc atgactccaa caatgcatcc catgggattt    2340
ggggttcccc agatctgggg cttgtaggcc tgactctccc ctgtgcacac gtctcataca    2400
cgcatgcgtg caccccattgc ctgccccgcc ccttgcacag ggagtcagca gggaggactg    2460
ggttatgccc tgcttatcag cagcttccca gcttcctctg cctggattct tagaggcctg    2520
gggtcctaga acgagctggt gcacgtggct tcccaaagat ctctcagata atgagaggaa    2580
atgcagtcat cagtttgcag aaggctaggg attctgggcc atagctcaga cctgcgccca    2640
ccatctccct ccaggcagcc cttggctggt ccctgcgagc ccgtggagac tgccagtcag    2700
cgctgctgga tctcgggctg gaggccacca tgcagatcga tgtccacc tgctttttc    2760
tgtgcctgct gcggttctgc ttcagcgcca cccggcggta ctacctgggc gccgtggagc    2820
tgtcctggga ctacatgcag agcgacctgg gcgagctgcc cgtggacgcc cggttccccc    2880
ccagagtgcc caagagcttc cccttcaaca ccagcgtggg gtacaagaaa accctgttcg    2940
tggagttcac cgaccacctg ttcaatatcg ccaagcccag gcccccctgg atgggcctgc    3000
tgggccccac catccaggcc gaggtgtacg acaccgtggt gatcacccctg aagaacatgc    3060
ccagccaccc cgtgagcctg cacgccgtgg gcgtgagcta ctggaaggcc agcgagggcg    3120
ccgagtacga cgaccagacc agccagcggg agaaagaaga tgacaaggtg ttccctggcg    3180
gcagccacac ctacgtgtgg caggtgctga agaaaaacgg ccccatggcc tccgaccccc    3240
tgtgcctgac ctacagctac ctgagccacg tggacctggt gaaggacctg aacagcggcc    3300
tgatcggcgc tctgctcgtc tgccggggag gcagcctggc caaagagaaa acccagaccc    3360
tgcacaagtt catcctgctg ttccgccgtgt tcgacgaggg caagagctgg cacagcgaga    3420
caaagaacag cctgatgcag gaccgggacg ccgcctctgc cagagcctgg cccaagatgc    3480
acaccgtgaa cggctacgtg aacagaagcc tgcccggcct gattggctgc caccggaaga    3540
gcgtgtactg gcacgtgatc ggcatgggca ccacacccga ggtgcacagc atctttctgg    3600
aagggcacac ctttctggtc cggaaccacc ggcaggccag cctggaaatc agccctatca    3660
ccttcctgac cgcccagaca ctgctgatgg acctgggcca gttcctgctg ttttgccaca    3720
tcagctctca ccagcacgac ggcatgaagg cctacgtgaa ggtggactct tgccccgacg    3780
aaccccagct gcggatgaag aacaacgagg aagccgagga ctacgacgac gacctgaccg    3840
acagcgagat ggacgtggtg cggttcgacg acgacaacag ccccagcttc atccagatca    3900
gaagcgtggc caagaagcac cccaagacct gggtgcacta tatcgccgcc gaggaagagg    3960
actgggacta cgcccccctg gtgctggccc ccgacgacag aagctacaag agccagtacc    4020
tgaacaatgg ccccagcagg atcggccgga gtacaagaa agtgcggttc atggcctaca    4080
ccgacgagac attcaagacc cgggaggcca tccagcacga gagcggcatc ctgggccccc    4140
tgctgtacgg cgaagtgggc gacacactgc tgatcatctt caagaaccag gctagccggc    4200
cctacaacat ctacccccac ggcatcaccg acgtgcggcc cctgtacagc aggcggctgc    4260
ccaagggcgt gaagcacctg aaggacttcc ccatcctgcc cggcgagatc ttcaagtaca    4320
agtggaccgt gaccgagga gaccgcccca ccaagagcgac ctgaccggt ctgacccggt    4380
actacagcag cttcgtgaac atggaacggg acctggcctc cgggctgatc ggacctctgt    4440
tgatctgcta caaagaaagc gtggaccagc ggggcaacca gatcatgagc gacaagcgga    4500
acgtgatcct gttcagcgtg ttcgatgaga ccggtcctg gtatctgacc gagaacatcc    4560
agcggtttct gcccaaccct gccggcgtgc agctggaaga tcccgagttc caggccagca    4620
acatcatgca ctccatcaat ggctacgtgt tcgactctct gcagctctcc gtgtgtctgc    4680
```

```
acgaggtggc ctactggtac atcctgagca tcggcgccca gaccgacttc ctgagcgtgt  4740
tcttcagcgg ctacaccttc aagcacaaga tggtgtacga ggacaccctg accctgttcc  4800
ctttcagcgg cgagacagtg ttcatgagca tggaaaaccc cggcctgtgg attctgggct  4860
gccacaacac cgacttccgg aaccggggca tgaccgccct gctgaaggtg tccagctgcg  4920
acaagaacac cggcgactac tacgaggaca gctacgagga tatcagcgcc tacctgctgt  4980
ccaagaacaa cgccatcgaa ccccggagct tcagccagaa ccccccgtg ctgacgcgtc  5040
accagcggga gatcacccgg acaaccctgc agtccgacca ggaagagatc gattacgacg  5100
acaccatcag cgtggagatg aagaaagagg atttcgatat ctacgacgag gacgagaacc  5160
agagcccag aagcttccag aagaaaaccc ggcactactt cattgccgcc gtggagaggc  5220
tgtgggacta cggcatgagt tctagccccc acgtgctgcg gaaccgggcc cagagcgaga  5280
gcgtgcccca gttcaagaaa gtggtgttcc aggaattcac agacggcagc ttcacccagc  5340
ctctgtatag aggcgagctg aacgagcacc tggggctgct ggggccctac atcagggccg  5400
aagtggagga caacatcatg gtgaccttcc ggaatcaggc cagcagaccc tactccttct  5460
acagcagcct gatcagctac gaagaggacc agcggcaggg gccgaaccc cggaagaact  5520
tcgtgaagcc caacgaaacc aagacctact tctggaaagt gcagcaccac atggccccca  5580
ccaaggacga gttcgactgc aaggcctggg cctacttcag cgacgtggat ctggaaaagg  5640
acgtgcactc tggactgatt ggcccactcc tggtctgcca cactaacacc ctcaaccccg  5700
cccacggccg ccaggtgacc gtgcaggaat tcgccctgtt cttcaccatc ttcgacgaga  5760
caaagtcctg gtacttcacc gagaatatgg aacggaactg cagagccccc tgcaacatcc  5820
agatggaaga tcctaccttc aaaagagaact accggttcca cgccatcaac ggctacatca  5880
tggacaccct gcctggcctg gtgatggccc aggaccagag aatccggtgg tatctgctgt  5940
ccatggcag caacgagaat atccacagca tccacttcag cggccacgtg ttcaccgtgc  6000
ggaagaaaga agagtacaag atggcccgt acaacctgta ccccggcctg ttcgagacag  6060
tggagatgct gcccagcaag gccggcatct ggcgggtgga gtgtctgatc ggcgagcacc  6120
tgcacgctgg catgagcacc ctgtttctgg tgtacagcaa caagtgccag accccactgg  6180
gcatggcctc tggccacatc cgggacttcc agatcaccgc ctccgacac tacggccagt  6240
gggccccaa gctggccaga ctgcactaca gcggcagcat caacgcctgg tccaccaaag  6300
agcccttcag ctggatcaag gtggacctgc tggcccctat gatcatccac ggcattaaga  6360
cccagggcgc caggcagaag ttcagcagcc tgtacatcag ccagttcatc atcatgtaca  6420
gcctggacag caagaagtgg cagacctacc ggggcaacag caccggcacc ctgatggtgt  6480
tcttcggcaa tgtggacagc agcggcatca agcacaacat cttcaaccc cccatcattg  6540
cccggtacat ccggctgcac cccacccact acagcattag atccacactg agaatggaac  6600
tgatgggctg cgacctgaac tcctgcagca tgcctctggg catggaaagc aaggccatca  6660
gcgacgccca gatcacagcc agcagctact tcaccaacat gttcgccacc tggtcccct  6720
ccaaggccag gctgcacctg caggccggt ccaacgcctg gcggcctcag gtcaacaacc  6780
ccaaagaatg gctgcaggtg gactttcaga aaaccatgaa ggtgaccggc gtgaccaccc  6840
agggcgtgaa aagcctgctg accagcatgt acgtgaaaga gtttctgatc agcagctctc  6900
aggatggcca ccagtggacc ctgttctttc agaacggca ggtgaaagtg ttccagggca  6960
accaggactc cttcacccc gtggtgaact ccctggaccc ccccctgctg acccgctacc  7020
tgagaatcca cccccagtct tgggtgcacc agatcgccct caggatggaa gtcctgggat  7080
gtgaggccca ggatcgtac tgatgacgtc tggaacaatc aacctctgga ttacaaaatt  7140
tgtgaaagat tgactggtat tcttaactat gttgctcctt ttacgctatg tggatacgct  7200
gctttaatgc ctttgtatca tgctattgct tcccgtatgg ctttcatttt ctcctccttg  7260
tataaatcct ggttgctgtc tctttatgag gagttgtggc ccgttgtcag gcaacgtggc  7320
gtggtgtgca ctgtgtttgc tgacgcaacc cccactggtt ggggcattgc caccacctgt  7380
cagctccttt ccgggacttt cgctttcccc ctccctattg ccacggcgga actcatcgcc  7440
gcctgccttg cccgctgctg gacagggct cggctgttgg gcactgacaa ttccgtggtg  7500
ttgtcgggga agctgacgtc ctttccatgg ctgctcgcct gtgttgccac ctggattctg  7560
cgcgggacgt ccttctgcta cgtccctcg gccctcaatc cagcggacct tccttcccgc  7620
ggcctgctgc cggctctgcg gcctcttccg cgtcttcgcc ttcgccctca gacgagtcgg  7680
atctcccttt gggccgcctc cccgcctgga attaattctg cagtcgagac ctagaaaaac  7740
atggagcaat cacaagtagc aatacagcag ctaccaatgc tgattgtgcc tggctagaag  7800
cacaagagga ggaggaggtg ggttttccag tcacacctca ggtacctta agaccaatga  7860
cttacaaggc agctgtagat cttagccact ttttaaaaga aaagagggga ctggaagggc  7920
taattcactc ccaacgaaga caagatatcc ttgatctgtg gatctaccac acacaaggct  7980
acttccctga ttagcagaac tacacaccag ggccagggt cagatatcca ctgacctttg  8040
gatggtgcta caagctagta ccagttgagc cagataaggt agaagaggcc aataaaggag  8100
agaacaccag cttgttacac cctgtgagcc tgcatgggat ggatgacccg gagagagaag  8160
tgttagagtg gaggtttgac agccgcctag catttcatca cgtggcccga gagctgcatc  8220
cggagtactt caagaactgc tgatatcgag cttgctacaa gggactttcc gctggggact  8280
ttccagggag gcgtggcctg ggcgggactg gggagtggcg agccctcaga tcctgcatat  8340
aagcagctgc tttttgcctg tactgggtct ctctggttag accagatctg agcctgggag  8400
ctctctggct aactagggaa cccactgctt aagcctcaat aaagcttgcc ttgagtgctt  8460
caagtagtgt gtgcccgtct gttgtgtgac tctggtaact agagatccct cagacccttt  8520
tagtcagtgt ggaaaatctc tagcagtagt agttcatgtc atcttattat tcagtattta  8580
taacttgcaa agaaatgaat atcagagagt gagaggcctt gacattgcta gcgttttacc  8640
gtcgacctct agctagagct tggcgtaatc atggtcatag ctgtttcctg tgtgaaattg  8700
ttatccgctc acaattccac acaacatacg agccggaagc ataaagtgta aagcctgggg  8760
tgcctaatga gtgagctaac tcacattaat tgcgttgcgc tcactgcccg ctttccagtc  8820
gggaaacctg tcgtgccagc tgcattaatg aatcggccaa cgcgcgggga gaggcggttt  8880
gcgtattggg cgctcttccg cttcctcgct cactgactcg ctgcgctcgg tcgttcggct  8940
gcggcgagcg gtatcagctc actcaaaggc ggtaatacgg ttatccacag aatcagggga  9000
taacgcagga aagaacatgt gagcaaaagg ccagcaaaag gccaggaacc gtaaaaaggc  9060
cgcgttgctg gcgtttttcc ataggctccg cccccctgac gagcatcaca aaaatcgacg  9120
ctcaagtcag aggtggcgaa acccgacagg actataaaga taccaggcgt ttccccctgg  9180
aagctccctc gtgcgctctc ctgttccgac cctgccgctt accggatacc tgtccgcctt  9240
tctcccttcg ggaagcgtgg cgctttctca tagctcacgc tgtaggtatc tcagttcggt  9300
gtaggtcgtt cgctccaagc tgggctgtgt gcacgaaccc cccgttcagc ccgaccgctg  9360
cgccttatcc ggtaactatc gtcttgagtc caacccggta agacacgact tatcgccact  9420
```

-continued

```
ggcagcagcc actggtaaca ggattagcag agcgaggtat gtaggcggtg ctacagagtt  9480
cttgaagtgg tggcctaact acggctacac tagaagaaca gtatttggta tctgcgctct  9540
gctgaagcca gttaccttcg gaaaaagagt tggtagctct tgatccggca aacaaaccac  9600
cgctggtagc ggtggttttt ttgtttgcaa gcagcagatt acgcgcagaa aaaaaggatc  9660
tcaagaagat cctttgatct tttctacggg gtctgacgct cagtggaacg aaaactcacg  9720
ttaagggatt ttggtcatga gattatcaaa aaggatcttc acctagatcc ttttaaatta  9780
aaaatgaagt tttaaatcaa tctaaagtat atatgagtaa acttggtctg acagttacca  9840
atgcttaatc agtgaggcac ctatctcagc gatctgtcta tttcgttcat ccatagttgc  9900
ctgactcccc gtcgtgtaga taactacgat acgggagggc ttaccatctg gccccagtgc  9960
tgcaatgata ccgcgagacc cacgctcacc ggctccagat ttatcagcaa taaaccagcc  10020
agccggaagg gccgagcgca gaagtggtcc tgcaactta tccgcctcca tccagtctat  10080
taattgttgc cgggaagcta gagtaagtag ttcgccagtt aatagtttgc gcaacgttgt  10140
tgccattgct acaggcatcg tggtgtcacg ctcgtcgttt ggtatggctt cattcagctc  10200
cggttcccaa cgatcaaggc gagttacatg atccccatg ttgtgcaaaa aagcggttag  10260
ctccttcggt cctccgatcg ttgtcagaag taagttggcc gcagtgttat cactcatggt  10320
tatggcagca ctgcataatt ctcttactgt catgccatcc gtaagatgct tttctgtgac  10380
tggtgagtac tcaaccaagt cattctgaga atagtgtatg cggcgaccga gttgctcttg  10440
cccggcgtca atacgggata ataccgcgcc acatagcaga actttaaaag tgctcatcat  10500
tggaaaacgt tcttcggggc gaaaactctc aaggatctta ccgctgttga gatccagttc  10560
gatgtaaccc actcgtgcac ccaactgatc ttcagcatct tttactttca ccagcgtttc  10620
tgggtgagca aaaacaggaa ggcaaaatgc cgcaaaaaag ggaataaggg cgacacggaa  10680
atgttgaata ctcatactct tccttttca atattattga agcatttatc agggttattg  10740
tctcatgagc ggatacatat ttgaatgtat ttagaaaaat aaacaaatag gggttccgcg  10800
cacatttccc cgaaaagtgc cacctgacgt cgacggatcg ggagatcaac ttgtttattg  10860
cagcttataa tggttacaaa taaagcaata gcatcacaaa tttcacaaat aaagcatttt  10920
tttcactgca ttctagttgt ggtttgtcca aactcatcaa tgtatcttat catgtctgta  10980
tcaactggat aactcaagct aaccaaaatc atcccaaact tcccacccca taccctatta  11040
ccactgccaa ttacctgtgg tttcatttac tctaaacctg tgattcctct gaattatttt  11100
cattttaaag aaattgtatt tgttaaatat gtactacaaa cttagtagtt tttaaagaaa  11160
ttgtatttgt taaatatgta ctacaaactt agtagt                           11196
```

```
SEQ ID NO: 46          moltype = DNA  length = 8303
FEATURE                Location/Qualifiers
misc_feature           1..8303
                       note = vector
source                 1..8303
                       mol_type = other DNA
                       organism = synthetic construct
SEQUENCE: 46
tggaagggct aattcactcc caaagaagac aagatatcct tgatctgtgg atctaccaca  60
cacaaggcta cttccctgat tagcagaact acacaccagg gccagggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgag  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccaggagg cgtggcctgg gcgggactgg ggagtggcga gccctcagat  420
cctcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agacccttt agtcagtgtg gaaaatctct agcagtggcg cccgaacagg gacttgaaag  660
cgaaaggtaa accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca gggggaaaga aaaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag ttttttgctgt  1860
actttctata gtgaatagag ttaggcaggg atattcacca ttatcgtttc agacccacct  1920
cccaaccccg aggggggacc cgacaggccc gaaggaatag aagaagaagg tggagagaga  1980
gacagagaca gatccattcg attagtgaac ggatctcgac ggtcgccaaa tggcagtatt  2040
catccacaat tttaaaagaa aagggggggat tggggggtac agtgcagggg aagaaatagt  2100
agacataata gcaacagaca tacaaactaa agaattacaa aaacaaatta caaaaattca  2160
aaatttcgg gttattaca gggacagcag agatccagtt tggatcgata agcttgatat  2220
cgaattcctg cgcggccgct cgaacgcgc gcgatgcatc atatgcgtac gcggtctaga  2280
attcctgcag ggcccactag tctcccaggc atgactccaa caatgcatcc catgggattt  2340
ggggttcccc agatctgggg cttgtaggcc tgactctccc ctgtgcacac gtctcataca  2400
```

```
cgcatgcgtg cacccattgc ctgccccgcc ccttgcacag ggagtcagca gggaggactg   2460
ggttatgccc tgcttatcag cagcttccca gcttcctctg cctggattct tagaggcctg   2520
gggtcctaga acgagctggt gcacgtggct tcccaaagat ctctcagata atgagaggaa   2580
atgcagtcat cagtttgcag aaggctaggg attctgggcc atagctcaga cctgcgccca   2640
ccatctccct ccaggcagcc cttggctggt ccctgcgagc ccgtggagac tgccagtcag   2700
cgctgctgga tctcgggctc gaggccacca tggaagatgc caaaaacatt aagaagggcc   2760
cagcgccatt ctacccactc gaagacggga ccgccggcga gcagctgcac aaagccatga   2820
agcgctacgc cctggtgccc ggcaccatcg cctttaccga cgcacatatc gaggtggaca   2880
ttacctacgc cgagtacttc gagatgagcg ttcggctggc agaagctatg aagcgctatg   2940
ggctgaatac aaaccatcgg atcgtggtgt gcagcgagaa tagcttgcag ttcttcatgc   3000
ccgtgttggg tgccctgttc atcggtgtgg ctgtggcccc agctaacgac atctacaacg   3060
agcgcgagct gctgaacagc atgggcatca gccagcccac cgtcgtattc gtgagcaaga   3120
aagggctgca aaagatcctc aacgtgcaaa agaagctacc gatcatacaa aagatcatca   3180
tcatggatag caagaccgac taccaggget tccaaagcat gtacaccttc gtgacttccc   3240
atttgccacc cggcttcaac gagtacgact tcgtgcccga gagcttcgac cgggacaaaa   3300
ccatcgccct gatcatgaac agtagtggca gtaccggatt gcccaagggc gtagccctac   3360
cgcaccgcac cgcttgtgtc cgattcagtc atgcccgcga ccccatcttc ggcaaccaga   3420
tcatccccga caccgctatc tcagcgtgg tgccatttca ccacggcttc ggcatgttca   3480
ccacgctggg ctacttgatc tgcggctttc gggtcgtgct catgtaccgc ttcgaggagg   3540
agctattctt gcgcagcttg caagactata agattcaatc tgccctgctg gtgcccacac   3600
tatttagctt cttcgctaag agcactctca tcgacaagta cgacctaagc aacttgcacg   3660
agatcgccag cggcggggcg ccgctcagca aggaggtagg tgaggccgtg gccaaacgct   3720
tccacctacc aggcatccgc cagggctacg gcctgacaga aacaaccagc gccattctga   3780
tcaccccga aggggacgac aagcctggcc cagtaggcaa ggtggtgccc ttcttcgagg   3840
ctaaggtggt ggacttggac accggtaaga cactgggtgt gaaccagcgc ggcgagctgt   3900
gcgtccgtgg cccatgatc atgagcggct acgttaacaa ccccgaggct acaaacgtc   3960
tcatcgacaa ggacggctgg ctgcacagcg gcgacatcgc ctactgggac gaggacgagc   4020
acttcttcat cgtggaccgg ctgaagagcc tgatcaaata caagggctac caggtagccc   4080
cagccgaact ggagagcatc ctgctgcaac accccaacat cttcgacgcc ggggtcgccg   4140
gcctgcccga cgacgatgcc ggcgagctgc ccgccgcagt cgtcgtgctg gaacacggta   4200
aaaccatgac cgagaaggag atcgtggact atgtggccag ccaggttaca accgccaaga   4260
agctgcgcgg tggtgttgtg ttcgtggacg aggtgcctaa aggactgacc ggcaagttgg   4320
acgcccgcaa gatccgcgag attctcatta aggccaagaa gggcggcaag atcgccgtgt   4380
aaatgcaagc tagggtatac gatatcaagc ttatcgtcga caatcaacct ctggattaca   4440
aaatttgtga aagattgact ggtattctta actatgttgc tccttttacg ctatgtggat   4500
acgctgcttt aatgcctttg tatcatgcta ttgcttcccg tatggctttc attttctcct   4560
ccttgtataa atcctggttg ctgtctcttt atgaggagtt gtggcccgtt gtcaggcaac   4620
gtggcgtggt gtgcactgtg tttgctgacg caaccccac tggttggggc attgccacca   4680
cctgtcagct cctttccggg actttcgctt tccccctccc tattgccacg gcggaactca   4740
tcgccgcctg ccttgcccgc tgctggacag gggctcggct gttgggcact gacaattccg   4800
tggtgttgtc ggggaagctg acgtcctttc catggctgct cgcctgtgtt gccacctgga   4860
ttctgcgcgg gacgtccttc tgctacgtcc cttcggccct caatccagcg gaccttcctt   4920
cccgcggcct gctgccggct caagataggt cctttaaga ccaatgactt acaaggcagc   4980
tgtagatctt agccactttt taaaagaaaa gaggggactg gaagggctaa ttcactccca   5040
acgaagacaa gatatccttg atctgtggat ctaccacaca caaggctact ccctgattaa   5100
gcagaactac acaccagggc caggggtcag atatccactg acctttggat ggtgctacaa   5160
gctagtacca gttgagccag ataaggtaga agaggccaat aaaggagaga acaccagctt   5220
gttacacct gtgagcctgc atgggatgga tgacccggag agagaagtgt tagagtggag   5280
gtttgacagc cgcctagcat ttcatcacgt ggcccgagag ctgcatccgg agtacttcaa   5340
gaactgctga tatcgagctt gctacaaggg actttccgct ggggactttc cagggaggcg   5400
tggcctgggc gggactgggg agtggcgagc cctcagatcc tgcatataag cagctgcttt   5460
ttgcctgtac tgggtctctc tggttagacc agatctgagc ctgggagctc tctggctaac   5520
tagggaaccc actgcttaag cctcaataaa gcttgccttg agtgcttcaa gtagtgtgtg   5580
cccgtctgtt gtgtgactct ggtaactaga tccctcag acccttttag tcagtgtgga   5640
aaatctctag cagtagtagt tcatgtcatc ttattattca gtatttataa cttgcaaaga   5700
aatgaatatc agagagtgag aggccttgac attgctagcg ttttaccgtc gacctctagc   5760
tagagcttgg cgtaatcatg gtcatagctg tttcctgtgt gaaattgtta tccgctcaca   5820
attccacaca acatacgagc cggaagcata aagtgtaaag cctggggtgc ctaatgagtg   5880
agctaactca cattaattgc gttgcgctca ctgcccgctt tccagtcggg aaacctgtcg   5940
tgccagctgc attaatgaat cggccaacgc gcggggagag gcggtttgcg tattgggcgc   6000
tcttccgctt cctcgctcac tgactcgctg cgctcggtcg ttcggctgcg gcgagcggta   6060
tcagctcact caaaggcggt aatacggtta tccacagaat caggggataa cgcaggaaag   6120
aacatgtgag caaaaggcca gcaaaaggcc aggaaccgta aaaaggccgc gttgctggcg   6180
tttttccata ggctccgccc cctgacgag catcacaaaa atcgacgctc aagtcagagg   6240
tggcgaaacc cgacaggact ataaagatac caggcgtttc ccctggaag ctccctcgtg   6300
cgctctcctg ttccgaccct gccgcttacc ggatacctgt ccgcctttct cccttcggga   6360
agcgtggcgc tttctcatag ctcacgctgt aggtatctca gttcggtgta ggtcgttcgc   6420
tccaagctgg gctgtgtgca cgaacccccc gttcagcccg accgctgcgc cttatccggt   6480
aactatcgtc ttgagtccaa cccggtaaga cacgacttat cgccactggc agcagccact   6540
ggtaacagga ttagcagagc gaggtatgta ggcggtgcta cagagttctt gaagtggtgg   6600
cctaactacg gctacactag aagaacagta tttggtatct gcgctctgct gaagccagtt   6660
accttcggaa aaagagttgg tagctcttga tccggcaaac aaaccaccgc tggtagcggt   6720
ggtttttttg tttgcaagca gcagattacg cgcagaaaaa aaggatctca agaagatcct   6780
ttgatctttt ctacggggtc tgacgctcag tggaacgaaa actcacgtta agggatttg   6840
gtcatgagat tatcaaaaag gatcttcacc tagatccttt taaattaaaa atgaagtttt   6900
aaatcaatct aaagtatata tgagtaaact tggtctgaca gttaccaatg cttaatcagt   6960
gaggcaccta tctcagcgat ctgtctattt cgttcatcca tagttgcctg actccccgtc   7020
gtgtagataa ctacgatacg ggagggctta ccatctggcc ccagtgctgc aatgataccg   7080
cgagacccac gctcaccggc tccagattta tcagcaataa accagccagc cggaagggcc   7140
```

-continued

```
gagcgcagaa gtggtcctgc aactttatcc gcctccatcc agtctattaa ttgttgccgg   7200
gaagctagag taagtagttc gccagttaat agtttgcgca acgttgttgc cattgctaca   7260
ggcatcgtgg tgtcacgctc gtcgtttggt atggcttcat tcagctccgg ttcccaacga   7320
tcaaggcgag ttacatgatc ccccatgttg tgcaaaaaag cggttagctc cttcggtcct   7380
ccgatcgttg tcagaagtaa gttggccgca gtgttatcac tcatggttat ggcagcactg   7440
cataattctc ttactgtcat gccatccgta agatgctttt ctgtgactgg tgagtactca   7500
accaagtcat tctgagaata gtgtatgcgg cgaccgagtt gctcttgccc ggcgtcaata   7560
cgggataata ccgcgccaca tagcagaact ttaaaagtgc tcatcattgg aaaacgttct   7620
tcggggcgaa aactctcaag gatcttaccg ctgttgagat ccagttcgat gtaacccact   7680
cgtgcaccca actgatcttc agcatctttt actttcacca gcgtttctgg gtgagcaaaa   7740
acaggaaggc aaaatgccgc aaaaaaggga ataagggcga cacggaaatg ttgaatactc   7800
atactcttcc tttttcaata ttattgaagc atttatcagg gttattgtct catgagcgga   7860
tacatatttg aatgtattta gaaaaataaa caaataggg ttccgcgcac atttccccga   7920
aaagtgccac ctgacgtcga cggatccggga gatcaacttg tttattgcag cttataatgg   7980
ttacaaataa agcaatagca tcacaaattt cacaaataaa gcatttttt cactgcattc   8040
tagttgtggt ttgtccaaac tcatcaatgt atcttatcat gtctggatca actggataac   8100
tcaagctaac caaaatcatc ccaaacttcc caccccatac cctattacca ctgccaatta   8160
cctgtggttt catttactct aaacctgtga ttcctctgaa ttatttcat tttaaagaaa   8220
ttgtatttgt taaatatgta ctacaaactt agtagttttt aaagaaattg tatttgttaa   8280
atatgtacta caaacttagt agt                                           8303
```

SEQ ID NO: 47              moltype = DNA   length = 8379
FEATURE                    Location/Qualifiers
misc_feature               1..8379
                           note = vector
source                     1..8379
                           mol_type = other DNA
                           organism = synthetic construct
SEQUENCE: 47

```
tggaaggct aattcactcc caaagaagac aagatatcct tgatctgtgg atctaccaca   60
cacaaggcta cttccctgat tagcagaact acacaccagg gccagggtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgaccgg   240
agagagaagt gttagagtgg aggtttgaca gccgcctagc atttcatcac gtggcccgag   300
agctgcatcc ggagtacttc aagaactgct gatatcgatc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agacccttt agtcagtgtg gaaaatctct agcagtggcg cccgaacagg gacttgaaag   660
cgaaaggaaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaatataa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat   1020
cattatataa tacagtagca accctctatt gtgtgcataa aggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagaagaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttgggGtc gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aaggggggat tggggggtac agtgcaggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatgccct cacaaaggaa   2280
caataacagg aaaccatccc aggggggaagt gggccagggc cagctggaaa acctgaaggg   2340
gcgtacgcgg tctagaattc ctgcaggccc cactagtctc ccaggcatga ctccaacaat   2400
gcatcccatg ggatttgggg ttccccagat ctggggcttg taggcctgac tctcccctgt   2460
gcacacgtct catacacgca tgcgtgcacc cattgcctgc ccgccccctt gcacaggag   2520
tcagcaggga ggactgggtt atgccctgct tatcagcagc ttcccagctt cctctgcctt   2580
gattcttaga ggcctggggt cctagaacga gctggtgcac gtggcttccc aaagatctct   2640
cagataatga gaggaaatgc agtcatcagt ttgcagaagg tggggattc tgggccatag   2700
ctcagacctg cgccaccat ctccctccag gcagcccttg gctggtccct gcgagcccgt   2760
ggagactgcc agtcagcgct gctggatctc gggctcgagg ccaccatgga agatgccaaa   2820
aacattaaga agggcccagc gccattctac ccactcgaag acgggaccgc cggcgagcag   2880
ctgcacaaag ccatgaagcg ctacgccctg gtgcccggca ccatcgcctt taccgacgca   2940
catatcgagg tggacattac ctacgccgag tacttcgaga tgagcgttcg gctggcagaa   3000
```

-continued

```
gctatgaagc gctatgggct gaatacaaac catcggatcg tggtgtgcag cgagaatagc   3060
ttgcagttct tcatgcccgt gttgggtgcc ctgttcatcg gtgtggctgt ggccccagct   3120
aacgacatct acaacgagcg cgagctgctg aacagcatgg gcatcagcca gcccaccgtc   3180
gtattcgtga gcaagaaagg gctgcaaaag atcctcaacg tgcaaaagaa gctaccgatc   3240
atacaaaaga tcatcatcat ggatagcaag accgactacc agggcttcca aagcatgtac   3300
accttcgtga cttcccattt gccacccggc ttcaacgagt acgacttcgt gcccgagagc   3360
ttcgaccggg acaaaaccat cgccctgatc atgaacagta gtggcagtac cggattgccc   3420
aagggcgtag ccctaccgca ccgcaccgct tgtgtccgat tcagtcatgc ccgcgacccc   3480
atcttcggca accagatcat ccccgacacc gctatcctca gcgtggtgcc atttcaccac   3540
ggcttcggca tgttcaccac gctgggctac ttgatctgcg gctttcgggt cgtgctcatg   3600
taccgcttcg aggaggagct attcttgcgc agcttgcaag actataagat tcaatctgcc   3660
ctgctggtgc ccacactatt tagcttcttc gctaagagca ctctcatcga caagtacgac   3720
ctaagcaact tgcacgagat cgccagcggc ggggcgccgc tcagcaagga ggtaggtgag   3780
gccgtggcca aacgcttcca cctaccaggc atccgcaggg gctacggcct gacagaaaca   3840
accagcgcca ttctgatcac ccccgaaggg gacgacaagc ctggcgcagt aggcaaggtg   3900
gtgcccttct tcgaggctaa ggtggtggac ttggacaccg gtaagacact gggtgtgaac   3960
cagcgcgcg agctgtgcgt ccgtggcccc atgatcatga gcggctacgt taacaacccc   4020
gaggctacaa acgctctcat cgacaaggac ggctggctgc acagcggcga catcgcctac   4080
tgggacgagg acgagcactt cttcatccgtg gaccggctga agagcctgat caaatacaag   4140
ggctaccagg tagccccagc cgaactggag agcatcctgc tgcaacaccc caacatcttc   4200
gacgccgggg tcgccggcct gcccgacgac gatgccggcg agctgcccgc cgcagtcgtc   4260
gtgctggaac acggtaaaac catgaccgag aaggagatcg gccatggt gccagccag   4320
gttacaaccg ccaagaagct gcgcggtggt gttgtgttcg tggacgaggt gcctaaagga   4380
ctgaccggca agtggacgc ccgcaagatc cgcgagattc tcattaaggc caagaagggc   4440
ggcaagatcg ccgtgtaaat gcagcctagg gtatacgata tcaagcttat cgtcgacaat   4500
caacctctgg attacaaaat ttgtgaaaga ttgactggta ttcttaacta tgttgctcct   4560
tttacgctat gtggatacgc tgctttaatg cctttgtatc atgctattgc ttcccgtatg   4620
gctttcattt tctcctcctt gtataaatcc tggttgctgt ctctttatga ggagttgtgg   4680
cccgttgtca ggcaacgtgg cgtggtgtgc actgtgtttg ctgacgcaac ccccactggt   4740
tggggcattg ccaccacctg tcagctcctt tccgggactt tcgctttccc cctccctatt   4800
gccacggcgg aactcatcgc cgcctgcctt gcccgctgct ggacaggggc tcggctgttg   4860
ggcactgaca attccgtggt gttgtcgggg aagctgacgt cctttccatg gctgctcgcc   4920
tgtgttgcca cctggattct gcgcgggacg tccttctgct acgtcccttc ggccctcaat   4980
ccagcggacc ttccttcccg cggcctgctg ccggctctgc ataggaccct ttaagaccaa   5040
tgacttacaa ggcagctgta gatcttagcc actttttaaa agaaaagagg ggactggaag   5100
ggctaattca ctcccaacga agacaagata tccttgatct gtggatctac cacacacaag   5160
gctacttccc tgattagcag aactacacac cagggccagg ggtcagatat ccactgacct   5220
ttggatggtg ctacaagcta gtaccagttg agccagataa ggtagaagag gccaataaag   5280
gagagaacac cagcttgtta caccctgtga gcctgcatg gatggatgac cggagagag   5340
aagtgttaga gtggaggttt gacagccgcc tagcatttca tcacgtggcc cgagagctgc   5400
atccggagta cttcaagaac tgctgatatc gagcttgcta caagggactt tccgctgggg   5460
actttccagg gaggcgtggc ctgggcggga ctggggagtg cgagccctc agatcctgca   5520
tataagcagc tgcttttgc ctgtactggg tctctctggt tagaccagat ctgagcctgg   5580
gagctctctg gctaactagg gaacccactg cttaagcctc aataaagctt gccttgagtg   5640
cttcaagtag tgtgtgcccg tctgttgtgt gactctggta actagagatc cctcagaccc   5700
tttttagtcag tgtggaaaat ctctagcagt agtagttcat gtcatcttat tattcagtat   5760
ttataacttg caaagaaatg aatatcagag agtgagagac cttgacattg ctagcgtttt   5820
accgtcgacc tctagctaga gcttggcgta atcatggtca tagctgtttc ctgtgtgaaa   5880
ttgttatccg ctcacaattc cacacaacat acgagccgga agcataaagt gtaaagcctg   5940
gggtgcctaa tgagtgagct aactcacatt aattgcgttg cgctcactgc ccgctttcca   6000
gtcgggaaac ctgtcgtgcc agctgcatta atgaatcggc caacgcgcgg ggagaggcgg   6060
tttgcgtatt gggcgctctt ccgcttcctc gctcactgac tcgctgcgct cggtcgttcg   6120
gctgcggcga gcggtatcag ctcactcaaa ggcggtaata cggttatcca cagaatcagg   6180
ggataacgca ggaaagaaca tgtgagcaaa aggccagcaa aaggccagga accgtaaaaa   6240
ggccgcgttg ctggcgtttt tccataggct ccgcccccct gacgagcatc acaaaaatcg   6300
acgctcaagt cagaggtggc gaaacccgac aggactataa agataccagg cgtttccccc   6360
tggaagctcc ctcgtgcgct ctcctgttcc gaccctgccg cttaccggat acctgtccgc   6420
ctttctccct tcgggaagcg tggcgctttc tcatagctca cgctgtaggt atctcagttc   6480
ggtgtaggtc gttcgctcca agctgggctg tgtgcacgaa ccccccgttc agcccgaccg   6540
ctgcgcctta tccggtaact atcgtcttga gtccaacccg gtaagacacg acttatcgcc   6600
actggcagca gccactggta acaggattag cagagcgagg tatgtaggcg gtgctacaga   6660
gttcttgaag tggtggccta actacggcta cactagaaga acagtatttg gtatctgcgc   6720
tctgctgaag ccagttacct tcggaaaaag agttggtagc tcttgatccg gcaaacaaac   6780
caccgctggt agcggtggtt tttttgtttg caagcagcag attacgcgca gaaaaaaagg   6840
atctcaagaa gatcctttga tcttttctac ggggtctgac gctcagtgga acgaaaactc   6900
acgttaaggg attttggtca tgagattatc aaaaaggatc ttcacctaga tccttttaaa   6960
ttaaaaatga agttttaaat caatctaaag tatatatgag taaacttggt ctgacagtta   7020
ccaatgctta atcagtgagg cacctatctc agcgatctgt ctatttcgtt catccatagt   7080
tgcctgactc cccgtcgtgt agataactac gatacgggag ggcttaccat ctggccccag   7140
tgctgcaatg ataccgcgag acccacgctc accggctcca gatttatcag caataaacca   7200
gccagccgga agggccgagc gcagaagtgg tcctgcaact ttatccgcct ccatccagtc   7260
tattaattgt tgccgggaag ctagagtaag tagttcgcca gttaatagtt tgcgcaacgt   7320
tgttgccatt gctacaggca tcgtggtgtc acgctcgtcg tttggtatgg cttcattcag   7380
ctccggttcc caacgatcaa ggcgagttac atgatccccc atgttgtgca aaaaagcggt   7440
tagctccttc ggtcctccga tcgttgtcag aagtaagttg gccgcagtgt tatcactcat   7500
ggttatggca gcactgcata attctcttac tgtcatgcca tccgtaagat gcttttctgt   7560
gactggtgag tactcaacca agtcattctg agaatagtgt atgcggcgac cgagttgctc   7620
ttgcccggcg tcaatacggg ataataccgc gccacatagc agaactttaa aagtgctcat   7680
cattggaaaa cgttcttcgg ggcgaaaact ctcaaggatc ttaccgctgt tgagatccag   7740
```

-continued

```
ttcgatgtaa cccactcgtg cacccaactg atcttcagca tcttttactt tcaccagcgt   7800
ttctgggtga gcaaaaacag gaaggcaaaa tgccgcaaaa aagggaataa gggcgacacg   7860
gaaatgttga atactcatac tcttcctttt tcaatattat tgaagcattt atcagggtta   7920
ttgtctcatg agcggataca tatttgaatg tatttagaaa aataaacaaa taggggttcc   7980
gcgcacattt ccccgaaaag tgccacctga cgtcgacgga tcgggagatc aacttgttta   8040
ttgcagctta taatggttac aaataaagca atagcatcac aaatttcaca aataaagcat   8100
tttttttcact gcattctagt tgtggtttgt ccaaactcat caatgtatct tatcatgtct   8160
ggatcaactg gataactcaa gctaaccaaa atcatcccaa acttcccacc ccataccct   8220
ttaccactgc caattacctg tggtttcatt tactctaaac ctgtgattcc tctgaattat   8280
tttcattta aagaaattgt atttgttaaa tatgtactac aaacttagta gttttaaag   8340
aaattgtatt tgttaaatat gtactacaaa cttagtagt                        8379
```

SEQ ID NO: 48              moltype = DNA   length = 11272
FEATURE                    Location/Qualifiers
misc_feature               1..11272
                           note = vector
source                     1..11272
                           mol_type = other DNA
                           organism = synthetic construct
SEQUENCE: 48

```
tggaagggct aattcactcc caaagaagac aagatatcct tgatctgtgg atctaccaca   60
cacaaggcta cttccctgat tagcagaact acacaccagg gccaggggtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgaccccgg   240
agagagaagt gttagagtgg aggtttgaca gccgcctagc atttcatcac gtggcccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agacccttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaataaa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaacccg agggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aagggggggat tggggggtac agtgcagggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatggccct cacaaaggaa   2280
caataacagg aaaccatccc aggggggaagt gggccagggc cagctggaaa acctgaaggg   2340
gcgtacgcgg tctagaattc ctgcgaggcc cactagtctc ccaggcatga ctccaacat   2400
gcatcccatg ggatttgggg ttccccagat ctggggcttg taggcctgac tctcccctgt   2460
gcacgtct catacacgca tgcgtgcacc cattgcctgc cccgccctt gcacaggag   2520
tcagcaggga ggactgggtt atgccctgct tatcagcagc ttcccagctt cctctgcctg   2580
gattcttaga ggcctggggt cctagaacga gctggtgcac ggcgcttccc aaagatctct   2640
cagataatga gaggaaatgc agtcatcagt ttgcagaagg ctaggattc tgggcccatag   2700
ctcagacctg cgcccaccat ctccctccag gcagcccttg gctggtccct gcgagccgt   2760
ggagactgcc agtcagcgct gctggatctc gggctcgagg ccaccatgca gatcgagctg   2820
tccacctgct tttttctgtg cctgctgcgg ttctgcttca gcgcgcacccg gcggtactac   2880
ctgggcgccg tggagctgtc ctgggactac atgcagagcg acctgggcga gctgcccgtg   2940
gacgccggt tccccccccag agtgcccaag agcttcccct tcaacaccag cgtggtgtac   3000
aagaaaaccc tgttcgtgga gttcaccgac cacctgttca atatcgccaa gcccaggccc   3060
ccctggatgg gcctgctggg ccccaccatc caggccgagt gtacgacac cgtggtgatc   3120
accctgaaga acatggccag ccacccgtg agcctgcacg ccgtggggcgt gagctactgg   3180
aaggcagcg agggcgccga gtacgacgac cagaagaccg agggcgagaa agaagatgac   3240
aaggtgttcc ctggcggcag ccacacctac gtgtggcagg tgctgaaaga aaacggcccc   3300
atggcctccg accccctgtg cctgacctac agctacctga gccacgtgga cctggtgaag   3360
gacctgaaca gcggcctgat cggcgctctg ctcgtctgcc gggagggcag cctgcccaaa   3420
gagaaaaccc agaccctgca caagttcatc ctgctgttcg ccgtgttcga cgagggcaag   3480
agctggcaca gcgagacaaa gaacagcctg atgcaggacc gggacgccgc ctctgccaga   3540
```

-continued

```
gcctggccca agatgcacac cgtgaacggc tacgtgaaca gaagcctgcc cggcctgatt 3600
ggctgccacc ggaagagcgt gtactggcac gtgatcggca tgggcaccac acccgaggtg 3660
cacagcatct ttctggaagg gcacaccttt ctggtccgga accaccggca ggccagcctg 3720
gaaatcagcc ctatcacctt cctgaccgcc cagacactgc tgatggacct gggccagttc 3780
ctgctgtttt gccacatcag ctctcaccag cacgacggca tggaagccta cgtgaaggtg 3840
gactcttgcc ccgaggaacc ccagctgcgg atgaagaaca acgaggaagc cgaggactac 3900
gacgacgacc tgaccgacag cgagatggac gtggtcggt tcgacgacga caacagcccc 3960
agcttcatcc agatcagaag cgtggccaag aagcacccca agacctgggt gcactatatc 4020
gccgccgagg aagaggactg ggactacgcc ccctggtgc tggcccccga cgacagaagc 4080
tacaagagcc agtacctgaa caatgcccc cagcgggatcg gccggaagta caagaaagtg 4140
cggttcatgg cctacaccga cgagacattc aagacccggg aggccatcca gcacgagagc 4200
ggcatcctgg gcccctgct gtacggcgaa gtgggcgaca cactgctgat catcttcaag 4260
aaccaggcta gccggcccta caacatctac ccccacggca tcaccgacgt gcggcccctg 4320
tacagcaggc ggctgcccaa gggcgtgaag cacctgaagg acttccccat cctgcccggc 4380
gagatcttca agtacaagtg gaccgtgacc gtggaggacg gccccaccaa gagcgacccc 4440
agatgcctga cccggtacta cagcagcttc gtgaacatgg aacgggacct ggcctccggg 4500
ctgatcggac ctctgctgat ctgctacaaa gaaagcgtgg accagcgggg caaccagatc 4560
atgagcgaca agcggaacgt gatcctgttc agcgtgttcg atgagaaccg gtcctggtat 4620
ctgaccgaga acatccagcg gtttctgccc aaccctgccg gcgtgcagct ggaagatccc 4680
gagttccagg ccagcaacat catgcactcc atcaatggct acgtgttcga ctctctgcag 4740
ctctccgtgt gtctgcacga ggtggcctac tggtacatcc tgagcatcgg cgcccagacc 4800
gacttcctga gcgtgttctt cagcggctac accttcaagc acaagatggt gtacgaggac 4860
accctgaccc tgttcccttt cagcggcgag acagtgttca tgagcatgga aaaccccggc 4920
ctgtggattc tgggctgcca caacagcgac ttccggaacc ggggcatgac cgccctgctg 4980
aaggtgtcca gctgcgacaa gaacaccggc gactactacg aggacagcta cgaggatatc 5040
agcgcctacc tgctgtccaa gaacaacgcc atcgaaccc gacgcttcag ccagaacccc 5100
cccgtgctga cgcgtcacca gcgggagatc acccggacaa ccctgcagtc cgaccaggaa 5160
gagatcgatt acgacgacac catcagccgtg gagatgaaga aagaggattt cgatatctac 5220
gacgaggacg agaaccagag ccccagaagc ttccagaaga aaacccggca ctacttcatt 5280
gccgccggg agaggctgtg ggactacggc atgagttcta gcccccacgt gctgcggaac 5340
cgggcccaga gcggcagcgt gccccagttc aagaaagtgg tgttccagga attcacagac 5400
ggcagcttca cccagcctct gtatagaggc gagctgaacg agcacctggg gctgctgggg 5460
ccctacatca gggccgaagt ggaggacaac atcatggtga ccttccggaa tcaggccagc 5520
agaccctact ccttctacag cagcctgatc agctacgaag aggaccagcg gcagggcgcc 5580
gaacccggga agaacttcgt gaagcccaac gaaaccaaga cctacttctg gaaagtgcag 5640
caccacatgg cccccaccaa ggacgagttc gactgcaagg cctgggccta cttcagcgac 5700
gtggatctgg aaaaggacgt gcactctgga ctgattggcc cactcctggt ctgccacact 5760
aacaccctca accccgccca cggccgccag gtgaccgtgc aggaattcgc cctgttcttc 5820
accatcttcg acgagacaaa gtcctggtac ttcaccgaga atatggaacg gaactgcaga 5880
gcccctgca acatccagat ggaagatcct accttcaaag agaactaccg gttccacgcc 5940
atcaacggct acatcatgga caccctgcct ggcctggtga tggcccagga ccagagaatc 6000
cggtggtatc tgctgtccat gggcagcaac gagaatatcc acagcatcca cttcagcggc 6060
cacgtgttca ccgtgcggaa gaaagaagag tacaagatgg ccctgtacaa cctgtacccc 6120
ggcgtgttcg agacagtgga gatgctgccc agcaaggccg gcatctggcg ggtggagtgt 6180
ctgatcggcg agcacctgca cgctggcatg agcacctgt ttctggtgta cagcaacaag 6240
tgccagaccc cactgggcat ggcctctggc cacatccggg acttccagat caccgcctcc 6300
ggccagtacg gccagtgggc ccccaagctg gccagactgc actacagcgg cagcatcaac 6360
gcctggtcca ccaaagagcc cttcagctgg atcaaggtgg acctgctggc ccctatgatc 6420
atccacggca ttaagaccca ggggcccagg cagaagttca gcagcctgta catcagccag 6480
ttcatcatca tgtacagcct ggacggcaag aagtggcaga cctaccgggg caacagcacc 6540
ggcaccctga tggtgttctt cggcaatgtg gacagcagcg gcatcaagca caatcatctc 6600
aacccccca tcattgcccg gtacatccgg ctgcaccca cccactacag cattagatcc 6660
acactgagaa tggaactgat gggctgcgac ctgaactcct gcagcatgcc tctgggcatg 6720
gaaagcaagg ccatcagcga cgcccagatc acagccagca gctacttcac caacatgttc 6780
gccacctggt cccctccaa ggccaggctg cacctgcagg gcggtccaa cgcctggcgg 6840
cctcaggtca acaaccccaa agaatggctg caggtggact ttcagaaaac catgaaggtg 6900
accggcgtga ccacccaggg cgtgaaaagc ctgctgacca gcatgtacgt gaaagagttt 6960
ctgatcagca gctctcagga tggccaccag tggacctgt tctttcagaa cggcaaggtg 7020
aaagtgttcc agggcaacca ggactccttc accccgtgg tgaactccct ggacccccca 7080
ctgctgaccc gctacctgag aatccacccc cagtcttcgg tgcaccagat cgccctcagg 7140
atggaagtcc tgggatgtga ggcccaggat ctgtactgat gacgtctgga caatcaacc 7200
tctggattac aaaatttgtg aaagattgac tggtattctt aactatgttg ctccttttac 7260
gctatgtgga tacgctgctt taatgccttt gtatcatgct attgcttccc gtatggcttt 7320
cattttctcc tccttgtata aatcctggtt gctgtctctt tatgaggagt tgtggcccgt 7380
tgtcaggcaa cgtggcgtgg tgtgcactgt gtttgctgac gcaacccca ctggttgggg 7440
cattgccacc acctgtcagc tcctttccgg gactttcgct ttccctcc ctattgccac 7500
ggcggaactc atcgccgcct gccttgcccg ctgctggaca ggggctcggc tgttgggcac 7560
tgacaattcc gtggtgttgt cggggaagct gacgtccttt ccatggctgc tcgcctgtgt 7620
tgccacctgg attctgcgcg ggacgtcctt ctgctacgtc cctcggccc tcaatccac 7680
ggaccttcct tcccgcggcc tgctgccggc tctgcggcct cttccgcgtc ttcgccttcg 7740
ccctcagacg agtcggatct cccttttggc cgcctccccg cctggaatta ttctctgcagt 7800
cgagacctag aaaaacatgg agcaatcaca agtagcaata cagcagctac caatgctgat 7860
tgtgcctggc tagaagcaca agaggaggag gaggtgggt ttccagtcac acctcaggta 7920
cctttaagac caatgactta caaggcagct gtagatctta gccactttt aaaagaaaag 7980
aggggactgg aagggctaat tcactcccaa cgaagacaag atatccttga tctgtggatc 8040
taccacacac aaggctactt ccctgattag cagaactaca caccagggcc aggggtcaga 8100
tatccactga cctttggatg gtgctacaag ctagtaccag ttgagccaga taaggtagaa 8160
gaggccaata aaggagagaa caccagcttg ttacaccctg tgagcctgca tgggatggat 8220
gacccggaga gagaagtgtt agagtggagg tttgacagcc gcctagcatt tcatcacgtg 8280
```

-continued

```
gcccgagagc tgcatccgga gtacttcaag aactgctgat atcgagcttg ctacaaggga    8340
ctttccgctg gggactttcc agggaggcgt ggcctgggcg ggactgggga gtggcgagcc    8400
ctcagatcct gcatataagc agctgctttt tgcctgtact gggtctctct ggttagacca    8460
gatctgagcc tgggagctct ctggctaact agggaaccca ctgcttaagc ctcaataaag    8520
cttgccttga gtgcttcaag tagtgtgtgc ccgtctgttg tgtgactctg gtaactagag    8580
atccctcaga cccttttagt cagtgtggaa aatctctagc agtagtagtt catgtcatct    8640
tattattcag tatttataac ttgcaaagaa atgaatatca gagagtgaga ggccttgaca    8700
ttgctagcgt tttaccgtcg acctctagct agagcttggc gtaatcatgg tcatagctgt    8760
ttcctgtgtg aaattgttat ccgctcacaa ttccacacaa catacgagcc ggaagcataa    8820
agtgtaaagc ctggggtgcc taatgagtga gctaactcac attaattgcg ttgcgctcac    8880
tgcccgcttt ccagtcggga aacctgtcgt gccagctgca ttaatgaatc ggccaacgcg    8940
cggggagagg cggtttgcgt attgggcgct cttccgcttc ctcgctcact gactcgctgc    9000
gctcggtcgt tcggctgcgg cgagcggtat cagctcactc aaaggcggta atacggttat    9060
ccacagaatc aggggataac gcaggaaaga acatgtgagc aaaaggccag caaaaggcca    9120
ggaaccgtaa aaaggccgcg ttgctggcgt ttttccatag gctccgcccc cctgacgagc    9180
atcacaaaaa tcgacgctca agtcagaggt ggcgaaaccc gacaggacta taaagatacc    9240
aggcgtttcc ccctggaagc tccctcgtgc gctctcctgt tccgaccctg ccgcttaccg    9300
gatacctgtc cgcctttctc ccttcgggaa gcgtggcgct ttctcatagc tcacgctgta    9360
ggtatctcag ttcggtgtag gtcgttcgct ccaagctggg ctgtgtgcac gaaccccccg    9420
ttcagcccga ccgctgcgcc ttatccggta actatcgtct tgagtccaac ccggtaagac    9480
acgacttatc gccactggca gcagccactg gtaacaggat tagcagagcg aggtatgtag    9540
gcggtgctac agagttcttg aagtggtggc ctaactacgg ctacactaga agaacagtat    9600
ttggtatctg cgctctgctg aagccagtta ccttcggaaa aagagttggt agctcttgat    9660
ccggcaaaca aaccaccgct ggtagcggtg gttttttgt ttgcaagcag cagattacgc    9720
gcagaaaaaa aggatctcaa gaagatcctt tgatcttttc tacggggtct gacgctcagt    9780
ggaacgaaaa ctcacgttaa gggattttgg tcatgagatt atcaaaaagg atcttcacct    9840
agatcctttt aaattaaaaa tgaagtttta aatcaatcta agtatatat gagtaaactt    9900
ggtctgacag ttaccaatgc ttaatcagtg aggcacctat ctcagcgatc tgtctatttc    9960
gttcatccat agttgcctga ctccccgtcg tgtagataac tacgatacgg gagggcttac   10020
catctggccc cagtgctgca atgataccgc gagacccacg ctcaccggct ccagatttat   10080
cagcaataaa ccagccagcc ggaagggccg agcgcagaag tggtcctgca actttatccg   10140
cctccatcca gtctattaat tgttgccggg aagctagagt aagtagttcg ccagttaata   10200
gtttgcgcaa cgttgttgcc attgctacag gcatcgtggt gtcacgctcg tcgtttggta   10260
tggcttcatt cagctccggt tcccaacgat caaggcgagt tacatgatcc cccatgttgt   10320
gcaaaaaagc ggttagctcc ttcggtcctc cgatcgttgt cagaagtaag ttggccgcag   10380
tgttatcact catggttatg gcagcactgc ataattctct tactgtcatg ccatccgtaa   10440
gatgcttttc tgtgactggt gagtactcaa ccaagtcatt ctgagaatag tgtatgcggc   10500
gaccgagttg ctcttgcccg gcgtcaatac gggataatac cgcgccacat agcagaactt   10560
taaaagtgct catcattgga aaacgttctt cggggcgaaa actctcaagg atcttaccgc   10620
tgttgagatc cagttcgatg taacccactc gtgcacccaa ctgatcttca gcatctttta   10680
ctttcaccag cgtttctggg tgagcaaaaa caggaaggca aaatgccgca aaaaagggaa   10740
taagggcgac acggaaatgt tgaatactca tactcttcct ttttcaatat tattgaagca   10800
tttatcaggg ttattgtctc atgagcggat acatatttga atgtatttag aaaaataaac   10860
aaataggggt tccgcgcaca tttccccgaa aagtgccacc tgacgtcgac ggatcgggag   10920
atcaacttgt ttattgcagc ttataatggt tacaaataaa gcaatagcat cacaaatttc   10980
acaaataaag cattttttc actgcattct agttgtggtt tgtccaaact catcaatgta   11040
tcttatcatg tctggatcaa ctggataact caagctaact aaaatcatcc caaacttccc   11100
accccatacc ctattaccac tgccaattac ctgtggtttc atttactcta aacctgtgat   11160
tcctctgaat tattttcatt ttaaagaaat tgtatttgtt aaatatgtac tacaaactta   11220
gtagtttta aagaaattgt atttgttaaa tatgtactac aaacttagta gt           11272
```

SEQ ID NO: 49 moltype = DNA length = 10725
FEATURE Location/Qualifiers
misc_feature 1..10725
  note = Vector
source 1..10725
  mol_type = other DNA
  organism = synthetic construct
SEQUENCE: 49

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agacccttt agtcagtgtg gaaaatctct agcagtggcg    420
cccgaacagg gacctgaaag cgaaaggaa accagagctc tctcgacgca ggactcggct    480
tgctgaagcg cgcacggcaa gaggcgaggg gcggcgactg gtgagtacgc caaaaatttt    540
gactagcgga ggctagaagg agagatggg tgcgcagagg tcagtatta agcgggggag    600
aattagatcg cgatgggaaa aaattcggtt aaggccaggg ggaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaaaatag aaaacaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
```

-continued

```
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatccgaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggttaacttt   1800
taaaagaaaa gggggggattg gggggtacag tgcaggggaa agaatagtag acataatagc   1860
aacagacata caaactaaag aattacaaaa acaaattaca aaaattcaaa attttatcga   1920
tagcgcggcc gcttcgaacg cgcgcgatgc atcatatgcg tacgcggtct agaattcctg   1980
cagggcccac tagtctccca ggcatgactc caacaatgca tcccatggga tttggggttc   2040
cccagatctg gggcttgtag gcctgactct cccctgtgca cacgtctcat acacgcatgc   2100
gtgcacccat tgcctgcccc gccccttgca cagggagtca gcagggagga ctgggttatg   2160
ccctgcttat cagcagcttc ccagcttcct ctgcctggat tcttagaggc ctggggtcct   2220
agaacgagct ggtgcacgtg gcttcccaaa gatctctcag ataatgagag gaaatgcagt   2280
catcagtttg cagaaggcta gggattctgg gccatagctc agacctgcgc ccaccatctc   2340
cctccaggca gcccttggct ggtccctgcg agcccgtgga gactgccagt cagcgctgct   2400
ggatctcggg ctcgaggcca ccatgcagat cgagctgtcc acctgctttt ttctgtgcct   2460
gctgcgggttc tgcttcagcg ccacccggcg gtactacctg gggcgcgtgg agctgtcctg   2520
ggactacatg cagagcgacc tgggcgagct gcccgtggac gcccggttcc ccccagagt   2580
gcccaagagc ttccccttca acaccagcgt ggtgtacaag aaaaccctgt tcgtggagtt   2640
caccgaccac ctgttcaata tcgccaagcc caggcccccc tggatgggcc tgctgggccc   2700
caccatccag gccgaggtgt agacaccgt ggtgatcacc ctgaagaaca tggccagcca   2760
ccccgtgagc ctgcacgccg tgggcgtgag ctactggaag gccagcgagg cgcgccgagta   2820
cgacgaccag accagccagc gggagaaaga agatgacaag gtgttccctg gcggcagcca   2880
cacctacgtg tggcaggtgc tgaaagaaaa cggccccatg gcctccgacc ccctgtgcct   2940
gacctacagc tacctgagcc acgtggacct ggtgaaggac ctgaacagcg gcctgatcgg   3000
cgctctgctc gtctgccggg agggcagcct ggccaaagag aaaacccaga ccctgcacaa   3060
gttcatcctg ctgttcgccg tgttcgacga gggcaagagc tggcacacg agacaaagaa   3120
cagcctgatg caggaccggg acgccgcctc tgccagagcc tggcccaaga tgcacaccgt   3180
gaacggctac gtgaacagaa gcctgcccgg cctgattggc tgccaccgga agagcgtgca   3240
ctggcacgtg atcggcatgg gcaccacacc cgaggtgcac agcatctttc tggaagggca   3300
caccttctg gtccggaacc accggcaggc cagcctggaa atcagcccta tcaccttcct   3360
gaccgcccag acactgctga tggacctggg ccagttcctg ctgttttgcc acatcagctc   3420
tcaccagcac gacggcatgg aagcctacg gaaggtggac tcttgccccg aggaaccca   3480
gctgcgggatg aagaacaacg aggaagccga ggactacgac gacgacctga ccgacagcga   3540
gatggacgtg gtgcggttcg acgacgacaa cagcccagc ttcatccaga tcagaagcgt   3600
ggccaagaag caccccaaga cctgggtgca ctatatcgcc gccgaggaag aggactggga   3660
ctacgccccc ctggtgctgg cccccgacga cagaagctac aagagccagt acctgaacaa   3720
tggccccag cggatcggcc ggaagtacaa gaaagtgcgg ttcatggcct acaccgacga   3780
gacattcaag acccgggagg ccatccagca cgagagcggc atcctgggcc cctgctgta   3840
cggcgaagtg ggcgacacac tgctgatcat cttcaagaac caggctagcc ggccctacaa   3900
catctacccc cacggcatca ccgacgtgcg gcccctgtac agcaggcggc tgcccaaggg   3960
cgtgaagcac ctgaaggact tccccatcct gcccggcgag atcttcaagt acaagtggac   4020
cgtgaccgtg gaggacggcc ccaccaagag cgaccccaga tgcctgaccc ggtactacag   4080
cagcttcgtg aacatggaac gggacctggc ctccgggctg atcggacctc tgctgatctg   4140
ctacaaagaa agcgtggacc agcggggcaa ccagatcatg agcgacaagc ggaacgtgat   4200
cctgttcagc gtgttcgatg agaaccggtc ctggtatctg accgagaaca tccagcggtt   4260
tctgcccaac cctgccggcg tgcagctgga agatcccgag ttccaggcca gcaacatcat   4320
gcactccatc aatggctacg tgttcgactc tctgcagctc tccgtgtgtc tgcacgaggt   4380
ggcctactgg tacatcctga gcatcggcgc ccagaccgac ttcctgagcg tgttcttcag   4440
cggctacacc ttcaagcaca agatggtgta cgaggacacc ctgacccgt tccctttcag   4500
cggcgagaca gtgttcatga gcatggaaaa ccccggcctg tggattctgg gctgccacaa   4560
cagcgacttc cggaaccggg gcatgaccgc cctgctgaag gtgtccagct gcgacaagaa   4620
caccggcgac tactacgagg acagctacga ggatatcagc gcctacctgc tgtccaagaa   4680
caacgccatc gaacccggga gcttcagcca gaacccccc gtgctgacgc gtcaccagcg   4740
gggagatcacc cggacaaccc tgcagtccga ccaggaagag atcgattacg acgacaccat   4800
cagcgtggag atgaagaaag aggatttcga tatctacgac gaggacgaga accagagccc   4860
cagaagcttc cagaagaaaa cccggcacta cttcattgcc gccgtggaga ggctgtggga   4920
ctacggcatg agttctagcc cccacgtgct gcggaaccgg gcccagagcg gcagcgtgcc   4980
ccagttcaag aaagtggtgt tccaggaatt cacagacggc agcttcaccc agcctctgta   5040
tagaggcgag ctgaacgagc acctgggggct gctggggccc tacatcaggg ccgaagtgga   5100
ggacaacatc atggtgacct tccggaatca ggccagcaga ccctactcct tctacagcag   5160
cctgatcagc tacgaagagg accagcggca gggcgccgaa ccccggaaga acttcgtgaa   5220
gcccaacgaa accaagacct acttctggaa agtgcagcac cacatggccc ccaccaagga   5280
cgagttcgac tgcaaggcct gggcctactt cagcgacgtg gatctggaaa aggacgtgca   5340
ctctggactg attggcccac tcctggtctg ccacactaac accctcaacc ccgcccacgg   5400
ccgccaggtg accgtgcagg aattcgccct gttcttcacc atcttcgacg agacaaagtc   5460
ctggtacttc accgagaata tggaacggaa ctgcagagcc ccctgcaaca tccagatgga   5520
agatcctacc ttcaaagaga actaccggtt ccacgccatc aacggctaca tcatggacac   5580
cctgcctggc ctggtgatgg cccaggacca gagaatccgg tggtatctgc tgtccatggg   5640
cagcaacgag aatatccaca gcatccactt cagcggccac gtgttcaccg tgcggaagaa   5700
agaagagtac aagatggccc tgtacaacct gtaccccggc gtgttcgaga cagtggagat   5760
gctgcccagc aaggccggca tctggcgggt ggagtgtctg atcggcgagc acctgcacgc   5820
tggcatgagc accctgtttc tggtgtacag caacaagtgc cagacccccac tgggcatggc   5880
ctctggccac atccgggact ccagatcac cgcctccggc cagtacggcc agtgggcccc   5940
```

-continued

```
caagctggcc agactgcact acagcggcag catcaacgcc tggtccacca aagagccctt   6000
cagctggatc aaggtggacc tgctggcccc tatgatcatc cacggcatta agacccaggg   6060
cgccaggcag aagttcagca gcctgtacat cagccagttc atcatcatgt acagcctgga   6120
cggcaagaag tggcagacct accggggcaa cagcaccggc accctgatgg tgttcttcgg   6180
caatgtggac agcagcggca tcaagcacaa catcttcaac ccccccatca ttgcccggta   6240
catccggctg caccccaccc actacagcat tagatccaca ctgagaatgg aactgatggc   6300
ctgcgacctg aactcctgca gcatgcctct gggcatggaa agcaaggcca tcagcgacgc   6360
ccagatcaca gccagcagct acttcaccaa catgttcgcc acctggtccc cctccaaggc   6420
caggctgcac ctgcagggcc ggtccaacgc ctggcggcct caggtcaaca accccaaaga   6480
atggctgcag gtggactttc agaaaaccat gaaggtgacc ggcgtgacca cccagggcgt   6540
gaaaagcctg ctgaccagca tgtacgtgaa agagtttctg atcagcagct ctcaggatgg   6600
ccaccagtgg accctgttct ttcagaacgg caaggtgaaa gtgttccagg gcaaccagga   6660
ctccttcacc cccgtggtga actccctgga cccccccctg ctgacccgct acctgagaat   6720
ccaccccag tcttgggtgc accagatcgc cctcaggatg gaagtcctgg gatgtgaggc   6780
ccaggatctg tactgatgac gtctggaacg cgtcgacaat caacctctgg attacaaaat   6840
ttgtgaaaga ttgactggta ttcttaacta tgttgctcct tttacgctat gtggatacgc   6900
tgctttaatg cctttgtatc atgctattgc ttcccgtatg gctttcattt tctcctcctt   6960
gtataaatcc tggttgctgt ctctttatga ggagttgtgg cccgttgtca ggcaacgtgg   7020
cgtggtgtgc actgtgtttg ctgacgcaac ccccactggt tggggcattg ccaccacctg   7080
tcagctcctt tccgggactt tcgctttccc cctccctatt gccacggcgg aactcatcgc   7140
cgcctgcctt gcccgctgct ggacagggggc tcggctgttg ggcactgaca attccgtggt   7200
gttgtcgggg aaatcatcgt cctttccttg gctgctccgc tgtgttgcca cctggattct   7260
gcgcgggacg tccttctgct acgtcccttc ggccctcaat ccagcggacc ttccttcccg   7320
cggcctgctg ccggctctgc ggcctcttcc gcgtcttcgc cttcgccctc agacgagtcg   7380
gatctcccctt tgggccgcct ccccgcctgg tacctttaag accaatgact tacaaggcag   7440
ctgtagatct tagccacttt ttaaaagaaa aggggggact ggaagggcta attcactccc   7500
aacgaaaata agatctgctt tttgcttgta ctgggtctct ctggttagac cagatctgag   7560
cctgggagct ctctggctaa ctagggaacc cactgcttaa gcctcaataa agcttgcctt   7620
gagtgcttca agtagtgtgt gcccgtctgt tgtgtgactc tggtaactag agatccctca   7680
gacccttttta gtcagtgtgg aaaatctcta gcagtagtag ttcatgtcat cttattattc   7740
agtatttata acttgcaaag aaatgaatat cagagagtga gaggaacttg tttattgcag   7800
cttataatgg ttacaaataa agcaatagca tcacaaattt cacaaataaa gcattttttt   7860
cactgcattc tagttgtggt ttgtccaaac tcatcaatgt atcttatcat gtctggctct   7920
agctatcccg cccctaactc cgcccagttc cgcccattct ccgccccatg gctgactaat   7980
tttttttatt tatgcagagg ccgaggccgc ctcggcctct gagctattcc agaagtagtg   8040
aggaggcttt tttggaggcc tagacttttg cagagacggc ccaaattcgt aatcatggtc   8100
atagctgttt cctgtgtgaa attgttatcc gctcacaatt ccacacaaca tacgagccgg   8160
aagcataaag tgtaaagcct ggggtgccta atgagtgagc taactcacat taattgcgtt   8220
gcgctcactg cccgctttcc agtcgggaaa cctgtcgtgc cagctgcatt aatgaatcgg   8280
ccaacgcgcg gggagaggcg gtttgcgtat tgggcgctct tccgcttcct cgctcactga   8340
ctcgctgcgc tcggtcgttc ggctgcggcg agcggtatca gctcactcaa aggcggtaat   8400
acggttatcc acagaatcag gggataacgc aggaaagaac atgtgagcaa aaggccagca   8460
aaaggccagg aaccgtaaaa aggccgcgtt gctggcgttt ttccataggc tccgcccccc   8520
tgacgagcat cacaaaaatc gacgctcaag tcagaggtgg cgaaacccga caggactata   8580
aagataccag gcgtttcccc ctggaagctc cctcgtgcgc tctcctgttc cgaccctgcc   8640
gcttaccgga tacctgtccg cctttctccc ttcgggaagc gtggcgcttt ctcatagctc   8700
acgctgtagg tatctcagtt cggtgtaggt cgttcgctcc aagctgggct gtgtgcacga   8760
acccccgtt cagcccgacc gctgcgcctt atccggtaac tatcgtcttg agtccaaccc   8820
ggtaagacac gacttatcgc cactggcagc agccactggt aacaggatta gcagagcgag   8880
gtatgtaggc ggtgctacag agttcttgaa gtggtggcct aactacggct acactagaag   8940
gacagtattt ggtatctgcg ctctgctgaa gccagttacc ttcggaaaaa gagttggtag   9000
ctcttgatcc ggcaaacaaa ccaccgctgg tagcggtggt ttttttgttt gcaagcagca   9060
gattacgcgc agaaaaaaag gatctcaaga agatcctttg atcttttcta cggggtctga   9120
cgctcagtgg aacgaaaact cacgttaagg gattttggtc atgagattat caaaaaggat   9180
cttcacctag atccttttaa attaaaaatg aagttttaaa tcaatctaaa gtatatatga   9240
gtaaacttgg tctgacagtt accaatgctt aatcagtgag gcacctatct cagcgatctg   9300
tctatttcgt tcatccatag ttgcctgact ccccgtcgtg tagataacta cgatacggga   9360
gggcttacca tctggcccca gtgctgcaat gataccgcga cccacgct caccggctcc   9420
agatttatca gcaataaacc agccagccgg aagggccgag cgcagaagtg gtcctgcaac   9480
tttatccgcc tccatccagt ctattaattg ttgccgggaa gctagagtaa gtagttcgcc   9540
agttaatagt ttgcgcaacg ttgttgccat tgctacaggc atcgtggtgt cacgctcgtc   9600
gtttggtatg gcttcattca gctccggttc ccaacgatca aggcgagtta catgatcccc   9660
catgttgtgc aaaaaagcgg ttagctcctt cggtcctccg atcgttgtca gaagtaagtt   9720
ggccgcagtg ttatcactca tggttatggc agcactgcat aattctctta ctgtcatgcc   9780
atccgtaaga tgcttttctg tgactggtga gtactcaacc aagtcattct gagaatagtg   9840
tatgcggcga ccgagttgct cttgcccggc gtcaatacgg gataataccg cgccacatag   9900
cagaacttta aaagtgctca tcattggaaa acgttcttcg gggcgaaaac tctcaaggat   9960
cttaccgctg ttgagatcca gttcgatgta acccactcgt gcacccaact gatcttcagc   10020
atcttttact ttcaccagcg tttctgggtg agcaaaaaca ggaaggcaaa atgccgcaaa   10080
aaagggaata agggcgacac ggaaatgttg aatactcata ctcttccttt ttcaatatta   10140
ttgaagcatt tatcagggtt attgtctcat gagcggatac atatttgaat gtatttagaa   10200
aaataaacaa atagggggttc cgcgcacatt ccccgaaaa gtgccacctg acgtctaaga   10260
aaccattatt atcatgacat taacctataa aaataggcgt atcacgaggc cctttcgtct   10320
cgcgcgtttc ggtgatgacg gtgaaaacct ctgacacatg cagctcccgg agacggtcac   10380
agcttgtctg taagcggatg ccgggagcag acaagcccgt cagggcgcgt cagcgggtgt   10440
tggcgggtgt cggggctggc ttaactatgc ggcatcagag cagattgtac tgagagtgca   10500
ccatatatgc ggtgtgaaat accgcacaga tgcgtaagga gaaaataccg catcaggcgc   10560
cattcgccat tcaggctgcg caactgttgg gaagggcgat cggtgcgggc ctcttcgcta   10620
ttacgccagc tggcgaaagg gggatgtgct gcaaggcgat taagttgggt aacgccaggg   10680
```

```
ttttcccagt cacgacgttg taaaacgacg gccagtgcca agctg                 10725

SEQ ID NO: 50            moltype = DNA   length = 10895
FEATURE                  Location/Qualifiers
misc_feature             1..10895
                         note = Vector
source                   1..10895
                         mol_type = other DNA
                         organism = synthetic construct
SEQUENCE: 50
acgcgtgtag tcttatgcaa tactcttgta gtcttgcaac atggtaacga tgagttagca    60
acatgcctta caaggagaga aaaagcaccg tgcatgccga ttggtggaag taaggtggta   120
cgatcgtgcc ttattaggaa ggcaacagac gggtctgaca tggattggac gaaccactga   180
attgccgcat tgcagagata ttgtatttaa gtgcctagct cgatacaata aacgggtctc   240
tctggttaga ccagatctga gcctgggagc tctctggcta actagggaac ccactgctta   300
agcctcaata aagcttgcct tgagtgcttc aagtagtgtg tgcccgtctg ttgtgtgact   360
ctggtaacta gagatccctc agacccttt agtcagtgtg gaaaatctct agcagtggcg   420
cccgaacagg gacctgaaag cgaaagggaa accagagctc tctcgacgca ggactcggct   480
tgctgaagcg cgcacggcaa gaggcgaggg gcggcgactg gtgagtacgc caaaaatttt   540
gactagcgga ggctagaagg agagagatgg gtgcgagagc gtcagtatta agcggggggag   600
aattagatcg cgatgggaaa aaattcggtt aaggccaggg ggaaagaaaa aatataaatt   660
aaaacatata gtatgggcaa gcagggagct agaacgattc gcagttaatc ctggcctgtt   720
agaaacatca gaaggctgta gacaaatact gggacagcta caaccatccc ttcagacagg   780
atcagaagaa cttagatcat tatataatac agtagcaacc ctctattgtg tgcatcaaag   840
gatagagata aaagacacca aggaagcttt agacaagata gaggaagagc aaaacaaaag   900
taagaccacc gcacagcaag cggccactga tcttcagacc tggaggagga gatatgaggg   960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agttttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggttaacttt  1800
taaaagaaaa gggggggattg gggggtacag tgcaggggaa agaatagtag acataatagc  1860
aacagacata caaactaaag aattacaaaa acaaattaca aaaattcaaa attttatcga  1920
tagcgcggcc gcttcgaacg cgcgcgatgc atcatatgag ggaactccct gtgctgggcc  1980
tacccagctg accccatcgc tggaaacaat gggggtcagg caacacttcc ccactctctc  2040
ccgccgggct gtgctcactt ccttcctgct ggctgcctga ggaagtgtcc ctgccctggg  2100
acagtctggc ctagcctttg tttccccgcg tacgcggtct agaattcctg cagggcccac  2160
tagtctccca ggcatgactc caacaatgca tcccatgggg tttggggtc cccagatctg  2220
gggcttgtag gcctgactct cccctgtgca cacgtctcat acacgcatgc gtgcacccat  2280
tgcctgcccc gcccccttgca cagggagtca gcagggagga ctgggttatg ccctgcttat  2340
cagcagcttc ccagcttcct ctgcctggat tcttagaggc ctgggtcct agaacgagct  2400
ggtgcacgtg gcttcccaaa gatctctcag ataatgaagg gaaatgcagt catcagtttg  2460
cagaaggcta gggattctgg gccatagctc agacctgcgc ccaccatctc cctccaggca  2520
gcccttggct ggtccctgcg agccgtgga gactgccagt cagcgctgct ggatctcggg  2580
ctcgaggcca ccatgcagat cgagctgtcc acctgctttt ttctgtgcct gctgcggttc  2640
tgcttcagcg ccaccggcg gtactacctg ggcgccgtgg agctgtcctg ggactacatg  2700
cagagcgacc tgggcgagct gcccgtggac gcccggttcc cccccagagt gcccaagagc  2760
ttcccccttca acaccagcgt ggtgtacaag aaaacccgt tcgtggagtt caccgaccac  2820
ctgttcaata tcgccaagcc caggcccccc tggatgggcc tgctgggccc caccatccag  2880
gccgaggtgt acgacaccgt ggtgatcacc ctgaagaaca tggccagcca ccccgtgagc  2940
ctgcacgccg tgggcgtgag ctactggaag gccagcgagg gcgccgagta cgacgaccag  3000
accagccagc gggagaaaga agatgacaag gtgttccctg gcgccagcca cacctacgtg  3060
tggcaggtgc tgaaagaaaa cggccccatg gcctccgacc ccctgtgcct gacctacagc  3120
tacctgagc acgtggacct ggtgaaggac ctgaacagcg gcctgatcgg cgctctgctc  3180
gtctgccggg agggcagcct ggccaaagag aaaacccaga ccctgcacaa gttcatcctg  3240
ctgttcgccg tgttcgacga gggcaagagc tggcacagcg agacaaagaa cagcctgatg  3300
caggaccggg acgccgcctc tgccagagcc tggcccaaga tgcacaccgt gaacggctac  3360
gtgaacagaa gcctgcccgg cctgattggc tgccaccgga agagcgtgta ctggcacgtg  3420
atcggcatgg gcaccacacc cgaggtgcac agcatctttc tggaagggca caccttttctg  3480
gtccggaacc accggcaggc cagcctggaa atcagcccta tcaccttcct gaccgcccag  3540
acactgctga tggaccctgg gccagttcctg ctgtttttgcc acatcagctc tcaccagcac  3600
gacggcatgg aagcctacgt gaaggtggac tcttgccccg aggaacccca gctgcgcatg  3660
aagaacaacg aggaagccga ggactacgac gacgacctga ccgacagcga gatggacgtg  3720
gtgcggttcg acgacgacaa cagccccagc ttcatccaga tcagaagcgt ggccaagaag  3780
cacccccaaga cctgggtgca ctatatctcgc gccgaggaag aggactggga ctacgccccc  3840
ctggtgctgg ccccgacga cagaagctac aagagccagt acctgaacaa tggccccag  3900
cggatcggcc ggaagtacaa gaaagtgcgg ttcatggcct acaccgacga gacattcaag  3960
acccgggagg ccatccagca cgagagcggc atcctgggcc cctgctgta cggcgaagtg  4020
ggcgacacac tgctgatcat cttcaagaac caggctagcc ggcctacaa catctacccc  4080
cacggcatca ccgacgtgcg gcccctgtac agcaggcggc tgcccaaggg cgtgaagcac  4140
```

-continued

```
ctgaaggact tccccatcct gcccggcgag atcttcaagt acaagtggac cgtgaccgtg   4200
gaggacggcc ccaccaagag cgaccccaga tgcctgaccc ggtactacag cagcttcgtg   4260
aacatggaac gggacctggc ctccgggctg atcggacctc tgctgatctg ctacaaagaa   4320
agcgtggacc agcgggggcaa ccagatcatg agcgacaagc ggaacgtgat cctgttcagc   4380
gtgttcgatg agaaccggtc ctggtatctg accgagaaca tccagcggtt tctgcccaac   4440
cctgccggcg tgcagctgga agatcccgag ttccaggcca gcaacatcat gcactccatc   4500
aatggctacg tgttcgactc tctgcagctc tccgtgtgtc tgcacgaggt ggcctactgg   4560
tacatcctga gcatcggccgc ccagaccgac ttcctgagcg tgttcttcag cggctacacc   4620
ttcaagcaca agatggtgta cgaggacgac ctgacctgt tccctttcag cggcgagaca   4680
gtgttcatga gcatggaaaa cccggccctg tggattctgg gctgccacaa cagcgacttc   4740
cggaaccggg gcatgaccgc cctgctgaag gtgtccagct gcgacaagaa caccggcgac   4800
tactacgagg acagctacga ggatatcagc gcctacctgc tgtccaagaa caacgccatc   4860
gaaccccgga gcttcagcca gaacccccc gtgctgacgc gtcaccagcg ggagatcacc   4920
cggacaaccc tgcagtccga ccaggaagag atcgattacg acgacaccat cagcgtggag   4980
atgaagaaag aggatttcga tatctacgac gaggacgaga accagagccc cagaagcttc   5040
cagaagaaaa cccggcacta cttcattgcc gccgtggaga ggctgtggga ctacggcatg   5100
agttctagcc cccacgtgct gcggaaccgg gcccagagcg gcagcgtgcc ccagttcaag   5160
aaagtggtgt tccaggaatt cacagacggc agcttcaccc agcctctgta tagaggcgag   5220
ctgaacgagc acctggggct gctggggccc tacatcaggg ccgaagtgga ggacaacatc   5280
atggtgacct tccggaatca ggccagcaga ccctactcct tctacagcag cctgatcagc   5340
tacgaagagg accagcggca gggcgccgaa ccccggaaga acttcgtgaa gcccaacgaa   5400
accaagacct acttctggaa agtgcagcac cacatggccc ccaccaagga cgagttcgac   5460
tgcaaggcct gggcctactt cagcgacgtg gatctgcgaaa aggacgtgca ctctggactg   5520
attggcccac tcctggtctg ccacactaac accctcaacc ccgccacgg ccgccaggtg   5580
accgtgcagg aattcgccct gttcttcacc atcttcgacg agacaaagtc ctggtacttc   5640
accgagaata tggaacggaa ctgcagagcc ccctgcaaca tccagatgga agatctacc   5700
ttcaaagaga actaccggtt ccacgccatc aacggctaca tcatggacac cctgcctggc   5760
ctggtgatgg cccaggacca gagaatccgg tggtatctgc tgtccatggg cagcaacgag   5820
aatatccaca gcatccactt cagcggccac gtgttcaccg tgcggaagaa agaagagtac   5880
aagatggccc tgtacaacct gtaccccggc gtgttcgaga cagtggagat gctgcccagc   5940
aaggccggca tctggcgggt gggagtgtctg atcggcgagc acctgcacgc tggcatgagc   6000
accctgtttc tggtgtacag caacaagtgc cagaccccac tgggcatggc ctctggccac   6060
atccgggact tccagatcac cgcctccggc cagtacggcc agtgggcccc caagctggcc   6120
agactgcact acagcggcag catcaacgcc tggtccacca aagagcctt cagctggatc   6180
aaggtggacc tgctggcccc tatgatcatc cacggcatta agacccaggg cgccaggcag   6240
aagttcagca gcctgtacat cagccagttc atcatcatgt acagcctgga cggcaagaag   6300
tggcagacct accggggcaa cagcaccggc accctgatgg tgttcttcgg caatgtggac   6360
agcagcggca tcaagcacaa catcttcaac ccccccatca ttgcccggta catccggctg   6420
caccccaccc actacagcat tagatcccaca ctgagaatgg aactgatggg ctgcgacctg   6480
aactcctgca gcatgcctct gggcatggaa agcaaggcca tcagcgacgc ccagatcaca   6540
gccagcagct acttccacca catgttcgcc acctggtccc cctccaaggc caggctgcac   6600
ctgcagggcc ggtccaacgc ctggcggcct caggtcaaca accccaaaga atggctgcag   6660
gtggactttc agaaaaccat gaaggtgacc ggcgtgacca ccccagggcgt gaaaagcctg   6720
ctgaccagca tgtacgtgaa agagtttctg atcagcagct ctcaggatgg ccaccagtgg   6780
accctgttct ttcagaacgg caaggtgaaa gtgttccagg gcaaccagga ctccttcacc   6840
cccgtggtga actccctgga cccccccctg ctgacccgct acctgagaat ccacccccag   6900
tcttgggtgc accagatcgc cctcaggatg gaagtcctgg gatgtgaggc ccaggatctg   6960
tactgatgac gtctggaacg cgtcgacaat caacctctgg attacaaaat ttgtgaaaga   7020
ttgactggta ttcttaacta tgttgctcct tttacgctat gtggatacgc tgctttaatg   7080
cctttgtatc atgctattgc ttcccgtatg gctttcattt tctcctcctt gtataaatcc   7140
tggttgctgt ctctttatga ggagttgtgg cccgttgtca ggcaacgtgg cgtggtgtgc   7200
actgtgtttg ctgacgcaac ccccactggt tggggcattg ccaccacctg tcagctcctt   7260
tccgggactt tcgctttccc cctccctatt gccacggcgg aactcatcgc cgcctgcctt   7320
gcccgctgct ggacaggggc tcggctgttg ggcactgaca attccgtggt gttgtcgggg   7380
aaatcatcgt cctttccttg gctgctcgcc tgtgttgcca cctggattct gcgcgggacg   7440
tccttctgct acgtcccttc ggccctcaat ccagcggacc ttccttcccg cggcctgctg   7500
ccggctctgc ggcctcttcc gcgtcttcgc cttcgccctc agacgagtcg gatctccctt   7560
tgggccgcct ccccgcctgg tacctttaag accaatgact tacaaggcag ctgtagatct   7620
tagccacttt ttaaaagaaa aggggggact ggaagggcta attcactccc aacgaaaata   7680
agatctgctt tttgcttgta ctgggtctct ctggttagac cagatctgag cctgggagct   7740
ctctggctaa ctagggaacc cactgcttaa gcctcaataa agcttgcctt gagtgcttca   7800
agtagtgtgt gcccgtctgt tgtgtgactc tggtaactag agatccctca gacccttttta   7860
gtcagtgtgg aaaatctcta gcagtagtag ttcatgtcat cttattattc agtatttata   7920
acttgcaaag aaatgaatat cagagagtga gaggaacttg tttattgcag cttataatgg   7980
ttacaaataa agcaatagca tcacaaattt cacaaataaa gcatttttt cactgcattc   8040
tagttgtggt ttgtccaaac tcatcaatgt atcttatcat gtctggctct agctatcccg   8100
cccctaactc cgcccagttc cgcccattct ccgccccatg gctgactaat tttttttatt   8160
tatgcagagg ccgaggccgc ctcggcctct gagctattcc agaagtagtg aggaggcttt   8220
tttggaggcc tagactttctg cagagacggc ccaaattcgt aatcatggtc atagctgttt   8280
cctgtgtgaa attgttatcc gctcacaatt ccacacaaca tacgagccgg aagcataaag   8340
tgtaaagcct ggggtgccta atgagtgagc taactcacat taattgcgtt gcgctcactg   8400
cccgctttcc agtcgggaaa cctgtcgtgc cagctgcatt aatgaatcgg ccaacgcgcg   8460
gggagaggcg gtttgcgtat tgggcgctct ccgcttcct cgctcactga ctcgctgcgc   8520
tcggtcgttc ggctgcggcg agcggtatca gctcactcaa aggcggtaat acggttatcc   8580
acagaatcag gggataacgc aggaaagaac atgtgagcaa aaggccagca aaaggccagg   8640
aaccgtaaaa aggccgcgtt gctggcgttt ttccataggc tccgcccccc tgacgagcat   8700
cacaaaaatc gacgctcaag tcagaggtgg cgaaacccga caggactata aagataccag   8760
gcgtttcccc ctggaagctc cctcgtgcgc tctcctgttc cgaccctgcc gcttaccgga   8820
tacctgtccg cctttctccc ttcgggaagc gtggcgcttt ctcatagctc acgctgtagg   8880
```

-continued

```
tatctcagtt cggtgtaggt cgttcgctcc aagctgggct gtgtgcacga acccccgtt      8940
cagcccgacc gctgcgcctt atccggtaac tatcgtcttg agtccaaccc ggtaagacac      9000
gacttatcgc cactggcagc agccactggt aacaggatta gcagagcgag gtatgtaggc      9060
ggtgctacag agttcttgaa gtggtggcct aactacggct acactagaag gacagtattt      9120
ggtatctgcg ctctgctgaa gccagttacc ttcggaaaaa gagttggtag ctcttgatcc      9180
ggcaaacaaa ccaccgctgg tagcggtggt tttttttgttt gcaagcagca gattacgcgc      9240
agaaaaaaag gatctcaaga agatcctttg atcttttcta cggggtctga cgctcagtgg      9300
aacgaaaact cacgttaagg gattttggtc atgagattat caaaaaggat cttcacctag      9360
atcctttaa attaaaaatg aagttttaaa tcaatctaaa gtatatatga gtaaacttgg      9420
tctgacagtt accaatgctt aatcagtgag gcacctatct cagcgatctg tctatttcgt      9480
tcatccatag ttgcctgact cccgtcgtg tagataacta cgatacggga gggcttacca      9540
tctggcccca gtgctgcaat gataccgcga gacccacgct caccggctcc agatttatca      9600
gcaataaacc agccagccgg aagggccgag cgcagaagtg gtcctgcaac tttatccgcc      9660
tccatccagt ctattaattg ttgccgggaa gctagagtaa gtagttcgcc agttaatagt      9720
ttgcgcaacg ttgttgccat tgctacaggc atcgtggtgt cacgctcgtc gtttggtatg      9780
gcttcattca gctccggttc ccaacgatca aggcgagtta catgatcccc catgttgtgc      9840
aaaaaagcgg ttagctcctt cggtcctccg atcgttgtca gaagtaagtt ggccgcagtg      9900
ttatcactca tggttatggc agcactgcat aattctctta ctgtcatgcc atccgtaaga      9960
tgcttttctg tgactggtga gtactcaacc aagtcattct gagaatagtg tatgcggcga     10020
ccgagttgct cttgcccggc gtcaatacgg gataataccg cgccacatag cagaacttta     10080
aaagtgctca tcattggaaa acgttcttcg gggcgaaaac tctcaaggat cttaccgctg     10140
ttgagatcca gttcgatgta acccactcgt gcacccaact gatcttcagc atcttttact     10200
ttcaccagcg tttctgggtg agcaaaaaca ggaaggcaaa atgccgcaaa aaagggaata     10260
agggcgacac ggaaatgttg aatactcata ctcttccttt ttcaatatta ttgaagcatt     10320
tatcaggggt tattgtctcat gagcggatac atatttgaat gtatttagaa aaataaacaa     10380
ataggggttc cgcgcacatt tccccgaaaa gtgccacctg acgtctaaga aaccattatt     10440
atcatgacat taacctataa aaataggcgt atcacgaggc cctttcgtct cgcgcgtttc     10500
ggtgatgacg gtgaaaacct ctgacacatg cagctcccgg agacggtcac agcttgtctg     10560
taagcggatg ccgggagcag acaagcccgt caggcgcgt cagcgggtgt tggcgggtgt     10620
cggggctggc ttaactatgc ggcatcagag cagattgtac tgagagtgca ccatatatgc     10680
ggtgtgaaat accgcacaga tgcgtaagga gaaaataccg catcaggcgc cattcgccat     10740
tcaggctgcg caactgttgg gaagggcgat cggtgcgggc ctcttcgcta ttacgccagc     10800
tggcgaaagg gggatgtgct gcaaggcgat taagttgggt aacgccaggg ttttcccagt     10860
cacgacgttg taaaacgacg gccagtgcca agctg                                10895
```

```
SEQ ID NO: 51          moltype = DNA   length = 11195
FEATURE                Location/Qualifiers
misc_feature           1..11195
                       note = Vector
source                 1..11195
                       mol_type = other DNA
                       organism = synthetic construct
SEQUENCE: 51
acgcgtgtag tcttatgcaa tactcttgta gtcttgcaac atggtaacga tgagttagca        60
acatgcctta caaggagaga aaaagcaccg tgcatgccga ttggtggaag taaggtggta       120
cgatcgtgcc ttattaggaa ggcaacagac gggtctgaca tggattggac gaaccactga       180
attgccgcat tgcagagata ttgtatttaa gtgcctagct gatacaata aacgggtctc       240
tctggttaga ccagatctga gcctgggagc tctctggcta actagggaac ccactgctta       300
agcctcaata aagcttgcct tgagtgcttc aagtagtgtg tgcccgtctg ttgtgtgact       360
ctggtaacta gagatccctc agacccttt agtcagtgtg gaaaatctct agcagtggcg       420
cccgaacagg gacctgaaag cgaaaggaa accagagctc tctcgacgca ggactcggct       480
tgctgaagcg cgcacggcaa gaggcgaggg gcggcgactg gtgagtacgc caaaaattt       540
gactagcgga ggctagaagg agagagatgg gtgcgagagc gtcagtatta agcggggag       600
aattagatcg cgatgggaaa aaattcggtt aaggccaggg ggaaagaaaa aatataaatt       660
aaaacatata gtatgggcaa gcagggagct agaacgattc gcagttaatc ctggccttgtt       720
agaaacatca gaaggctgta gacaaatact gggacagcta caaccatccc ttcagacagg       780
atcagaagaa cttagatcat tatataatac agtagcaacc ctctattgtg tgcatcaaag       840
gatagagata aaagacacca aggaagcttt agacaagata gaggaagagc aaaacaaaag       900
taagaccacc gcacagcaag cggccactga tcttcagacc tggaggagga gatatgaggg       960
acaattggag aagtgaatta tataaatata aagtagtaaa aattgaacca ttaggagtag      1020
cacccaccaa ggcaaagaga agagtggtgc agagagaaaa aagagcagtg ggaataggag      1080
ctttgttcct tgggttcttg ggagcagcag gaagcactat gggcgcagcc tcaatgacgc      1140
tgacggtaca ggccagacaa ttattgtctg gtatagtgca gcagcagaac aatttgctga      1200
gggctattga ggcgcaacag catctgttgc aactcacagt ctggggcatc aagcagctcc      1260
aggcaagaat cctggctgtg gaaagatacc taaaggatca acagctcctg gggatttggg      1320
gttgctctgg aaaactcatt tgcaccactg ctgtgccttg gaatgctagt tggagtaata      1380
aatctctgga acagattgga atcacacgac ctggatggag tgggacagag aaattaacaa      1440
ttacacaagc ttaatacact ccttaattga agaatcgcaa aaccagcaag aaaagaatga      1500
acaagaatta ttggaattag ataaatgggc aagtttgtgg aattggttta acataacaaa      1560
ttggctgtgg tatataaaat attcataat gatagtagga ggcttggtag gtttaagaat      1620
agttttgct gtactttcta tagtgaatag agttaggcag ggatattcac cattatcgtt      1680
tcagacccac ctcccaaccc cgaggggacc cgacaggccc gaaggaatag aagaagaagg      1740
tggagagaga gacagagaca gatccattcg attagtgaac ggatctcgac ggttaacttt      1800
taaaagaaaa gggggattg gggggtacag tgcagggaga agaatagtag acataatagc      1860
aacagacata caaactaaag aattacaaaa acaaattaca aaaattcaaa attttatcga      1920
tagcgcggcc gcttcgaacg cgcgcgatgc atcatatgga caggcttctg agtgtaggga      1980
gctggtctgc cagtctttcg gaggtttgaa cttgtcaagg ctaggcagg atcaccatat      2040
ccagcctgga cttgcagttc tgtggggtgc ctccccatac ccccataaga tgccaaacat      2100
gaggccctgt catcctccat ggtccccctc tactggctgt tcaaggccca gggctctccc      2160
```

```
atgccagata gcatcctgtc tcctaccacc actgtcccag cctgagggaa ctccctgtgc  2220
tgggcctacc cagctgaccc catcgctgga aacaatgggg gtcaggcaac acttccccac  2280
tctctcccgc cgggctgtgc tcacttcctt cctgctggct gcctgaggaa gtgtccctgc  2340
cctgggacag tctggcctag cctttgtttc cccgggggtc cccacccatg gagctttcaa  2400
ggcttctggc ccctgtgaag ccagcacacg tacgcggtct agaattcctg cagggcccac  2460
tagtctccca ggcatgactc caacaatgca tcccatggga tttgggggttc cccagatctg  2520
gggcttgtag gcctgactct cccctgtgca cacgtctcat acacgcatgc gtgcacccat  2580
tgcctgcccc gccccttgca cagggagtca gcagggagga ctgggttatg ccctgcttat  2640
cagcagcttc ccagcttcct ctgcctggat tcttagagac ctggggtcct agaacgagct  2700
ggtgcacgtg gcttcccaaa gatctctcag ataatgagag gaaatgcagt catcagtttg  2760
cagaaggcta gggattctgg gccatagctc agacctgcgc ccaccatctc cctccaggca  2820
gcccttggct ggtccctgcg agccgtggga gactgccagt cagcgctgct ggatctcggg  2880
ctcgaggcca ccatgcagat cgagctgtcc acctgctttt ttctgtgcct gctgcggttc  2940
tgcttcagcg ccacccggcg gtactacctg ggcgccgtgg agctgtcctg ggactacatg  3000
cagagcgacc tgggcgagct gcccgtggac gcccggttcc cccccagagt gcccaagagc  3060
ttccccttca acaccagcgt ggtgtacaag aaaaccctgt tcgtggagtt caccgaccac  3120
ctgttcaata tcgccaagcc caggcccccc tggatgggcc tgctgggccc caccatccag  3180
gccgaggtgt acgacaccgt ggtgatcacc ctgaagaaca tggccagcca ccccgtgagc  3240
ctgcacgccg tgggcgtgag ctactggaag gccagcgagg gcgccgagta cgacgaccag  3300
accagccagc gggagaaaga agatgacaag gtgttccctg gcggcagcca cacctacgtg  3360
tggcaggtgc tgaaagaaaa cggcccccatg gcctccgacc ccctgtgcct gacctacagc  3420
tacctgagcc acgtggacct ggtgaaggac ctgaacagcg gcctgatcgg cgctctgctc  3480
gtctgccggg agggcagcct ggccaaagag aaaaacccaga ccctgcacaa gttcatcctg  3540
ctgttcgccg tgttcgacga gggcaagagc tggcacagcg agacaaagaa cagcctgatg  3600
caggaccggg acgccgcctc tgccagagcc tggcccaaga tgcacaccgt gaacggctac  3660
gtgaacagaa gcctgcccgg cctgattggc tgccaccgga agagcgtgta ctggcacgtg  3720
atcggcatgg gcaccacacc cgaggtgcac agcatctttc tggaagggca cacctttctg  3780
gtccggaacc accggcaggc cagcctggaa atcagcccta tcacctttcct gaccgcccag  3840
acactgctga tggacctggg ccagttcctg ctgttttgcc acatcagctc tcaccagcac  3900
gacggcatgg aagcctacgt gaaggtggac tcttgccccg aggaacccca gctgcggatg  3960
aagaacaacg aggaagccga ggactacgac gacgacctga ccgacagcga gatggacgtg  4020
gtgcggttcg acgacgacaa cagccccagc ttcatccaga tcagaagcgt ggccaagaag  4080
cacccccaaga cctgggtgca ctatatcgcc gccgaggaag aggactggga ctacgccccc  4140
ctggtgctgg cccccgacga cagaagctac aagagccagt acctgaacaa tggcccccag  4200
cggatcggcc ggaagtacaa gaaagtgcgg ttcatggcct acaccgacga gacattcaag  4260
acccgggagg ccatccagca cgagagcggc atcctgggcc ccctgctgta cggcgaagtg  4320
ggcgacacac tgctgatcat cttcaagaac caggctagcc ggcctacaa catctacccc  4380
cacggcatca ccgacgtgcg gccctgtac agcaggcggc tgcccaaggg cgtgaagcac  4440
ctgaaggact tccccatcct gcccgcggag atcttcaagt acaagtggac cgtgaccgtg  4500
gaggacggcc ccaccaagag cgaccccaga tgcctgaccc ggtactacag cagcttcgtg  4560
aacatggaac gggacctggc ctccgggctg atcggacctc tgctgatctg ctacaaagaa  4620
agcgtggacc agcggggcaa ccagatcatg agcgacaagc ggaacgtgat cctgttcagc  4680
gtgttcgatg agaaccggtc ctggtatctg accgagaaca tccagcggtt tctgcccaac  4740
cctgccggcg tgcagctgga agatcccgag ttccaggcca gcaacatcat gcactccatc  4800
aatggctacg tgttcgactc tctgcagctc tccgtgtgtc tgcacgaggt ggcctactgg  4860
tacatcctga gcatcggccg ccagaccgac ttcctgagcg tgttcttcag cggctacacc  4920
ttcaagcaca agatggtgta cgaggacacc ctgaccctgt tccctttcag cggcgagaca  4980
gtgttcatga gcatggaaaa ccccggcctg tggattctgg gctgccacaa cagcgacttc  5040
cggaaccggg gcatgaccgc cctgctgaag gtgtccagct gcgacaagaa caccggcgac  5100
tactacgagg acagctacga ggatatcagc gcctacctgc tgtccaagaa caacgccatc  5160
gaaccccgga gcttcagcca gaacccccccc gtgctgaacg gtcaccagcg ggagatcaac  5220
cggacaaccc tgcagtccga ccaggaagag atcgattacg acgacaccat cagcgtggag  5280
atgaagaaag aggatttcga tatctacgac gaggacgaga accagagccc cagaagcttc  5340
cagaagaaaa cccggcacta cttcattgcc gcgtggaga ggctgtggga ctacggcatg  5400
agttctagcc cccacgtgct gcggaaccgg gcccagagcg gcagcgtgcc ccagttcaag  5460
aaagtggtgt tccaggaatt cacagacggc agcttcaccc agcctctgta tagaggcgag  5520
ctgaacgagc acctgggggct gctggggccc tacatcaggg ccgaagtgga ggacaacatc  5580
atggtgacct tccggaatca ggccagcaga ccctactcct tctacagcag cctgatcagc  5640
tacgaagagg accagcggca gggcgccgaa ccccggaaga acttcgtgaa gcccaacgaa  5700
accaagacct acttctggaa agtgcagcac cacatggccc ccaccaagga cgagttcgac  5760
tgcaaggcct gggcctactt cagcgacgtg gatctggaaa aggacgtgca ctctggactg  5820
attggcccac tcctggtctg ccacactaac accctcaacc ccgcccacgg ccgccaggtg  5880
accgtgcagg aattcgccct gttcttcacc atcttcgacg agacaaagtc ctggtacttc  5940
accgagaata tggaacggaa ctgcagagcc ccctgcaaca tccagatgga agatcctacc  6000
ttcaaagaga actaccggtt ccacgccatc aacggctaca tcatggacac cctgcctggc  6060
ctggtgatgg cccaggacca gagaatccgg tggtatctgc tgtccatggg cagcaacgag  6120
aatatccaca gcatccactt cagcggccac gtgttcaccg tgcggaagaa agaagagtac  6180
aagatggccc tgtacaacct gtaccccggc gtgttcgaga cagtggagt gctgcccagc  6240
aaggccggca tctggcggt ggagtgtctg atcggcgagc acctgcacgc tggcatgagc  6300
accctgtttc tggtgtacag caacaagtgc cagacccccac tgggcatggc ctctggccac  6360
atccgggact tccagatcac cgcctccgcc cagtacggcc agtgggcccc caagctggcc  6420
agactgcact acagcggcag catcaacgcc tggtccacca agagcccttt cagctggatc  6480
aaggtggacc tgctggcccc tatgatcatc cacggcatta gacccagggg cgccaggcag  6540
aagttcagca gcctgtacat cagccagttc atcatcatgt acagcctgga cggcaagaag  6600
tggcagacct accgggtgca cagcaccggc acccctgatg tgttcttcgg caatgtggac  6660
agcagcggca tcaagcacaa catcttcaac cccccccatca ttgcccggta catccggctg  6720
caccccaccc actacagcat tagatccaca ctgagaatgg aactgatggg ctgcgacctg  6780
aactcctgca gcatgcctct gggcatggaa agcaaggcca tcagcgacgc ccagatcaca  6840
gccagcagct acttcaccaa catgttcgcc acctggtccc cctccaaggc caggctgcac  6900
```

```
ctgcagggcc ggtccaacgc ctggcggcct caggtcaaca accccaaaga atggctgcag  6960
gtggactttc agaaaaccat gaaggtgacc ggcgtgacca cccagggcgt gaaaagcctg  7020
ctgaccagca tgtacgtgaa agagtttctg atcagcagct ctcaggatgg ccaccagtgg  7080
accctgttct ttcagaacgg caaggtgaaa gtgttccagg gcaaccagga ctccttcacc  7140
cccgtggtga actccctgga cccccccctg ctgacccgct acctgagaat ccaccccccag  7200
tcttgggtgc accagatcgc cctcaggatg gaagtcctgg gatgtgaggc ccaggatctg  7260
tactgatgac gtctggaacg cgtcgacaat caacctctgg attacaaaat ttgtgaaaga  7320
ttgactggta ttcttaacta tgttgctcct tttacgctat gtggatacgc tgctttaatg  7380
cctttgtatc atgctattgc ttcccgtatg gctttcattt tctcctcctt gtataaatcc  7440
tggttgctgt ctctttatga ggagttgtgg cccgttgtca ggcaacgtgg cgtggtgtgc  7500
actgtgtttg ctgacgcaac ccccactggt tggggcattg ccaccacctg tcagctcctt  7560
tccgggactt tcgctttccc cctccctatt gccacggcgg aactcatcgc cgcctgcctt  7620
gcccgctgct ggacaggggc tcggctgttg ggcactgaca attccgtggt gttgtcgggg  7680
aaatcatcgt cctttccttg gctgctcgcc tgtgttgcca tcggattct gcgcgggacg  7740
tccttctgct acgtcccttc ggccctcaat ccagcggacc ttccttcccg cggcctgctg  7800
ccggctctgc ggcctcttcc gcgtcttcgc cttcgccctc agacgagtcg gatctccctt  7860
tgggccgcct ccccgcctgg tacctttaag accaatgact tacaaggcag ctgtagatct  7920
tagccacttt ttaaaagaaa aggggggact ggaagggcta attcactccc aacgaaaata  7980
agatctgctt tttgcttgta ctgggtctct ctggttagac cagatctgag cctgggagct  8040
ctctggctaa ctagggaacc cactgcttaa gcctcaataa agcttgcctt gagtgcttca  8100
agtagtgtgt gcccgtctgt tgtgtgactc tggtaactag agatccctca gacccttta  8160
gtcagtgtgg aaaatctcta gcagtagtag ttcatgtcat cttattattc agtatttata  8220
acttgcaaag aaatgaatat cagagagtga gaggaacttg tttattgcag cttataatgg  8280
ttacaaataa agcaatagca tcacaaattt cacaaataaa gcattttttt cactgcattc  8340
tagttgtggt ttgtccaaac tcatcaatgt atcttatcat gtctggctct agctatcccg  8400
cccctaactc cgcccagttc cgcccattct ccgccccatg cctgactaat tttttttatt  8460
tatgcagagg ccgaggccgc ctcggcctct gagctattcc agaagtagtg aggaggcttt  8520
tttggaggcc tagactttg cagagacggc ccaaattcgt aatcatggtc atagctgttt  8580
cctgtgtgaa attgttatcc gctcacaatt ccacacaaca tacgagccgg aagcataaag  8640
tgtaaagcct ggggtgccta aatgagtgagc taactcacat taattgcgtt gcgctcactg  8700
cccgctttcc agtcgggaaa cctgtcgtgc cagctgcatt aatgaatcgg ccaacgcgcg  8760
gggagaggcg gtttgcgtat tgggcgctct tccgcttcct cgctcactga ctcgctgcgc  8820
tcggtcgttc ggctgcggcg agcggtatca gctcactcaa aggcggtaat acggttatcc  8880
acagaatcag gggataacgc aggaaagaac atgtgagcaa aaggccagca aaaggccagg  8940
aaccgtaaaa aggccgcgtt gctggcgttt tccataggc tccgcccccc tgacgagcat  9000
cacaaaaatc gacgctcaag tcagaggtgg cgaaacccga caggactata aagataccag  9060
gcgtttcccc ctggaagctc cctcgtgcgc tctcctgttc cgaccctgcc gcttaccgga  9120
tacctgtccg cctttctccc ttcgggaagc gtggcgcttt ctcatagctc acgctgtagg  9180
tatctcagtt cggtgtaggt cgttcgctcc aagctgggct gtgtgcacga accccccgtt  9240
cagcccgacc gctgcgcctt atccggtaac tatcgtcttg agtccaaccc ggtaagacac  9300
gacttatcgc cactggcagc agccactggt aacaggatta gcagagcgag gtatgtaggc  9360
ggtgctacag agttcttgaa gtggtggcct aactacggct acactagaag gacagtattt  9420
ggtatctgcg ctctgctgaa gccagttacc ttcggaaaaa gagttggtag ctcttgatcc  9480
ggcaaacaaa ccaccgctgg tagcggtggt ttttttgttt gcaagcagca gattacgcgc  9540
agaaaaaaag gatctcaaga agatcctttg atcttttcta cggggtctga cgctcagtgg  9600
aacgaaaact cacgttaagg gattttggtc atgagattat caaaaaggat cttcacctag  9660
atcctttaa attaaaaatg aagttttaaa tcaatctaaa gtatatatga gtaaacttgg  9720
tctgacagtt accaatgctt aatcagtgag gcacctatct cagcgatctg tctatttcgt  9780
tcatccatag ttgcctgact ccccgtcgtg tagataacta cgatacggga gggcttacca  9840
tctggcccca gtgctgcaat gataccgcga gacccacgct caccggctcc agatttatca  9900
gcaataaacc agccagccgg aagggccgcg cgcagaagtg gtcctgcaac tttatccgcc  9960
tccatccagt ctattaattg ttgccgggaa gctagagtaa gtagttcgcc agttaatagt 10020
ttgcgcaacg ttgttgccat tgctacaggc atcgtggtgt cacgctcgtc gtttggtatg 10080
gcttcattca gctccggttc ccaacgatca aggcgagtta catgatcccc catgttgtgc 10140
aaaaaagcgg ttagctcctt cggtcctccg atcgttgtca gaagtaagtt ggccgcagtg 10200
ttatcactca tggttatggc agcactgcat aattctctta ctgtcatgcc atccgtaaga 10260
tgcttttctg tgactggtga gtactcaacc aagtcattct gagaatagtg tatgcggcga 10320
ccgagttgct cttgcccggc gtcaatacgg gataataccg cgccacatag cagaacttta 10380
aaagtgctca tcattggaaa acgttcttcg gggcgaaaac tctcaaggat cttaccgctg 10440
ttgagatcca gttcgatgta acccactcgt gcacccaact gatcttcagc atcttttact 10500
ttcaccagcg tttctgggtg agcaaaaaca ggaaggcaaa atgccgcaaa aaagggaata 10560
agggcgacac ggaaatgttg aatactcata ctcttccttt tcaatatta ttgaagcatt 10620
tatcagggtt attgtctcat gagcggatac atatttgaat gtatttagaa aaataaacaa 10680
ataggggttc cgcgcacatt tccccgaaaa gtgccacctg acgtctaaga aaccattatt 10740
atcatgacat taacctataa aaataggcgt atcacgaggc cctttcgtct cgcgcgtttc 10800
ggtgatgacg gtgaaaacct ctgacacatg cagctcccgg agacggtcac agcttgtctg 10860
taagcggatg ccgggagcag acaagcccgt cagggcgcgt cagcgggtgt tggcgggtgt 10920
cggggctggc ttaactatgc ggcatcagag cagattgtac tgagagtgca ccatatatgc 10980
ggtgtgaaat accgcacaga tgcgtaagga gaaaataccg catcaggcgc cattcgccat 11040
tcaggctgcg caactgttgg gaagggcgat cggtgcgggc ctcttcgcta ttacgccagc 11100
tggcgaaagg gggatgtgct gcaaggcgat taagttgggt aacgccaggg ttttcccagt 11160
cacgacgttg taaaacgacg gccagtgcca agctg                             11195
```

SEQ ID NO: 52          moltype = DNA   length = 11295
FEATURE                Location/Qualifiers
misc_feature           1..11295
                       note = Vector
source                 1..11295
                       mol_type = other DNA -continued

```
                              organism = synthetic construct
SEQUENCE: 52
acgcgtgtag tcttatgcaa tactcttgta gtcttgcaac atggtaacga tgagttagca    60
acatgcctta caaggagaga aaaagcaccg tgcatgccga ttggtggaag taaggtggta   120
cgatcgtgcc ttattaggaa ggcaacagac gggtctgaca tggattggac gaaccactga   180
attgccgcat tgcagagata ttgtatttaa gtgcctagct cgatacaata aacgggtctc   240
tctggttaga ccagatctga gcctgggagc tctctggcta actagggaac ccactgctta   300
agcctcaata aagcttgcct tgagtgcttc aagtagtgtg tgcccgtctg ttgtgtgact   360
ctggtaacta gagatccctc agaccctttt agtcagtgtg gaaaatctct agcagtggcg   420
cccgaacagg gacctgaaag cgaaagggaa accagagctc tctcgacgca ggactcggct   480
tgctgaagcg cgcacggcaa gaggcgaggg gcggcgactc gtgagtacgc caaaaatttt   540
gactagcgga ggctagaagg agagagatgg gtgcgagagc gtcagtatta agcgggggag   600
aattagatcg cgatgggaaa aaattcggtt aaggccaggg ggaaagaaaa aatataaatt   660
aaaacatata gtatgggcaa gcagggagct agaacgattc gcagttaatc ctggcctgtt   720
agaaacatca gaaggctgta gacaaatact gggacagcta caaccatccc ttcagacagg   780
atcagaagaa cttagatcat tatataatac agtagcaacc ctctattgtg tgcatcaaag   840
gatagagata aaagacacca aggaagcttt agacaagata gaggaagagc aaaacaaaag   900
taagaccacc gcacagcaag cggccactga tcttcagacc tggaggagga gatatgaggg   960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggttaacttt  1800
taaaagaaaa ggggggattg gggggtacag tgcagggaa agaatagtag acataatagc  1860
aacagacata caaactaaag aattacaaaa acaaattaca aaaattcaaa attttatcga  1920
tagcgcggcc gcttcgaacg cgcgcgatgc atcatatgga gactttttt gaaaaacgaa  1980
acatctgcct atcgcaagga ctactattat tctgaaaatc accttcttca ttagaaagta  2040
atatttatca ttttattata gaactttgat cttacttctt gtgacttcat tctgcgtaga  2100
gcacactccc atccttgaat taaatgacaa agcattttat attaactgac aatgactgat  2160
gccatgggca aatcctattt ctgtaaataa ctgaattttc ttctggactg cgcatgaggg  2220
gagaaagatg tctgcagttt cggtttcctg gaaaatgaaa cctatctcat ttgttgcctg  2280
tgtcaagggg cagtgcttca gtcggggtgg agctgcttaa aaggcctggg atcacaccct  2340
ttgggaacac atccaagctt aagacggtga ggtcagcttc acattctcag gaactctcct  2400
tctttgggta agactgggag ggtgggcagg agctaccctt cccgtggccc cggaccttga  2460
gtgggctgtg ggctcaggga gcggagggga ggccttaagc atccactctc tgcccggtgt  2520
ttttgttccg tacgcggtct agaattcctg cagggcccac tagtctccca ggcatgactc  2580
caacaatgca tcccatggga tttggggttc cccagatctg gggcttgtag gcctgactct  2640
ccctgtgca cacgtctcat acacgcatgc gtgcacccat tgcctgcccc gccccttgca  2700
cagggagtca gcagggagga ctgggttatg ccctgcttat cagcagcttc ccagcttcct  2760
ctgcctggat tcttagaggc ctggggtcct agaacgagct ggtgcacgtg gcttcccaaa  2820
gatctctcag ataatgagag gaaatgcagt catcagtttg cagaaggcta gggattctgg  2880
gccatagctc agacctgcgc ccaccatctc cctccaggca gcccttggct ggtccctgcg  2940
agcccgtgga gactgccagt cagcgctgct ggatctcggg ctcgaggcca ccatgcagat  3000
cgagctgtcc acctgctttt ttctgtgcct gctgcggttc tgcttcagcg ccaccccggcg  3060
gtactacctg ggcgccgtgg agctgtcctg ggactacatg cagagcgacc tgggcgagct  3120
gcccgtggac gcccggttcc cccccagagt gcccaagagc ttcccccttca acaccagcgt  3180
ggtgtacaag aaaaccctgt tcgtggagtt caccgaccac ctgttcaata tcgccaagcc  3240
caggcccccc tggatgggcc tgctgggccc caccatccag gccgaggtgt acgacaccgt  3300
ggtgatcacc ctgaagaaca tggccagcca ccccgtgagc ctgcacgccg tgggcgtgag  3360
ctactggaag gccagcgagg gcgccgagta cgacgaccag accagccagc gggagaaaga  3420
agatgacaag gtgttccctg gcggcagcca cacctacgtg tggcaggtgc tgaaagaaaa  3480
cggcccccatg gcctccgacc ccctgtgcct gacctacagc tacctgagcc acgtggacct  3540
ggtgaaggac ctgaacagcg gcctgatcgg cgctctgctc gtctgccggg agggcagcct  3600
ggccaaagag aaaacccaga ccctgcacaa gttcatcctg ctgttcgccg tgttcgacga  3660
gggcaaagagc tggcacagcg agacaaagaa cagcctgatg caggaccggg acgccgcctc  3720
tgccagagcc tggccaaaga tgcacaccgt gaacggctac gtgaacagaa gcctgcccgg  3780
cctgattggc tgccaccgga gagcgtgta ctggcacgtg atcggcatgg gcaccacacc  3840
cgaggtgcac agcatctttc tggaagggca cacctttctg gtccggaacc accggcaggc  3900
cagcctggaa atcagcccta tcaccttcct gaccgcccag acactgctga tggacctggg  3960
ccagttcctg ctgtttgtcc acatcagctc tcaccagcac gacgccgtgg aagcctacgt  4020
gaaggtggac tcttgcccccg aggaacccca gctgcgggatg aagaacaacg aggaagccga  4080
ggactacgac gacgacctga ccgacagcga gatggacgtg gtgcggttcg acgacgacaa  4140
cagccccagc ttcatccaga tcagaagcgt ggccaagaag cacccccaaga cctgggtgca  4200
ctatatcgcc gccgaggaag aggactggga ctacgccccc ctggtgctgg cccccgacga  4260
cagaagctac aagagccagt acctgaacaa tggcccccag cggatcggcc ggaagtacaa  4320
gaaagtgcgc ttcatggcct acaccgacga gacattcaag acccgggagg gccatccagca  4380
cgagagcggc atcctgggcc ccctgctgta cggcgaagtg ggcgacacac tgctgatcat  4440
cttcaagaac caggctagcc ggccctacaa catctacccc cacggcatca ccgacgtgcg  4500
gccccctgtac agcaggcggc tgcccaaggg cgtgaagcac ctgaaggact cccccatcct  4560
gcccggcgag atcttcaagt acaagtggac cgtgaccgtg gaggacggcc ccaccaagag  4620
```

```
cgaccccaga tgcctgaccc ggtactacag cagcttcgtg aacatggaac gggacctggc   4680
ctccgggctg atcggacctc tgctgatctg ctacaaagaa agcgtggacc agcggggcaa   4740
ccagatcatg agcgacaagc ggaacgtgat cctgttcagc gtgttcgatg agaaccggtc   4800
ctggtatctg accgagaaca tccagcggtt tctgcccaac cctgccggcg tgcagctgga   4860
agatcccgag ttccaggcca gcaacatcat gcactccatc aatggctacg tgttcgactc   4920
tctgcagctc tccgtgtgtc tgcacgaggt ggcctactgg tacatcctga gcatcggcgc   4980
ccagaccgac ttcctgagcg tgttcttcag cggctacacc ttcaagcaca agatggtgta   5040
cgaggacacc ctgaccctgt tcccttttcag cggcgagaca gtgttcatga gcatggaaaa   5100
ccccggcctg tggattctgg gctgccacaa cagcgacttc cggaaccggg gcatgaccgc   5160
cctgctgaag gtgtccagct gcgacaagaa caccggcgac tactacgagg acagctacga   5220
ggatatcagc gcctacctgc tgtccaagaa caacgccatc gaaccccgga gcttcagcca   5280
gaaccccccc gtgctgacgc gtcaccacg ggagatcacc cggacaaccc tgcagtccga   5340
ccaggaagag atcgattacg acgacaccat cagcgtggag atgaagaaag aggatttcga   5400
tatctacgac gaggacgaga accagagccc cagaagcttc cagaagaaaa cccggcacta   5460
cttcattgcc gccgtggaga ggctgtggga ctacggcatg agttctagcc cccacgtgct   5520
gcggaaccgg gcccagagcg gcagcgtgcc ccagttcaag aaagtggtgt tccaggaatt   5580
cacagacggc agcttcaccc agcctctgta tagaggcgag ctgaacgagc acctgggggct   5640
gctggggccc tacatcaggg ccgaagtgga ggacaacatc atggtgacct tccggaatca   5700
ggccagcaga ccctactcct tctacagcag cctgatcagc tacgaagagg accagcggca   5760
gggcgccgaa ccccggaaga acttcgtgaa gcccaacgaa accaagacct acttctggaa   5820
agtgcagcac cacatggccc ccaccaagga cgagttcgac tgcaaggcct gggcctactt   5880
cagcgacgtg gatctggaaa ggacgtgca ctctggactg attggcccac tcctggtctg   5940
ccacactaac accctcaacc ccgcccacgg ccgccaggtg accgtgcagg aattcgccct   6000
gttcttcacc atcttcgacg agacaaagtc ctggtacttc accgagaata tggaacggaa   6060
ctgcagagcc ccctgcaaca tccagatgga agatcctacc ttcaaagaga actaccggtt   6120
ccacgccatc aacggctaca tcatggacac cctgcctggc ctggtgatgg cccaggacca   6180
gagaatccgg tggtatctgc tgtccatggg cagcaacgga aatatccaca gcatccactt   6240
cagcggccac gtgttcaccg tgcggaagaa agaaagagtac aagatggccc tgtacaacct   6300
gtaccccggc gtgttcgaga cagtggagat gctgcccagc aaggccggca tctggcgggt   6360
ggagtgtctg atcggcgagc acctgcacgc tggcatgagc accctgtttc tggtgtacag   6420
caacaagtgc cagacccccac tgggcatggc ctctggccac atccgggact tccagatcac   6480
cgcctccggc cagtacggcc agtgggcccc caagctggcc agactgcact acagcggcag   6540
catcaacgcc tggtccacca aagagcctt cagctggatc aaggtggacc tgctggcccc   6600
tatgatcatc cacggcatta agaccccagg cgccaggcag aagttcagca gcctgtacat   6660
cagccagttc atcatcatgt acagcctgga cggcaagaag tggcagacct accgggggcaa   6720
cagcaccggc accctgatgg tgttcttcgg caatgtggac agcagcggca tcaagcacaa   6780
catcttcaac cccccccatca ttgcccggta catccggctg cacccaccc actacagcat   6840
tagatccaca ctgagaatgg aactgatggg ctgcgacctg aactcctgca gcatgcctct   6900
gggcatggaa agcaaggcca tcagcgacgc ccagatcaca gccagcagct acttcaccaa   6960
catgttcgcc acctggtccc cctccaaggc caggctgcac ctgcagggcc ggtccaacgc   7020
ctggcgggcct caggtcaaca accccaaaga atggctgcag gtggactttc agaaaaccat   7080
gaaggtgacc ggcgtgacca cccagggcgt gaaaagcctg ctgaccagca tgtacgtgaa   7140
agagtttctg atcagcagct ctcaggatgg ccaccagtgg acctgttct ttcagaacgg   7200
caaggtgaaa gtgttccagg gcaaccagga ctccttcacc cccgtggtga actccctgga   7260
ccccccccctg ctgacccgct acctgagaat ccaccccccag tcttgggtgc accagatcgc   7320
cctcaggatg gaagtcctgg gatgtgaggc ccaggatctg tactgatgac gtctggaacg   7380
cgtcgacaat caacctctgg attacaaaat ttgtgaaaga ttgactggta ttcttaacta   7440
tgttgctcct tttacgctat gtggatacgc tgctttaatg cctttgtatc atgctattgc   7500
ttcccgtatg gctttcattt tctcctcctt gtataaatcc tggttgctgt ctctttatga   7560
ggagttgtg cccgttgtca ggcaacgtgg cgtggtgtgc actgtgtttg ctgacgcaac   7620
ccccactggt tggggcattg ccaccacctg tcagctcctt tccgggactt tcgctttcc   7680
cctccctatt gccacggcgg aactcatcgc cgcctgcctt gcccgctgct ggacaggggc   7740
tcggctgttg ggcactgaca attccgtggt gttgtcgggg aaatcatcgt cctttccttg   7800
gctgctcgcc tgtgttgcca cctggattct gcgcgggacg tccttctgct acgtcccttc   7860
ggccctcaat ccagcggacc ttccttcccg cggcctgctg ccggctctgc ggcctcttcc   7920
gcgtcttcgc cttcgccctc agacgagtcg gatctccctt tgggccgcct ccccgcctgg   7980
tacctttaag accaatgact acaaggcag ctgtagatct tagccacttt ttaaaagaaa   8040
aggggggact ggaagggcta attcactccc aacgaaaata agatctgctt tttgcttgta   8100
ctgggtctct ctggttagac cagatctgag cctgggagct ctctggctaa ctagggaacc   8160
cactgcttaa gcctcaataa agcttgcctt gagtgcttca agtagtgtgt gcccgtctgt   8220
tgtgtgactc tggtaactag agatccctca gacccttttta gtcagtgtgg aaaatctcta   8280
gcagtagtag ttcatgtcat cttattattc agtatttata acttgcaaag aaatgaatat   8340
cagagagtga gaggaacttg tttattgcag cttataatgg ttacaaataa agcaatagca   8400
tcacaaattt cacaaataaa gcatttttt cactgcattc tagttgtggt ttgtccaaa   8460
tcatcaatgt atcttatcat gtctggctct agctatcccg ccctaactc cgcccagttc   8520
cgcccattct ccgccccatg gctgactaat tttttttatt tatgcagagg ccgaggccgc   8580
ctcggcctct gagctattcc agaagtagtg aggaggcttt tttggaggcc tagacttttg   8640
cagagacggc ccaaattcgt aatcatggtc atagctgttt cctgtgtgaa attgttatcc   8700
gctcacaatt ccacacaaca tacgagccgg aagcataaag tgtaaagcct ggggtgccta   8760
atgagtgagc taactcacat taattgcgtt gcgctcactg cccgctttcc agtcgggaaa   8820
cctgtcgtgc cagctgcatt aatgaatcgg ccaacgcgcg gggagaggcg gtttgcgtat   8880
tgggcgctct tccgcttcct cgctcactga ctcgctgcgc tcggtcgttc ggctgcggcg   8940
agcggtatca gctcactcaa aggcggtaat acggttatcc acagaatcag gggataacgc   9000
aggaaagaac atgtgagcaa aaggccagca aaaggccagg aaccgtaaaa aggccgcgtt   9060
gctggcgttt ttccataggc tccgcccccc tgacgagcat cacaaaaatc gacgctcaag   9120
tcagaggtgg cgaaacccga caggactata aagataccag gcgtttcccc ctggaagctc   9180
cctcgtgcgc tctcctgttc cgaccctgcc gcttaccgga tacctgtccg cctttctccc   9240
ttcgggaagc gtggcgcttt ctcatagctc acgctgtagg tatctcagtt cggtgtaggt   9300
cgttcgctcc aagctgggct gtgtgcacga accccccgtt cagcccgacc gctgcgcctt   9360
```

```
atccggtaac tatcgtcttg agtccaaccc ggtaagacac gacttatcgc cactggcagc    9420
agccactggt aacaggatta gcagagcgag gtatgtaggc ggtgctacag agttcttgaa    9480
gtggtggcct aactacggct acactagaag gacagtattt ggtatctgcg ctctgctgaa    9540
gccagttacc ttcggaaaaa gagttggtag ctcttgatcc ggcaaacaaa ccaccgctgg    9600
tagcggtggt ttttttgttt gcaagcagca gattacgcgc agaaaaaaag gatctcaaga    9660
agatcctttg atcttttcta cggggtctga cgctcagtgg aacgaaaact cacgttaagg    9720
gattttggtc atgagattat caaaaaggat cttcacctag atccttttaa attaaaaatg    9780
aagtttttaaa tcaatctaaa gtatatatga gtaaacttgg tctgacagtt accaatgctt    9840
aatcagtgag gcacctatct cagcgatctg tctatttcgt tcatccatag ttgcctgact    9900
ccccgtcgtg tagataacta cgatacggga gggcttacca tctggcccca gtgctgcaat    9960
gataccgcga gaccacgct caccggctcc agatttatca gcaataaacc agccagccgg    10020
aagggccgag cgcagaagtg gtcctgcaac tttatccgcc tccatccagt ctattaattg    10080
ttgccgggaa gctagagtaa gtagttcgcc agttaatagt ttgcgcaacg ttgttggccat    10140
tgctacaggc atcgtggtgt cacgctcgtc gtttggtatg gcttcattca gctccggttc    10200
ccaacgatca aggcgagtta catgatcccc catgttgtgc aaaaaagcgg ttagctcctt    10260
cggtcctccg atcgttgtca gaagtaagtt ggccgcagtg ttatcactca tggttatggc    10320
agcactgcat aattctctta ctgtcatgcc atccgtaaga tgcttttctg tgactggtga    10380
gtactcaacc aagtcattct gagaatagtg tatgcggcga ccgagttgct cttgcccggc    10440
gtcaatacgg gataataccg cgccacatag cagaacttta aaagtgctca tcattggaaa    10500
acgttcttcg gggcgaaaac tctcaaggat cttaccgctg ttgagatcca gttcgatgta    10560
acccactcgt gcacccaact gatcttcagc atcttttact ttcaccagcg tttctggggtg    10620
agcaaaaaca ggaaggcaaa atgccgcaaa aaagggaata aggggcgacac ggaaatgttg    10680
aatactcata ctcttccttt ttcaatatta ttgaagcatt tatcagggtt attgtctcat    10740
gagcggatac atatttgaat gtatttagaa aaataaacaa ataggggttc cgcgcacatt    10800
tccccgaaaa gtgccacctg acgtctaaga aaccattatt atcatgacat taacctataa    10860
aaataggcgt atcacgaggc cctttcgtct cgcgcgtttc ggtgatgacg gtgaaaacct    10920
ctgacacatg cagctcccgg agacggtcac agcttgtctg taagcggatg ccgggagcag    10980
acaagcccgt cagggcgcgt cagcgggtgt tggcgggtgt cggggctggc ttaactatgc    11040
ggcatcagag cagattgtac tgagagtgca ccatatatgc ggtgtgaaat accgcacaga    11100
tgcgtaagga gaaaataccg catcaggcgc cattcgccat tcaggctgcg caactgttgg    11160
gaagggcgat cggtgcgggc ctcttcgcta ttacgccagc tggcgaaagg gggatgtgct    11220
gcaaggcgat taagttgggt aacgccaggg tttttcccagt cacgacgttg taaaacgacg    11280
gccagtgcca agctg                                                     11295

SEQ ID NO: 53              moltype = DNA   length = 20
FEATURE                    Location/Qualifiers
misc_feature               1..20
                           note = Primer
source                     1..20
                           mol_type = other DNA
                           organism = synthetic construct
SEQUENCE: 53
aacggctacg tgaacagaag                                                    20

SEQ ID NO: 54              moltype = DNA   length = 20
FEATURE                    Location/Qualifiers
misc_feature               1..20
                           note = Primer
source                     1..20
                           mol_type = other DNA
                           organism = synthetic construct
SEQUENCE: 54
gatagggctg atttccaggc                                                    20

SEQ ID NO: 55              moltype = DNA   length = 19
FEATURE                    Location/Qualifiers
misc_feature               1..19
                           note = Primer
source                     1..19
                           mol_type = other DNA
                           organism = synthetic construct
SEQUENCE: 55
gaaggtgaag gtcggagtc                                                     19

SEQ ID NO: 56              moltype = DNA   length = 20
FEATURE                    Location/Qualifiers
misc_feature               1..20
                           note = Primer
source                     1..20
                           mol_type = other DNA
                           organism = synthetic construct
SEQUENCE: 56
gaagatggtg atgggatttc                                                    20
```